United States Patent
Asami et al.

(10) Patent No.: US 9,260,500 B2
(45) Date of Patent: Feb. 16, 2016

(54) PEPTIDE AND USE THEREOF

(75) Inventors: Taiji Asami, Kanagawa (JP); Naoki Nishizawa, Kanagawa (JP); Ayumu Niida, Kanagawa (JP); Yusuke Adachi, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 354 days.

(21) Appl. No.: 13/381,737

(22) PCT Filed: Jul. 1, 2010

(86) PCT No.: PCT/JP2010/061274
§ 371 (c)(1),
(2), (4) Date: Dec. 30, 2011

(87) PCT Pub. No.: WO2011/002066
PCT Pub. Date: Jan. 6, 2011

(65) Prior Publication Data
US 2012/0172293 A1 Jul. 5, 2012

(30) Foreign Application Priority Data
Jul. 2, 2009 (JP) ................................. 2009-158278

(51) Int. Cl.
*A61K 38/10* (2006.01)
*A61P 3/04* (2006.01)
*C07K 7/08* (2006.01)
*C07K 14/575* (2006.01)
*A61K 38/00* (2006.01)

(52) U.S. Cl.
CPC ............... *C07K 14/575* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 5,604,203 | A | 2/1997 | Balasubramaniam |
| 6,046,167 | A | 4/2000 | Balasubramaniam |
| 7,608,245 | B2 | 10/2009 | Lin |
| 2007/0197445 | A1 | 8/2007 | Balasubramaniam |
| 2008/0194486 | A1 | 8/2008 | Bridon et al. |

FOREIGN PATENT DOCUMENTS

| | | |
|---|---|---|
| WO | 03/026591 | 4/2003 |
| WO | 2004/056314 | 7/2004 |
| WO | 2004/066966 | 8/2004 |
| WO | 2005/080433 | 9/2005 |
| WO | 2005/089789 | 9/2005 |
| WO | 2006/007412 | 1/2006 |
| WO | 2006/049681 | 5/2006 |
| WO | 2006/066024 | 6/2006 |
| WO | 2006/077035 | 7/2006 |
| WO | 2006/091505 | 8/2006 |
| WO | 2007/065808 | 6/2007 |
| WO | 2009/138511 | 11/2009 |
| WO | 2010/031707 | 3/2010 |
| WO | 2010/052144 | 5/2010 |

OTHER PUBLICATIONS

Ioannides-Demos et al. (Drugs, 2005 (10); 1391-1418).*
Mayo Clinic—Obesity Risk Factors, http://www.mayoclinic.com/health/obesity/DS00314, accessed Nov. 13, 2013.*
Lawlor et al. (International Journal of Epidemiology 2006; 35: pp. 3-9.*
International Search Report issued Sep. 21, 2010 in International (PCT) Application No. PCT/JP2010/061274.
A. Balasubramaniam et al., "Structure-Activity Studies of Peptide YY (22-36): N-α-Ac[Phe$^{27}$]PYY(22-36), A Potent Antisecretory Peptide in Rat Jejunum", Peptides, vol. 14, No. 5, pp. 1011-1016, Sep. 1993.
A. Balasubramaniam et al., "Neuropeptide Y (NPY) Y$_2$ Receptor-Selective Agonist Inhibits Food Intake and Promotes Fat Metabolism in Mice: Combined Anorectic Effects of Y$_2$ and Y$_4$ Receptor-Selective Agonists", Peptides, vol. 28, No. 2, pp. 235-240, 2007.
Extended European Search Report issued Apr. 22, 2014 in corresponding Application No. 10 79 4234.4.
Beck-Sickinger et al., "A novel cyclic analog of neuropeptide Y specific for the Y$_2$ receptor", European Journal of Biochemistry, 1992, vol. 206, No. 3, pp. 957-964.
Batterham et al., "Gut hormone PYY$_{3-36}$ physiologically inhibits food intake", Nature, 2002, vol. 418, pp. 650-654.

* cited by examiner

*Primary Examiner* — James H Alstrum Acevedo
*Assistant Examiner* — Tara Martinez
(74) *Attorney, Agent, or Firm* — Wenderoth, Lind & Ponack, L.L.P.

(57) ABSTRACT

The present invention aims to provide a peptide having a superior Y2 receptor agonist action and useful as an agent for the prophylaxis or treatment of obesity and the like.
A peptide represented by the formula:

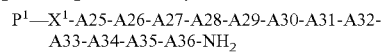

P$^1$—X$^1$-A25-A26-A27-A28-A29-A30-A31-A32-A33-A34-A35-A36-NH$_2$ wherein each symbol is as described in the specification, or a salt thereof.

10 Claims, No Drawings

PEPTIDE AND USE THEREOF

This application is a U.S. national stage of International Application No. PCT/JP2010/061274 filed Jul. 1, 2010.

TECHNICAL FIELD

The present invention relates to a peptide having a Y2 receptor agonist action and use thereof.

BACKGROUND OF THE INVENTION

Peptide YY (PYY) is a peptide consisting of 36 amino acid residues, which is isolated from the porcine upper small intestine. PYY belongs to the pancreatic polypeptide (PP) family together with neuropeptide Y (NPY) isolated from the porcine brain.

It is known that PYY is secreted from the gastrointestinal tract endocrine cell (L cell) along with the diet ingestion, and shows a feeding suppressive action via Y2 receptor. As this action pathways, the intestine-hypothalamus pathway via Y2 receptor of hypothalamic actuate nucleus NPY/AgRP expression nerve cell, and the vagal afferent pathway via Y2 receptor of vagal nerve ending have been reported.

In addition, it has been reported that patients with Anorexia Nervosa (AN) having bad eating behavior show high PYY level in the cerebrospinal fluid, and patients with Bulimia Nervosa (BN) show extremely slow postprandial increase of blood PYY level as compared to that of healthy individuals. Furthermore, it is known that the blood PYY level of obesity patients is lower than that of healthy individuals (Nature, 418, 650-654 (2002), N. Engl. Med., 349, 941-948 (2003) (non-patent documents 1-2)).

On the other hand, the following reports are available.

WO2006/049681 (patent document 1) describes peptide represented by the following formula or a salt thereof.

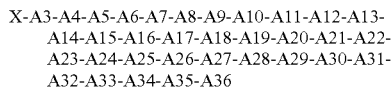

wherein,
X is an N-terminal modifying group;
A3 is Ile, Ser or deleted;
A4 is Lys or deleted;
A5 is Pro or deleted;
A6 is Glu, Asp or deleted;
A7 is Ala, Asn or deleted;
A8 is Pro or deleted;
A9 is Gly or deleted;
A10 is Glu or deleted;
A11, is Asp or deleted;
A12 is Ala or deleted;
A13 is Ser, Pro or deleted;
A14 is Pro, Ala or deleted;
A15 is Glu or deleted;
A16 is Glu, Asp or deleted;
A17 is Leu, Met or deleted;
A18 is Asn, Ala or deleted;
A19 is Arg or deleted;
A20 is Tyr or deleted;
A21 is Tyr or deleted;
A22 is Ala, Ser or deleted;
A23 is Ser, Ala or deleted;
A24 is Leu or deleted;
A25 is Arg or deleted;
A26 is His or deleted;
A27 is Tyr or deleted;
A28 is Leu, Ile or deleted;
A29 is Asn or deleted;
A30 is Leu or deleted;
A31 is Val, Ile or deleted;
A32 is Thr;
A33 is Arg;
A34 is Gln;
A35 is Arg; and
A36 is Tyr.

U.S. Pat. No. 5,604,203 (patent document 2) describes a compound represented by the following formula or a pharmacologically acceptable salt thereof.

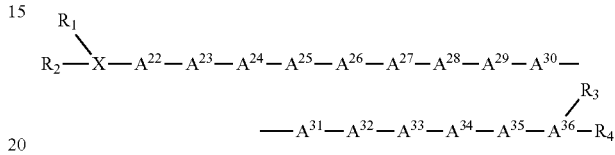

wherein X is Cys or deleted;
each of $R_1$ and $R_2$ is bonded to a nitrogen atom of an α-amino group of the N-terminal amino acid;
$R_1$ is H, $C_1$-$C_{12}$ alkyl, $C_6$-$C_{18}$ aryl, $C_1$-$C_{12}$ acyl, $C_7$-$C_{18}$ aralkyl, or $C_7$-$C_{18}$ alkaryl;
$R_2$ is H, $C_1$-$C_{12}$ alkyl, $C_6$-$C_{18}$ aryl, $C_1$-$C_{12}$ acyl, $C_7$-$C_{18}$ aralkyl, or $C_7$-$C_{18}$ alkaryl;
$A^{22}$ is aromatic amino acid, Ala, Aib, Anb, N-Me-Ala, or deleted;
$A^{23}$ is Ser, Thr, Ala, Aib, N-Me-Ser, N-Me-Thr, N-Me-Ala, D-Trp, or deleted;
$A^{24}$ is Leu, Gly, Ile, Val, Tip, Nle, Nva, Aib, Anb, N-Me-Leu, or deleted;
$A^{25}$ is Arg, Lys, homo-Arg, diethyl-homo-Arg, Lys-ε-NH—R (where R is H, a branched or straight chain $C_1$-$C_{10}$ alkyl group, or an aryl group), Orn, or deleted;
$A^{26}$ is Ala, His, Thr, 3-Me-His, 1-Me-His, β-pyrozolylalanine, N-Me-His, Arg, Lys, homo-Arg, diethyl-homo-Arg, Lys-ε-NH—R (R is H, branched chain or straight chain $C_1$-$C_{10}$ alkyl group, or an aryl group), Orn, or deleted;
$A^{27}$ is Nal, Bip, Pcp, Tic, Trp, Bth, Thi, or Dip;
$A^{28}$ is Leu, Val, Trp, Nle, Nva, Aib, Anb, or N-Me-Leu;
$A^{29}$ is Asn, Ala, Gln, Gly, Trp, or N-Me-Asn;
$A^{30}$ is Leu, Ile, Val, Trp, Nle, Nva, Aib, Anb, or N-Me-Leu;
$A^{31}$ is Val, Leu, Ile, Trp, Nle, Nva, Aib, Anb, or N-Me-Val;
$A^{32}$ is Thr, Ser, N-Me-Ser, N-Me-Thr, or D-Trp;
$A^{33}$ is Cys, Arg, Lys, homo-Arg, diethyl-homo-Arg, Lys-ε-NH—R (where R is H, branched chain or straight chain $C_1$-$C_{10}$ alkyl group, or $C_6$-$C_{18}$ aryl group), or Orn;
$A^{34}$ is Cys, Gln, Asn, Ala, Gly, N-Me-Gln, Aib, or Anb;
$A^{35}$ is Cys, Arg, Lys, homo-Arg, diethyl-homo-Arg, Lys-ε-NH—R (where R is H, branched chain or straight chain $C_1$-$C_{10}$ alkyl group, or $C_6$-$C_{18}$ aryl group), or Orn;
$A^{36}$ is an aromatic amino acid or Cys;
$R_3$ is H, $C_1$-$C_{12}$ alkyl, $C_6$-$C_{18}$ aryl, $C_1$-$C_{12}$ acyl, $C_7$-$C_{18}$ aralkyl, or $C_7$-$C_{18}$ alkaryl; and
$R_4$ is H, $C_1$-$C_{12}$ alkyl, $C_6$-$C_{18}$ aryl, $C_1$-$C_{12}$ acyl, $C_7$-$C_{18}$ aralkyl, or $C_7$-$C_{18}$ alkaryl.

U.S. Pat. No. 6,046,167 (patent document 3) describes the following compound or a pharmaceutically acceptable salt thereof.

N-α$R^1$—[Nle$^{24,28,30}$, Trp$^{27}$, Nva$^{31}$, ψ$^{35/36}$]PYY(22-36)-NH$_2$,

N-α$R^1$—[Nle$^{24,28}$, Trp$^{27,30}$, Nva$^{31}$, ψ$^{35/36}$]PYY(22-36)-NH$_2$,

N-αR¹—[Nle$^{24,28,30}$, Phe$^{27}$, Nva$^{31}$, ψ$^{35/36}$]PYY(22-36)-NH$_2$,

N-αR¹—[Nle$^{24,28}$, Phe$^{27}$, Trp$^{30}$, Nva$^{31}$, ψ$^{35/36}$]PYY(22-36)-NH$_2$,

N-α-R¹—[Trp$^{30}$, ψ$^{35/36}$]PYY(25-36)-NH$_2$,

N-α-R¹—[Trp$^{30}$]PYY(25-36)-NH$_2$,

N-α-R¹—[Nle$^{24,28}$, Trp$^{30}$, Nva$^{31}$, ψ$^{35/36}$]PYY(22-36)-NH$_2$ and N-α-R¹—[Nle$^{28}$, Trp$^{30}$, Nva31, ψ$^{35/36}$]PYY(22-36)-NH$_2$, wherein R$_1$ is H, (C$_1$-C$_{12}$)alkyl or (C$_1$-C$_{12}$)acyl;

Ψ is a pseudopeptide bond selected from the group consisting of —CH$_2$—NH—, —CH$_2$—S—, —CH$_2$—CH$_2$—, —CH$_2$—O—, and —CH$_2$—CO—.

WO2004/056314 (patent document 4) describes "a transmucosal Y2 receptor-binding peptide formulation capable of raising the concentration of the Y2 receptor-binding peptide in the plasma of a mammal by at least 5 pmoles per liter of plasma or more when a dose containing at least 50 μg of the Y2 receptor-binding agonist is administered transmucosally to said mammal".

WO2005/080433 (patent document 5) describes "a pharmaceutical composition product comprising: a. an aqueous solution formulation of a Y2 receptor binding compound at a concentration sufficient to produce therapeutically effective plasma concentrations and; b. an actuator able to produce an aerosol of said solution, wherein the spray pattern ellipticity ratio of said aerosol is between 1.00 and 1.40 when measured at a height of between 0.5 cm and 10 cm distance from the actuator tip".

WO2006/007412 (patent document 6) describes "an aqueous Y2 receptor-binding peptide formulation suitable for transmucosal administration, comprising a Y2 receptor-binding peptide, a cyclodextrin and an effective amount of an anti-microbial preservative".

US2008/0194486 (patent document 7) describes "a compound comprising a PYY peptide or a functional derivative thereof which is coupled to a reactive group, said reactive group being capable of reacting with an amino group, a hydroxyl group or a thiol group on a blood component so as to form a stable covalent bond therewith, thereby substantially preventing said PYY peptide or functional derivative thereof from crossing the blood brain barrier".

DOCUMENT LIST

Patent Documents patent document 1: WO2006/049681
patent document 2: U.S. Pat. No. 5,604,203
patent document 3: U.S. Pat. No. 6,046,167
patent document 4: WO2004/056314
patent document 5: WO2005/080433
patent document 6: WO2006/007412
patent document 7: US2008/0194486

Non-Patent Documents non-patent document 1: Nature, 418, 650-654 (2002)
non-patent document 2: N. Engl. Med., 349, 941-948 (2003)

SUMMARY OF THE INVENTION

Problems to be Solved by the Invention

The present invention aims to provide a peptide having a superior Y2 receptor agonist action, and useful as an agent for the prophylaxis or treatment of obesity and the like.

Means of Solving the Problems

The present inventors have conducted intensive studies about peptide having a superior Y2 receptor agonist action, and useful as an agent for the prophylaxis or treatment of obesity and the like, and found that a peptide represented by the following formula (I) and the like have a superior Y2 receptor agonist action, which resulted in the completion of the present invention.

Accordingly, the present invention relates to

[1] a peptide represented by the formula (I):

P¹—X¹-A25-A26-A27-A28-A29-A30-A31-A32-A33-A34-A35-A36-NH$_2$  (I)

wherein

P¹ is a group represented by the formula:

—R$^{A1}$,
—CO—R$^{A1}$,
—CO—OR$^{A1}$,
—CO—COR$^{A1}$,
—SO—R$^{A1}$,
—SO$_2$—R$^{A1}$,
—SO$_2$—OR$^{A1}$,
—CO—NR$^{A2}$R$^{B2}$,
—SO$_2$—NR$^{A2}$R$^{B2}$, or
—C(=NR$^{A1}$)—NR$^{A2}$R$^{B2}$ wherein R$^{A1}$, R$^{A2}$ and R$^{B2}$ are each independently a hydrogen atom, an optionally substituted hydrocarbon group, or an optionally substituted heterocyclic group;

X¹ is (1) a group represented by the formula:

—X²-L¹-C(J¹)(Q¹)-Y¹—C(J²)(Q²)-Y²—C(J³)(Q³)-Y³—C(J⁴)(Q⁴)-C(=Z¹)—, or

—X²-A21-A22-A23-A24- wherein

X² is a group represented by the formula:
(i) —X³-A17-A18-A19-A20-,
(ii) -A17-A18-A19-A20-,
(iii) -A18-A19-A20-,
(iv) -A19-A20-, or
(v) -A20- wherein
A17 is Leu, or Tyr;
A18 is Ala, Asn, or Pro;
A19 is Arg, D-Arg, Ile, or Acp;
A20 is Arg, Tyr, D-Arg, Lys, or Acp; and
X³ shows any amino acid residue(s) bound continuously or discontinuously to each other from the C-terminal of the 10th-16th amino acid of the amino acid sequence shown by SEQ ID NO:1;

L¹ is NH optionally substituted by a C$_{1-6}$ alkyl group, or CH$_2$ optionally substituted by a C$_{1-6}$ alkyl group, O, or S;

J¹, J², J³ and J⁴ are each independently a hydrogen atom or a C$_{1-3}$ alkyl group;

Q¹, Q², Q³ and Q⁴ are each independently a hydrogen atom or an optionally substituted C$_{1-10}$ alkyl group;

J¹ and Q¹, J² and Q², J³ and Q³, and J⁴ and Q⁴, or L¹ and Q¹, Y¹ and Q², Y² and Q³, and Y³ and Q⁴ are optionally bonded to form a ring;

Y¹, Y² and Y³ are each independently a group represented by the formula: —CON(J⁵)-, —CSN(J⁶)-, —C(J⁷)(J⁸)N(J⁹)-, —N(J¹⁰)CO—, or —C(J¹¹)=C(J¹²)- wherein J⁵, J⁶, J⁷, J⁸, J⁹, J¹⁰, J¹¹ and J¹² are each independently a hydrogen atom or a $C_{1-3}$ alkyl group;

Z¹ is O or S;

A21 is D-Tyr, Tyr, Acp, Pro, Ambz(4), Lys or Arg;

A22 is Ala, Acp, Phe, Dap, Leu, Lys, D-Ala, Ile, Lys[Hexadecanoyl-(PEG2)], Tyr, Aib, Ambz(4), Pic(4), Gly, PEG2 or Adc(12);

A23 is Ser, Glu, Gln, Arg, Acp, Thr, Asp, Lys, D-Arg, D-Ser, Gly, Ser(Me), Abu, Phe, Asn, β-Ala, Aoc(8), PEG2, Pic(4), Hyp, NMeSer, N(iBu)Gly, N(2-hydroxyethyl)Gly, Hse, D-Thr, Aad, Lys(Me₂), Tyr, Lys(Ac), Iva or D-Iva; and A24 is D-Pro, D-Hyp, Aib, D-Iva, Iva, β-Ala, DL-β-HOAla, Aipe, Ambz(4), Leu, Acp, D-Leu, Phe, D-Phe, Cha, D-Cha, Pro, Abz(2), Pic(4), N(iBu)Gly, NMeAla, D-NMeAla, Sar, Gly, Aze(3), D-cisHyp, D-Pic(2), D-Aze(2), α-MePro, D-α-MePro or GABA, (2) a group represented by the formula:

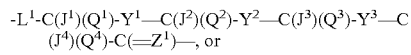

-A21-A22-A23-A24- wherein each symbol is as defined above, (3) a group represented by the formula:

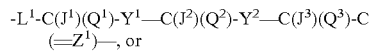

-A22-A23-A24- wherein each symbol is as defined above, (4) a group represented by the formula:

-L¹-C(J¹)(Q¹)-Y¹—C(J²)(Q²)-C(=Z¹)—, or

-A23-A24- wherein each symbol is as defined above, (5) a group represented by the formula:

-L¹-C(J¹)(Q¹)-C(=Z¹)—, or

-A24- wherein each symbol is as defined above, or (6) a bond;

A25 is Iva, Arg, Nle, Arg(Me), Ala(4Pip), Cit, Aib, Nar, Lys(Ac), Har, D-Iva, D-Arg, Orn, Lys, D-Ala(4Pip) or a bond;

A26 is Pya(4), His, Abu, Ala(4Pip), Phe, Pya(2), Cha, Gln, Aib, Ala, Arg, Pro, Ala(cPr), Gly, Dap, Ser, Ser(Me), Asn, Hse, Thr, Pya(3), Alb, Orn, Glu, Cit, Iva, D-Iva, D-Ala(4Pip), Tyr, Trp, Tyr(Me), Nle or a bond;

A27 is Cha, Nal(2), Phe(4F), Nal(1), Ala(4Pip), Tyr, Glu, Arg, Gln, Nle, Pya(4), Trp, Phe(4NH₂), Aib, D-Ala(4Pip), Dap, Nva, His, Cit, Iva, D-Iva, Abu, Gly or a bond;

A28 is Aib, Iva, Leu(Me), Cha, α-MePhe, D-Iva, Tyr, Ile, Leu, Nle, Phe, Trp, Lys, Ala, Nal(1), Ala(cPr), Phe(4F), Pya(4), Gln, His, Hse, Acpc, Nva, Gly(cPr), Ser or a bond;

A29 is Asn, Aib, Asn(Me), D-Iva or a bond;

A30 is Lys, Har, Arg(Me), Ala(4Pip), Cha, Lys(Me), Orn, Lys(Ac), Arg, Leu, Nle, Cit, Lys(Hexyl), Trp, Hse, Thr, Ala, Gly, Aib, Phe, Nal(1), Nal(2), Tyr, Phe(4F), Dap, Pya(4), Phe(4NH₂), Ala(cPr), Leu(Me), Ser, Gln, Abu, His, Dab, Lys(Me₂), Iva or a bond;

A31 is Aib, D-Iva, Iva, Ile, Lys, Ala, Val, Phg, Cha, Nle, Phe, Arg, Dap, Arg(Me), Pya(4), Phe(4NH₂), Pya(3), Gly(cPr), Acpc or a bond;

A32 is Thr, Glu, Nva, Leu, Thr(Me), Abu, Ser or a bond;

A33 is Arg, Arg(Me) or a bond;

A34 is Gln or a bond;

A35 is Arg, Arg(Me) or a bond; and

A36 is Cha, Phe(2,6-Me₂), Phe(3Me), Phe(2Me), Tyr, Phe(2F), Phe, Phe(3F), Leu(Me), homoLeu, threo-PhSer, Trp, Tyr(Me), Phe(4Cl), Phe(4NH₂), Nal(1), Nal(2), Phe(4Me), Tyr(2F), Tyr(3F), NMePhe, Tic or a bond, wherein side chains of two amino acid residues selected from A25, A26, A27, A28, A29, A30, A31, A32, A33, A34, A35 and A36 are optionally bonded to form a ring, provided that 3 or more groups selected from A25, A26, A27, A28, A29, A30, A31, A32, A33, A34, A35 and A36 are not bonds at the same time, and PYY(10-36), PYY(11-36), PYY(12-36), PYY(13-36), PYY(14-36), PYY(15-36), PYY(16-36), PYY(17-36), PYY(18-36), PYY(19-36), PYY(20-36), PYY(21-36), PYY(22-36), PYY(23-36), PYY(24-36), PYY(25-36), PYY(26-36), PYY(27-36), Ac—PYY(22-36), Ac—PYY(25-36), Ac—PYY(26-36), Ac—PYY(27-36), Ac-[Trp27]-PYY(22-36), Ac-[Trp28]-PYY(22-36), Ac-[Trp30]-PYY(22-36), Ac-[Trp30]-PYY(25-36) and MPA-PYY(25-36) are excluded, or a salt thereof (hereinafter sometimes to be abbreviated as compound (A));

[2] the peptide of the above-mentioned [1], wherein P¹ is acetyl, 3-carboxypropionyl, 4-imidazolecarbonyl, tetrahydro-2H-pyran-4-ylcarbonyl, 3-carboxypropylcarbamoyl, carboxymethylcarbamoyl, [(1S)-1-carboxy-3-methylbutyl]carbamoyl, tetrahydro-2H-pyran-4-ylcarbamoyl, 2-hydroxyethyl, glycoloyl, 2-methylbutanoyl, isobutanoyl, 4-pyridinecarbonyl, morpholinocarbonyl, (cis-2,6-dimethylmorpholin-4-yl)carbonyl, piperidinocarbonyl, 2-carboxyethylcarbamoyl, 1,3-dihydroxypropan-2-ylcarbamoyl, 5-carboxypentylcarbamoyl, tetrahydro-2H-pyran-4-ylmethylcarbamoyl, carbamoylmethylcarbamoyl, [(1S)-1-carboxy-2-hydroxyethyl]carbamoyl, [(1S)-1-carboxy-2-(4-hydroxyphenyl)ethyl]carbamoyl, benzoyl, D-pyroglutamyl, carbamoyl, or amidino, or a salt thereof;

[3] the peptide of the above-mentioned [1] or [2], wherein X¹ is a group represented by the formula:

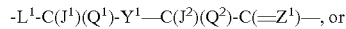

-A23-A24- wherein each symbol is as described in the above-mentioned [1], or a salt thereof;

[4] the peptide of any one of the above-mentioned [1] to [3], wherein X¹ is (1) -Gly-ψ[(E)CH=CH]-Leu-, or (2) a group represented by the formula:

-A23-A24- wherein each symbol is as described in the above-mentioned [1], or a salt thereof;

[5] the peptide of any one of the above-mentioned [1] to [4], wherein X¹ is a group represented by the formula:

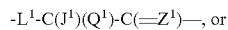

-A23-A24- wherein A23 is Ser, Glu, Gln, Arg, Acp, Thr, or Asp; and A24 is D-Pro, D-Hyp, Aib, D-Iva, Iva, β-Ala, DL-β-HOAla, Aipe or Ambz(4), or a salt thereof;

[6] the peptide of any one of the above-mentioned [1] to [5], wherein A25 is Iva, Arg, Nle, Arg(Me), Ala(4Pip), Cit, Aib, Nar, Lys(Ac), or Har, or a salt thereof;

[7] the peptide of any one of the above-mentioned [1] to [6], wherein A26 is Pya(4), His, Abu, Ala(4Pip), Phe, Pya(2), Cha, Gln, or Aib, or a salt thereof;
[8] the peptide of any one of the above-mentioned [1] to [7], wherein A27 is Cha, Nal(2), Phe(4F), Nal(1), or Ala(4Pip), or a salt thereof;
[9] the peptide of any one of the above-mentioned [1] to [8], wherein A28 is Aib, Iva, Leu(Me), Cha, α-MePhe, or D-Iva, or a salt thereof;
[10] the peptide of any one of the above-mentioned [1] to [9], wherein A30 is Lys, Har, Arg(Me), Ala(4Pip), Cha, Lys(Me), Orn, Lys(Ac), Arg, Leu, Nle, Cit, Lys(Hexyl), Trp, Hse, or Thr, or a salt thereof;
[11] the peptide of any one of the above-mentioned [1] to [10], wherein A31 is Aib, D-Iva, or Iva, or a salt thereof;
[12] the peptide of any one of the above-mentioned [1] to [11], wherein A36 is Cha, Phe(2,6-Me$_2$), Phe(3Me), or Phe(2Me), or a salt thereof;
[13] a peptide represented by the formula (II):

P$^1$-X$^4$-A23-A24-A25-A26-A27-A28-Asn-A30-A31-Thr-Arg-Gln-Arg-A36-NH$_2$ (SEQ ID NO: 187) (II)

wherein
P$^1$ is acetyl, 3-carboxypropionyl, 4-imidazolecarbonyl, tetrahydro-2H-pyran-4-ylcarbonyl, 3-carboxypropylcarbamoyl, carboxymethylcarbamoyl, [(1S)-1-carboxy-3-methylbutyl]carbamoyl, tetrahydro-2H-pyran-4-ylcarbamoyl, 2-hydroxyethyl, glycoloyl, 2-methylbutanoyl, isobutanoyl, 4-pyridinecarbonyl, morpholinocarbonyl, (cis-2,6-dimethylmorpholin-4-yl)carbonyl, piperidinocarbonyl, 2-carboxyethylcarbamoyl, 1,3-dihydroxypropan-2-ylcarbamoyl, 5-carboxypentylcarbamoyl, tetrahydro-2H-pyran-4-ylmethylcarbamoyl, carbamoylmethylcarbamoyl, [(1S)-1-carboxy-2-hydroxyethyl]carbamoyl, [(1S)-1-carboxy-2-(4-hydroxyphenyl)ethyl]carbamoyl, benzoyl, D-pyroglutamyl, carbamoyl or amidino;
X$^4$ shows
(1) a bond, or
(2) any amino acid residue(s) bound continuously or discontinuously to each other from the C-terminal of the 1st-22nd amino acid of the amino acid sequence shown by SEQ ID NO: 1;
A23 is Ser, Glu, Gln, Arg, Acp, Thr or Asp;
A24 is D-Pro, D-Hyp, Aib, D-Iva, Iva, β-Ala, DL-β-HOAla, Aipe or Ambz(4);
A25 is Iva, Arg, Nle, Arg(Me), Ala(4Pip), Cit, Aib, Nar, Lys(Ac) or Har;
A26 is Pya(4), His, Abu, Ala(4Pip), Phe, Pya(2), Cha, Gln or Aib;
A27 is Cha, Nal(2), Phe(4F), Nal(1) or Ala(4Pip);
A28 is Aib, Iva, Leu(Me), Cha, α-MePhe or D-Iva;
A30 is Lys, Har, Arg(Me), Ala(4Pip), Cha, Lys(Me), Orn, Lys(Ac), Arg, Leu, Nle, Cit, Lys(Hexyl), Trp, Hse or Thr;
A31 is Aib, D-Iva or Iva; and
A36 is Cha, Phe(2,6-Me$_2$), Phe(3Me) or Phe(2Me), or a salt thereof (hereinafter sometimes to be abbreviated as compound (B));
[14] the peptide of the above-mentioned [13], wherein X$^4$ is a bond, or a salt thereof;
[15] Thp(4)-NHCO-Ser-D-Pro-Arg-Pya(4)-Cha-Aib-Asn-Lys-Aib-Thr-Arg-Gln-Arg-Cha-NH$_2$ or a salt thereof;
[16] Ac-Ser-D-Hyp-Iva-Pya(4)-Cha-Iva-Asn-Lys-Aib-Thr-Arg-Gln-Arg-Cha-NH$_2$ or a salt thereof;
[17] 4-imidazolecarbonyl-Ser-D-Hyp-Iva-Pya(4)-Cha-Leu(Me)-Asn-Lys-Aib-Thr-Arg-Gln-Arg-Cha-NH$_2$ or a salt thereof;
[18] CC(GABA)-Ser-D-Hyp-Iva-Pya(4)-Cha-Leu(Me)-Asn-Lys-Aib-Thr-Arg-Gln-Arg-Cha-NH$_2$ or a salt thereof;
[19] a prodrug of the peptide of any one of the above-mentioned [1] to [18] or a salt thereof;
[20] a pharmaceutical drug comprising the peptide of any one of the above-mentioned [1] to [18] or a salt thereof or a prodrug thereof;
[21] the pharmaceutical drug of the above-mentioned [20], which is a Y2 receptor agonist;
[22] the pharmaceutical drug of the above-mentioned [20], which is a feeding suppressant;
[23] the pharmaceutical drug of the above-mentioned [20], which is an agent for the prophylaxis or treatment of obesity;
[24] a method for the prophylaxis or treatment of obesity in a mammal, comprising administering an effective amount of the peptide of any one of the above-mentioned [1] to [18] or a salt thereof or a prodrug thereof to the mammal;
[25] use of the peptide of any one of the above-mentioned [1] to [18] or a salt thereof or a prodrug thereof for the production of an agent for the prophylaxis or treatment of obesity; and the like.

Effect of the Invention

The peptide of the present invention has a superior Y2 receptor agonist action, and is useful as an agent for the prophylaxis or treatment of obesity and the like.

DETAILED DESCRIPTION OF THE INVENTION

The definition of each symbol in the formula (I) and the formula (II) is described in detail in the following.
In the present specification, the "halogen atom" means, unless otherwise specified, a fluorine atom, a chlorine atom, a bromine atom or an iodine atom.
In the present specification, the "$C_{1-3}$ alkylenedioxy group" means, unless otherwise specified, methylenedioxy, ethylenedioxy and the like.
In the present specification, the "$C_{1-6}$ alkyl group" means, unless otherwise specified, methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl and the like.
In the present specification, the "$C_{1-6}$ alkoxy group" means, unless otherwise specified, methoxy, ethoxy, propoxy, isopropoxy, butoxy, isobutoxy, sec-butoxy, tert-butoxy and the like.
In the present specification, the "$C_{1-6}$ alkoxy-carbonyl group" means, unless otherwise specified, methoxycarbonyl, ethoxycarbonyl, propoxycarbonyl, tert-butoxycarbonyl and the like.
In the present specification, the "$C_{1-6}$ alkyl-carbonyl group" means, unless otherwise specified, acetyl, propanoyl, butanoyl, isobutanoyl, pentanoyl, isopentanoyl, hexanoyl and the like.
In the present specification, the "$C_{6-14}$ aryl-carbonyl group" means, unless otherwise specified, benzoyl, naphthylcarbonyl, biphenylcarbonyl and the like.
P$^1$ is a group represented by the formula:
—R$^{41}$,
—CO—R$^{41}$,
—CO—OR$^{41}$,
—CO—COR$^{41}$, —SO—R^{A1},
—SO_2—R^{A1},
—SO_2—OR^{A1},
—CO—NR^{A2}R^{B2},
—SO_2—NR^{A2}R^{B2} or
—C(=NR^{A1})—NR^{A2}R^{B2}
wherein $R^{A1}$, $R^{A2}$ and $R^{B2}$ are each independently a hydrogen atom, an optionally substituted hydrocarbon group, or optionally substituted heterocyclic group.

Examples of the "hydrocarbon group" of the "optionally substituted hydrocarbon group" for $R^{A1}$, $R^{A2}$ or $R^{B2}$ include $C_{1-10}$ alkyl group, $C_{2-10}$ alkenyl group, $C_{2-10}$ alkynyl group, $C_{3-10}$ cycloalkyl group, $C_{3-10}$ cycloalkenyl group, $C_{4-10}$ cycloalkadienyl group, $C_{6-14}$ aryl group, $C_{7-16}$ aralkyl group, $C_{8-16}$ arylalkenyl group and the like.

Examples of the "$C_{1-10}$ alkyl group" include methyl, ethyl, propyl, isopropyl, butyl, isobutyl, sec-butyl, tert-butyl, pentyl, isopentyl, neopentyl, hexyl, heptyl, octyl, nonanyl, decanyl and the like.

Examples of the "$C_{2-10}$ alkenyl group" include vinyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl and the like.

Examples of the "$C_{2-10}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like.

Examples of the "$C_{3-10}$ cycloalkyl group" include cyclopropyl, cyclobutyl, cyclopentyl, cyclohexyl, cycloheptyl, cyclooctyl and the like.

Examples of the "$C_{3-10}$ cycloalkenyl group" include 2-cyclopenten-1-yl, 3-cyclopenten-1-yl, 2-cyclohexen-1-yl, 3-cyclohexen-1-yl and the like.

Examples of the "$C_{4-10}$ cycloalkadienyl group" include 2,4-cyclopentadien-1-yl, 2,4-cyclohexadien-1-yl, 2,5-cyclohexadien-1-yl and the like.

The above-mentioned $C_{3-10}$ cycloalkyl group, $C_{3-10}$ cycloalkenyl group and $C_{4-10}$ cycloalkadienyl group may be each condensed with a benzene ring to form a fused ring group, and examples of such fused ring group include indanyl, dihydronaphthyl, tetrahydronaphthyl, fluorenyl and the like.

The above-mentioned $C_{3-10}$ cycloalkyl group, $C_{3-10}$ cycloalkenyl group and $C_{4-10}$ cycloalkadienyl group may be $C_{7-10}$ crosslinked hydrocarbon group. Examples of the $C_{7-10}$ crosslinked hydrocarbon group include bicyclo[2.2.1]heptyl (norbornyl), bicyclo[2.2.2]octyl, bicyclo[3.2.1]octyl, bicyclo[3.2.2]nonyl, bicyclo[3.3.1]nonyl, bicyclo[4.2.1]nonyl, bicyclo[4.3.1]decyl, adamantyl and the like.

Moreover, the above-mentioned $C_{3-10}$ cycloalkyl group, $C_{3-10}$ cycloalkenyl group and $C_{4-10}$ cycloalkadienyl group may each form a spiro ring group with $C_{3-10}$ cycloalkane, $C_{3-10}$ cycloalkene or $C_{4-10}$ cycloalkadiene. Here, as the $C_{3-10}$ cycloalkane, $C_{3-10}$ cycloalkene and $C_{4-10}$ cycloalkadiene, rings corresponding to the above-mentioned $C_{3-10}$ cycloalkyl group, $C_{3-10}$ cycloalkenyl group and $C_{4-10}$ cycloalkadienyl group can be mentioned. Examples of such spiro ring group include spiro[4.5]decan-8-yl and the like.

Examples of the "$C_{6-14}$ aryl group" include phenyl, naphthyl, anthryl, phenanthryl, acenaphthylenyl and the like.

Examples of the "$C_{7-16}$ aralkyl group" include benzyl, phenethyl, diphenylmethyl, 1-naphthylmethyl, 2-naphthylmethyl, 2,2-diphenylethyl, 3-phenylpropyl, 4-phenylbutyl, 5-phenylpentyl, 2-biphenylylmethyl, 3-biphenylylmethyl, 4-biphenylylmethyl and the like.

Examples of the "$C_{8-16}$ arylalkenyl group" include styryl and the like.

The $C_{1-10}$ alkyl group, $C_{2-10}$ alkenyl group and $C_{2-10}$ alkynyl group exemplified as the aforementioned "hydrocarbon group" optionally have 1 to 3 substituents at substitutable position(s).

Examples of such substituent include
(1) a $C_{3-10}$ cycloalkyl group (e.g., cyclopropyl, cyclohexyl);
(2) a $C_{6-14}$ aryl group (e.g., phenyl, naphthyl) optionally substituted by 1 to 3 substituents selected from
   (a) a $C_{1-6}$ alkyl group (e.g., methyl, tert-butyl) optionally substituted by 1 to 3 substituents selected from
      (i) a halogen atom, and
      (ii) an amino group,
   (b) a hydroxy group,
   (c) a $C_{1-6}$ alkoxy group optionally substituted by 1 to 3 halogen atoms,
   (d) a halogen atom, and
   (e) a cyano group;
(3) an aromatic heterocyclic group (e.g., thienyl, furyl, pyridyl, pyrazolyl, pyrrolyl, imidazolyl, tetrazolyl, oxazolyl, thiazolyl, oxadiazolyl, thiadiazolyl) optionally substituted by 1 to 3 substituents selected from
   (a) a $C_{1-6}$ alkyl group optionally substituted by 1 to 3 halogen atoms,
   (b) a hydroxy group,
   (c) a $C_{1-6}$ alkoxy group optionally substituted by 1 to 3 halogen atoms, and
   (d) a halogen atom;
(4) a nonaromatic heterocyclic group (e.g., tetrahydrofuryl, tetrahydropyranyl, morpholinyl, thiomorpholinyl, piperidinyl, pyrrolidinyl, piperazinyl) optionally substituted by 1 to 3 substituents selected from
   (a) a $C_{1-6}$ alkyl group optionally substituted by 1 to 3 halogen atoms,
   (b) a hydroxy group,
   (c) a $C_{1-6}$ alkoxy group optionally substituted by 1 to 3 halogen atoms,
   (d) a halogen atom, and
   (e) an oxo group;
(5) an amino group optionally mono- or di-substituted by substituent(s) selected from
   (a) a $C_{1-6}$ alkyl group optionally substituted by 1 to 3 halogen atoms,
   (b) a $C_{1-6}$ alkyl-carbonyl group optionally substituted by 1 to 3 halogen atoms,
   (c) a $C_{1-6}$ alkoxy-carbonyl group optionally substituted by 1 to 3 halogen atoms,
   (d) a $C_{1-6}$ alkylsulfonyl group (e.g., methylsulfonyl) optionally substituted by 1 to 3 halogen atoms,
   (e) a carbamoyl group optionally mono- or di-substituted by a $C_{1-6}$ alkyl group optionally substituted by 1 to 3 halogen atoms, and
   (f) an aromatic heterocyclic group (e.g., thienyl, furyl, pyridyl, pyrazolyl, imidazolyl, tetrazolyl, oxazolyl, thiazolyl, oxadiazolyl, thiadiazolyl);
(6) a $C_{1-6}$ alkyl-carbonyl group (e.g., acetyl) optionally substituted by 1 to 3 substituents selected from
   (a) a halogen atom, and
   (b) an amino group;
(7) a $C_{1-6}$ alkoxy-carbonyl group (e.g., methoxycarbonyl) optionally substituted by 1 to 3 substituents selected from
   (a) a halogen atom,
   (b) a $C_{1-6}$ alkoxy group,
   (c) a $C_{6-14}$ aryl group (e.g., phenyl), and
   (d) a heterocyclic group (e.g., tetrahydrofuryl);

(8) a $C_{1-6}$ alkylsulfonyl group (e.g., methylsulfonyl, ethylsulfonyl, isopropylsulfonyl) optionally substituted by 1 to 3 halogen atoms;
(9) a carbamoyl group optionally mono- or di-substituted by a $C_{1-6}$ alkyl group optionally substituted by 1 to 3 halogen atoms;
(10) a thiocarbamoyl group optionally mono- or di-substituted by a $C_{1-6}$ alkyl group optionally substituted by 1 to 3 halogen atoms;
(11) a sulfamoyl group optionally mono- or di-substituted by a $C_{1-6}$ alkyl group optionally substituted by 1 to 3 halogen atoms;
(12) a carboxy group;
(13) a hydroxy group;
(14) a $C_{1-6}$ alkoxy group (e.g., methoxy, ethoxy) optionally substituted by 1 to 3 substituents selected from
    (a) a halogen atom,
    (b) a carboxy group,
    (c) a $C_{1-6}$ alkoxy group,
    (d) a $C_{1-6}$ alkoxy-carbonyl group optionally substituted by 1 to 3 $C_{6-14}$ aryl groups (e.g., phenyl),
    (e) an amino group optionally mono- or di-substituted by substituent(s) selected from a $C_{1-6}$ alkyl group and a $C_{1-6}$ alkoxy-carbonyl group,
    (f) a heterocyclic group (e.g., tetrahydrofuryl),
    (g) a $C_{3-10}$ cycloalkyl group (e.g., cyclopropyl, cyclohexyl), and
    (h) a hydroxy group;
(15) a $C_{2-6}$ alkenyloxy group (e.g., ethenyloxy) optionally substituted by 1 to 3 halogen atoms;
(16) a $C_{7-13}$ aralkyloxy group (e.g., benzyloxy);
(17) a $C_{6-14}$ aryloxy group (e.g., phenyloxy, naphthyloxy);
(18) a $C_{1-6}$ alkyl-carbonyloxy group (e.g., acetyloxy, tert-butylcarbonyloxy);
(19) a $C_{6-14}$ aryl-carbonyl group (e.g., benzoyl) optionally substituted by 1 to 3 substituents selected from
    (a) a halogen atom, and
    (b) a $C_{1-6}$ alkyl group optionally substituted by 1 to 3 halogen atoms;
(20) a nonaromatic heterocyclic carbonyl group (e.g., pyrrolidinylcarbonyl, morpholinylcarbonyl) optionally substituted by 1 to 3 substituents selected from a $C_{1-6}$ alkyl group optionally substituted by 1 to 3 halogen atoms;
(21) a mercapto group;
(22) a $C_{1-6}$ alkylthio group (e.g., methylthio, ethylthio) optionally substituted by 1 to 3 substituents selected from
    (a) a halogen atom, and
    (b) a $C_{1-6}$ alkoxy-carbonyl group;
(23) a $C_{7-13}$ aralkylthio group (e.g., benzylthio);
(24) a $C_{6-14}$ arylthio group (e.g., phenylthio, naphthylthio);
(25) a cyano group;
(26) a nitro group;
(27) a halogen atom;
(28) a $C_{1-3}$ alkylenedioxy group;
(29) a $C_{1-3}$ alkyleneoxy group (e.g., methyleneoxy, ethyleneoxy);
(30) an aromatic heterocyclic carbonyl group (e.g., pyrazolylcarbonyl, pyrazinylcarbonyl, isoxazolylcarbonyl, pyridylcarbonyl, thiazolylcarbonyl) optionally substituted by 1 to 3 substituents selected from a $C_{1-6}$ alkyl group optionally substituted by 1 to 3 halogen atoms;
(31) a $C_{3-10}$ cycloalkyloxy group (e.g., cyclopropyloxy, cyclopentyloxy) optionally substituted by 1 to 3 substituents selected from
    (a) a halogen atom (e.g., fluorine atom), and
    (b) a $C_{1-6}$ alkoxy group (e.g., methoxy),
(32) an amidino group;
(33) a guanidino group; and the like.

When the number of the substituents is 2 or more, respective substituents may be the same or different.

In addition, the $C_{3-10}$ cycloalkyl group, $C_{3-10}$ cycloalkenyl group, $C_{4-10}$ cycloalkadienyl group, $C_{6-14}$ aryl group, $C_{7-16}$ aralkyl group and $C_{8-16}$ arylalkenyl group exemplified as the aforementioned "hydrocarbon group" optionally have 1 to 3 substituents at substitutable position(s).

Examples of such substituent include
(1) the groups exemplified as the substituent of the aforementioned $C_{1-10}$ alkyl group and the like;
(2) a $C_{1-10}$ alkyl group (e.g., methyl, ethyl, isopropyl, sec-butyl, pentyl, nonanyl) optionally substituted by 1 to 3 substituents selected from
    (a) a halogen atom,
    (b) a carboxy group,
    (c) a hydroxy group,
    (d) a $C_{1-6}$ alkoxy-carbonyl group,
    (e) a $C_{1-6}$ alkoxy group,
    (f) an amino group optionally mono- or di-substituted by a $C_{1-6}$ alkyl group,
    (g) a $C_{6-14}$ aryl group (e.g., phenyl, naphthyl, anthryl, phenanthryl, acenaphthylenyl),
    (h) a guadinino group,
    (i) a ureido group, and
    (j) a 5- or 6-membered nonaromatic heterocyclic group (e.g., piperidyl);
(3) a $C_{2-6}$ alkenyl group (e.g., ethenyl, 1-propenyl) optionally substituted by 1 to 3 substituents selected from
    (a) a halogen atom,
    (b) a carboxy group,
    (c) a hydroxy group,
    (d) a $C_{1-6}$ alkoxy-carbonyl group,
    (e) a $C_{1-6}$ alkoxy group, and
    (f) an amino group optionally mono- or di-substituted by $C_{1-6}$ alkyl group(s);
(4) a $C_{7-13}$ aralkyl group (e.g., benzyl) optionally substituted by 1 to 3 substituents selected from
    (a) a $C_{1-6}$ alkyl group optionally substituted by 1 to 3 halogen atoms,
    (b) a hydroxy group,
    (c) a $C_{1-6}$ alkoxy group, and
    (d) a halogen atom; and the like. When the number of the substituents is 2 or more, respective substituents may be the same or different.

As the "heterocyclic group" of the "optionally substituted heterocyclic group" for $R^{A1}$, $R^{A2}$ or $R^{B2}$, an aromatic heterocyclic group and a nonaromatic heterocyclic group can be mentioned.

Examples of the "aromatic heterocyclic group" include a 5- to 7-membered monocyclic aromatic heterocyclic group containing, as a ring-constituting atom besides carbon atoms, 1 to 4 heteroatoms selected from an oxygen atom, a sulfur atom and a nitrogen atom, and a fused aromatic heterocyclic group. Examples of the fused aromatic heterocyclic group include a group derived from a fused ring wherein a ring corresponding to such 5- to 7-membered monocyclic aromatic heterocyclic group, and 1 or 2 rings selected from a 5- or 6-membered aromatic heterocycle containing 1 or 2 nitrogen atoms (e.g., pyrrole, imidazole, pyrazole, pyrazine, pyridine, pyrimidine), a 5-membered aromatic heterocycle containing one sulfur atom (e.g., thiophene) and a benzene ring are condensed, and the like.

Preferable examples of the "aromatic heterocyclic group" include monocyclic aromatic heterocyclic groups such as furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl(e.g., 4-isothiazolyl), oxazolyl (e.g., 2-oxazolyl, 4-oxazolyl, 5-oxazolyl), isoxazolyl (e.g., 3-isoxazolyl), oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl (e.g., 1,2,4-triazin-1-yl, 1,2,4-triazin-3-yl, 1,3,5-triazin-1-yl) and the like; condensed aromatic heterocyclic groups such as quinolyl (e.g., 2-quinolyl, 3-quinolyl, 4-quinolyl, 6-quinolyl), isoquinolyl (e.g., 3-isoquinolyl), quinazolyl (e.g., 2-quinazolyl, 4-quinazolyl), quinoxalyl (e.g., 2-quinoxalyl, 6-quinoxalyl), benzofuranyl (e.g., 2-benzofuranyl, 3-benzofuranyl), benzothiophenyl (e.g., 2-benzothiophenyl, 3-benzothiophenyl), benzoxazolyl (e.g., 2-benzoxazolyl), benzisooxazolyl (e.g., 7-benzisooxazolyl), benzothiazolyl (e.g., 2-benzothiazolyl), benzimidazolyl (e.g., benzimidazol-1-yl, benzimidazol-2-yl, benzimidazol-5-yl), benzotriazolyl (e.g., 1H-1,2,3-benzotriazol-5-yl), indolyl (e.g., indol-1-yl, indol-2-yl, indol-3-yl, indol-5-yl), indazolyl(e.g., 1H-indazol-3-yl), pyrrolopyrazinyl (e.g., 1H-pyrrolo[2,3-b]pyrazin-2-yl, 1H-pyrrolo[2,3-b]pyrazin-6-yl), imidazopyridinyl (e.g., 1H-imidazo[4,5-b]pyridin-2-yl, 1H-imidazo[4,5-c]pyridin-2-yl, 2H-imidazo[1,2-a]pyridin-3-yl), imidazopyrazinyl(e.g., 1H-imidazo[4,5-b]pyrazin-2-yl), pyrazolopyridinyl (e.g., 1H-pyrazolo[4,3-c]pyridin-3-yl), pyrazolothienyl(e.g., 2H-pyrazolo[3,4-b]thiophen-2-yl), pyrazolotriazinyl (e.g., pyrazolo[5,1-c][1,2,4]triazin-3-yl) and the like; and the like.

Examples of the "nonaromatic heterocyclic group" include a 5- to 7-membered monocyclic nonaromatic heterocyclic group containing, as a ring-constituting atom besides carbon atoms, 1 to 4 heteroatoms selected from an oxygen atom, a sulfur atom (the sulfur atom may be oxidized) and a nitrogen atom, and a fused nonaromatic heterocyclic group. Examples of the fused nonaromatic heterocyclic group include a group derived from a fused ring wherein a ring corresponding to such 5- to 7-membered monocyclic nonaromatic heterocyclic group, and 1 or 2 rings selected from a 5- or 6-membered aromatic or nonaromatic heterocycle containing 1 or 2 nitrogen atoms (e.g., pyrrole, imidazole, pyrazole, pyrazine, pyridine, pyrimidine), a 5-membered aromatic or nonaromatic heterocycle containing one sulfur atom (e.g., thiophene) and a benzene ring are condensed, a group obtained by partial saturation of the group and the like.

Preferable examples of the nonaromatic heterocyclic group include monocyclic nonaromatic heterocyclic groups such as tetrahydrofuryl (e.g., 2-tetrahydrofuryl), pyrrolidinyl (e.g., 1-pyrrolidinyl), 1,1-dioxidotetrahydrothienyl (e.g., 1,1-dioxidotetrahydro-3-thienyl), piperidinyl (e.g., piperidino), morpholinyl (e.g., morpholino), thiomorpholinyl (e.g., thiomorpholino), 1,1-dioxidothiomorpholinyl (e.g., 1,1-dioxidothiomorpholino), piperazinyl (e.g., 1-piperazinyl), hexamethyleniminyl (e.g., hexamethylenimin-1-yl), oxazolinyl (e.g., 2,5-dihydrooxazol-3-yl, 3,4-dihydrooxazol-3-yl), thiazolinyl (e.g., 2,5-dihydrothiazol-3-yl, 3,4-dihydrothiazol-3-yl), imidazolinyl (e.g., 2-imidazolin-3-yl), oxazolidinyl (e.g., oxazolidin-3-yl), thiazolidinyl (e.g., thiazolidin-3-yl, thiazolidin-5-yl), imidazolidinyl (e.g., imidazolidin-3-yl), dioxolyl (e.g., 1,3-dioxol-4-yl), dioxolanyl (e.g., 1,3-dioxolan-4-yl), dihydrooxadiazolyl (e.g., 4,5-dihydro-1,2,4-oxadiazol-3-yl), thiooxooxazolidinyl (e.g., 2-thioxo-1,3-oxazolidin-5-yl), tetrahydropyranyl (e.g., 4-tetrahydropyranyl), tetrahydrothiopyranyl (e.g., 4-tetrahydrothiopyranyl), 1,1-dioxidotetrahydrothiopyranyl (e.g., 1,1-dioxidotetrahydrothiopyran-4-yl), pyrazolidinyl (e.g., pyrazolidin-1-yl), oxotetrahydropyridazinyl (e.g., 3-oxo-2,3,4,5-tetrahydropyridazin-4-yl) and the like;

fused nonaromatic heterocyclic groups such as dihydroisoindolyl (e.g., 1,3-dihydro-2H-isoindol-2-yl), dihydrobenzofuranyl (e.g., 2,3-dihydro-1-benzofuran-5-yl), dihydrobenzodioxynyl (e.g., 2,3-dihydro-1,4-benzodioxyn-2-yl), dihydrobenzodioxepinyl (e.g., 3,4-dihydro-2H-1,5-benzodioxepin-2-yl), tetrahydrobenzofuranyl (e.g., 4,5,6,7-tetrahydro-1-benzofuran-3-yl), tetrahydrobenzothiazolyl (e.g., 4,5,6,7-tetrahydro-1-benzothiazol-2-yl), tetrahydrobenzoxazolyl (e.g., 4,5,6,7-tetrahydro-1-benzoxazol-2-yl), chromenyl (e.g., 4H-chromen-2-yl, 2H-chromen-3-yl), dihydroquinolinyl (e.g., 1,2-dihydroquinolin-2-yl), tetrahydroquinolinyl (e.g., 1,2,3,4-tetrahydroquinolin-2-yl), dihydroisoquinolinyl (e.g., 1,2-dihydroisoquinolin-2-yl), tetrahydroisoquinolinyl (e.g., 1,2,3,4-tetrahydroisoquinolin-4-yl, 1,2,3,4-tetrahydroisoquinolin-2-yl), dihydrophthalazinyl (e.g., 1,4-dihydrophthalazin-4-yl), tetrahydroindazolyl (e.g., 4,5,6,7-tetrahydro-2H-indazol-2-yl), tetrahydroquinazolinyl (e.g., 5,6,7,8-tetrahydroquinazolin-6-yl), tetrahydrothiazolopyridinyl (e.g., 4,5,6,7-tetrahydrothiazolo[5.4-c]pyridin-6-yl), tetrahydroimidazopyridinyl (e.g., 1,2,3,4-tetrahydroimidazo[4.5-c]pyridin-2-yl), tetrahydropyrazolopyridinyl (e.g., 1,2,3,4-tetrahydropyrazolo[3.4-c]pyridin-2-yl), tetrahydrotriazolopyrazinyl (e.g., 1,2,3,4-tetrahydrotriazolo[4.3-a]pyrazin-2-yl), tetrahydroimidazopyrazinyl (e.g., 1,2,3,4-tetrahydroimidazo[1.2-a]pyrazin-2-yl, 1,2,3,4-tetrahydroimidazo[3.4-a]pyrazin-2-yl), tetrahydropyridopyrimidinyl (e.g., 5,6,7,8-tetrahydropyrido[5.4-c]pyrimidin-6-yl) and the like.

The "heterocyclic group" of the "optionally substituted heterocyclic group" for $R^{A1}$, $R^{A2}$ or $R^{B2}$ optionally has 1 to 3 substituents at substitutable position(s). Examples of such substituent include those similar to the substituent that the $C_{3-10}$ cycloalkyl group and the like exemplified as the "hydrocarbon group" of the "optionally substituted hydrocarbon group" for $R^{A1}$, $R^{A2}$ or $R^{B2}$ optionally have. When the "heterocyclic group" is a "nonaromatic heterocyclic group", the substituent further includes an oxo group. When the number of the substituents is 2 or more, respective substituents may be the same or different.

$R^{A1}$, $R^{A2}$ and $R^{B2}$ are preferably each independently (1) a hydrogen atom;
(2) an optionally substituted $C_{1-10}$ alkyl group
(3) an optionally substituted $C_{3-10}$ cycloalkyl group
(4) an optionally substituted $C_{6-14}$ aryl group
(5) an optionally substituted 5- or 6-membered aromatic heterocyclic group
(6) an optionally substituted 5- or 6-membered nonaromatic heterocyclic group
and the like.

$R^{A1}$, $R^{A2}$ and $R^{B2}$ are preferably each independently (1) a hydrogen atom;
(2) a $C_{1-10}$ alkyl group (e.g., methyl, ethyl, propyl, isopropyl, isobutyl, 1-ethyl-3-methylbutyl, sec-butyl, pentyl, isopentyl, hexyl, heptyl, octyl, nonanyl) optionally substituted by 1 to 3 substituents selected from (a) a hydroxy group,
(b) a $C_{1-5}$ alkoxy group (e.g., methoxy, ethoxy) optionally substituted by 1 to 3 substituents selected from
  (i) a hydroxy group, and
  (ii) a carboxy group,
(c) a carboxy group,
(d) a $C_{6-14}$ aryl group (e.g., phenyl, naphthyl) optionally substituted by 1 to 3 substituents selected from
  (i) a hydroxy group,
  (ii) a cyano group, and
  (iii) a $C_{1-6}$ alkyl group (e.g., methyl, tert-butyl) optionally substituted by an amino group,
(e) a 5- or 6-membered nonaromatic heterocyclic group (e.g., piperidyl, tetrahydropyranyl)
(f) a 5- or 6-membered aromatic heterocyclic group (e.g., pyridyl)
(g) a carbamoyl group, and
(h) $C_{1-6}$ alkoxy-carbonyl (e.g., methoxycarbonyl);
(3) a $C_{3-10}$ cycloalkyl group (e.g., cyclopropyl, cyclohexyl);
(4) a $C_{6-14}$ aryl group (e.g., phenyl, naphthyl) optionally substituted by 1 to 5 substituents selected from
  (a) a halogen atom (e.g., fluorine atom),
  (b) a hydroxy group, and
  (c) a $C_{1-6}$ alkyl group (e.g., methyl) optionally substituted by 1 to 3 substituents selected from
    (i) an amino group,
    (ii) a guadinino group, and
    (iii) a ureido group;
(5) a 5- or 6-membered aromatic heterocyclic group (e.g., imidazolyl, pyridyl, furyl, pyrrolyl, thiophenyl); or
(6) a 5- or 6-membered nonaromatic heterocyclic group (e.g., tetrahydropyranyl, morpholinyl, piperidinyl, pyrrolidinyl, tetrahydropyrimidinyl) optionally substituted by 1 to 3 substituents selected from
  (a) an oxo group,
  (b) a $C_{1-6}$ alkyl group (e.g., methyl),
  (c) an amidino group, and
  (d) a $C_{1-6}$ alkyl-carbonyl group (e.g., acetyl) optionally substituted by an amino group;
and the like.

When $P^1$ is a group represented by the formula: —$R^{A1}$, $R^{A1}$ is preferably
(1) an optionally substituted $C_{1-10}$ alkyl group, or
(2) an optionally substituted 5- or 6-membered aromatic heterocyclic group.
$R^{A1}$ is more preferably
(1) a $C_{1-10}$ alkyl group (e.g., methyl, ethyl, hexyl, heptyl, octyl) optionally substituted by 1 to 3 substituents selected from
  (a) a hydroxy group,
  (b) a $C_{1-6}$ alkoxy group (e.g., ethoxy) optionally substituted by a hydroxy group, and
  (c) a $C_{6-14}$ aryl group (e.g., phenyl), or
(2) a 5- or 6-membered aromatic heterocyclic group (e.g., pyridyl).

When $P^1$ is a group represented by the formula: —CO—$R^{A1}$, $R^{A1}$ is preferably
(1) a hydrogen atom,
(2) an optionally substituted $C_{1-20}$ alkyl group,
(3) an optionally substituted $C_{3-10}$ cycloalkyl group,
(4) an optionally substituted $C_{6-14}$ aryl group,
(5) an optionally substituted 5- or 6-membered aromatic heterocyclic group, or
(6) an optionally substituted 5- or 6-membered nonaromatic heterocyclic group.

$R^{A1}$ is more preferably
(1) a hydrogen atom,
(2) a $C_{1-10}$ alkyl group (e.g., methyl, ethyl, isopropyl, sec-butyl, pentyl, nonanyl) optionally substituted by 1 to 3 substituents selected from
  (a) a hydroxy group,
  (b) a carboxy group,
  (c) a $C_{6-14}$ aryl group (e.g., phenyl), and
  (d) a 5- or 6-membered nonaromatic heterocyclic group (e.g., piperidyl),
(3) a $C_{3-10}$ cycloalkyl group (e.g., cyclopropyl, cyclohexyl),
(4) a $C_{6-14}$ aryl group (e.g., phenyl, naphthyl)) optionally substituted by 1 to 5 substituents selected from
  (a) a halogen atom (e.g., fluorine atom),
  (b) a hydroxy group, and
  (c) a $C_{1-6}$ alkyl group (e.g., methyl) optionally substituted by 1 to 3 substituents selected from
    (i) an amino group,
    (ii) a guadinino group, and
    (iii) a ureido group,
(5) a 5- or 6-membered aromatic heterocyclic group (e.g., imidazolyl, pyridyl, furyl, pyrrolyl, thiophenyl), or
(6) a 5- or 6-membered nonaromatic heterocyclic group (e.g., tetrahydropyranyl, morpholinyl, piperidinyl, pyrrolidinyl, tetrahydropyrimidinyl) optionally substituted by 1 to 3 substituents selected from
  (a) an oxo group,
  (b) a $C_{1-6}$ alkyl group (e.g., methyl),
  (c) an amidino group, and
  (d) a $C_{1-6}$ alkyl-carbonyl group (e.g., acetyl) optionally substituted by an amino group.

When $P^1$ is a group represented by the formula: —CO—$OR^{A1}$, $R^{A1}$ is preferably an optionally substituted $C_{1-10}$ alkyl group (e.g., methyl), more preferably, or a $C_{1-10}$ alkyl group (e.g. methyl) optionally substituted by a $C_{6-14}$ aryl group (e.g., phenyl).

When $P^1$ is a group represented by the formula: —$SO_2$—$R^{A1}$, $R^{A1}$ is preferably an optionally substituted $C_{1-10}$ alkyl group (e.g., methyl group), more preferably a $C_{1-10}$ alkyl group (e.g., methyl group).

When $P^1$ is a group represented by the formula: —CO—$NR^{A2}R^{B2}$, $R^{A2}$ is preferably
(1) a hydrogen atom,
(2) an optionally substituted $C_{1-10}$ alkyl group, or
(3) an optionally substituted 5- or 6-membered nonaromatic heterocyclic group, and
$R^{B2}$ is
(1) a hydrogen atom, or
(2) an optionally substituted $C_{1-10}$ alkyl group.

More preferably, $R^{A2}$ is
(1) a hydrogen atom,
(2) a $C_{1-10}$ alkyl group (e.g., methyl, ethyl, propyl, isopropyl, isobutyl, 1-ethyl-3-methylbutyl, pentyl, isopentyl) optionally substituted by 1 to 3 substituents selected from
  (a) a hydroxy group,
  (b) a carboxy group,
  (c) a carbamoyl group,
  (d) a $C_{6-14}$ aryl group (e.g., phenyl, naphthyl) optionally substituted by a hydroxy group,
  (e) a $C_{1-6}$ alkoxy (e.g., methoxy, ethoxy) optionally substituted by a carboxy group,
  (f) a $C_{1-6}$ alkoxy-carbonyl (e.g., methoxycarbonyl), and
  (g) a 5- or 6-membered nonaromatic heterocyclic group (e.g., tetrahydropyranyl), or (3) a 5- or 6-membered nonaromatic heterocyclic group (e.g., tetrahydropyranyl), and
$R^{B2}$ is
(1) a hydrogen atom, or
(2) a $C_{1-10}$ alkyl group (e.g., ethyl).
When $P^1$ is a group represented by the formula: —C(=NR$^{A1}$)—NR$^{A2}$R$^{B2}$,
$R^{A1}$ is preferably (1) a hydrogen atom, and
$R^{A2}$ and $R^{B2}$ are each independently
(1) a hydrogen atom, or
(2) an optionally substituted $C_{1-10}$ alkyl group.
More preferably, $R^{A1}$ is (1) a hydrogen atom, and
$R^{A2}$ and $R^{B2}$ are each independently
(1) a hydrogen atom, or
(2) a $C_{1-10}$ alkyl group (e.g., methyl, isobutyl, octyl) optionally substituted by 1 to 3 substituents selected from
    (a) a hydroxy group,
    (b) a $C_{6-14}$ aryl group (e.g., phenyl) optionally substituted by 1 to 3 substituents selected from
        (i) a cyano group, and
        (ii) a $C_{1-6}$ alkyl group (e.g., methyl, tert-butyl) optionally substituted by an amino group, and
    (c) a 5- or 6-membered aromatic heterocyclic group (e.g., pyridyl).
$P^1$ is preferably
(1) a hydrogen atom,
(2) an optionally substituted $C_{1-10}$ alkyl group,
(3) an optionally substituted 5- or 6-membered aromatic heterocyclic group,
(4) a formyl group
(5) an optionally substituted $C_{1-10}$ alkyl-carbonyl group,
(6) an optionally substituted $C_{3-10}$ cycloalkyl-carbonyl group,
(7) an optionally substituted $O_{6-14}$ aryl-carbonyl group,
(8) an optionally substituted 5- or 6-membered aromatic heterocyclic carbonyl group,
(9) an optionally substituted 5- or 6-membered nonaromatic heterocyclic carbonyl group,
(10) an optionally substituted $C_{1-10}$ alkoxy-carbonyl group,
(11) an optionally substituted $C_{1-10}$ alkyl-sulfonyl group,
(12) a carbamoyl group optionally mono- or di-substituted by substituent(s) selected from
    (a) an optionally substituted $C_{1-10}$ alkyl group, and
    (b) an optionally substituted 5- or 6-membered nonaromatic heterocyclic group,
(13) an amidino group optionally mono-, di- or tri-substituted by an optionally substituted $C_{1-10}$ alkyl group, or the like.
$P^1$ is more preferably
(1) a hydrogen atom,
(2) a $C_{1-10}$ alkyl group (e.g., methyl, ethyl, hexyl, heptyl, octyl) optionally substituted by 1 to 3 substituents selected from
    (a) a hydroxy group,
    (b) a $C_{1-6}$ alkoxy group (e.g., ethoxy) optionally substituted by a hydroxy group, and
    (c) a $C_{6-14}$ aryl group (e.g., phenyl),
(3) a 5- or 6-membered aromatic heterocyclic group (e.g., pyridyl),
(4) a formyl group,
(5) a $C_{1-10}$ alkyl-carbonyl group (e.g., acetyl, ethylcarbonyl, isopropylcarbonyl, sec-butylcarbonyl, pentylcarbonyl, nonanylcarbonyl) optionally substituted by 1 to 3 substituents selected from
    (a) a hydroxy group,
    (b) a carboxy group,
    (c) a $C_{6-14}$ aryl group (e.g., phenyl), and
    (d) a 5- or 6-membered nonaromatic heterocyclic group (e.g., piperidyl),
(6) a $C_{3-10}$ cycloalkyl-carbonyl group (e.g., cyclopropylcarbonyl, cyclohexyl-carbonyl),
(7) a $C_{6-14}$ aryl-carbonyl group (e.g., benzoyl, naphthylcarbonyl) optionally substituted by 1 to 5 substituents selected from
    (a) a halogen atom (e.g., fluorine atom),
    (b) a hydroxy group, and
    (c) a $C_{1-6}$ alkyl group (e.g., methyl) optionally substituted by 1 to 3 substituents selected from
        (i) an amino group,
        (ii) a guadinino group, and
        (iii) a ureido group,
(8) a 5- or 6-membered aromatic heterocyclic carbonyl group (e.g., imidazolylcarbonyl, pyridylcarbonyl, furylcarbonyl, pyrrolylcarbonyl, thiophenylcarbonyl),
(9) a 5- or 6-membered nonaromatic heterocyclic carbonyl group (e.g., tetrahydropyranylcarbonyl, morpholinylcarbonyl, piperidinylcarbonyl, pyrrolidinylcarbonyl, tetrahydropyrimidinylcarbonyl) optionally substituted by 1 to 3 substituents selected from
    (a) an oxo group,
    (b) $C_{1-6}$ alkyl group (e.g., methyl),
    (c) an amidino group, and
    (d) a $C_{1-6}$ alkyl-carbonyl group (e.g., acetyl) optionally substituted by an amino group,
(10) a $C_{1-10}$ alkoxy-carbonyl group (e.g., methoxycarbonyl) optionally substituted by a $C_{6-14}$ aryl group (e.g., phenyl),
(11) a $C_{1-10}$ alkyl-sulfonyl group (e.g., methylsulfonyl),
(12) a carbamoyl group optionally mono- or di-substituted by substituent(s) selected from
    (a) a $C_{1-10}$ alkyl group (e.g., methyl, ethyl, propyl, isopropyl, isobutyl, 1-ethyl-3-methylbutyl, pentyl, isopentyl) optionally substituted by 1 to 3 substituents selected from
        (i) a hydroxy group,
        (ii) a carboxy group
        (iii) a carbamoyl group,
        (iv) a $C_{6-14}$ aryl group (e.g., phenyl, naphthyl) optionally substituted by a hydroxy group,
        (v) a $C_{1-6}$ alkoxy (e.g., methoxy, ethoxy) optionally substituted by a carboxy group,
        (vi) $C_{1-6}$ alkoxy-carbonyl (e.g., methoxycarbonyl), and
        (vii) a 5- or 6-membered nonaromatic heterocyclic group (e.g., tetrahydropyranyl), and
    (b) a 5- or 6-membered nonaromatic heterocyclic group (e.g., tetrahydropyranyl),
(13) an amidino group optionally mono-, di- or tri-substituted by a $C_{1-10}$ alkyl group (e.g., methyl, isobutyl, octyl) optionally substituted by 1 to 3 substituents selected from
    (a) a hydroxy group,
    (b) a $C_{6-14}$ aryl group (e.g., phenyl) optionally substituted by 1 to 3 substituents selected from
        (i) a cyano group, and
        (ii) a $C_{1-6}$ alkyl group (e.g., methyl, tert-butyl) optionally substituted by an amino group, and
    (c) a 5- or 6-membered aromatic heterocyclic group (e.g., pyridyl),
or the like.
$P^1$ is more preferably
(1) a $C_{1-10}$ alkyl group (e.g., ethyl) optionally substituted by 1 to 3 substituents selected from
    (a) a hydroxy group, and
    (b) a $C_{1-6}$ alkoxy group (e.g., ethoxy) optionally substituted by a hydroxy group, (2) a $C_{1-10}$ alkyl-carbonyl group (e.g., acetyl, ethylcarbonyl, isopropylcarbonyl, sec-butylcarbonyl) optionally substituted by 1 to 3 substituents selected from
    (a) a hydroxy group,
    (b) a carboxy group, and
    (c) a $C_{6-14}$ aryl group (e.g., phenyl),
(3) a $C_{6-14}$ aryl-carbonyl group (e.g., benzoyl),
(4) a 5- or 6-membered aromatic heterocyclic carbonyl group (e.g., imidazolylcarbonyl, pyridylcarbonyl),
(5) a 5- or 6-membered nonaromatic heterocyclic carbonyl group (e.g., tetrahydropyranylcarbonyl, morpholinylcarbonyl, piperidinylcarbonyl, pyrrolidinylcarbonyl) optionally substituted by 1 to 3 substituents selected from
    (a) an oxo group, and
    (b) a $C_{1-6}$ alkyl group (e.g., methyl),
(6) a carbamoyl group optionally mono- or di-substituted by substituent(s) selected from
    (a) a $C_{1-10}$ alkyl group (e.g., methyl, ethyl, propyl, pentyl, isopentyl) optionally substituted by 1 to 3 substituents selected from
        (i) a hydroxy group,
        (ii) a carboxy group
        (iii) a carbamoyl group,
        (iv) a $C_{6-14}$ aryl group (e.g., phenyl) optionally substituted by a hydroxy group, and
        (v) a 5- or 6-membered nonaromatic heterocyclic group (e.g., tetrahydropyranyl), and
    (b) a 5- or 6-membered nonaromatic heterocyclic group (e.g., tetrahydropyranyl),
(7) an amidino group
or the like.

$P^1$ is more preferably
(1) a $C_{1-10}$ alkyl group (e.g., ethyl) optionally substituted by 1 to 3 substituents selected from
    (a) a hydroxy group, and
    (b) a $C_{1-6}$ alkoxy group (e.g., ethoxy) optionally substituted by a hydroxy group,
(2) a $C_{1-10}$ alkyl-carbonyl group (e.g., acetyl, ethylcarbonyl, isopropylcarbonyl, sec-butylcarbonyl) optionally substituted by 1 to 3 substituents selected from
    (a) a hydroxy group,
    (b) a carboxy group, and
    (c) a $C_{6-14}$ aryl group (e.g., phenyl),
(3) a 5- or 6-membered aromatic heterocyclic carbonyl group (e.g., imidazolylcarbonyl, pyridylcarbonyl),
(4) a 5- or 6-membered nonaromatic heterocyclic carbonyl group (e.g., tetrahydropyranylcarbonyl, morpholinylcarbonyl, piperidinylcarbonyl) optionally substituted by 1 to 3 substituents selected from
    (a) an oxo group, and
    (b) a $C_{1-6}$ alkyl group (e.g., methyl),
(5) a carbamoyl group optionally mono- or di-substituted by substituent(s) selected from
    (a) a $C_{1-10}$ alkyl group (e.g., methyl, ethyl, propyl, pentyl, isopentyl) optionally substituted by 1 to 3 substituents selected from
        (i) a hydroxy group,
        (ii) a carboxy group
        (iii) a carbamoyl group,
        (iv) a $C_{6-14}$ aryl group (e.g., phenyl) optionally substituted by a hydroxy group, and
        (v) a 5- or 6-membered nonaromatic heterocyclic group (e.g., tetrahydropyranyl), and
    (b) a 5- or 6-membered nonaromatic heterocyclic group (e.g., tetrahydropyranyl)
or the like.

$P^1$ is particularly preferably
(1) a $C_{1-10}$ alkyl-carbonyl group (e.g., acetyl, ethylcarbonyl) optionally substituted by 1 to 3 substituents selected from
    (a) a hydroxy group, and
    (b) a carboxy group,
(2) a 5- or 6-membered aromatic heterocyclic carbonyl group (e.g., imidazolylcarbonyl),
(3) a 5- or 6-membered nonaromatic heterocyclic carbonyl group (e.g., tetrahydropyranylcarbonyl),
(4) a carbamoyl group optionally mono- or di-substituted by substituent(s) selected from
    (a) a $C_{1-10}$ alkyl group (e.g., methyl, ethyl, isopentyl) optionally substituted by 1 to 3 carboxy groups, and
    (b) a 5- or 6-membered nonaromatic heterocyclic group (e.g., tetrahydropyranyl)
or the like.

Specific examples of $P^1$ include 2-hydroxyethyl, heptyl, hexyl, benzyl, octyl, 2-ethoxyethyl, 2-(2-hydroxyethoxy) ethyl, 4-pyridinyl, formyl, acetyl, 3-carboxypropionyl, glycoloyl, 2-methylbutanoyl, isobutanoyl, benzoyl, hexanoyl, 4-aminomethylbenzoyl, 4-guanidinomethylbenzoyl, 4-ureidomethylbenzoyl, phenylacetyl, cyclohexanecarbonyl, 1-naphthoyl, 2-naphthoyl, 4-fluorobenzoyl, 4-hydroxybenzoyl, diphenylacetyl, pentafluorobenzoyl, cyclopropanecarbonyl, piperidinoacetyl, propanoyl, L-lactoyl, decanoyl, (S)-2-methylbutanoyl, 4-imidazolecarbonyl, tetrahydro-2H-pyran-4-ylcarbonyl (Thp(4)-CO), 4-pyridinecarbonyl, morpholinocarbonyl, (cis-2,6-dimethylmorpholin-4-yl)carbonyl, piperidinocarbonyl, D-pyroglutamyl, pyroglutamyl, 2-pyridinecarbonyl, piperidine-4-carbonyl, N-acetylpiperidine-4-carbonyl, N-amidinopiperidine-4-carbonyl, N-glycylpiperidine-4-carbonyl, hydroorotyl, D-hydroorotyl, 3-pyridinecarbonyl, 3-furoyl, 3-pyrrolecarbonyl, 2-pyrrolecarbonyl, 2-thiophenecarbonyl, Z, mesyl, carbamoyl, 3-carboxypropylcarbamoyl (CC(GABA)), carboxymethylcarbamoyl (CC(Gly)), 2-carboxyethylcarbamoyl (CC(β-Ala)), 1,3-dihydroxypropan-2-ylcarbamoyl, 5-carboxypentylcarbamoyl(CC(Acp)), tetrahydro-2H-pyran-4-ylmethylcarbamoyl (Thp(4)-CH₂NHCO), carbamoylmethylcarbamoyl (NH₂—CC(Gly)) [(1S)-1-carboxy-2-hydroxyethyl]carbamoyl (CC(Ser)), [(1S)-1-carboxy-3-methylbutyl]carbamoyl (CC(Leu)), [(1S)-1-carboxy-2-(4-hydroxyphenyl)ethyl]carbamoyl (CC(Tyr)), isobutylcarbamoyl, 2-hydroxyethylcarbamoyl, benzylcarbamoyl, (S)-2-hydroxy-1-(methoxycarbonyl)ethylcarbamoyl, 2-hydroxy-1-(hydroxymethyl)ethylcarbamoyl, [(1S)-1-(2-hydroxyethyl)-3-methylbutyl]carbamoyl, 2-(4-hydroxyphenyl)ethylcarbamoyl, [(2R)-1-hydroxy-4-methylpentan-2-yl]carbamoyl, 2-ethoxyethyl-carbamoyl, diethylcarbamoyl, [(2S)-1-(carboxymethoxy)-4-methylpentan-2-yl]carbamoyl, [(2S)-1-hydroxy-3-phenylpropan-2-yl]carbamoyl, [(2S)-1-hydroxypropan-2-yl]carbamoyl, tetrahydro-2H-pyran-4-ylcarbamoyl (Thp(4)-NHCO), amidino, octylamidino, 4-tert-butylbenzylamidino, methylamidino, isobutylamidino, benzylamidino, 4-cyanobenzylamidino, 4-pyridinylmethylamidino, 4-aminomethylbenzylamidino and the like.

$P^1$ is preferably acetyl, 3-carboxypropionyl, 4-imidazolecarbonyl, Thp(4)-CO, CC(GABA), CC(Gly), CC(Leu), Thp(4)-NHCO, 2-hydroxyethyl, glycoloyl, 2-methylbutanoyl, isobutanoyl, 4-pyridinecarbonyl, morpholinocarbonyl, (cis-2,6-dimethylmorpholin-4-yl)carbonyl, piperidinocarbonyl, CC(β-Ala), 1,3-dihydroxypropan-2-ylcarbamoyl, CC(Acp), Thp(4)-CH₂NHCO, NH₂—CC(Gly), CC(Ser), CC(Tyr), benzoyl, D-pyroglutamyl, carbamoyl, amidino and the like.

$P^1$ is more preferably acetyl, 3-carboxypropionyl, 4-imidazolecarbonyl, Thp(4)-CO, CC(GABA), CC(Gly), CC(Leu), Thp(4)-NHCO, 2-hydroxyethyl, glycoloyl, 2-methylbutanoyl, isobutanoyl, 4-pyridinecarbonyl, morpholinocarbonyl, (cis-2,6-dimethylmorpholin-4-yl)carbonyl, piperidinocarbonyl, CC(β-Ala), 1,3-dihydroxypropan-2-ylcarbamoyl, CC(Acp), Thp(4)-CH$_2$NHCO, NH$_2$—CC(Gly), CC(Ser), CC(Tyr) and the like.

$P^1$ is more preferably acetyl, 3-carboxypropionyl, 4-imidazolecarbonyl, Thp(4)-CO, CC(GABA), CC(Gly), CC(Leu), Thp(4)-NHCO and the like.

$X^1$ is (1) a group represented by the formula:

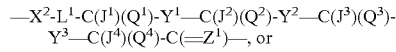, or

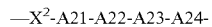

wherein $X^2$ is a group represented by the formula:
(i) —$X^3$-A17-A18-A19-A20-,
(ii) -A17-A18-A19-A20-,
(iii) -A18-A19-A20-,
(iv) -A19-A20-, or
(v) -A20-
wherein
A17 is Leu or Tyr;
A18 is Ala, Asn, or Pro;
A19 is Arg, D-Arg, Ile, or Acp;
A20 is Arg, Tyr, D-Arg, Lys, or Acp; and
$X^3$ shows any amino acid residue(s) bound continuously or discontinuously to each other from the C-terminal of the 10th-16th amino acid of the amino acid sequence shown by SEQ ID NO:1;
$L^1$ is NH optionally substituted by a $C_{1-6}$ alkyl group, CH$_2$ optionally substituted by a $C_{1-6}$ alkyl group, O, or S;
$J^1$, $J^2$, $J^3$ and $J^4$ are each independently a hydrogen atom or a $C_{1-3}$ alkyl group;
$Q^1$, $Q^2$, $Q^3$ and $Q^4$ are each independently a hydrogen atom or an optionally substituted $C_{1-10}$ alkyl group;
$J^1$ and $Q^1$, $J^2$ and $Q^2$, $J^3$ and $Q^3$, and $J^4$ and $Q^4$, or $L^1$ and $Q^1$, $Y^1$ and $Q^2$, $Y^2$ and $Q^3$, $Y^3$ and $Q^4$ may be bonded to foam a ring;
$Y^1$, $Y^2$ and $Y^3$ are each independently a group represented by the formula: —CON($J^5$)-, —CSN($J^6$)-, —C($J^7$)($J^8$)N($J^9$)-, —N($J^{10}$)CO—, or —C($J^{11}$)=C($J^{12}$)-
wherein $J^5$, $J^6$, $J^7$, $J^8$, $J^9$, $J^{10}$, $J^{11}$ and $J^{12}$ are each independently a hydrogen atom or a $C_{1-3}$ alkyl group;
$Z^1$ is O or S;
A21 is D-Tyr, Tyr, Acp, Pro, Ambz(4), Lys or Arg;
A22 is Ala, Acp, Phe, Dap, Leu, Lys, D-Ala, Ile, Lys[Hexadecanoyl-(PEG2)], Tyr, Aib, Ambz(4), Pic(4), Gly, PEG2 or Adc(12);
A23 is Ser, Glu, Gln, Arg, Acp, Thr, Asp, Lys, D-Arg, D-Ser, Gly, Ser(Me), Abu, Phe, Asn, β-Ala, Aoc(8), PEG2, Pic(4), Hyp, NMeSer, N(iBu)Gly, N(2-hydroxyethyl)Gly, Hse, D-Thr, Aad, Lys(Me$_2$), Tyr, Lys(Ac), Iva or D-Iva; and
A24 is D-Pro, D-Hyp, Aib, D-Iva, Iva, β-Ala, DL-β-HOAla, Aipe, Ambz(4), Leu, Acp, D-Leu, Phe, D-Phe, Cha, D-Cha, Pro, Abz(2), Pic(4), N(iBu)Gly, NMeAla, D-NMeAla, Sar, Gly, Aze(3), D-cisHyp, D-Pic(2), D-Aze(2), α-MePro, D-α-MePro or GABA, (2) a group represented by the formula:

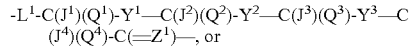, or

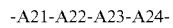

wherein each symbol is as defined above, (3) a group represented by the formula:

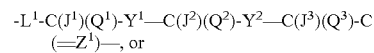, or

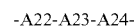

wherein each symbol is as defined above,
(4) a group represented by the formula:

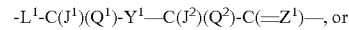, or

wherein each symbol is as defined above,
(5) a group represented by the formula:

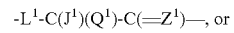, or

wherein each symbol is as defined above, or
(6) a bond.

$X^2$ is a group represented by the formula:
(i) —$X^3$-A17-A18-A19-A20-,
(ii) -A17-A18-A19-A20-,
(iii) -A18-A19-A20-,
(iv) -A19-A20-, or
(v) -A20-
wherein
A17 is Leu or Tyr;
A18 is Ala, Asn, or Pro;
A19 is Arg, D-Arg, Ile, or Acp;
A20 is Arg, Tyr, D-Arg, Lys, or Acp; and
$X^3$ shows any amino acid residue(s) bound continuously or discontinuously to each other from the C-terminal of the 10th-16th amino acid of the amino acid sequence shown by SEQ ID NO:1;

A17 is Leu or Tyr, A18 is Ala, Asn, or Pro, A19 is Arg, D-Arg, Ile, or Acp, A20 is Arg, Tyr, D-Arg, Lys, or Acp, preferably Arg or Tyr.

$X^3$ shows any amino acid residue(s) bound continuously or discontinuously to each other from the C-terminal of the 10th-16th amino acid of the amino acid sequence shown by SEQ ID NO:1;

As the "amino acid residue(s) bound continuously or discontinuously to each other from the C-terminal of the 10th-16th amino acid of the amino acid sequence shown by SEQ ID NO:1" for $X^3$ is specifically (1) Glu- (2) Glu-Glu- (3) Pro-Glu-Glu- (4) Ser-Pro-Glu-Glu- (SEQ ID NO: 2)

(5) Ala-Ser-Pro-Glu-Glu- (SEQ ID NO: 3)

(6) Asp-Ala-Ser-Pro-Glu-Glu- (SEQ ID NO: 4)

(7) Glu-Asp-Ala-Ser-Pro-Glu-Glu- (SEQ ID NO: 5)

or the like.

$L^1$ is (1) NH optionally substituted by a $C_{1-6}$ alkyl group, (2) CH$_2$ optionally substituted by a $C_{1-6}$ alkyl group, (3) O, or (4) S.

As $L^1$, NH optionally substituted by a $C_{1-6}$ alkyl group is preferable, and NH is more preferable.

$J^1$, $J^2$, $J^3$ and $J^4$ are each independently a hydrogen atom or a $C_{1-3}$ alkyl group.

As the "$C_{1-3}$ alkyl group" for $J^1$, $J^2$, $J^3$ or $J^4$, methyl, ethyl, propyl and isopropyl can be mentioned.

$J^1$ is preferably a hydrogen atom or methyl.
$J^2$ is preferably a hydrogen atom or methyl.
$J^3$ is preferably a hydrogen atom or methyl.
$J^4$ is preferably a hydrogen atom or methyl.

$Q^1$, $Q^2$, $Q^3$ and $Q^4$ are each independently a hydrogen atom or an optionally substituted $C_{1-10}$ alkyl group.

As the "$C_{1-10}$ alkyl group" of the "optionally substituted $C_{1-10}$ alkyl group" for $Q^1$, $Q^2$, $Q^3$ or $Q^4$, methyl, ethyl, propyl, isopropyl, butyl, isobutyl, sec-butyl, tert-butyl, pentyl, isopentyl, neopentyl, hexyl, heptyl, octyl, nonanyl, decanyl and the like can be mentioned.

The "$C_{1-10}$ alkyl group" of the "optionally substituted $C_{1-10}$ alkyl group" for $Q^1$, $Q^2$, $Q^3$ or $Q^4$ optionally has 1 to 5 substituents at substitutable position(s). Examples of such substituent include those similar to the substituent that the $C_{1-10}$ alkyl group and the like exemplified as the "hydrocarbon group" of the "optionally substituted hydrocarbon group" optionally have. When the number of the substituents is 2 or more, respective substituents may be the same or different.

$Q^1$, $Q^2$, $Q^3$ and $Q^4$ are preferably each independently
(1) a hydrogen atom;
(2) a $C_{1-10}$ alkyl group (e.g., methyl, ethyl, propyl, isopropyl, butyl, isobutyl, sec-butyl, tert-butyl, pentyl, isopentyl, neopentyl, hexyl, heptyl, octyl, nonanyl, decanyl) optionally substituted by 1 to 3 substituents selected from
  (a) a $C_{3-10}$ cycloalkyl group (e.g., cyclopropyl, cyclohexyl),
  (b) a $C_{6-14}$ aryl group (e.g., phenyl, naphthyl) optionally substituted by 1 to 3 substituents selected from
    (i) a $C_{1-6}$ alkyl group (e.g., methyl, tert-butyl),
    (ii) a hydroxy group, and
    (iii) a $C_{1-6}$ alkoxy group;
  (c) an aromatic heterocyclic group (e.g., imidazolyl, indolyl) optionally substituted by 1 to 3 substituents selected from
    (i) a $C_{1-6}$ alkyl group,
    (ii) a hydroxy group, and
    (iii) a $C_{1-6}$ alkoxy group;
  (d) an amino group optionally mono- or di-substituted by substituent(s) selected from
    (i) a $C_{1-6}$ alkyl group (e.g., methyl),
    (ii) a $C_{1-6}$ alkyl-carbonyl group, and
    (iii) a $C_{1-6}$ alkoxy-carbonyl group;
  (e) a carbamoyl group optionally mono- or di-substituted by a $C_{1-6}$ alkyl group (e.g., methyl) optionally substituted by 1 to 3 halogen atoms;
  (f) a carboxy group;
  (g) a hydroxy group;
  (h) a $C_{1-6}$ alkoxy group (e.g., methoxy, ethoxy) optionally substituted by 1 to 3 substituents selected from
    (i) a $C_{1-6}$ alkyl group,
    (ii) a hydroxy group, and
    (iii) a $C_{1-6}$ alkoxy group;
  (i) a mercapto group;
  (j) a $C_{1-6}$ alkylthio group (e.g., methylthio, ethylthio); and
  (k) guanidino;
or the like.

$Y^1$, $Y^2$ and $Y^3$ are each independently a group represented by the formula: —CON($J^5$)—, —CSN($J^6$)—, —C($J^7$)($J^8$)N($J^9$)—, —N($J^{10}$)CO—, or —C($J^{11}$)=C($J^{12}$)—.

$J^5$, $J^6$, $J^7$, $J^8$, $J^9$, $J^{10}$, $J^{11}$ and $J^{12}$ are each independently a hydrogen atom or a $C_{1-3}$ alkyl group.

As the "$C_{1-3}$ alkyl group" for $J^5$, $J^6$, $J^7$, $J^8$, $J^9$, $J^{10}$, $J^{11}$ or $J^{12}$, methyl, ethyl, propyl and isopropyl can be mentioned.

$J^5$ is preferably a hydrogen atom or methyl.
$J^6$ is preferably a hydrogen atom.
$J^7$ is preferably a hydrogen atom.
$J^8$ is preferably a hydrogen atom.
$J^9$ is preferably a hydrogen atom.
$J^{10}$ is preferably a hydrogen atom.
$J^{11}$ is preferably a hydrogen atom.
$J^{12}$ is preferably a hydrogen atom.

As $Y^1$, —CONH—, —CON(CH$_3$)—, —CH$_2$NH—, —CH=CH— and the like are preferable.
As $Y^2$, —CONH—, —CON(CH$_3$)—, —CH$_2$NH—, —CH=CH— and the like are preferable.
As $Y^3$, —CONH—, —CON(CH$_3$)—, —CH$_2$NH—, —CH=CH— and the like are preferable.

$Z^1$ is O or S.

$J^1$ and $Q^1$, $J^2$ and $Q^2$, $J^3$ and $Q^3$, and $J^4$ and $Q^4$ may be bonded to form a ring. In this case, C($J^1$)($Q^1$), C($J^2$)($Q^2$), C($J^3$)($Q^3$) or C($J^4$)($Q^4$) forms, for example, a ring such as cyclopentane, cyclohexane, piperidine and the like.

Alternatively, $L^1$ and $Q^1$, $Y^1$ and $Q^2$, $Y^2$ and $Q^3$, and $Y^3$ and $Q^4$ may be bonded to form a ring.

When $L^1$ and $Q^1$ are bonded to form a ring, $L^1$-C($J^1$)($Q^1$) forms, for example, a ring such as azetidine, pyrrolidine, hydroxypyrrolidine, piperidine, thiazolidine and the like.

When $Y^1$ and $Q^2$, $Y^2$ and $Q^3$, and $Y^3$ and $Q^4$ are bonded to form a ring, $Y^1$—C($J^2$)($Q^2$), $Y^2$—C($J^3$)($Q^3$) or $Y^3$—C($J^4$)($Q^4$) forms, for example, a ring such as azetidine, pyrrolidine, hydroxypyrrolidine, piperidine, thiazolidine and the like.

A21 is D-Tyr, Tyr, Acp, Pro, Ambz(4), Lys or Arg, preferably, D-Tyr.

A22 is Ala, Acp, Phe, Dap, Leu, Lys, D-Ala, Ile, Lys [Hexadecanoyl-(PEG2)], Tyr, Aib, Ambz(4), Pic(4), Gly, PEG2 or Adc(12), preferably, Ala, Acp, Phe, Dap, Leu or Lys, more preferably, Ala or Acp.

A23 is Ser, Glu, Gln, Arg, Acp, Thr, Asp, Lys, D-Arg, D-Ser, Gly, Ser(Me), Abu, Phe, Asn, β-Ala, Aoc(8), PEG2, Pic(4), Hyp, NMeSer, N(iBu)Gly, N(2-hydroxyethyl)Gly, Hse, D-Thr, Aad, Lys(Me$_2$), Tyr, Lys(Ac), Iva or D-Iva, preferably Ser, Glu, Gln, Arg, Acp, Thr or Asp, more preferably Ser, Glu, Gln, Arg, Acp or Thr, particularly preferably Ser or Glu.

A24 is D-Pro, D-Hyp, Aib, D-Iva, Iva, β-Ala, DL-β-HOAla, Aipe, Ambz(4), Leu, Acp, D-Leu, Phe, D-Phe, Cha, D-Cha, Pro, Abz(2), Pic(4), N(iBu)Gly, NMeAla, D-NMeAla, Sar, Gly, Aze(3), D-cisHyp, D-Pic(2), D-Aze(2), α-MePro, D-α-MePro or GABA, preferably, D-Pro, D-Hyp, Aib, D-Iva, Iva, β-Ala, DL-β-HOAla, Aipe or Ambz(4), more preferably D-Pro, D-Hyp, Aib, D-Iva, Iva or β-Ala, particularly preferably D-Pro or D-Hyp.

Examples of the group represented by
(1) the formula for $X^1$:

—$X^2$-$L^1$-C($J^1$)($Q^1$)-$Y^1$—C($J^2$)($Q^2$)-$Y^2$—C($J^3$)($Q^3$)-$Y^3$—C($J^4$)($Q^4$)-C(=$Z^1$)—, or

—$X^2$-A21-A22-A23-A24- include

Glu-Asp-Ala-Ser-Pro-Glu-Glu-Leu-Ala-Arg-Tyr-Tyr-Ala-Ser-Leu (SEQ ID NO: 6),

Glu-Asp-Ala-Ser-Pro-Glu-Glu-Leu-Asn-Arg-Tyr-Tyr-Ala-Ser-Leu (SEQ ID NO: 7),

-continued

Glu-Asp-Ala-Ser-Pro-Glu-Glu-Leu-Ala-Arg-Tyr-Tyr-Ala-Ser-D-Pro,

Glu-Asp-Ala-Ser-Pro-Glu-Glu-Leu-Asn-Arg-Tyr-Tyr-Ala-Ser-D-Pro,

Glu-Glu-Leu-Ala-Arg-Tyr-Tyr-Ala-Ser-Leu, (SEQ ID NO: 8)

Leu-Asn-Arg-Tyr-Tyr-Ala-Ser-Leu (SEQ ID NO: 9),

Tyr-Pro-Ile-Lys-Acp-Ala-Ser-Leu (SEQ ID NO: 10),

Asn-Arg-Tyr-Tyr-Ala-Ser-Leu (SEQ ID NO: 11),

Arg-Tyr-D-Tyr-Ala-Ser-D-Pro,

D-Arg-Tyr-D-Tyr-Ala-Ser-D-Pro,

Arg-Tyr-Tyr-Ala-Ser-Leu (SEQ ID NO: 12),

D-Arg-Tyr-Tyr-Ala-Ser-Leu,

Arg-Arg-Tyr-Ala-Ser-Leu (SEQ ID NO: 13),

Ile-Lys-Acp-Ala-Ser-Leu (SEQ ID NO: 14),

Arg-Tyr-Tyr-Ala-Ser-D-Pro,

Arg-Tyr-Tyr-Ala-Ser-D-Leu,

Acp-Arg-D-Tyr-Ala-Ser-D-Pro,

Arg-D-Tyr-Ala-Ser-D-Pro,

Tyr-D-Tyr-Ala-Ser-D-Pro,

D-Arg-D-Tyr-Ala-Ser-D-Pro,

Arg-Tyr-Ala-Ser-Leu (SEQ ID NO: 15),

Tyr-Tyr-Ala-Ser-Leu (SEQ ID NO: 16),

D-Arg-Tyr-Ala-Ser-Leu,

Tyr-Pro-Ile-Lys-Acp (SEQ ID NO: 17),

Acp-Arg-Acp-Ser-D-Pro and the like,
preferably

Arg-Tyr-Tyr-Ala-Ser-Leu (SEQ ID NO: 12),

Tyr-Tyr-Ala-Ser-Leu (SEQ ID NO: 16),

Arg-D-Tyr-Ala-Ser-D-Pro,

Tyr-D-Tyr-Ala-Ser-D-Pro and the like.

Examples of the group represented by (2) the formula for $X^1$:

$-L^1-C(J^1)(Q^1)-Y^1-C(J^2)(Q^2)-Y^2-C(J^3)(Q^3)-Y^3-C(J^4)(Q^4)-C(=Z^1)-$, or

-A21-A22-A23-A24- include

D-Tyr-Ala-Ser-D-Pro,

Tyr-Ala-Ser-D-Pro,

Tyr-D-Ala-Ser-D-Pro,

D-Tyr-D-Ala-Ser-D-Pro,

Acp-Acp-Ser-D-Pro,

Ambz(4)-Acp-Ser-D-Pro,

Lys-Acp-Ser-D-Pro,

Acp-Pic(4)-Ser-D-Pro

PEG2-Dap-Ser-Leu and the like,
preferably

D-Tyr-Ala-Ser-D-Pro and the like.

Examples of the group represented by (3) the formula for $X^1$:

$-L^1-C(J^1)(Q^1)-Y^1-C(J^2)(Q^2)-Y^2-C(J^3)(Q^3)-C(=Z^1)-$, or

-A22-A23-A24- include

Ala-Ser-D-Pro,

Ala-Glu-D-Pro,

Acp-Ser-D-Pro,

Phe-Ser-D-Pro,

Acp-Glu-D-Pro,

Dap-Ser-D-Pro,

Leu-Ser-D-Pro,

Lys-Ser-D-Pro,

Ala-Ser-Leu,

D-Ala-Ser-Leu,

Ile-Lys-Acp,

Lys(Hexadecanoyl)-Ser-Leu,

Lys[Hexadecanoyl-(PEG2)]-Ser-Leu,

Ala-Ser-D-Leu,

Ala-Asp-D-Pro,

D-Ala-Ser-D-Pro,

Tyr-Ser-D-Pro,

Aib-Ser-D-Pro,

Ala-MeSer-D-Pro,

D-Ala-MeSer-D-Pro,

Ambz(4)-Ser-D-Pro,

Pic(4)-Ser-D-Pro,

Acp-Pic(4)-D-Pro,

Gly-Ser-D-Pro,

-continued

PEG2-Ser-D-Pro,

Adc(12)-Ser-D-Pro and the like,
preferably

Ala-Ser-Leu,

D-Ala-Ser-Leu,

Ala-MeSer-D-Pro,

Acp-Ser-D-Pro,

Acp-Glu-D-Pro,

Ala-Ser-D-Pro,

Ala-Glu-D-Pro,

Lys-Ser-D-Pro,

Dap-Ser-D-Pro,

Phe-Ser-D-Pro,

Ile-Lys-Acp and the like.

Examples of the group represented by (4) the formula for $X^1$:

-$L^1$-C($J^1$)($Q^1$)-$Y^1$—C($J^2$)($Q^2$)-C(=$Z^1$)—, or

-A23-A24- include

Ser-D-Pro,

Ser-D-Hyp,

Glu-D-Pro,

Ser-Aib,

Glu-D-Hyp,

Gln-D-Pro,

Ser-D-Iva,

Ser-Iva,

Arg-D-Pro,

Acp-D-Pro,

Ser-β-Ala,

Thr-D-Pro,

Ser-DL-β-HOAla,

Asp-D-Hyp,

Ser-Aipe,

Glu-β-Ala,

Asp-D-Pro,

Arg-Leu,

Arg-D-Leu,

D-Arg-Leu,

D-Arg-D-Leu,

Ser-Leu,

D-Ser-Leu,

Gly-Pic(4),

Ser-D-Leu,

D-Ser-D-Pro,

Abu-D-Leu,

Ser(Me)-D-Leu,

Phe-D-Leu,

Asp-D-Leu,

Abu-D-Pro,

Ser(Me)-D-Pro,

Phe-D-Pro,

D-Arg-D-Pro,

Ser-N(iBu)Gly,

Ser-NMeAla,

D-Ser-NMeAla,

Ser-D-NMeAla,

D-Ser-D-NMeAla,

Ser-Sar,

D-Ser-Sar,

D-Ser-Aib,

Ser-Gly,

D-Ser-Gly,

Ser-Aze(3),

D-Ser-Aze(3),

Asn-D-Pro,

Ser-Pic(4),

β-Ala-D-Pro,

Aoc(8)-D-Pro, (PEG2)-D-Pro,

Ser-D-cisHyp,

Glu-D-cisHyp,

Ser-D-Pic(2),

Glu-D-Pic(2),

Gly-ψ[(E)CH=CH]-Leu-,

Ser-MeAla,

Ser-D-MeAla,

Pic(4)-D-Pro,

Hyp-D-Pro,

-continued

MeSer-D-Pro,

N(iBu)Gly-D-Pro,

N(2-hydroxyethyl)Gly-D-Pro,

Ser-Pro,

Ser-D-Aze(2),

Ser-Abz(2),

Ser-α-MePro,

Ser-D-α-MePro,

Ser-GABA,

Hse-D-Pro,

D-Thr-D-Pro,

Aad-D-Pro,

Lys-D-Pro,

Lys(Me$_2$)-D-Pro,

Tyr-D-Pro,

Lys(Ac)-D-Pro, and

Iva-D-Pro, preferably,

D-Arg-Leu,

D-Ser-Leu,

Gly-Pic(4),

Abu-D-Pro,

Ser(Me)-D-Pro,

Phe-D-Pro,

Ser-N(iBu)Gly,

D-Ser-NMeAla,

Ser-D-NMeAla,

D-Ser-Sar,

Ser-Gly,

Ser-Aze(3),

Ser-D-Hyp,

Asn-D-Pro,

β-Ala-D-Pro,

Aoc(8)-D-Pro, (PEG2)-D-Pro,

Ser-D-Pic(2),

Glu-D-Pic(2),

Gly-ψ[(E)CH=CH]-Leu,

Ser-MeAla,

Ser-D-MeAla,

-continued

Pic(4)-D-Pro,

Hyp-D-Pro,

Asp-D-Hyp,

Ser-D-Pro,

N(iBu)Gly-D-Pro,

N(2-hydroxyethyl)Gly-D-Pro,

Glu-D-Pro,

Ser-D-Aze(2),

Ser-α-MePro,

Ser-D-α-MePro,

Ser-GABA,

Hse-D-Pro,

D-Thr-D-Pro,

Aad-D-Pro,

Lys(Me$_2$)-D-Pro,

Asp-D-Pro,

Tyr-D-Pro,

Lys(Ac)-D-Pro,

Iva-D-Pro,

D-Iva-D-Pro,

Glu-D-Hyp,

Gln-D-Pro,

Thr-D-Pro,

Ser-β-Ala,

Glu-β-Ala,

Ser-Aib,

Ser-Iva,

Ser-D-Iva,

Ser-Aipe,

Ser-DL-β-HOAla,

Acp-D-Pro,

Arg-D-Pro and the like.

Examples of the group represented by (5) the formula for $X^1$:

$$-L^1-C(J^1)(Q^1)-C(=Z^1)-, \text{ or}$$

$$-A24-$$

include

D-Leu, Ambz(4), Phe, D-Phe, Cha, D-Cha, Pro, Abz(2), D-Pro and the like.

$X^1$ is preferably a group represented by the formula:

-L$^1$-C(J$^1$)(Q$^1$)-Y$^1$—C(J$^2$)(Q$^2$)-C(=Z$^1$)—, or

-A23-A24- wherein each symbol is as defined above.
$X^1$ is more preferably a group represented by the formula:
(1) -Gly-Ψ[(E)CH=CH]-Leu-, or
(2) the formula:

-A23-A24- wherein each symbol is as defined above.
$X^1$ is particularly preferably a group represented by the formula:

-A23-A24- wherein
A23 is Ser, Glu, Gln, Arg, Acp, Thr or Asp; and
A24 is D-Pro, D-Hyp, Aib, D-Iva, Iva, β-Ala, DL-β-HOAla, Aipe or Ambz (4).
In addition, specific examples of $X^1$ include Glu-Asp-Ala-Ser-Pro-Glu-Glu-Leu-Ala-Arg-Tyr-Tyr-Ala-Ser-Leu (SEQ ID NO: 6), Glu-Asp-Ala-Ser-Pro-Glu-Glu-Leu-Asn-Arg-Tyr-Tyr-Ala-Ser-Leu (SEQ ID NO: 7), Glu-Asp-Ala-Ser-Pro-Glu-Glu-Leu-Ala-Arg-Tyr-Tyr-Ala-Ser-D-Pro, Glu-Asp-Ala-Ser-Pro-Glu-Glu-Leu-Asn-Arg-Tyr-Tyr-Ala-Ser-D-Pro, Glu-Glu-Leu-Ala-Arg-Tyr-Tyr-Ala-Ser-Leu (SEQ ID NO: 8), Leu-Asn-Arg-Tyr-Tyr-Ala-Ser-Leu (SEQ ID NO: 9), Tyr-Pro-Ile-Lys-Acp-Ala-Ser-Leu (SEQ ID NO: 10), Asn-Arg-Tyr-Tyr-Ala-Ser-Leu (SEQ ID NO: 11), Arg-Tyr-D-Tyr-Ala-Ser-D-Pro, D-Arg-Tyr-D-Tyr-Ala-Ser-D-Pro, Arg-Tyr-Tyr-Ala-Ser-Leu (SEQ ID NO: 12), D-Arg-Tyr-Tyr-Ala-Ser-Leu, Arg-Arg-Tyr-Ala-Ser-Leu (SEQ ID NO: 13), Ile-Lys-Acp-Ala-Ser-Leu (SEQ ID NO: 14), Arg-Tyr-Tyr-Ala-Ser-D-Pro, Arg-Tyr-Tyr-Ala-Ser-D-Leu, Acp-Arg-D-Tyr-Ala-Ser-D-Pro, Arg-D-Tyr-Ala-Ser-D-Pro, Tyr-D-Tyr-Ala-Ser-D-Pro, D-Arg-D-Tyr-Ala-Ser-D-Pro, Arg-Tyr-Ala-Ser-Leu (SEQ ID NO: 15), Tyr-Tyr-Ala-Ser-Leu (SEQ ID NO: 16), D-Arg-Tyr-Ala-Ser-Leu, Tyr-Pro-Ile-Lys-Acp (SEQ ID NO: 17), Acp-Arg-Acp-Ser-D-Pro, D-Tyr-Ala-Ser-D-Pro, Tyr-Ala-Ser-D-Pro, Tyr-D-Ala-Ser-D-Pro, D-Tyr-D-Ala-Ser-D-Pro, Acp-Acp-Ser-D-Pro, Ambz(4)-Acp-Ser-D-Pro, Lys-Acp-Ser-D-Pro, Acp-Pic(4)-Ser-D-Pro, PEG2-Dap-Ser-Leu, Ala-Ser-D-Pro, Ala-Glu-D-Pro, Acp-Ser-D-Pro, Phe-Ser-D-Pro, Acp-Glu-D-Pro, Dap-Ser-D-Pro, Leu-Ser-D-Pro, Lys-Ser-D-Pro, Ala-Ser-Leu, D-Ala-Ser-Leu, Ile-Lys-Acp, Lys(Hexadecanoyl)-Ser-Leu, Lys[Hexadecanoyl-(PEG2)]-Ser-Leu, Ala-Ser-D-Leu, Ala-Asp-D-Pro, D-Ala-Ser-D-Pro, Tyr-Ser-D-Pro, Aib-Ser-D-Pro, Ala-MeSer-D-Pro, D-Ala-MeSer-D-Pro, Ambz(4)-Ser-D-Pro, Pic(4)-Ser-D-Pro, Acp-Pic(4)-D-Pro, Gly-Ser-D-Pro, PEG2-Ser-D-Pro, Adc(12)-Ser-D-Pro, Ser-D-Pro, Ser-D-Hyp, Glu-D-Pro, -continued Ser-Aib,
Glu-D-Hyp,
Gln-D-Pro,
Ser-D-Iva,
Ser-Iva,
Arg-D-Pro,
Acp-D-Pro,
Ser-β-Ala,
Thr-D-Pro,
Ser-DL-β-HOAla,
Asp-D-Hyp,
Ser-Aipe,
Glu-β-Ala,
Asp-D-Pro,
Arg-Leu,
Arg-D-Leu,
D-Arg-Leu,
D-Arg-D-Leu,
Ser-Leu,
D-Ser-Leu,
Gly-Pic(4),
Ser-D-Leu,
D-Ser-D-Pro,
Abu-D-Leu,
Ser(Me)-D-Leu,
Phe-D-Leu,
Asp-D-Leu,
Abu-D-Pro,
Ser(Me)-D-Pro,
Phe-D-Pro,
D-Arg-D-Pro,
Ser-N(iBu)Gly,
Ser-NMeAla,
D-Ser-NMeAla,
Ser-D-NMeAla,
D-Ser-D-NMeAla,
Ser-Sar,
D-Ser-Sar,
D-Ser-Aib,
Ser-Gly,
D-Ser-Gly, -continued Ser-Aze(3),
D-Ser-Aze(3),
Asn-D-Pro,
Ser-Pic(4),
β-Ala-D-Pro,
Aoc(8)-D-Pro,
(PEG2)-D-Pro,
Ser-D-cisHyp,
Glu-D-cisHyp,
Ser-D-Pic(2),
Glu-D-Pic(2),
Gly-ψ[(E)CH=CH]-Leu-,
Ser-MeAla,
Ser-D-MeAla,
Pic(4)-D-Pro,
Hyp-D-Pro,
MeSer-D-Pro,
N(iBu)Gly-D-Pro,
N(2-hydroxyethyl)Gly-D-Pro,
Ser-Pro,
Ser-D-Aze(2),
Ser-Abz(2),
Ser-α-MePro,
Ser-D-α-MePro,
Ser-GABA,
Hse-D-Pro,
D-Thr-D-Pro,
Aad-D-Pro,
Lys-D-Pro,
Lys(Me$_2$)-D-Pro,
Tyr-D-Pro,
Lys(Ac)-D-Pro,
Iva-D-Pro and the like,
preferably, Arg-Tyr-Tyr-Ala-Ser-Leu (SEQ ID NO: 12),
Tyr-Tyr-Ala-Ser-Leu (SEQ ID NO: 16),
Arg-D-Tyr-Ala-Ser-D-Pro,
Tyr-D-Tyr-Ala-Ser-D-Pro,
D-Tyr-Ala-Ser-D-Pro, -continued Ala-Ser-Leu, D-Ala-Ser-Leu, Ala-MeSer-D-Pro, Acp-Ser-D-Pro, Acp-Glu-D-Pro, Ala-Ser-D-Pro, Ala-Glu-D-Pro, Lys-Ser-D-Pro, Dap-Ser-D-Pro, Phe-Ser-D-Pro, Ile-Lys-Acp, D-Arg-Leu, D-Ser-Leu, Gly-Pic(4), Abu-D-Pro, Ser(Me)-D-Pro, Phe-D-Pro, Ser-N(iBu)Gly, D-Ser-NMeAla, Ser-D-NMeAla, D-Ser-Sar, Ser-Gly, Ser-Aze(3), Ser-D-Hyp, Asn-D-Pro, β-Ala-D-Pro, Aoc(8)-D-Pro, (PEG2)-D-Pro, Ser-D-Pic(2), Glu-D-Pic(2), Gly-ψ[(E)CH=CH]-Leu, Ser-MeAla, Ser-D-MeAla, Pic(4)-D-Pro, Hyp-D-Pro, Asp-Hyp, Ser-D-Pro, N(iBu)Gly-D-Pro, N(2-hydroxyethyl)Gly-D-Pro, Glu-D-Pro, Ser-D-Aze(2), -continued Ser-α-MePro, Ser-D-α-MePro, Ser-GABA, Hse-D-Pro, D-Thr-D-Pro, Aad-D-Pro, Lys(Me$_2$)-D-Pro, Asp-D-Pro, Tyr-D-Pro, Lys(Ac)-D-Pro, Iva-D-Pro, D-Iva-D-Pro, Glu-D-Hyp, Gln-D-Pro, Thr-D-Pro, Ser-β-Ala, Glu-β-Ala, Ser-Aib, Ser-Iva, Ser-D-Iva, Ser-Aipe, Ser-DL-β-HOAla, Acp-D-Pro, Arg-D-Pro, D-Leu, Ambz(4), Phe, D-Phe, Cha, D-Cha, Pro, Abz(2), D-Pro and the like.

A25 is Iva, Arg, Nle, Arg(Me), Ala(4Pip), Cit, Aib, Nar, Lys(Ac), Har, D-Iva, D-Arg, Orn, Lys, D-Ala(4Pip) or a bond, preferably, Iva, Arg, Nle, Arg(Me), Ala(4Pip), Cit, Aib, Nar, Lys(Ac) or Har, more preferably, Iva, Arg, Nle, Arg(Me), Ala(4Pip), Cit or Aib, particularly preferably Iva, Arg or Nle.

A26 is Pya(4), His, Abu, Ala(4Pip), Phe, Pya(2), Cha, Gln, Aib, Ala, Arg, Pro, Ala(cPr), Gly, Dap, Ser, Ser(Me), Asn, Hse, Thr, Pya(3), Alb, Orn, Glu, Cit, Iva, D-Iva, D-Ala(4Pip), Tyr, Trp, Tyr(Me), Nle or a bond, preferably, Pya(4), His, Abu, Ala(4Pip), Phe, Pya(2), Cha, Gln or Aib, more preferably Pya(4), His, Abu, Ala(4Pip), Phe, Pya(2) or Cha, particularly preferably Pya(4) or His.

A27 is Cha, Nal(2), Phe(4F), Nal(1), Ala(4Pip), Tyr, Glu, Arg, Gln, Nle, Pya(4), Trp, Phe(4NH$_2$), Aib, D-Ala(4Pip), Dap, Nva, His, Cit, Iva, D-Iva, Abu, Gly or a bond, preferably Cha, Nal(2), Phe(4F), Nal(1) or Ala(4Pip), more preferably Cha.

A28 is Aib, Iva, Leu(Me), Cha, α-MePhe, D-Iva, Tyr, Ile, Leu, Nle, Phe, Trp, Lys, Ala, Nal(1), Ala(cPr), Phe(4F), Pya (4), Gln, His, Hse, Acpc, Nva, Gly(cPr), Ser or a bond, preferably Aib, Iva, Leu(Me), Cha, α-MePhe or D-Iva, more preferably, Aib, Iva or Leu(Me).

A29 is Asn, Aib, Asn(Me), D-Iva or a bond, preferably Asn.

A30 is Lys, Har, Arg(Me), Ala(4Pip), Cha, Lys(Me), Orn, Lys(Ac), Arg, Leu, Nle, Cit, Lys(Hexyl), Trp, Hse, Thr, Ala, Gly, Aib, Phe, Nal(1), Nal(2), Tyr, Phe(4F), Dap, Pya(4), Phe(4NH$_2$), Ala(cPr), Leu(Me), Ser, Gln, Abu, His, Dab, Lys(Me$_2$), Iva or a bond, preferably, Lys, Har, Arg(Me), Ala (4Pip), Cha, Lys(Me), Orn, Lys(Ac), Arg, Leu, Nle, Cit, Lys (Hexyl), Trp, Hse or Thr, more preferably, Lys, Har, Arg(Me), Ala(4Pip), Cha, Lys(Me) or Orn, particularly preferably Lys.

A31 is Aib, D-Iva, Iva, Ile, Lys, Ala, Val, Phg, Cha, Nle, Phe, Arg, Dap, Arg(Me), Pya(4), Phe(4NH$_2$), Pya(3), Gly (cPr), Acpc or a bond, preferably, Aib, D-Iva, or Iva, more preferably Aib.

A32 is Thr, Glu, Nva, Leu, Thr(Me), Abu, Ser or a bond, preferably Thr.

A33 is Arg, Arg(Me) or a bond, preferably Arg.

A34 is Gln or a bond, preferably Gln.

A35 is Arg, Arg(Me) or a bond, preferably Arg.

A36 is Cha, Phe(2,6-Me$_2$), Phe(3Me), Phe(2Me), Tyr, Phe (2F), Phe, Phe(3F), Leu(Me), homoLeu, threo-PhSer, Trp, Tyr(Me), Phe(4Cl), Phe(4NH$_2$), Nal(1), Nal(2), Phe(4Me), Tyr(2F), Tyr(3F), NMePhe, Tic or a bond, preferably, Cha, Phe(2,6-Me$_2$), Phe(3Me), or Phe(2Me), more preferably, Cha or Phe(2,6-Me$_2$), particularly preferably Cha.

Among A25, A26, A27, A28, A29, A30, A31, A32, A33, A34, A35 and A36, 3 or more groups are not bonds at the same time.

Side chains which two amino acid residues selected from A25, A26, A27, A28, A29, A30, A31, A32, A33, A34, A35 and A36 have may be bonded to form a ring.

Preferable examples of compound (A) include the following peptide or a salt thereof.

[Compound (A)-1]

Compound (A) wherein P$^1$ is
(1) a hydrogen atom,
(2) a $C_{1-10}$ alkyl group (e.g., methyl, ethyl, hexyl, heptyl, octyl) optionally substituted by 1 to 3 substituents selected from
  (a) a hydroxy group,
  (b) a $C_{1-6}$ alkoxy group (e.g., ethoxy) optionally substituted by a hydroxy group, and
  (c) a $C_{6-14}$ aryl group (e.g., phenyl).
(3) a 5- or 6-membered aromatic heterocyclic group (e.g., pyridyl),
(4) a formyl group,
(5) a $C_{1-10}$ alkyl-carbonyl group (e.g., acetyl, ethylcarbonyl, isopropylcarbonyl, sec-butylcarbonyl, pentylcarbonyl, nonanylcarbonyl) optionally substituted by 1 to 3 substituents selected from
  (a) a hydroxy group,
  (b) a carboxy group,
  (c) a $C_{6-14}$ aryl group (e.g., phenyl), and
  (d) a 5- or 6-membered nonaromatic heterocyclic group (e.g., piperidyl),
(6) a $C_{3-10}$ cycloalkyl-carbonyl group (e.g., cyclopropylcarbonyl, cyclohexyl-carbonyl),
(7) a $C_{6-14}$ aryl-carbonyl group (e.g., benzoyl, naphthylcarbonyl) optionally substituted by 1 to 5 substituents selected from
  (a) a halogen atom (e.g., fluorine atom),
  (b) a hydroxy group, and
  (c) a $C_{1-6}$ alkyl group (e.g., methyl) optionally substituted by 1 to 3 substituents selected from
    (i) an amino group,
    (ii) a guadinino group, and
    (iii) a ureido group,
(8) a 5- or 6-membered aromatic heterocyclic carbonyl group (e.g., imidazolylcarbonyl, pyridylcarbonyl, furylcarbonyl, pyrrolylcarbonyl, thiophenylcarbonyl),
(9) a 5- or 6-membered nonaromatic heterocyclic carbonyl group (e.g., tetrahydropyranylcarbonyl, morpholinylcarbonyl, piperidinylcarbonyl, pyrrolidinylcarbonyl, tetrahydropyrimidinylcarbonyl) optionally substituted by 1 to 3 substituents selected from
  (a) an oxo group,
  (b) a $C_{1-6}$ alkyl group (e.g., methyl),
  (c) an amidino group, and
  (d) a $C_{1-6}$ alkyl-carbonyl group (e.g., acetyl) optionally substituted by an amino group,
(10) a $C_{1-10}$ alkoxy-carbonyl group (e.g., a methoxycarbonyl group) optionally substituted by a $C_{6-14}$ aryl group (e.g., phenyl group),
(11) a $C_{1-10}$ alkyl-sulfonyl group (e.g., a methylsulfonyl group),
(12) a carbamoyl group optionally mono- or di-substituted by substituent(s) selected from
  (a) a $C_{1-10}$ alkyl group (e.g., methyl, ethyl, propyl, isopropyl, isobutyl, 1-ethyl-3-methylbutyl, pentyl, isopentyl) optionally substituted by 1 to 3 substituents selected from
    (i) a hydroxy group,
    (ii) a carboxy group
    (iii) a carbamoyl group,
    (iv) a $C_{6-14}$ aryl group (e.g., phenyl, naphthyl) optionally substituted by a hydroxy group,
    (v) a $C_{1-6}$ alkoxy (e.g., methoxy, ethoxy) optionally substituted by a carboxy group,
    (vi) a $C_{1-6}$ alkoxy-carbonyl (e.g., methoxycarbonyl), and
    (vii) a 5- or 6-membered nonaromatic heterocyclic group (e.g., tetrahydropyranyl), and
  (b) a 5- or 6-membered nonaromatic heterocyclic group (e.g., tetrahydropyranyl), or
(13) an amidino group optionally mono-, di- or tri-substituted by a $C_{1-10}$ alkyl group (e.g., methyl, isobutyl, octyl) optionally substituted by 1 to 3 substituents selected from
  (a) a hydroxy group,
  (b) a $C_{6-14}$ aryl group (e.g., phenyl) optionally substituted by 1 to 3 substituents selected from
    (i) a cyano group, and
    (ii) a $C_{1-6}$ alkyl group (e.g., methyl, tert-butyl) optionally substituted by an amino group, and
  (c) a 5- or 6-membered aromatic heterocyclic group (e.g., pyridyl);

$Q^1$, $Q^2$, $Q^3$ and $Q^4$ are each independently
(1) a hydrogen atom, or
(2) a $C_{1-10}$ alkyl group (e.g., methyl, ethyl, propyl, isopropyl, butyl, isobutyl, sec-butyl, tert-butyl, pentyl, isopentyl, neopentyl, hexyl, heptyl, octyl, nonanyl, decanyl) optionally substituted by 1 to 3 substituents selected from
  (a) a $C_{3-10}$ cycloalkyl group (e.g., cyclopropyl, cyclohexyl), (b) a C<sub>6-14</sub> aryl group (e.g., phenyl, naphthyl) optionally substituted by 1 to 3 substituents selected from
  (i) a C$_{1-6}$ alkyl group (e.g., methyl, tert-butyl),
  (ii) a hydroxy group, and
  (iii) a C$_{1-6}$ alkoxy group;
(c) an aromatic heterocyclic group (e.g., imidazolyl, indolyl) optionally substituted by 1 to 3 substituents selected from
  (i) a C$_{1-6}$ alkyl group,
  (ii) a hydroxy group, and
  (iii) a C$_{1-6}$ alkoxy group;
(d) an amino group optionally mono- or di-substituted by substituent(s) selected from
  (i) a C$_{1-6}$ alkyl group (e.g., methyl),
  (ii) a C$_{1-6}$ alkyl-carbonyl group, and
  (iii) a C$_{1-6}$ alkoxy-carbonyl group;
(e) a carbamoyl group optionally mono- or di-substituted by a C$_{1-6}$ alkyl group (e.g., methyl) optionally substituted by 1 to 3 halogen atoms;
(f) a carboxy group;
(g) a hydroxy group;
(h) a C$_{1-6}$ alkoxy group (e.g., methoxy, ethoxy) optionally substituted by 1 to 3 substituents selected from
  (i) a C$_{1-6}$ alkyl group,
  (ii) a hydroxy group, and
  (iii) a C$_{1-6}$ alkoxy group;
(i) a mercapto group;
(j) a C$_{1-6}$ alkylthio group (e.g., methylthio, ethylthio); and
(k) guanidino.

[Compound (A)-2]
Compound (A) wherein P$^1$ is
(1) a C$_{1-10}$ alkyl group (e.g., ethyl) optionally substituted by 1 to 3 substituents selected from
  (a) a hydroxy group, and
  (b) a C$_{1-6}$ alkoxy group (e.g., ethoxy) optionally substituted by a hydroxy group,
(2) a C$_{1-10}$ alkyl-carbonyl group (e.g., acetyl, ethylcarbonyl, isopropylcarbonyl, sec-butylcarbonyl) optionally substituted by 1 to 3 substituents selected from
  (a) a hydroxy group,
  (b) a carboxy group, and
  (c) a C$_{6-14}$ aryl group (e.g., phenyl),
(3) a C$_{6-14}$ aryl-carbonyl group (e.g., benzoyl)
(4) a 5- or 6-membered aromatic heterocyclic carbonyl group (e.g., imidazolylcarbonyl, pyridylcarbonyl),
(5) a 5- or 6-membered nonaromatic heterocyclic carbonyl group (e.g., tetrahydropyranylcarbonyl, morpholinylcarbonyl, piperidinylcarbonyl, pyrrolidinylcarbonyl) optionally substituted by 1 to 3 substituents selected from
  (a) an oxo group, and
  (b) a C$_{1-6}$ alkyl group (e.g., methyl),
(6) a carbamoyl group optionally mono- or di-substituted by substituent(s) selected from
  (a) a C$_{1-10}$ alkyl group (e.g., methyl, ethyl, propyl, pentyl, isopentyl) optionally substituted by 1 to 3 substituents selected from
    (i) a hydroxy group,
    (ii) a carboxy group
    (iii) a carbamoyl group,
    (iv) a C$_{6-14}$ aryl group (e.g., phenyl) optionally substituted by a hydroxy group, and
    (v) a 5- or 6-membered nonaromatic heterocyclic group (e.g., tetrahydropyranyl), and
  (b) a 5- or 6-membered nonaromatic heterocyclic group (e.g., tetrahydropyranyl), or
(7) an amidino group;

X$^1$ is

Glu-Asp-Ala-Ser-Pro-Glu-Glu-Leu-Ala-Arg-Tyr-Tyr-Ala-Ser-Leu (SEQ ID NO: 6),

Glu-Asp-Ala-Ser-Pro-Glu-Glu-Leu-Asn-Arg-Tyr-Tyr-Ala-Ser-Leu (SEQ ID NO: 7),

Glu-Asp-Ala-Ser-Pro-Glu-Glu-Leu-Ala-Arg-Tyr-Tyr-Ala-Ser-D-Pro,

Glu-Asp-Ala-Ser-Pro-Glu-Glu-Leu-Asn-Arg-Tyr-Tyr-Ala-Ser-D-Pro,

Glu-Glu-Leu-Ala-Arg-Tyr-Tyr-Ala-Ser-Leu (SEQ ID NO: 8),

Leu-Asn-Arg-Tyr-Tyr-Ala-Ser-Leu (SEQ ID NO: 9),

Tyr-Pro-Ile-Lys-Acp-Ala-Ser-Leu (SEQ ID NO: 10),

Asn-Arg-Tyr-Tyr-Ala-Ser-Leu (SEQ ID NO: 11),

Arg-Tyr-D-Tyr-Ala-Ser-D-Pro,

D-Arg-Tyr-D-Tyr-Ala-Ser-D-Pro,

Arg-Tyr-Tyr-Ala-Ser-Leu (SEQ ID NO: 12),

D-Arg-Tyr-Tyr-Ala-Ser-Leu,

Arg-Arg-Tyr-Ala-Ser-Leu (SEQ ID NO: 13),

Ile-Lys-Acp-Ala-Ser-Leu (SEQ ID NO: 14),

Arg-Tyr-Tyr-Ala-Ser-D-Pro,

Arg-Tyr-Tyr-Ala-Ser-D-Leu,

Acp-Arg-D-Tyr-Ala-Ser-D-Pro,

Arg-D-Tyr-Ala-Ser-D-Pro,

Tyr-D-Tyr-Ala-Ser-D-Pro,

D-Arg-D-Tyr-Ala-Ser-D-Pro,

Arg-Tyr-Ala-Ser-Leu (SEQ ID NO: 15),

Tyr-Tyr-Ala-Ser-Leu (SEQ ID NO: 16),

D-Arg-Tyr-Ala-Ser-Leu,

Tyr-Pro-Ile-Lys-Acp (SEQ ID NO: 17),

Acp-Arg-Acp-Ser-D-Pro,

D-Tyr-Ala-Ser-D-Pro,

Tyr-Ala-Ser-D-Pro,

Tyr-D-Ala-Ser-D-Pro,

D-Tyr-D-Ala-Ser-D-Pro,

Acp-Acp-Ser-D-Pro,

Ambz(4)-Acp-Ser-D-Pro,

Lys-Acp-Ser-D-Pro,

Acp-Pic(4)-Ser-D-Pro,

PEG2-Dap-Ser-Leu,

Ala-Ser-D-Pro,
Ala-Glu-D-Pro,
Acp-Ser-D-Pro,
Phe-Ser-D-Pro,
Acp-Glu-D-Pro,
Dap-Ser-D-Pro,
Leu-Ser-D-Pro,
Lys-Ser-D-Pro,
Ala-Ser-Leu,
D-Ala-Ser-Leu,
Ile-Lys-Acp,
Lys(Hexadecanoyl)-Ser-Leu,
Lys[Hexadecanoyl-(PEG2)]-Ser-Leu,
Ala-Ser-D-Leu,
Ala-Asp-D-Pro,
D-Ala-Ser-D-Pro,
Tyr-Ser-D-Pro,
Aib-Ser-D-Pro,
Ala-MeSer-D-Pro,
D-Ala-MeSer-D-Pro,
Ambz(4)-Ser-D-Pro,
Pic(4)-Ser-D-Pro,
Acp-Pic(4)-D-Pro,
Gly-Ser-D-Pro,
PEG2-Ser-D-Pro,
Adc(12)-Ser-D-Pro,
Ser-D-Pro,
Ser-D-Hyp,
Glu-D-Pro,
Ser-Aib,
Glu-D-Hyp,
Gln-D-Pro,
Ser-D-Iva,
Ser-Iva,
Arg-D-Pro,
Acp-D-Pro,
Ser-β-Ala,
Thr-D-Pro,
Ser-DL-β-HOAla,
Asp-D-Hyp,
Ser-Aipe,
Glu-β-Ala,
Asp-D-Pro,
Arg-Leu,
Arg-D-Leu,
D-Arg-Leu,
D-Arg-D-Leu,
Ser-Leu,
D-Ser-Leu,
Gly-Pic(4),
Ser-D-Leu,
Abu-D-Leu,
D-Ser-D-Pro,
Phe-D-Leu,
Ser(Me)-D-Leu,
Asp-D-Leu,
Abu-D-Pro,
Ser(Me)-D-Pro,
Phe-D-Pro,
D-Arg-D-Pro,
Ser-N(iBu)Gly,
Ser-NMeAla,
D-Ser-NMeAla,
Ser-D-NMeAla,
D-Ser-D-NMeAla,
Ser-Sar,
D-Ser-Sar,
D-Ser-Aib,
Ser-Gly,
D-Ser-Gly,
Ser-Aze(3),
D-Ser-Aze(3),
Asn-D-Pro,
Ser-Pic(4),
β-Ala-D-Pro,
Aoc(8)-D-Pro,
(PEG2)-D-Pro,
Ser-D-cisHyp,
Glu-D-cisHyp,
Ser-D-Pic(2),
Glu-D-Pic(2),
Gly-ψ[(E)CH=CH]-Leu-, -continued

```
Ser-MeAla,
Ser-D-MeAla,
Pic(4)-D-Pro,
Hyp-D-Pro,
MeSer-D-Pro,
N(iBu)Gly-D-Pro,
N(2-hydroxyethyl)Gly-D-Pro,
Ser-Pro,
Ser-D-Aze(2),
Ser-Abz(2),
Ser-α-MePro,
Ser-D-α-MePro,
Ser-GABA,
Hse-D-Pro,
D-Thr-D-Pro,
Aad-D-Pro,
Lys-D-Pro,
Lys(Me₂)-D-Pro,
Tyr-D-Pro,
Lys(Ac)-D-Pro,
or
Iva-D-Pro.
```

[Compound (A)-3]
Peptide represented by the formula (I):

$$P^1\text{—}X^1\text{-}A25\text{-}A26\text{-}A27\text{-}A28\text{-}A29\text{-}A30\text{-}A31\text{-}A32\text{-}A33\text{-}A34\text{-}A35\text{-}A36\text{-}NH_2 \quad (I)$$

wherein
P1 is
(1) a $C_{1-10}$ alkyl group (e.g., ethyl) optionally substituted by $C_{1-6}$ alkoxy group (e.g., ethoxy) optionally substituted by 1 to 3 hydroxy groups,
(2) a $C_{1-10}$ alkyl-carbonyl group (e.g., acetyl, ethylcarbonyl, isopropylcarbonyl, sec-butylcarbonyl) optionally substituted by 1 to 3 substituents selected from
    (a) a hydroxy group,
    (b) a carboxy group, and
    (c) a $C_{6-14}$ aryl group (e.g., phenyl),
(3) a $C_{6-14}$ aryl-carbonyl group (e.g., benzoyl),
(4) a 5- or 6-membered aromatic heterocyclic carbonyl group (e.g., imidazolylcarbonyl, pyridylcarbonyl),
(5) a 5- or 6-membered nonaromatic heterocyclic carbonyl group (e.g., tetrahydropyranylcarbonyl, morpholinylcarbonyl, piperidinylcarbonyl, pyrrolidinylcarbonyl) optionally substituted by 1 to 3 substituents selected from
    (a) an oxo group, and
    (b) a $C_{1-6}$ alkyl group (e.g., methyl),
(6) a carbamoyl group optionally mono- or di-substituted by substituent(s) selected from
    (a) a $C_{1-10}$ alkyl group (e.g., methyl, ethyl, propyl, pentyl, isopentyl) optionally substituted by 1 to 3 substituents selected from
        (i) a hydroxy group,
        (ii) a carboxy group,
        (iii) a carbamoyl group,
        (iv) a $C_{6-14}$ aryl group (e.g., phenyl) optionally substituted by a hydroxy group, and
        (v) a 5- or 6-membered nonaromatic heterocyclic group (e.g., tetrahydropyranyl), and
    (b) a 5- or 6-membered nonaromatic heterocyclic group (e.g., tetrahydropyranyl), or
(7) an amidino group;
$X^1$ is

```
Arg-Tyr-Tyr-Ala-Ser-Leu (SEQ ID NO: 12),
Tyr-Tyr-Ala-Ser-Leu (SEQ ID NO: 16),
Arg-D-Tyr-Ala-Ser-D-Pro,
Tyr-D-Tyr-Ala-Ser-D-Pro,
D-Tyr-Ala-Ser-D-Pro,
Ala-Ser-Leu,
D-Ala-Ser-Leu,
Ala-MeSer-D-Pro,
Acp-Ser-D-Pro,
Acp-Glu-D-Pro,
Ala-Ser-D-Pro,
Ala-Glu-D-Pro,
Lys-Ser-D-Pro,
Dap-Ser-D-Pro,
Phe-Ser-D-Pro,
Ile-Lys-Acp,
D-Arg-Leu,
D-Ser-Leu,
Gly-Pic(4),
Abu-D-Pro,
Ser(Me)-D-Pro,
Phe-D-Pro,
Ser-N(iBu)Gly,
D-Ser-NMeAla,
Ser-D-NMeAla,
D-Ser-Sar,
Ser-Gly,
Ser-Aze(3),
Ser-D-Hyp,
Asn-D-Pro,
β-Ala-D-Pro,
Aoc(8)-D-Pro,
(PEG2)-D-Pro,
Ser-D-Pic(2),
```

Glu-D-Pic(2),
Gly-ψ[(E)CH=CH]-Leu,
Ser-MeAla,
Ser-D-MeAla,
Pic(4)-D-Pro,
Hyp-D-Pro,
Asp-D-Hyp,
Ser-D-Pro,
N(iBu)Gly-D-Pro,
N(2-hydroxyethyl)Gly-D-Pro,
Glu-D-Pro,
Ser-D-Aze(2),
Ser-α-MePro,
Ser-D-α-MePro,
Ser-GABA,
Hse-D-Pro,
D-Thr-D-Pro,
Aad-D-Pro,
Lys(Me₂)-D-Pro,
Asp-D-Pro,
Tyr-D-Pro,
Lys(Ac)-D-Pro,
Iva-D-Pro,
D-Iva-D-Pro,
Glu-D-Hyp,
Gln-D-Pro,
Thr-D-Pro,
Ser-β-Ala,
Glu-β-Ala,
Ser-Aib,
Ser-Iva,
Ser-D-Iva,
Ser-Aipe,
Ser-DL-β-HOAla,
Acp-D-Pro,
Arg-D-Pro,
D-Leu,
Ambz(4),
Phe,
D-Phe,
Cha,
D-Cha,
Pro,
Abz(2),
or
D-Pro;

A25 is Iva, Arg, Nle, Arg(Me), Ala(4Pip), Cit, Aib, Nar, Lys(Ac) or Har;
A26 is Pya(4), His, Abu, Ala(4Pip), Phe, Pya(2), Cha, Gln or Aib;
A27 is Cha, Nal(2), Phe(4F), Nal(1) or Ala(4Pip);
A28 is Aib, Iva, Leu(Me), Cha, α-MePhe or D-Iva;
A29 is Asn;
A30 is Lys, Har, Arg(Me), Ala(4Pip), Cha, Lys(Me), Orn, Lys(Ac), Arg, Leu, Nle, Cit, Lys(Hexyl), Trp, Hse or Thr;
A31 is Aib, D-Iva, Iva;
A32 is Thr;
A33 is Arg;
A34 is Gln;
A35 is Arg;
A36 is Cha, Phe(2,6-Me₂), Phe(3Me), Phe(2Me),
or a salt thereof.

As compound (A), moreover, any peptide having any combination of the groups of the aforementioned respective symbols can be preferably used. Of these, peptides shown by the following compound Nos. are preferable.

In the present specification, PYY(1-36) shows a peptide having the amino acid sequence shown by SEQ ID NO:1. That is, PYY(1-36) shows Tyr-Pro-Ile-Lys-Pro-Glu-Ala-Pro-Gly-Glu-Asp-Ala-Ser-Pro-Glu-Glu-Leu-Asn-Arg-Tyr-Tyr-Ala-Ser-Leu-Arg-His-Tyr-Leu-Asn-Leu-Val-Thr-Arg-Gln-Arg-Tyr-NH₂.

In addition, the position of Tyr at the N-terminal of PYY (1-36) is to be counted as the 1-position, and Tyr at the C-terminal is to be counted as the 36-position.

Tyr-Pro-Ile-Lys-Pro-Glu-Ala-Pro-Gly-Glu-Asp-Ala-Ser-Pro-Glu-
 1   2   3   4   5   6   7   8   9  10  11  12  13  14  15

Glu-Leu-Asn-Arg-Tyr-Tyr-Ala-Ser-Leu-Arg-His-Tyr-Leu-Asn-Leu-
 16  17  18  19  20  21  22  23  24  25  26  27  28  29  30

Val-Thr-Arg-Gln-Arg-Tyr-NH₂
 31  32  33  34  35  36

Here, PYY(23-36) is a peptide having the 23-position-the 36-position amino acid sequence of PYY(1-36) (SEQ ID NO:1). That is, PYY(23-36) shows Ser-Leu-Arg-His-Tyr-Leu-Asn-Leu-Val-Thr-Arg-Gln-Arg-Tyr-NH$_2$ (SEQ ID NO:18).

In addition, Ac—PYY(23-36) is a peptide having the 23-position-the 36-position amino acid sequence of PYY(1-36) (SEQ ID NO:1), wherein the amino group of the N-terminal (the 23-position) amino acid residue (Ser) of the amino acid sequence is modified by Ac. That is, Ac—PYY(23-36) shows Ac-Ser-Leu-Arg-His-Tyr-Leu-Asn-Leu-Val-Thr-Arg-Gln-Arg-Tyr-NH$_2$ (SEQ ID NO:19).

Furthermore, Ac-[Ala26, Ile28, 31, Arg(Me)35]-PYY(23-36) is a peptide having the 23-position-the 36-position amino acid sequence of PYY(1-36) (SEQ ID NO:1), wherein the amino group of the N-terminal (the 23-position) amino acid residue (Ser) of the amino acid sequence is modified by Ac, and the 26-position amino acid residue (His)PYY(1-36) (SEQ ID NO:1) is substituted by Ala, the 28-position and the 31-position amino acid residues (Leu and Val) are substituted by Ile, and the 35-position amino acid residue (Arg) is substituted by Arg(Me). That is, Ac-[Ala26, Ile28,31, Arg(Me)35]-PYY(23-36) shows Ac-Ser-Leu-Arg-Ala-Tyr-Ile-Asn-Leu-Ile-Thr-Arg-Gln-Arg(Me)-Tyr-NH$_2$ (SEQ ID NO:20).

Moreover, cyclo(27-31)-4-Aminomethylbenzoyl-[Glu27, Ile28, Lys31]-PYY(25-36) is a cyclic peptide having the 25-position-the 36-position amino acid sequence of PYY(1-36) (SEQ ID NO:1), wherein the amino group of the N-terminal (the 25-position) amino acid residue (Ser) of the amino acid sequence is modified by 4-Aminomethylbenzoyl, and the 27-position amino acid residue (Tyr) of PYY(1-36) (SEQ ID NO:1) is substituted by Glu, the 28-position amino acid residue (Leu) of PYY(1-36) (SEQ ID NO:1) is substituted by Ile, the 31-position amino acid residue (Val) of PYY(1-36) (SEQ ID NO:1) is substituted by Lys, and the side chain functional group (carboxyl group) of the 27-position amino acid residue (Glu) is bound (amide bond) to the side chain functional group (amino group) of the 31-position amino acid residue (Lys). That is, cyclo(27-31)-4-Aminomethylbenzoyl-[Glu27, Ile28, Lys31]-PYY(25-36) shows

```
compound No. 4:
                                            (SEQ ID NO: 23)
4-Guanidinomethylbenzoyl-[Ala26, Ile28,31]-
PYY(25-36)
4-Guanidinomethylbenzoyl-Arg-Ala-Tyr-Ile-Asn-Leu-
Ile-Thr-Arg-Gln-Arg-Tyr-NH2 compound No. 5:
                                            (SEQ ID NO: 24)
Ac-[Ala26, Ile28,31]-PYY(20-36)
Ac-Tyr-Tyr-Ala-Ser-Leu-Arg-Ala-Tyr-Ile-Asn-Leu-
Ile-Thr-Arg-Gln-Arg-Tyr-NH2 compound No. 6:
                                            (SEQ ID NO: 25)
4-Aminomethylbenzoyl-[Ala26, Ile28,31, Phe36]-
PYY(25-36)
4-Aminomethylbenzoyl-Arg-Ala-Tyr-Ile-Asn-Leu-Ile-
Thr-Arg-Gln-Arg-Phe-NH2 compound No. 7:
                                            (SEQ ID NO: 26)
4-Aminomethylbenzoyl-[Ala26,
Ile28,31, Tyr(Me)36]-PYY(25-36)
4-Aminomethylbenzoyl-Arg-Ala-Tyr-Ile-Asn-Leu-Ile-
Thr-Arg-Gln-Arg-Tyr(Me)-NH2 compound No. 8:
                                            (SEQ ID NO: 27)
4-Aminomethylbenzoyl-[Ala26,
Ile28,31, Phe(4Cl)36]-PYY(25-36)
4-Aminomethylbenzoyl-Arg-Ala-Tyr-Ile-Asn-Leu-Ile-
Thr-Arg-Gln-Arg-Phe(4Cl)-NH2 compound No. 9:
4-Aminomethylbenzoyl-[D-Arg25, Ala26,
Ile28,31]-PYY(25-36)
4-Aminomethylbenzoyl-D-Arg-Ala-Tyr-Ile-Asn-Leu-
Ile-Thr-Arg-Gln-Arg-Tyr-NH2 compound No. 10:
                                            (SEQ ID NO: 28)
4-Aminomethylbenzoyl-[Orn25, Ala26,
Ile28,31]-PYY(25-36)
```

(SEQ ID NO: 152)

4-Aminomethylbenzoyl-Arg-Ala-Glu-Ile-Asn-Leu-Lys-Thr-Arg-Gln-Arg-Tyr-NH$_2$.

(with amide bond cyclization between positions 27 and 31 indicated by bracket)

Other PYY fragments, N-terminal modifications, and amino acid substitutions are also abbreviated in the same manner as the above.

```
compound No. 1:
                                            (SEQ ID NO: 21)
Ac-[Ala26, Ile28,31, Arg(Me)35]-PYY(22-36)
Ac-Ala-Ser-Leu-Arg-Ala-Tyr-Ile-Asn-Leu-Ile-Thr-
Gln-Arg-Arg(Me)-Tyr-NH2 compound No. 2:
                                            (SEQ ID NO: 22)
[Ala26, Ile28,31]-PYY(19-36)
Arg-Tyr-Tyr-Ala-Ser-Leu-Arg-Ala-Tyr-Ile-Asn-Leu-
Ile-Thr-Arg-Gln-Arg-Tyr-NH2 compound No. 3:
[D-Ala22, Ala26, Ile28,31, Arg(Me)35]-PYY(22-
36)
D-Ala-Ser-Leu-Arg-Ala-Tyr-Ile-Asn-Leu-Ile-Thr-
Arg-Gln-Arg(Me)-Tyr-NH2
```

```
-continued
4-Aminomethylbenzoyl-Orn-Ala-Tyr-Ile-Asn-Leu-Ile-
Thr-Arg-Gln-Arg-Tyr-NH2 compound No. 11:
                                            (SEQ ID NO: 29)
4-Aminomethylbenzoyl-[Ala26, Ile28,31,
Har33]-PYY(25-36)
4-Aminomethylbenzoyl-Arg-Ala-Tyr-Ile-Asn-Leu-Ile-
Thr-Har-Gln-Arg-Tyr-NH2 compound No. 12:
                                            (SEQ ID NO: 30)
4-Aminomethylbenzoyl-[Ala26, Ile28,31,
Phe(4NH2)36]-PYY(25-36)
4-Aminomethylbenzoyl-Arg-Ala-Tyr-Ile-Asn-Leu-Ile-
Thr-Arg-Gln-Arg-Phe(4NH2)-NH2 compound No. 13:
                                            (SEQ ID NO: 31)
4-Aminomethylbenzoyl-[Ala26, Ile28,31,
Nal(1)36]-PYY(25-36)
4-Aminomethylbenzoyl-Arg-Ala-Tyr-Ile-Asn-Leu-Ile-
Thr-Arg-Gln-Arg-Nal(1)-NH2
``` compound No. 14:
(SEQ ID NO: 32)
4-Aminomethylbenzoyl-[Ala26, Ile28,31, Nal(2)36]-PYY(25-36)
4-Aminomethylbenzoyl-Arg-Ala-Tyr-Ile-Asn-Leu-Ile-Thr-Arg-Gln-Arg-Nal(2)-NH$_2$ compound No. 15:
(SEQ ID NO: 33)
4-Aminomethylbenzoyl-[Ala26, Ile28,31, Phe(4Me)36]-PYY(25-36)
4-Aminomethylbenzoyl-Arg-Ala-Tyr-Ile-Asn-Leu-Ile-Thr-Arg-Gln-Arg-Phe(4Me)-NH$_2$ compound No. 16:
(SEQ ID NO: 34)
4-Aminomethylbenzoyl-[Ala26, Ile28,31, NMePhe36]-PYY(25-36)
4-Aminomethylbenzoyl-Arg-Ala-Tyr-Ile-Asn-Leu-Ile-Thr-Arg-Gln-Arg-NMePhe-NH$_2$ compound No. 17:
(SEQ ID NO: 35)
4-Aminomethylbenzoyl-[Ala26, Ile28,31, Tic36]-PYY(25-36)
4-Aminomethylbenzoyl-Arg-Ala-Tyr-Ile-Asn-Leu-Ile-Thr-Arg-Gln-Arg-Tic-NH$_2$ compound No. 18:
(SEQ ID NO: 36)
4-Aminomethylbenzoyl-[Arg26, Ile28,31]-PYY(25-36)
4-Aminomethylbenzoyl-Arg-Arg-Tyr-Ile-Asn-Leu-Ile-Thr-Arg-Gln-Arg-Tyr-NH$_2$ compound No. 19:
(SEQ ID NO: 37)
4-Aminomethylbenzoyl-[Pro26, Ile28,31]-PYY(25-36)
4-Aminomethylbenzoyl-Arg-Pro-Tyr-Ile-Asn-Leu-Ile-Thr-Arg-Gln-Arg-Tyr-NH$_2$ compound No. 20:
(SEQ ID NO: 38)
4-Aminomethylbenzoyl-[Ala26, Ile31]-PYY(25-36)
4-Aminomethylbenzoyl-Arg-Ala-Tyr-Leu-Asn-Leu-Ile-Thr-Arg-Gln-Arg-Tyr-NH$_2$ compound No. 21:
(SEQ ID NO: 39)
4-Aminomethylbenzoyl-[Ala26, Nle28, Ile31]-PYY(25-36)
4-Aminomethylbenzoyl-Arg-Ala-Tyr-Nle-Asn-Leu-Ile-Thr-Arg-Gln-Arg-Tyr-NH$_2$ compound No. 22:
(SEQ ID NO: 40)
4-Aminomethylbenzoyl-[Ala26, Phe28, Ile31]-PYY(25-36)
4-Aminomethylbenzoyl-Arg-Ala-Tyr-Phe-Asn-Leu-Ile-Thr-Arg-Gln-Arg-Tyr-NH$_2$ compound No. 23:
(SEQ ID NO: 41)
4-Aminomethylbenzoyl-[Ala26, Trp28, Ile31]-PYY(25-36)
4-Aminomethylbenzoyl-Arg-Ala-Tyr-Trp-Asn-Leu-Ile-Thr-Arg-Gln-Arg-Tyr-NH$_2$ compound No. 24:
[D-Leu24, Ala26, Ile28,31]-PYY(24-36)
D-Leu-Arg-Ala-Tyr-Ile-Asn-Leu-Ile-Thr-Arg-Gln-Arg-Tyr-NH$_2$ compound No. 25:
cyclo(27-31)-4-Aminomethylbenzoyl-[Glu27, Ile28, Lys31]-PYY(25-36)

(SEQ ID NO: 152)
4-Aminomethylbenzoyl-Arg-Ala-Glu-Ile-Asn-Leu-Lys-Thr-Arg-Gln-Arg-Tyr-NH$_2$
(cyclo between Glu and Lys)

compound No. 26:
cyclo(28-32)-4-Aminomethylbenzoyl-[Lys28, Ile31, Glu32]-PYY(25-36)

(SEQ ID NO: 171)
4-Aminomethylbenzoyl-Arg-Ala-Tyr-Lys-Asn-Leu-Ile-Glu-Arg-Gln-Arg-Tyr-NH$_2$
(cyclo between Lys and Glu)

compound No. 27:
[D-Arg23, Ala26, Ile28,31]-PYY(23-36)
D-Arg-Leu-Arg-Ala-Tyr-Ile-Asn-Leu-Ile-Thr-Arg-Gln-Arg-Tyr-NH$_2$ compound No. 28:
(SEQ ID NO: 42)
4-({[imino(octylamino)methyl]amino}methyl)benzoyl-[Ala26, Ile28,31]-PYY(25-36)
4-({[imino(octylamino)methyl]amino}methyl)benzoyl-Arg-Ala-Tyr-Ile-Asn-Leu-Ile-Thr-Arg-Gln-Arg-Tyr-NH$_2$ compound No. 29:
(SEQ ID NO: 43)
4-Aminomethylbenzoyl-[Ala26, Arg27, Ile28,31]-PYY(25-36)
4-Aminomethylbenzoyl-Arg-Ala-Arg-Ile-Asn-Leu-Ile-Thr-Arg-Gln-Arg-Tyr-NH$_2$ -continued compound No. 30:
(SEQ ID NO: 44)
4-Aminomethylbenzoyl-[Ala26, Gln27, Ile28,31]-
PYY(25-36)
4-Aminomethylbenzoyl-Arg-Ala-Gln-Ile-Asn-Leu-Ile-
Thr-Arg-Gln-Arg-Tyr-NH$_2$ compound No. 31:
(SEQ ID NO: 45)
4-Aminomethylbenzoyl-[Ala26,28, Ile31]-PYY(25-36)
4-Aminomethylbenzoyl-Arg-Ala-Tyr-Ala-Asn-Leu-Ile-
Thr-Arg-Gln-Arg-Tyr-NH$_2$ compound No. 32:
(SEQ ID NO: 46)
4-Aminomethylbenzoyl-[Ala26,30, Ile28,31]-PYY(25-
36)
4-Aminomethylbenzoyl-Arg-Ala-Tyr-Ile-Asn-Ala-Ile-
Thr-Arg-Gln-Arg-Tyr-NH$_2$ compound No. 33:
(SEQ ID NO: 47)
4-Aminomethylbenzoyl-[Ala26,31, Ile28]-PYY(25-36)
4-Aminomethylbenzoyl-Arg-Ala-Tyr-Ile-Asn-Leu-Ala-
Thr-Arg-Gln-Arg-Tyr-NH$_2$ compound No. 34:
(SEQ ID NO: 48)
Ac-[Phe24, Ala26, Ile28,31]-PYY(24-36)
Ac-Phe-Arg-Ala-Tyr-Ile-Asn-Leu-Ile-Thr-Arg-Gln-
Arg-Tyr-NH$_2$ compound No. 35:
Ac-[D-Phe24, Ala26, Ile28,31]-PYY(24-36)
Ac-D-Phe-Arg-Ala-Tyr-Ile-Asn-Leu-Ile-Thr-Arg-Gln-
Arg-Tyr-NH$_2$ compound No. 36:
(SEQ ID NO: 49)
Ac-[Cha24, Ala26, Ile28,31]-PYY(24-36)
Ac-Cha-Arg-Ala-Tyr-Ile-Asn-Leu-Ile-Thr-Arg-Gln-
Arg-Tyr-NH$_2$ compound No. 37:
Ac-[D-Cha24, Ala26, Ile28,31]-PYY(24-36)
Ac-D-Cha-Arg-Ala-Tyr-Ile-Asn-Leu-Ile-Thr-Arg-Gln-
Arg-Tyr-NH$_2$ compound No. 38:
(SEQ ID NO: 50)
Ac-[Pro24, Ala26, Ile28,31]-PYY(24-36)
Ac-Pro-Arg-Ala-Tyr-Ile-Asn-Leu-Ile-Thr-Arg-Gln-
Arg-Tyr-NH$_2$ compound No. 39:
(SEQ ID NO: 51)
4-Aminomethylbenzoyl-[Ala26, Ile28, VAl31]-PYY(25-
36)
4-Aminomethylbenzoyl-Arg-Ala-Tyr-Ile-Asn-Leu-Val-
Thr-Arg-Gln-Arg-Tyr-NH$_2$ compound No. 40:
(SEQ ID NO: 52)
4-Aminomethylbenzoyl-[Ala26, Ile28, Phg31]-PYY(25-
36)
4-Aminomethylbenzoyl-Arg-Ala-Tyr-Ile-Asn-Leu-Phg-
Thr-Arg-Gln-Arg-Tyr-NH$_2$ compound No. 41:
(SEQ ID NO: 53)
4-Aminomethylbenzoyl-[Ala26, Ile28, Cha31]-PYY(25-
36)
4-Aminomethylbenzoyl-Arg-Ala-Tyr-Ile-Asn-Leu-Cha-
Thr-Arg-Gln-Arg-Tyr-NH$_2$ compound No. 42:
(SEQ ID NO: 54)
4-Aminomethylbenzoyl-[Ala26, Ile28, Nle31]-PYY(25-
36)
4-Aminomethylbenzoyl-Arg-Ala-Tyr-Ile-Asn-Leu-Nle-
Thr-Arg-Gln-Arg-Tyr-NH$_2$ compound No. 43:
(SEQ ID NO: 55)
4-Aminomethylbenzoyl-[Ala26, Nle27, Ile28,31]-
PYY(25-36)
4-Aminomethylbenzoyl-Arg-Ala-Nle-Ile-Asn-Leu-Ile-
Thr-Arg-Gln-Arg-Tyr-NH$_2$ compound No. 44:
(SEQ ID NO: 56)
4-Aminomethylbenzoyl-[Ala26, Pya(4)27, Ile28,31]-
PYY(25-36)
4-Aminomethylbenzoyl-Arg-Ala-Pya(4)-Ile-Asn-Leu-
Ile-Thr-Arg-Gln-Arg-Tyr-NH$_2$ compound No. 45:
(SEQ ID NO: 57)
4-Aminomethylbenzoyl-[Ala26, Ile28,31, Gly30]-
PYY(25-36)
4-Aminomethylbenzoyl-Arg-Ala-Tyr-Ile-Asn-Gly-Ile-
Thr-Arg-Gln-Arg-Tyr-NH$_2$ compound No. 46:
(SEQ ID NO: 58)
4-Aminomethylbenzoyl-[Ala26, Ile28,31, Aib29]-
PYY(25-36)
4-Aminomethylbenzoyl-Arg-Ala-Tyr-Ile-Aib-Leu-Ile-
Thr-Arg-Gln-Arg-Tyr-NH$_2$ compound No. 47:
(SEQ ID NO: 59)
4-Aminomethylbenzoyl-[Ala26, Ile28,31, Aib30]-
PYY(25-36)
4-Aminomethylbenzoyl-Arg-Ala-Tyr-Ile-Asn-Aib-Ile-
Thr-Arg-Gln-Arg-Tyr-NH$_2$ compound No. 48:
(SEQ ID NO: 60)
4-Aminomethylbenzoyl-[Ala(cPr)26, Ile28,32]-
PYY(25-36)
4-Aminomethylbenzoyl-Arg-Ala(cPr)-Tyr-Ile-Asn-Leu-
Ile-Thr-Arg-Gln-Arg-Tyr-NH$_2$ compound No. 49:
(SEQ ID NO: 61)
4-Aminomethylbenzoyl-[Lys25, Ala26, Ile28,31]-
PYY(25-36)
4-Aminomethylbenzoyl-Lys-Ala-Tyr-Ile-Asn-Leu-Ile-
Thr-Arg-Gln-Arg-Tyr-NH$_2$ compound No. 50:
(SEQ ID NO: 62)
4-Aminomethylbenzoyl-[Gly26, Ile28,31]-PYY(25-36)
4-Aminomethylbenzoyl-Arg-Gly-Tyr-Ile-Asn-Leu-Ile-
Thr-Arg-Gln-Arg-Tyr-NH$_2$ compound No. 51:
(SEQ ID NO: 63)
4-Aminomethylbenzoyl-[Ala26, Trp27, Ile28,31]-
PYY(25-36)
4-Aminomethylbenzoyl-Arg-Ala-Trp-Ile-Asn-Leu-Ile-
Thr-Arg-Gln-Arg-Tyr-NH$_2$ compound No. 52:
(SEQ ID NO: 64)
4-Aminomethylbenzoyl-[Ala26, Phe(4NH$_2$)27,
Ile28,31]-PYY(25-36)
4-Aminomethylbenzoyl-Arg-Ala-Phe(4NH$_2$)-Ile-Asn-
Leu-Ile-Thr-Arg-Gln-Arg-Tyr-NH$_2$ compound No. 53:
(SEQ ID NO: 65)
4-Aminomethylbenzoyl-[Ala26, Aib27, Ile28,31]-
PYY(25-36)
4-Aminomethylbenzoyl-Arg-Ala-Aib-Ile-Asn-Leu-Ile-
Thr-Arg-Gln-Arg-Tyr-NH$_2$ compound No. 54:
(SEQ ID NO: 66)
4-Aminomethylbenzoyl-[Ala26, Ile28,31, Phe30]-
PYY(25-36)
4-Aminomethylbenzoyl-Arg-Ala-Tyr-Ile-Asn-Phe-Ile-
Thr-Arg-Gln-Arg-Tyr-NH$_2$ compound No. 55:
(SEQ ID NO: 67)
4-Aminomethylbenzoyl-[Ala26, Ile28,31, Nal(1)30]-
PYY(25-36)
4-Aminomethylbenzoyl-Arg-Ala-Tyr-Ile-Asn-Nal(1)-
Ile-Thr-Arg-Gln-Arg-Tyr-NH$_2$ compound No. 56:
(SEQ ID NO: 68)
4-Aminomethylbenzoyl-[Ala26, Ile28,31, Nal(2)30]-
PYY(25-36)
4-Aminomethylbenzoyl-Arg-Ala-Tyr-Ile-Asn-Nal(2)-
Ile-Thr-Arg-Gln-Arg-Tyr-NH$_2$ compound No. 57:
(SEQ ID NO: 69)
4-Aminomethylbenzoyl-[Ala26, Ile28,31, Tyr30]-
PYY(25-36)
4-Aminomethylbenzoyl-Arg-Ala-Tyr-Ile-Asn-Tyr-Ile-
Thr-Arg-Gln-Arg-Tyr-NH$_2$ compound No. 58:
(SEQ ID NO: 70)
4-Aminomethylbenzoyl-[Ala26, Ile28,31, Phe(4F)30]-
PYY(25-36)
4-Aminomethylbenzoyl-Arg-Ala-Tyr-Ile-Asn-Phe(4F)-
Ile-Thr-Arg-Gln-Arg-Tyr-NH$_2$ compound No. 59:
(SEQ ID NO: 71)
4-Aminomethylbenzoyl-[Ala26, Ile28, Phe31]-PYY(25-
36)
4-Aminomethylbenzoyl-Arg-Ala-Tyr-Ile-Asn-Leu-Phe-
Thr-Arg-Gln-Arg-Tyr-NH$_2$ compound No. 60:
(SEQ ID NO: 72)
4-Aminomethylbenzoyl-[Ala26, Ile28,31, Ser32]-
PYY(25-36)
4-Aminomethylbenzoyl-Arg-Ala-Tyr-Ile-Asn-Leu-Ile-
Ser-Arg-Gln-Arg-Tyr-NH$_2$ compound No. 61:
(SEQ ID NO: 73)
4-Aminomethylbenzoyl-[Ala26, Ile28,31, Nva32]-
PYY(25-36)
4-Aminomethylbenzoyl-Arg-Ala-Tyr-Ile-Asn-Leu-Ile-
Nva-Arg-Gln-Arg-Tyr-NH$_2$ compound No. 62:
(SEQ ID NO: 74)
4-Aminomethylbenzoyl-[Ala26, Ile28,31, Leu32]-
PYY(25-36)
4-Aminomethylbenzoyl-Arg-Ala-Tyr-Ile-Asn-Leu-Ile-
Leu-Arg-Gln-Arg-Tyr-NH$_2$ compound No. 63:
(SEQ ID NO: 75)
Benzoyl-[Cha27,36, Nal(1)28, Aib31]-PYY(25-36)
Benzoyl-Arg-His-Cha-Nal(1)-Asn-Leu-Aib-Thr-Arg-
Gln-Arg-Cha-NH$_2$ compound No. 64:
(SEQ ID NO: 76)
Benzoyl-[Cha27,28,36, Aib31]-PYY(25-36)
Benzoyl-Arg-His-Cha-Cha-Asn-Leu-Aib-Thr-Arg-Gln-
Arg-Cha-NH$_2$ compound No. 65:
(SEQ ID NO: 77)
Benzoyl-[Cha27,36, Ile28, Arg31]-PYY(25-36)
Benzoyl-Arg-His-Cha-Ile-Asn-Leu-Arg-Thr-Arg-Gln-
Arg-Cha-NH$_2$ compound No. 66:
(SEQ ID NO: 78)
Benzoyl-[Ala(4Pip)27, Ile28,31, Trp30, Cha36]-
PYY(25-36)
Benzoyl-Arg-His-Ala(4Pip)-Ile-Asn-Trp-Ile-Thr-Arg-
Gln-Arg-Cha-NH$_2$ wherein Ala(4Pip) in peptide of
compound No. 66 is any of D-form and L-form.

compound No. 67:
(SEQ ID NO: 79)
Benzoyl-[Dap27, Ile28,31, Trp30, Cha36]-PYY(25-36)
Benzoyl-Arg-His-Dap-Ile-Asn-Trp-Ile-Thr-Arg-Gln-
Arg-Cha-NH$_2$ compound No. 68:
(SEQ ID NO: 80)
[Abz(2)24, Cha27,36, Ile28,31, Trp30]-PYY(24-36)
Abz(2)-Arg-His-Cha-Ile-Asn-Trp-Ile-Thr-Arg-Gln-
Arg-Cha-NH$_2$ compound No. 69:
(SEQ ID NO: 81)
Benzoyl-[Cha27,36, Ile28, Dap31]-PYY(25-36)
Benzoyl-Arg-His-Cha-Ile-Asn-Leu-Dap-Thr-Arg-Gln-
Arg-Cha-NH$_2$ compound No. 70:
(SEQ ID NO: 82)
Benzoyl-[Cha27,36, Ile28, Arg(Me)31]-PYY(25-36)
Benzoyl-Arg-His-Cha-Ile-Asn-Leu-Arg(Me)-Thr-Arg-
Gln-Arg-Cha-NH$_2$ compound No. 71:
(SEQ ID NO: 83)
Benzoyl-[Cha27,36, Ile28, Pya(4)31]-PYY(25-36)
Benzoyl-Arg-His-Cha-Ile-Asn-Leu-Pya(4)-Thr-Arg-
Gln-Arg-Cha-NH$_2$ compound No. 72:
(SEQ ID NO: 84)
Benzoyl-[Cha27,36, Ile28, Phe(4NH$_2$)31]-PYY(25-36)
Benzoyl-Arg-His-Cha-Ile-Asn-Leu-Phe(4NH$_2$)-Thr-Arg-
Gln-Arg-Cha-NH$_2$ compound No. 73:
(SEQ ID NO: 85)
Benzoyl-[Cha27,36, Ile28,31, Phe(4NH$_2$)30]-PYY(25-
36)
Benzoyl-Arg-His-Cha-Ile-Asn-Phe(4NH$_2$)-Ile-Thr-Arg-
Gln-Arg-Cha-NH$_2$ compound No. 74:
(SEQ ID NO: 86)
4-Aminomethylbenzoyl-[Ala26, Ile28,31, Thr(Me)32]-
PYY(25-36)
Benzoyl-Arg-Ala-Tyr-Ile-Asn-Leu-Ile-Thr(Me)-Arg-
Gln-Arg-Tyr-NH$_2$ compound No. 75:
(SEQ ID NO: 87)
Cyclohexanecarbonyl-[Cha27,36, Ile28,31,
Asn(Me)29]-PYY(25-36)
Cyclohexanecarbonyl-Arg-His-Cha-Ile-Asn(Me)-Leu-
Ile-Thr-Arg-Gln-Arg-Cha-NH$_2$ compound No. 76:
(SEQ ID NO: 88)
4-Guanidinomethylbenzoyl-[Nle25, Cha27,28,31,36,
Arg30]-PYY(25-36)
4-Guanidinomethylbenzoyl-Nle-His-Cha-Cha-Asn-Arg-
Cha-Thr-Arg-Gln-Arg-Cha-NH$_2$ compound No. 77:
(SEQ ID NO: 89)
Cyclohexanecarbonyl-[Nle26, Cha27,28,36, Aib31]-
PYY(25-36)
Cyclohexanecarbonyl-Arg-Nle-Cha-Cha-Asn-Leu-Aib-
Thr-Arg-Gln-Arg-Cha-NH$_2$ -continued compound No. 78:
(SEQ ID NO: 90)
Cyclohexanecarbonyl-[Cha27,36, Ala(cPr)28, Aib31]-PYY(25-36)
Cyclohexanecarbonyl-Arg-His-Cha-Ala(cPr)-Asn-Leu-Aib-Thr-Arg-Gln-Arg-Cha-NH$_2$ compound No. 79:
(SEQ ID NO: 91)
Isobutanoyl-[Abu26, Cha27,36, Phe(4F)28, Aib31]-PYY(25-36)
Isobutanoyl-Arg-Abu-Cha-Phe(4F)-Asn-Leu-Aib-Thr-Arg-Gln-Arg-Cha-NH$_2$ compound No. 80:
(SEQ ID NO: 92)
Isobutanoyl-[Abu26, Cha27,28,36, Ala(cPr)30, Aib31]-PYY(25-36)
Isobutanoyl-Arg-Abu-Cha-Cha-Asn-Ala(cPr)-Aib-Thr-Arg-Gln-Arg-Cha-NH$_2$ compound No. 81:
(SEQ ID NO: 93)
Isobutanoyl-[Abu26, Cha27,28,36, Leu(Me)30, Aib31]-PYY(25-36)
Isobutanoyl-Arg-Abu-Cha-Cha-Asn-Leu(Me)-Aib-Thr-Arg-Gln-Arg-Cha-NH$_2$ compound No. 82:
(SEQ ID NO: 94)
Isobutanoyl-[Abu26, Cha27,28,36, Pya(3)31]-PYY(25-36)
Isobutanoyl-Arg-Abu-Cha-Cha-Asn-Leu-Pya(3)-Thr-Arg-Gln-Arg-Cha-NH$_2$ compound No. 83:
(SEQ ID NO: 95)
Isobutanoyl-[Abu26, Cha27,36, Pya(4)28, Aib31]-PYY(25-36)
Isobutanoyl-Arg-Abu-Cha-Pya(4)-Asn-Leu-Aib-Thr-Arg-Gln-Arg-Cha-NH$_2$ compound No. 84:
Ac-[D-Cha24, Abu26, Cha27,28,36, Aib31]-PYY(24-36)
Ac-D-Cha-Arg-Abu-Cha-Cha-Asn-Leu-Aib-Thr-Arg-Gln-Arg-Cha-NH$_2$ compound No. 85:
[D-Ser23, Abu26, Cha27,28,36, Aib31]-PYY(23-36)
D-Ser-Leu-Arg-Abu-Cha-Cha-Asn-Leu-Aib-Thr-Arg-Gln-Arg-Cha-NH$_2$ compound No. 86:
(SEQ ID NO: 96)
Isobutanoyl-[Abu26, Cha27,28, Aib31, Tyr(2F)36]-PYY(25-36)
Isobutanoyl-Arg-Abu-Cha-Cha-Asn-Leu-Aib-Thr-Arg-Gln-Arg-Tyr(2F)-NH$_2$ compound No. 87:
(SEQ ID NO: 97)
Isobutanoyl-[Abu26, Cha27,28, Aib31, Tyr(3F)36]-PYY(25-36)
Isobutanoyl-Arg-Abu-Cha-Cha-Asn-Leu-Aib-Thr-Arg-Gln-Arg-Tyr(3F)-NH$_2$ compound No. 88:
(SEQ ID NO: 98)
Isobutanoyl-[Abu26, Cha27,28,36, Gly(cPr)31]-PYY(25-36)
Isobutanoyl-Arg-Abu-Cha-Cha-Asn-Leu-Gly(cPr)-Thr-Arg-Gln-Arg-Cha-NH$_2$ compound No. 89:
(SEQ ID NO: 99)
Isobutanoyl-[Abu26, Cha27,28,36, Ser30, Aib31]-PYY(25-36)
Isobutanoyl-Arg-Abu-Cha-Cha-Asn-Ser-Aib-Thr-Arg-Gln-Arg-Cha-NH$_2$ compound No. 90:
(SEQ ID NO: 100)
Isobutanoyl-[Abu26, Cha27,28,36, Gln30, Aib31]-PYY(25-36)
Isobutanoyl-Arg-Abu-Cha-Cha-Asn-Gln-Aib-Thr-Arg-Gln-Arg-Cha-NH$_2$ compound No. 91:
(SEQ ID NO: 101)
Isobutanoyl-[Abu26, Cha27,28,36, Abu30, Aib31]-PYY(25-36)
Isobutanoyl-Arg-Abu-Cha-Cha-Asn-Abu-Aib-Thr-Arg-Gln-Arg-Cha-NH$_2$ compound No. 92:
(SEQ ID NO: 102)
Isobutanoyl-[Abu26, Cha27,28,36, His30, Aib31]-PYY(25-36)
Isobutanoyl-Arg-Abu-Cha-Cha-Asn-His-Aib-Thr-Arg-Gln-Arg-Cha-NH$_2$ compound No. 93:
(SEQ ID NO: 103)
Isobutanoyl-[Abu26, Cha27,36, Gly(cPr)28, Aib31]-PYY(25-36)
Isobutanoyl-Arg-Abu-Cha-Gly(cPr)-Asn-Leu-Aib-Thr-Arg-Gln-Arg-Cha-NH$_2$ compound No. 94:
(SEQ ID NO: 104)
Isobutanoyl-[Abu26,27, Cha28,36, Aib31]-PYY(25-36)
Isobutanoyl-Arg-Abu-Abu-Cha-Asn-Leu-Aib-Thr-Arg-Gln-Arg-Cha-NH$_2$ compound No. 95:
(SEQ ID NO: 105)
Isobutanoyl-[Abu26, Gly27, Cha28,36, Aib31]-PYY(25-36)
Isobutanoyl-Arg-Abu-Gly-Cha-Asn-Leu-Aib-Thr-Arg-Gln-Arg-Cha-NH$_2$ compound No. 96:
(SEQ ID NO: 106)
Amidino-[Gly23, Pic(4)24, Cha27,36, Ile 28,31, Trp30]-PYY(23-36)
Amidino-Gly-Pic(4)-Arg-His-Cha-Ile-Asn-Trp-Ile-Thr-Arg-Gln-Arg-Cha-NH$_2$ compound No. 97:
(SEQ ID NO: 107)
Benzoyl-[Ser26, Cha27,28,36, Aib31]-PYY(25-36)
Benzoyl-Arg-Ser-Cha-Cha-Asn-Leu-Aib-Thr-Arg-Gln-Arg-Cha-NH$_2$ compound No. 98:
(SEQ ID NO: 108)
Benzoyl-[Ser(Me)26, Cha27,28,36, Aib31]-PYY(25-36)
Benzoyl-Arg-Ser(Me)-Cha-Cha-Asn-Leu-Aib-Thr-Arg-Gln-Arg-Cha-NH$_2$ compound No. 99:
(SEQ ID NO: 109)
Benzoyl-[Asn26, Cha27,28,36, Aib31]-PYY(25-36)
Benzoyl-Arg-Asn-Cha-Cha-Asn-Leu-Aib-Thr-Arg-Gln-Arg-Cha-NH$_2$ compound No. 100:
(SEQ ID NO: 110)
Isobutanoyl-[Abu26, Cha27,36, Gln28, Aib31]-PYY(25-36)
Isobutanoyl-Arg-Abu-Cha-Gln-Asn-Leu-Aib-Thr-Arg-Gln-Arg-Cha-NH$_2$ compound No. 101:
(SEQ ID NO: 111)
Isobutanoyl-[Abu26, Cha27,36, His28, Aib31]-PYY(25-36)
Isobutanoyl-Arg-Abu-Cha-His-Asn-Leu-Aib-Thr-Arg-Gln-Arg-Cha-NH$_2$ -continued compound No. 102:
(SEQ ID NO: 112)
Isobutanoyl-[Abu26, Cha27,36, Ser28, Aib31]-
PYY(25-36)
Isobutanoyl-Arg-Abu-Cha-Ser-Asn-Leu-Aib-Thr-Arg-
Gln-Arg-Cha-NH$_2$ compound No. 103:
(SEQ ID NO: 113)
Benzoyl-[Nva27, Cha28,36, Aib31]-PYY(25-36)
Benzoyl-Arg-His-Nva-Cha-Asn-Leu-Aib-Thr-Arg-Gln-
Arg-Cha-NH$_2$ compound No. 104:
(SEQ ID NO: 114)
Benzoyl-[His27, Cha28,36, Aib31]-PYY(25-36)
Benzoyl-Arg-His-His-Cha-Asn-Leu-Aib-Thr-Arg-Gln-
Arg-Cha-NH$_2$ compound No. 105:
Ac-[Abu23, D-Pro24, Abu26, Cha27,28,36, Aib31]-
PYY(23-36)
Ac-Abu-D-Pro-Arg-Abu-Cha-Cha-Asn-Leu-Aib-Thr-Arg-
Gln-Arg-Cha-NH$_2$ compound No. 106:
Ac-[Ser(Me)23, D-Pro24, Abu26, Cha27,28,36,
Aib31]-PYY(23-36)
Ac-Ser(Me)-D-Pro-Arg-Abu-Cha-Cha-Asn-Leu-Aib-Thr-
Arg-Gln-Arg-Cha-NH$_2$ compound No. 107:
Ac-[Phe23, D-Pro24, Abu26, Cha27,28,36, Aib31]-
PYY(23-36)
Ac-Phe-D-Pro-Arg-Abu-Cha-Cha-Asn-Leu-Aib-Thr-Arg-
Gln-Arg-Cha-NH$_2$ compound No. 108:
(SEQ ID NO: 115)
Ac-[N(iBu)Gly24, Cha27,28,36, Aib31]-PYY(23-36)
Ac-Ser-N(iBu)Gly-Arg-His-Cha-Cha-Asn-Leu-Aib-Thr-
Arg-Gln-Arg-Cha-NH$_2$ compound No. 109:
Ac-[D-Ser23, MeAla24, Cha27,28,36, Aib31]-PYY(23-
36)
Ac-D-Ser-NMeAla-Arg-His-Cha-Cha-Asn-Leu-Aib-Thr-
Arg-Gln-Arg-Cha-NH$_2$ compound No. 110:
Ac-[D-MeAla24, Cha27,28,36, Aib31]-PYY(23-36)
Ac-Ser-D-NMeAla-Arg-His-Cha-Cha-Asn-Leu-Aib-Thr-
Arg-Gln-Arg-Cha-NH$_2$ compound No. 111:
Ac-[D-Ser23, Sar24, Cha27,28,36, Aib31]-PYY(23-36)
Ac-D-Ser-Sar-Arg-His-Cha-Cha-Asn-Leu-Aib-Thr-Arg-
Gln-Arg-Cha-NH$_2$ compound No. 112:
(SEQ ID NO: 116)
Ac-[Gly24, Cha27,28,36, Aib31]-PYY(23-36)
Ac-Ser-Gly-Arg-His-Cha-Cha-Asn-Leu-Aib-Thr-Arg-
Gln-Arg-Cha-NH$_2$ compound No. 113:
(SEQ ID NO: 117)
Ac-[Aze(3)24, Cha27,28,36, Aib31]-PYY(23-36)
Ac-Ser-Aze(3)-Arg-His-Cha-Cha-Asn-Leu-Aib-Thr-Arg-
Gln-Arg-Cha-NH$_2$ compound No. 114:
Ac-[D-Hyp24, Cha27,28,36, Aib31]-PYY(23-36)
Ac-Ser-D-Hyp-Arg-His-Cha-Cha-Asn-Leu-Aib-Thr-Arg-
Gln-Arg-Cha-NH$_2$ compound No. 115:
Ac-[Asn23, D-Pro24, Cha27,28,36, Aib31]-PYY(23-36)
Ac-Asn-D-Pro-Arg-His-Cha-Cha-Asn-Leu-Aib-Thr-Arg-
Gln-Arg-Cha-NH$_2$ compound No. 116:
[βAla23, D-Pro24, Cha27,28,36, Aib31]-PYY(23-36)
β-Ala-D-Pro-Arg-His-Cha-Cha-Asn-Leu-Aib-Thr-Arg-
Gln-Arg-Cha-NH$_2$ compound No. 117:
[Aoc(8)23, D-Pro24, Cha27,28,36, Aib31]-PYY(23-36)
Aoc(8)-D-Pro-Arg-His-Cha-Cha-Asn-Leu-Aib-Thr-Arg-
Gln-Arg-Cha-NH$_2$ compound No. 118:
[(PEG2)23, D-Pro24, Cha27,28,36, Aib31]-PYY(23-36)
(PEG2)-D-Pro-Arg-His-Cha-Cha-Asn-Leu-Aib-Thr-Arg-
Gln-Arg-Cha-NH$_2$ compound No. 119:
Ac-[D-Pic(2)24, Cha27,28,36, Aib31]-PYY(23-36)
Ac-Ser-D-Pic(2)-Arg-His-Cha-Cha-Asn-Leu-Aib-Thr-
Arg-Gln-Arg-Cha-NH$_2$ compound No. 120:
Ac-[Glu23, D-Pic(2)24, Cha27,28,36, Aib31]-PYY(23-
36)
Ac-Glu-D-Pic(2)-Arg-His-Cha-Cha-Asn-Leu-Aib-Thr-
Arg-Gln-Arg-Cha-NH$_2$ compound No. 121:
Ac-[D-Tyr21, D-Pro24, Cha27,28,36, Aib31]-PYY(21-
36)
Ac-D-Tyr-Ala-Ser-D-Pro-Arg-His-Cha-Cha-Asn-Leu-
Aib-Thr-Arg-Gln-Arg-Cha-NH$_2$ compound No. 122:
(SEQ ID NO: 118)
Ac-[Gly23-ψ[(E)—CH=CH]-Leu24, Cha27,28,36, Aib31]-
PYY(23-36)
Ac-Gly-ψ[(E)CH=CH]-Leu-Arg-His-Cha-Cha-Asn-Leu-
Aib-Thr-Arg-Gln-Arg-Cha-NH$_2$ compound No. 123:
[MeAla22, D-Pro24, Cha27,28,36, Aib31]-PYY(22-36)
MeAla-Ser-D-Pro-Arg-His-Cha-Cha-Asn-Leu-Aib-Thr-
Arg-Gln-Arg-Cha-NH$_2$ compound No. 124:
Ac-[D-MeAla22, D-Pro24, Cha27,28,36, Aib31]-
PYY(22-36)
Ac-D-MeAla-Ser-D-Pro-Arg-His-Cha-Cha-Asn-Leu-Aib-
Thr-Arg-Gln-Arg-Cha-NH$_2$ compound No. 125:
N-4-Pyridiniyl-[Pic(4)23, D-Pro24, Cha27,28,36,
Aib31]-PYY(23-36)
4-Pyridinyl-Pic(4)-D-Pro-Arg-His-Cha-Cha-Asn-Leu-
Aib-Thr-Arg-Gln-Arg-Cha-NH$_2$ compound No. 126:
Ac-[Hyp23, D-Pro24, Cha27,28,36, Aib31]-PYY(23-36)
Ac-Hyp-D-Pro-Arg-His-Cha-Cha-Asn-Leu-Aib-Thr-Arg-
Gln-Arg-Cha-NH$_2$ compound No. 127:
Isobutanoyl-[Asp23, D-Hyp24, Cha27,28,36, Aib31]-
PYY(23-36)
Isobutanoyl-Asp-D-Hyp-Arg-His-Cha-Cha-Asn-Leu-Aib-
Thr-Arg-Gln-Arg-Cha-NH$_2$ compound No. 128:
Ac-[D-Pro24, Hse26, Cha27,36, Aib28,31]-PYY(23-36)
Ac-Ser-D-Pro-Arg-Hse-Cha-Aib-Asn-Leu-Aib-Thr-Arg-
Gln-Arg-Cha-NH$_2$ compound No. 129:
Ac-[MeSer23, D-Pro24, Cha27,28,36, Aib31]-PYY(22-
36)
Ac-Ala-MeSer-D-Pro-Arg-His-Cha-Cha-Asn-Leu-Aib-
Thr-Arg-Gln-Arg-Cha-NH$_2$ -continued compound No. 130:
Carbamoyl-[D-Pro24, Cha27,28,36, Aib31]-PYY(23-36)
Carbamoyl-Ser-D-Pro-Arg-His-Cha-Cha-Asn-Leu-Aib-
Thr-Arg-Gln-Arg-Cha-NH$_2$ compound No. 131:
Ac-[D-Pro24, Cha27,28,36, Acpc31]-PYY(23-36)
Ac-Ser-D-Pro-Arg-His-Cha-Cha-Asn-Leu-Acpc-Thr-Arg-
Gln-Arg-Cha-NH$_2$ compound No. 132:
Ac-[D-Pro24, Cha27,28,36, Thr30, Aib31]-PYY(23-36)
Ac-Ser-D-Pro-Arg-His-Cha-Cha-Asn-Thr-Aib-Thr-Arg-
Gln-Arg-Cha-
NH$_2$ compound No. 133:
[N(iBu)Gly23, D-Pro24, Cha27,28,36, Aib31]-PYY(23-36)
N(iBu)Gly-D-Pro-Arg-His-Cha-Cha-Asn-Leu-Aib-Thr-
Arg-Gln-Arg-Cha-NH$_2$ compound No. 134:
[N(2-hydroxyethyl)Gly23, D-Pro24,
Cha27,28,36, Aib31]-PYY(23-36)
N(2-hydroxyethyl)Gly-D-Pro-Arg-His-Cha-Cha-Asn-
Leu-Aib-Thr-Arg-Gln-Arg-Cha-NH$_2$ compound No. 135:
Ac-[D-Pro24, Cha27,36, Aib28, Lys30, Aib31]-
PYY(23-36)
Ac-Ser-D-Pro-Arg-His-Cha-Aib-Asn-Lys-Aib-Thr-Arg-
Gln-Arg-Cha-NH$_2$ compound No. 136:
Ac-[D-Pro24, Cha27,36, Leu(Me)28, Lys30, Aib31]-
PYY(23-36)
Ac-Ser-D-Pro-Arg-His-Cha-Leu(Me)-Asn-Lys-Aib-Thr-
Arg-Gln-Arg-Cha-NH$_2$ compound No. 137:
Ac-[Glu23, D-Pro24, Cha27,28,36, Lys30,
Aib31]-PYY(23-36)
Ac-Glu-D-Pro-Arg-His-Cha-Cha-Asn-Lys-Aib-Thr-Arg-
Gln-Arg-Cha-NH$_2$ compound No. 138:
Ac-[D-Pro24, Pya(4)26, Cha27,36, Aib28,31, Lys30]-
PYY(23-36)
Ac-Ser-D-Pro-Arg-Pya(4)-Cha-Aib-Asn-Lys-Aib-Thr-
Arg-Gln-Arg-Cha-NH$_2$ compound No. 139:
Ac-[Glu23, D-Pro24, Pya(4)26, Cha27,36,
Tyr28, Lys30, Aib31]-PYY(23-36)
Ac-Glu-D-Pro-Arg-Pya(4)-Cha-Tyr-Asn-Lys-Aib-Thr-
Arg-Gln-Arg-Cha-NH$_2$ compound No. 140:
Ac-[D-Pro24, Nle25, Pya(4)26, Cha27,28,36, Aib31]-
PYY(23-36)
Ac-Ser-D-Pro-Nle-Pya(4)-Cha-Cha-Asn-Leu-Aib-Thr-
Arg-Gln-Arg-Cha-NH$_2$ compound No. 141:
Ac-[Glu23, D-Pro24, Pya(4)26, Cha27,28,36, Aib31]-
PYY(23-36)
Ac-Glu-D-Pro-Arg-Pya(4)-Cha-Cha-Asn-Leu-Aib-Thr-
Arg-Gln-Arg-Cha-NH$_2$ compound No. 142:
Ac-[D-Pro24, Cha27,28, Aib31]-PYY(23-36)
Ac-Ser-D-Pro-Arg-His-Cha-Cha-Asn-Leu-Aib-Thr-Arg-
Gln-Arg-Tyr-NH$_2$ compound No. 143:
Ac-[D-Pro24, Cha27,28, Aib31, Phe36]-PYY(23-36)
Ac-Ser-D-Pro-Arg-His-Cha-Cha-Asn-Leu-Aib-Thr-Arg-
Gln-Arg-Phe-NH$_2$ compound No. 144:
Ac-[D-Pro24, Cha27,36, Hse28, Aib31]-PYY(23-36)
Ac-Ser-D-Pro-Arg-His-Cha-Hse-Asn-Leu-Aib-Thr-Arg-
Gln-Arg-Cha-NH$_2$ compound No. 145:
Ac-[D-Pro24, Cha27,36, Acpc28, Aib31]-PYY(23-36)
Ac-Ser-D-Pro-Arg-His-Cha-Acpc-Asn-Leu-Aib-Thr-Arg-
Gln-Arg-Cha-NH$_2$ compound No. 146:
Ac-[D-Pro24, Cit27, Cha28,36, Aib31]-PYY(23-36)
Ac-Ser-D-Pro-Arg-His-Cit-Cha-Asn-Leu-Aib-Thr-Arg-
Gln-Arg-Cha-NH$_2$ compound No. 147:
Ac-[D-Pro24, Thr26, Cha27,28,36, Aib31]-PYY(23-36)
Ac-Ser-D-Pro-Arg-Thr-Cha-Cha-Asn-Leu-Aib-Thr-Arg-
Gln-Arg-Cha-NH$_2$ compound No. 148:
Ac-[D-Pro24, Pya(3)26, Cha27,28,36, Aib31]-PYY(23-36)
Ac-Ser-D-Pro-Arg-Pya(3)-Cha-Cha-Asn-Leu-Aib-Thr-
Arg-Gln-Arg-Cha-NH$_2$ compound No. 149:
Ac-[D-Pro24, Alb26, Cha27,28,36, Aib31]-PYY(23-36)
Ac-Ser-D-Pro-Arg-Alb-Cha-Cha-Asn-Leu-Aib-Thr-Arg-
Gln-Arg-Cha-NH$_2$ compound No. 150:
Ac-[D-Pro24, Orn26, Cha27,28,36, Aib31]-PYY(23-36)
Ac-Ser-D-Pro-Arg-Orn-Cha-Cha-Asn-Leu-Aib-Thr-Arg-
Gln-Arg-Cha-NH$_2$ compound No. 151:
Ac-[D-Pro24, Glu26, Cha27,28,36, Aib31]-PYY(23-36)
Ac-Ser-D-Pro-Arg-Glu-Cha-Cha-Asn-Leu-Aib-Thr-Arg-
Gln-Arg-Cha-NH$_2$ compound No. 152:
Ac-[D-Pro24, Cit26, Cha27,28,36, Aib31]-PYY(23-36)
Ac-Ser-D-Pro-Arg-Cit-Cha-Cha-Asn-Leu-Aib-Thr-Arg-
Gln-Arg-Cha-NH$_2$ compound No. 153:
Ac-[D-Aze(2)24, Cha27,28,36, Aib31]-PYY(23-36)
Ac-Ser-D-Aze(2)-Arg-His-Cha-Cha-Asn-Leu-Aib-Thr-
Arg-Gln-Arg-Cha-NH$_2$ compound No. 154: (SEQ ID NO: 119)
Ac-[αMePro24, Cha27,28,36, Aib31]-PYY(23-36)
Ac-Ser-αMePro-Arg-His-Cha-Cha-Asn-Leu-Aib-Thr-Arg-
Gln-Arg-Cha-NH2 compound No. 155:
Ac-[D-αMePro24, Cha27,28,36, Aib31]-PYY(23-36)
Ac-Ser-D-αMePro-Arg-His-Cha-Cha-Asn-Leu-Aib-Thr-
Arg-Gln-Arg-Cha-NH$_2$ compound No. 156: (SEQ ID NO: 120)
Ac-[GABA24, Cha27,28,36, Aib31]-PYY(23-36)
Ac-Ser-GABA-Arg-His-Cha-Cha-Asn-Leu-Aib-Thr-Arg-
Gln-Arg-Cha-NH$_2$ compound No. 157:
Ac-[Hse23, D-Pro24, Cha27,28,36, Aib31]-PYY(23-36)
Ac-Hse-D-Pro-Arg-His-Cha-Cha-Asn-Leu-Aib-Thr-Arg-
Gln-Arg-Cha-NH$_2$ compound No. 158:
Ac-[D-Thr23, D-Pro24, Cha27,36, Aib31]-PYY(23-36)
Ac-D-Thr-D-Pro-Arg-His-Cha-Cha-Asn-Leu-Aib-Thr-
Arg-Gln-Arg-Cha-NH$_2$ -continued compound No. 159:
Ac-[Aad23, D-Pro24, Cha27,28,36, Aib31]-PYY(23-36)
Ac-Aad-D-Pro-Arg-His-Cha-Cha-Asn-Leu-Aib-Thr-Arg-Gln-Arg-Cha-NH$_2$ compound No. 160:
Ac-[Lys(Me$_2$)23, D-Pro24, Cha27,28,36, Aib31]-PYY(23-36)
Ac-Lys(Me$_2$)-D-Pro-Arg-His-Cha-Cha-Asn-Leu-Aib-Thr-Arg-Gln-Arg-Cha-NH$_2$ compound No. 161:
Carbamoyl-[Asp23, D-Pro24, Cha27,28,36, Aib31]-PYY(23-36)
Carbamoyl-Asp-D-Pro-Arg-His-Cha-Cha-Asn-Leu-Aib-Thr-Arg-Gln-Arg-Cha-NH$_2$ compound No. 162:
Ac-[Tyr23, D-Pro24, Cha27,28,36, Aib31]-PYY(23-36)
Ac-Tyr-D-Pro-Arg-His-Cha-Cha-Asn-Leu-Aib-Thr-Arg-Gln-Arg-Cha-NH$_2$ compound No. 163:
[Lys(Ac)23, D-Pro24, Cha27,28,36, Aib31]-PYY(23-36)
Lys(Ac)-D-Pro-Arg-His-Cha-Cha-Asn-Leu-Aib-Thr-Arg-Gln-Arg-Cha-NH$_2$ compound No. 164:
Ac-[Arg20, D-Tyr21, D-Pro24, Cha27,28,36, Aib31]-PYY(20-36)
Ac-Arg-D-Tyr-Ala-Ser-D-Pro-Arg-His-Cha-Cha-Asn-Leu-Aib-Thr-Arg-Gln-Arg-Cha-NH$_2$ compound No. 165:
Ac-[D-Pro24, Cha27,28,36, Dab30, Aib31]-PYY(23-36)
Ac-Ser-D-Pro-Arg-His-Cha-Cha-Asn-Dab-Aib-Thr-Arg-Gln-Arg-Cha-NH$_2$ compound No. 166:
Ac-[D-Pro24, Cha27,28,36, Lys(Me$_2$)30, Aib31]-PYY(23-36)
Ac-Ser-D-Pro-Arg-His-Cha-Cha-Asn-Lys(Me$_2$)-Aib-Thr-Arg-Gln-Arg-Cha-NH$_2$ compound No. 167:
3-Carboxypropionyl-[D-Pro24, Cha27,28,36, Lys30, Aib31]-PYY(23-36)
3-Carboxypropionyl-Ser-D-Pro-Arg-His-Cha-Cha-Asn-Lys-Aib-Thr-Arg-Gln-Arg-Cha-NH$_2$ compound No. 168:
Ac-[Glu23, D-Pro24, Cha27,36, Leu(Me)28, Lys30, Aib31]-PYY(23-36)
Ac-Glu-D-Pro-Arg-His-Cha-Leu(Me)-Asn-Lys-Aib-Thr-Arg-Gln-Arg-Cha-NH$_2$ compound No. 169:
Ac-[Glu23, D-Pro24, Pya(4)26, Cha27,36, Leu(Me)28, Lys30, Aib31]-PYY(23-36)
Ac-Glu-D-Pro-Arg-Pya(4)-Cha-Leu(Me)-Asn-Lys-Aib-Thr-Arg-Gln-Arg-Cha-NH$_2$ compound No. 170:
Isobutanoyl-[Glu23, D-Pro24, Pya(4)26, Cha27,36, Leu(Me)28, Lys30, Aib31]-PYY(23-36)
Isobutanoyl-Glu-D-Pro-Arg-Pya(4)-Cha-Leu(Me)-Asn-Lys-Aib-Thr-Arg-Gln-Arg-Cha-NH$_2$ compound No. 171:
Ac-[Glu23, D-Pro24, Cha27,36, Aib28,31, Lys30]-PYY(23-36)
Ac-Glu-D-Pro-Arg-His-Cha-Aib-Asn-Lys-Aib-Thr-Arg-Gln-Arg-Cha-NH$_2$ compound No. 172:
Ac-[Glu23, D-Pro24, Nle25, Pya(4)26, Cha27,28,36, Lys30, Aib31]-PYY(23-36)
Ac-Glu-D-Pro-Nle-Pya(4)-Cha-Cha-Asn-Lys-Aib-Thr-Arg-Gln-Arg-Cha-NH$_2$ compound No. 173:
Morpholinocarbonyl-[Asp23, D-Pro24, Cha27,28,36, Aib31]-PYY(23-36)
Morpholinocarbonyl-Asp-D-Pro-Arg-His-Cha-Cha-Asn-Leu-Aib-Thr-Arg-Gln-Arg-Cha-NH$_2$ compound No. 174:
Morpholinocarbonyl-[Glu23, D-Pro24, Cha27,28,36, Aib31]-PYY(23-36)
Morpholinocarbonyl-Glu-D-Pro-Arg-His-Cha-Cha-Asn-Leu-Aib-Thr-Arg-Gln-Arg-Cha-NH$_2$ compound No. 175:
Ac-[D-Pro24, Iva27, Cha28,36, Aib31]-PYY(23-36)
Ac-Ser-D-Pro-Arg-His-Iva-Cha-Asn-Leu-Aib-Thr-Arg-Gln-Arg-Cha-NH$_2$ compound No. 176:
Ac-[D-Pro24, Iva26, Cha27,28,36, Aib31]-PYY(23-36)
Ac-Ser-D-Pro-Arg-Iva-Cha-Cha-Asn-Leu-Aib-Thr-Arg-Gln-Arg-Cha-NH$_2$ compound No. 177:
Ac-[D-Pro24, Iva25, Cha27,28,36, Aib31]-PYY(23-36)
Ac-Ser-D-Pro-Iva-His-Cha-Cha-Asn-Leu-Aib-Thr-Arg-Gln-Arg-Cha-NH$_2$ compound No. 178:
Ac-[Iva23, D-Pro24, Cha27,28,36, Aib31]-PYY(23-36)
Ac-Iva-D-Pro-Arg-His-Cha-Cha-Asn-Leu-Aib-Thr-Arg-Gln-Arg-Cha-NH$_2$ compound No. 179:
Ac-[D-Pro24, Cha27,28,36, D-Iva29, Aib31]-PYY(23-36)
Ac-Ser-D-Pro-Arg-His-Cha-Cha-D-Iva-Leu-Aib-Thr-Arg-Gln-Arg-Cha-NH$_2$ compound No. 180:
Ac-[D-Pro24, D-Iva27, Cha28,36, Aib31]-PYY(23-36)
Ac-Ser-D-Pro-Arg-His-D-Iva-Cha-Asn-Leu-Aib-Thr-Arg-Gln-Arg-Cha-NH$_2$ compound No. 181:
Ac-[D-Pro24, D-Iva26, Cha27,28,36, Aib31]-PYY(23-36)
Ac-Ser-D-Pro-Arg-D-Iva-Cha-Cha-Asn-Leu-Aib-Thr-Arg-Gln-Arg-Cha-NH$_2$ compound No. 182:
Ac-[D-Pro24, D-Iva25, Cha27,28,36, Aib31]-PYY(23-36)
Ac-Ser-D-Pro-D-Iva-His-Cha-Cha-Asn-Leu-Aib-Thr-Arg-Gln-Arg-Cha-NH$_2$ compound No. 183:
Ac-[D-Iva23, D-Pro24, Cha27,28,36, Aib31]-PYY(23-36)
Ac-D-Iva-D-Pro-Arg-His-Cha-Cha-Asn-Leu-Aib-Thr-Arg-Gln-Arg-Cha-NH$_2$ compound No. 184:
[(1S)-1-carboxy-3-methylbutyl]carbamoyl-[D-Pro24, Cha27,28,36, Aib31]-PYY(23-36)
[(1S)-1-Carboxy-3-methylbutyl]carbamoyl-Ser-D-Pro-Arg-His-Cha-Cha-Asn-Leu-Aib-Thr-Arg-Gln-Arg-Cha-NH$_2$ compound No. 185:
3-Carboxypropionyl-[Acp22, D-Pro24, Cha27,36, Leu(Me)28, Lys30, Aib31]-PYY(22-36)
3-Carboxypropionyl-Acp-Ser-D-Pro-Arg-His-Cha-Leu(Me)-Asn-Lys-Aib-Thr-Arg-Gln-Arg-Cha-NH$_2$ compound No. 186:
Amidino-[D-Pro24, Cha27,36, Leu(Me)28, Lys30, Aib31]-PYY(23-36)
Amidino-Ser-D-Pro-Arg-His-Cha-Leu(Me)-Asn-Lys-Aib-Thr-Arg-Gln-Arg-Cha-NH$_2$ -continued compound No. 187:
Morpholinocarbonyl-[D-Pro24, Cha27,36,
Leu(Me)28, Lys30, Aib31]-PYY(23-36)
Morpholinocarbonyl-Ser-D-Pro-Arg-His-Cha-Leu(Me)-
Asn-Lys-Aib-Thr-Arg-Gln-Arg-Cha-NH$_2$ compound No. 188:
2-Hydroxyethylcarbamoyl-[D-Pro24, Cha27,36,
Leu(Me)28, Lys30, Aib31]-PYY(23-36)
2-Hydroxyethylcarbamoyl-Ser-D-Pro-Arg-His-Cha-
Leu(Me)-Asn-Lys-Aib-Thr-Arg-Gln-Arg-Cha-NH$_2$ compound No. 189:
Ac-[Acp22, Glu23, D-Pro24, Cha27,28,36, Lys30,
Aib31]-PYY(22-36)
Ac-Acp-Glu-D-Pro-Arg-His-Cha-Cha-Asn-Lys-Aib-Thr-
Arg-Gln-Arg-Cha-NH$_2$ compound No. 190:
Amidino-[Glu23, D-Pro24, Cha27,28,36, Lys30,
Aib31]-PYY(23-36)
Amidino-Glu-D-Pro-Arg-His-Cha-Cha-Asn-Lys-Aib-Thr-
Arg-Gln-Arg-Cha-NH$_2$ compound No. 191:
Morpholinocarbonyl-[Glu23, D-Pro24,
Cha27,28,36, Lys30, Aib31]-PYY(23-36)
Morpholinocarbonyl-Glu-D-Pro-Arg-His-Cha-Cha-Asn-
Lys-Aib-Thr-Arg-Gln-Arg-Cha-NH$_2$ compound No. 192:
2-Hydroxyethylcarbamoyl-[Glu23, D-Pro24,
Cha27,28,36, Lys30, Aib31]-PYY(23-36)
2-Hydroxyethylcarbamoyl-Glu-D-Pro-Arg-His-Cha-Cha-
Asn-Lys-Aib-Thr-Arg-Gln-Arg-Cha-NH$_2$ compound No. 193:
Piperidinocarbonyl-[Glu23, D-Pro24, Pya(4)26,
Cha27,36, Aib28,31, Lys30]-PYY(23-36)
Piperidinocarbonyl-Glu-D-Pro-Arg-Pya(4)-Cha-Aib-
Asn-Lys-Aib-Thr-Arg-Gln-Arg-Cha-NH$_2$ compound No. 194:
Ac-[D-Pro24, Cha27,28, Aib31, Phe(2F)36]-PYY(23-
36)
Ac-Ser-D-Pro-Arg-His-Cha-Cha-Asn-Leu-Aib-Thr-Arg-
Gln-Arg-Phe(2F)-NH$_2$ compound No. 195:
Ac-[D-Pro24, Cha27,28, Aib31, Phe(3F)36]-PYY(23-
36)
Ac-Ser-D-Pro-Arg-His-Cha-Cha-Asn-Leu-Aib-Thr-Arg-
Gln-Arg-Phe(3F)-NH$_2$ compound No. 196:
Ac-[D-Pro24, Cha27,28, Aib31, Phe(2Me)36]-PYY(23-
36)
Ac-Ser-D-Pro-Arg-His-Cha-Cha-Asn-Leu-Aib-Thr-Arg-
Gln-Arg-Phe(2Me)-NH$_2$ compound No. 197:
Ac-[D-Pro24, Cha27,28, Aib31, Phe(3Me)36]-PYY(23-
36)
Ac-Ser-D-Pro-Arg-His-Cha-Cha-Asn-Leu-Aib-Thr-Arg-
Gln-Arg-Phe(3Me)-NH$_2$ compound No. 198:
Ac-[D-Pro24, Cha27,28, Aib31, Leu(Me)36]-PYY(23-
36)
Ac-Ser-D-Pro-Arg-His-Cha-Cha-Asn-Leu-Aib-Thr-Arg-
Gln-Arg-Leu(Me)-NH$_2$ compound No. 199:
Ac-[D-Pro24, Cha27,28, Aib31, homoLeu36]-PYY(23-
36)
Ac-Ser-D-Pro-Arg-His-Cha-Cha-Asn-Leu-Aib-Thr-Arg-
Gln-Arg-homoLeu-NH$_2$ compound No. 200:
Ac-[D-Pro24, Cha27,28, Aib31, threo-PhSer36]-
PYY(23-36)
Ac-Ser-D-Pro-Arg-His-Cha-Cha-Asn-Leu-Aib-Thr-Arg-
Gln-Arg-threo-PhSer-NH$_2$ compound No. 201:
Ac-[D-Pro24, Cha27,28, Aib31, DL-Phe(2,6-Me$_2$)36]-
PYY(23-36)
Ac-Ser-D-Pro-Arg-His-Cha-Cha-Asn-Leu-Aib-Thr-Arg-
Gln-Arg-DL-Phe(2,6-Me$_2$)-NH$_2$ compound No. 202:
Ac-[D-Pro24, Cha27,28,36, Iva30, Aib31]-PYY(23-36)
Ac-Ser-D-Pro-Arg-His-Cha-Cha-Asn-Iva-Aib-Thr-Arg-
Gln-Arg-Cha-NH$_2$ compound No. 203:
Ac-[D-Hyp24, Cha27,36, Leu(Me)28, Lys30, Aib31]-PYY
(23-36)
Ac-Ser-D-Hyp-Arg-His-Cha-Leu(Me)-Asn-Lys-Aib-Thr-
Arg-Gln-Arg-Cha-NH$_2$ compound No. 204:
Ac-[Glu23, D-Hyp24, Cha27,28,36, Lys30, Aib31]-
PYY(23-36)
Ac-Glu-D-Hyp-Arg-His-Cha-Cha-Asn-Lys-Aib-Thr-Arg-
Gln-Arg-Cha-NH$_2$ compound No. 205:
Ac-[D-Pro24, Pya(4)26, Cha27,36, Aib28,31, Trp30]-
PYY(23-36)
Ac-Ser-D-Pro-Arg-Pya(4)-Cha-Aib-Asn-Trp-Aib-Thr-
Arg-Gln-Arg-Cha-NH$_2$ compound No. 206:
Ac-[D-Pro24, Pya(4)26, Cha27,36, Aib28,31, Orn30]-
PYY(23-36)
Ac-Ser-D-Pro-Arg-Pya(4)-Cha-Aib-Asn-Orn-Aib-Thr-
Arg-Gln-Arg-Cha-NH$_2$ compound No. 207:
Ac-[D-Hyp24, Pya(4)26, Cha27,36, Aib28,31, Lys30]-
PYY(23-36)
Ac-Ser-D-Hyp-Arg-Pya(4)-Cha-Aib-Asn-Lys-Aib-Thr-
Arg-Gln-Arg-Cha-NH$_2$ compound No. 208:
Ac-[Glu23, D-Hyp24, Pya(4)26, Cha27,36,
Aib28,31, Lys30]-PYY(23-36)
Ac-Glu-D-Hyp-Arg-Pya(4)-Cha-Aib-Asn-Lys-Aib-Thr-
Arg-Gln-Arg-Cha-NH$_2$ compound No. 209:
Ac-[Glu23, D-Pro24, Pya(4)26, Cha27,36,
Aib28,31, Lys30]-PYY(23-36)
Ac-Glu-D-Pro-Arg-Pya(4)-Cha-Aib-Asn-Lys-Aib-Thr-
Arg-Gln-Arg-Cha-NH$_2$ compound No. 210:
Ac-[Gln23, D-Pro24, Pya(4)26, Cha27,36,
Aib28,31, Lys30]-PYY(23-36)
Ac-Gln-D-Pro-Arg-Pya(4)-Cha-Aib-Asn-Lys-Aib-Thr-
Arg-Gln-Arg-Cha-NH$_2$ compound No. 211:
Ac-[Thr23, D-Pro24, Pya(4)26, Cha27,36,
Aib28,31, Lys30]-PYY(23-36)
Ac-Thr-D-Pro-Arg-Pya(4)-Cha-Aib-Asn-Lys-Aib-Thr-
Arg-Gln-Arg-Cha-NH$_2$ compound No. 212:
Isobutanoyl-[D-Pro24, Pya(4)26, Cha27,36,
Aib28,31, Lys30]-PYY(23-36)
Isobutanoyl-Ser-D-Pro-Arg-Pya(4)-Cha-Aib-Asn-Lys-
Aib-Thr-Arg-Gln-Arg-Cha-NH$_2$ compound No. 213:
4-Imidazolecarbonyl-[D-Pro24, Pya(4)26,
Cha27,36, Aib28,31, Lys30]-PYY(23-36)
4-Imidazolecarbonyl-Ser-D-Pro-Arg-Pya(4)-Cha-Aib-
Asn-Lys-Aib-Thr-Arg-Gln-Arg-Cha-NH$_2$ -continued compound No. 214:
Isobutanoyl-[Glu23, D-Pro24, Pya(4)26,
Cha27,36, Aib28,31, Lys30]-PYY(23-36)
Isobutanoyl-Glu-D-Pro-Arg-Pya(4)-Cha-Aib-Asn-Lys-
Aib-Thr-Arg-Gln-Arg-Cha-NH$_2$ compound No. 215:
4-Pyridinecarbonyl-[Glu23, D-Pro24, Pya(4)26,
Cha27,36, Aib28,31, Lys30]-PYY(23-36)
4-Pyridinecarbonyl-Glu-D-Pro-Arg-Pya(4)-Cha-Aib-
Asn-Lys-Aib-Thr-Arg-Gln-Arg-Cha-NH$_2$ compound No. 216:
4-Imidazolecarbonyl-[Glu23, D-Pro24,
Pya(4)26, Cha27,36, Aib28,31, Lys30]-PYY(23-36)
4-Imidazolecarbonyl-Glu-D-Pro-Arg-Pya(4)-Cha-Aib-
Asn-Lys-Aib-Thr-Arg-Gln-Arg-Cha-NH$_2$ compound No. 217:
3-Carboxypropionyl-[D-Pro24, Pya(4)26,
Cha27,36, Aib28,31, Lys30]-PYY(23-36)
3-Carboxypropionyl-Ser-D-Pro-Arg-Pya(4)-Cha-Aib-
Asn-Lys-Aib-Thr-Arg-Gln-Arg-Cha-NH$_2$ compound No. 218:
3-Carboxypropionyl-[Gln23, D-Pro24, Pya(4)26,
Cha27,36, Aib28,31, Lys30]-PYY(23-36)
3-Carboxypropionyl-Gln-D-Pro-Arg-Pya(4)-Cha-Aib-
Asn-Lys-Aib-Thr-Arg-Gln-Arg-Cha-NH$_2$ compound No. 219:
Ac-[D-Pro24, Pya(4)26, Cha27,36, Aib28,31, Lys30]-
PYY(22-36)
Ac-Ala-Ser-D-Pro-Arg-Pya(4)-Cha-Aib-Asn-Lys-Aib-
Thr-Arg-Gln-Arg-Cha-NH$_2$ compound No. 220:
Ac-[Glu23, D-Pro24, Pya(4)26, Cha27,36,
Aib28,31, Lys30]-PYY(22-36)
Ac-Ala-Glu-D-Pro-Arg-Pya(4)-Cha-Aib-Asn-Lys-Aib-
Thr-Arg-Gln-Arg-Cha-NH$_2$ compound No. 221:
Ac-[D-Pro24, Gln26, Cha27,36, Aib28,31, Lys30]-
PYY(23-36)
Ac-Ser-D-Pro-Arg-Gln-Cha-Aib-Asn-Lys-Aib-Thr-Arg-
Gln-Arg-Cha-NH$_2$ compound No. 222:
(SEQ ID NO: 121)
Ac-[βAla24, Pya(4)26, Cha27,36, Aib28,31, Lys30]-
PYY(23-36)
Ac-Ser-βAla-Arg-Pya(4)-Cha-Aib-Asn-Lys-Aib-Thr-
Arg-Gln-Arg-Cha-NH$_2$ compound No. 223:
(SEQ ID NO: 122)
Ac-[Glu23, βAla24, Pya(4)26, Cha27,36,
Aib28,31, Lys30]-PYY(23-36)
Ac-Glu-βAla-Arg-Pya(4)-Cha-Aib-Asn-Lys-Aib-Thr-
Arg-Gln-Arg-Cha-NH$_2$ compound No. 224:
Ac-[D-Pro24, Nle25, Pya(4)26, Cha27,36,
Aib28,31, Lys30]-PYY(23-36)
Ac-Ser-D-Pro-Nle-Pya(4)-Cha-Aib-Asn-Lys-Aib-Thr-
Arg-Gln-Arg-Cha-NH$_2$ compound No. 225:
Ac-[D-Pro24, Cit25, Pya(4)26, Cha27,36,
Aib28,31, Lys30]-PYY(23-36)
Ac-Ser-D-Pro-Cit-Pya(4)-Cha-Aib-Asn-Lys-Aib-Thr-
Arg-Gln-Arg-Cha-NH$_2$ compound No. 226:
Ac-[D-Pro24, Cit25, Cha27,36, Aib28,31, Lys30]-
PYY(23-36)
Ac-Ser-D-Pro-Cit-His-Cha-Aib-Asn-Lys-Aib-Thr-Arg-
Gln-Arg-Cha-NH$_2$ compound No. 227:
Ac-[Glu23, D-Pro24, Nle25, Pya(4)26,
Cha27,36, Aib28,31, Lys30]-PYY(23-36)
Ac-Glu-D-Pro-Nle-Pya(4)-Cha-Aib-Asn-Lys-Aib-Thr-
Arg-Gln-Arg-Cha-NH$_2$ compound No. 228:
4-Pyridinecarbonyl-[Glu23, D-Pro24, Nle25,
Pya(4)26, Cha27,36, Aib28,31, Lys30]-PYY(23-36)
4-Pyridinecarbonyl-Glu-D-Pro-Nle-pya(4)-Cha-Aib-
Asn-Lys-Aib-Thr-Arg-Gln-Arg-Cha-NH$_2$ compound No. 229:
Tetrahydro-2H-pyran-4-yl-carbamoyl-[D-Pro24,
Cha27,36, Leu(Me)28, Lys30, Aib31]-PYY(23-36)
Thp(4)-NHCO-Ser-D-Pro-Arg-His-Cha-Leu(Me)-Asn-Lys-
Aib-Thr-Arg-Gln-Arg-Cha-NH$_2$ compound No. 230:
Tetrahydro-2H-pyran-4-yl-carbamoyl-[Glu23,
D-Pro24, Cha27,28,36, Lys30, Aib31]-PYY(23-36)
Thp(4)-NHCO-Glu-D-Pro-Arg-His-Cha-Cha-Asn-Lys-Aib-
Thr-Arg-Gln-Arg-Cha-NH$_2$ compound No. 231:
Ac-[D-Pro24, Pya(4)26, Cha27,36, Aib28, Lys30,
Iva31]-PYY(23-36)
Ac-Ser-D-Pro-Arg-Pya(4)-Cha-Aib-Asn-Lys-Iva-Thr-
Arg-Gln-Arg-Cha-NH$_2$ compound No. 232:
Ac-[D-Pro24, Pya(4)26, Cha27,36, Aib28, Lys30, D-
Iva31]-PYY(23-36)
Ac-Ser-D-Pro-Arg-Pya(4)-Cha-Aib-Asn-Lys-D-Iva-Thr-
Arg-Gln-Arg-Cha-NH$_2$ compound No. 233:
Ac-[D-Pro24, Pya(4)26, Cha27,36, Iva28, Lys30,
Aib31]-PYY(23-36)
Ac-Ser-D-Pro-Arg-Pya(4)-Cha-Iva-Asn-Lys-Aib-Thr-
Arg-Gln-Arg-Cha-NH$_2$ compound No. 234:
Ac-[D-Pro24, Pya(4)26, Cha27,36, D-Iva28, Lys30,
Aib31]-PYY(23-36)
Ac-Ser-D-Pro-Arg-Pya(4)-Cha-D-Iva-Asn-Lys-Aib-Thr-
Arg-Gln-Arg-Cha-NH$_2$ compound No. 235:
Ac-[D-Pro24, Aib26,28,31, Cha27,36, Lys30]-PYY(23-
36)
Ac-Ser-D-Pro-Arg-Aib-Cha-Aib-Asn-Lys-Aib-Thr-Arg-
Gln-Arg-Cha-NH$_2$ compound No. 236:
Ac-[D-Pro24, Aib25,28,31, Pya(4)26, Cha27,36,
Lys30]-PYY(23-36)
Ac-Ser-D-Pro-Aib-Pya(4)-Cha-Aib-Asn-Lys-Aib-Thr-
Arg-Gln-Arg-Cha-NH$_2$ compound No. 237:
Ac-[D-Pro24, Iva25, Pya(4)26, Cha27,36,
Aib28,31, Lys30]-PYY(23-36)
Ac-Ser-D-Pro-Iva-Pya(4)-Cha-Aib-Asn-Lys-Aib-Thr-
Arg-Gln-Arg-Cha-NH$_2$ compound No. 238:
Ac-[D-Pro24, Aib25,28,31, Cha27,36, Lys30]-PYY(23-
36)
Ac-Ser-D-Pro-Aib-His-Cha-Aib-Asn-Lys-Aib-Thr-Arg-
Gln-Arg-Cha-NH$_2$ compound No. 239:
Ac-[D-Pro24, Iva25, Cha27,36, Aib28,31, Lys30]-
PYY(23-36)
Ac-Ser-D-Pro-Iva-His-Cha-Aib-Asn-Lys-Aib-Thr-Arg-
Gln-Arg-Cha-NH$_2$ -continued compound No. 240:
(SEQ ID NO: 123)
Ac-[Aib24,28,31, Pya(4)26, Cha27,36, Lys30]-PYY(23-36)
Ac-Ser-Aib-Arg-Pya(4)-Cha-Aib-Asn-Lys-Aib-Thr-Arg-Gln-Arg-Cha-NH$_2$ compound No. 241:
(SEQ ID NO: 124)
Ac-[Iva24, Pya(4)26, Cha27,36, Aib28,31, Lys30]-PYY(23-36)
Ac-Ser-Iva-Arg-Pya(4)-Cha-Aib-Asn-Lys-Aib-Thr-Arg-Gln-Arg-Cha-NH$_2$ compound No. 242:
Ac-[D-Iva24, Pya(4)26, Cha27,36, Aib28,31, Lys30]-PYY(23-36)
Ac-Ser-D-Iva-Arg-Pya(4)-Cha-Aib-Asn-Lys-Aib-Thr-Arg-Gln-Arg-Cha-NH$_2$ compound No. 243:
(SEQ ID NO: 125)
Ac-[Aipe24, Pya(4)26, Cha27,36, Aib28,31, Lys30]-PYY(23-36)
Ac-Ser-Aipe-Arg-Pya(4)-Cha-Aib-Asn-Lys-Aib-Thr-Arg-Gln-Arg-Cha-NH$_2$ compound No. 244: Ac-[β-HOAla24, Pya(4)26, Cha27,36, Aib28,31, Lys30]-PYY(23-36) former peak
Ac-Ser-β-HOAla-Arg-Pya (4)-Cha-Aib-Asn-Lys-Aib-Thr-Arg-Gln-Arg-Cha-NH$_2$ (SEQ ID NO:126) former peak
provided that β-HOAla in peptide of compound No. 244 is any of D-form and L-form.

compound No. 245: Ac-[β-HOAla24, Pya(4)26, Cha27,36, Aib28,31, Lys30]-PYY(23-36) later peak
Ac-Ser-β-HOAla-Arg-Pya(4)-Cha-Aib-Asn-Lys-Aib-Thr-Arg-Gln-Arg-Cha-NH$_2$ (SEQ ID NO:126) later peak
provided that β-HOAla in peptide of compound No. 245 is any of D-form and L-form.

compound No. 246:
Ac-[D-Pro24, Pya(4)26, Cha27,36, Iva28,31, Lys30]-PYY(23-36)
Ac-Ser-D-Pro-Arg-Pya(4)-Cha-Iva-Asn-Lys-Iva-Thr-Arg-Gln-Arg-Cha-NH$_2$ compound No. 247:
Ac-[D-Pro24, Pya(4)26, Cha27,36, D-Iva28,31, Lys30]-PYY(23-36)
Ac-Ser-D-Pro-Arg-Pya(4)-Cha-D-Iva-Asn-Lys-D-Iva-Thr-Arg-Gln-Arg-Cha-NH$_2$ compound No. 248:
Ac-[D-Pro24, Pya(4)26, Cha27,36, D-Iva28, Lys30, Iva31]-PYY(23-36)
Ac-Ser-D-Pro-Arg-Pya(4)-Cha-D-Iva-Asn-Lys-Iva-Thr-Arg-Gln-Arg-Cha-NH$_2$ compound No. 249:
Ac-[D-Pro24, Pya(4)26, Cha27,36, Iva28, Lys30, D-Iva31]-PYY(23-36)
Ac-Ser-D-Pro-Arg-Pya(4)-Cha-Iva-Asn-Lys-D-Iva-Thr-Arg-Gln-Arg-Cha-NH$_2$ compound No. 250:
[D-pGlu24, Pya(4)26, Cha27,36, Aib28,31, Lys30]-PYY(24-36)
D-pGlu-Arg-Pya(4)-Cha-Aib-Asn-Lys-Aib-Thr-Arg-Gln-Arg-Cha-NH$_2$ compound No. 251:
Ac-[D-Pro24, Pya(4)26, Cha27,36, Aib28,31, Lys30]-PYY(24-36)
Ac-D-Pro-Arg-Pya(4)-Cha-Aib-Asn-Lys-Aib-Thr-Arg-Gln-Arg-Cha-NH$_2$ compound No. 252:
4-Guanidinomethylbenzoyl-[Iva25, Cha27,36, Aib28,31, Lys30]-PYY(25-36)
4-Guanidinomethylbenzoyl-Iva-His-Cha-Aib-Asn-Lys-Aib-Thr-Arg-Gln-Arg-Cha-NH$_2$ (SEQ ID NO: 127)

compound No. 253:
[(1S)-1-carboxy-3-methylbutyl]carbamoyl-[D-Pro24, Cha27,36, Leu(Me)28, Lys30, Aib31]-PYY(23-36)
CC(Leu)-Ser-D-Pro-Arg-His-Cha-Leu(Me)-Asn-Lys-Aib-Thr-Arg-Gln-Arg-Cha-NH$_2$ compound No. 254:
[(1S)-1-carboxy-3-methylbutyl]carbamoyl-[Glu23, D-Pro24, Cha27,28,36, Lys30, Aib31]-PYY(23-36)
CC(Leu)-Glu-D-Pro-Arg-His-Cha-Cha-Asn-Lys-Aib-Thr-Arg-Gln-Arg-Cha-NH$_2$ compound No. 255:
Ac-[D-Pro24, Cha27, Leu(Me)28, Lys30, Aib31, Phe(2Me)36]-PYY(23-36)
Ser-D-Pro-Arg-His-Cha-Leu(Me)-Asn-Lys-Aib-Thr-Arg-Gln-Arg-Phe(2Me)-NH$_2$ compound No. 256:
Ac-[Glu23, D-Pro24, Cha27,28, Lys30, Aib31, Phe(2Me)36]-PYY(23-36)
Glu-D-Pro-Arg-His-Cha-Cha-Asn-Lys-Aib-Thr-Arg-Gln-Arg-Phe(2Me)-NH$_2$ compound No. 257:
Ac-[D-Pro24, Pya(4)26, Cha27, Aib28,31, Lys30, Phe(2Me)36]-PYY(23-36)
Ser-D-Pro-Arg-Pya(4)-Cha-Aib-Asn-Lys-Aib-Thr-Arg-Gln-Arg-Phe(2Me)-NH$_2$ compound No. 258:
Ac-[D-Pro24, Cha27, Leu(Me)28, Lys30, Aib31, Phe(3Me)36]-PYY(23-36)
Ser-D-Pro-Arg-His-Cha-Leu(Me)-Asn-Lys-Aib-Thr-Arg-Gln-Arg-Phe(3Me)-NH$_2$ compound No. 259:
Ac-[Glu23, D-Pro24, Cha27,28, Lys30, Aib31, Phe(3Me)36]-PYY(23-36)
Ac-Glu-D-Pro-Arg-His-Cha-Cha-Asn-Lys-Aib-Thr-Arg-Gln-Arg-Phe(3Me)-NH$_2$ compound No. 260:
Ac-[D-Pro24, Pya(4)26, Cha27, Aib28,31, Lys30, Phe(3Me)36]-PYY(23-36)
Ac-Ser-D-Pro-Arg-Pya(4)-Cha-Aib-Asn-Lys-Aib-Thr-Arg-Gln-Arg-Phe(3Me)-NH$_2$ compound No. 261:
Ac-[Arg20, D-Tyr21, D-Pro24, Pya(4)26, Cha27, Aib28,31, Lys30, Phe(2Me)36]-PYY(20-36)
Ac-Arg-D-Tyr-Ala-Ser-D-Pro-Arg-Pya(4)-Cha-Aib-Asn-Lys-Aib-Thr-Arg-Gln-Arg-Phe(2Me)-NH$_2$ compound No. 262:
Ac-[Arg20, D-Tyr21, D-Pro24, Pya(4)26, Cha27, Aib28,31, Lys30, Phe(3Me)36]-PYY(20-36)
Ac-Arg-D-Tyr-Ala-Ser-D-Pro-Arg-Pya(4)-Cha-Aib-Asn-Lys-Aib-Thr-Arg-Gln-Arg-Phe(3Me)-NH$_2$ compound No. 263:
Ac-[D-Pro24, Pya(4)26, Cha27,36, Aib28,31, Arg30]-PYY(23-36)
Ac-Ser-D-Pro-Arg-Pya(4)-Cha-Aib-Asn-Arg-Aib-Thr-Arg-Gln-Arg-Cha-NH$_2$ compound No. 264:
Ac-[D-Pro24, Pya(4)26, Cha27,36, Aib28,31, Lys(Me$_2$)30]-PYY(23-36)
Ac-Ser-D-Pro-Arg-Pya(4)-Cha-Aib-Asn-Lys(Me$_2$)-Aib-Thr-Arg-Gln-Arg-Cha-NH$_2$ -continued compound No. 265:
Ac-[D-Pro24, Pya(4)26, Cha27,36, Aib28,31,
Hse30]-PYY(23-36)
Ac-Ser-D-Pro-Arg-Pya(4)-Cha-Aib-Asn-Hse-Aib-Thr-
Arg-Gln-Arg-Cha-NH$_2$ compound No. 266:
Ac-[D-Pro24, Pya(4)26, Cha27,36, Aib28,31,
Cit30]-PYY(23-36)
Ac-Ser-D-Pro-Arg-Pya(4)-Cha-Aib-Asn-Cit-Aib-Thr-
Arg-Gln-Arg-Cha-NH$_2$ compound No. 267:
Ac-[D-Pro24, Pya(4)26, Cha27,36, Aib28,31,
Nle30]-PYY(23-36)
Ac-Ser-D-Pro-Arg-Pya(4)-Cha-Aib-Asn-Nle-Aib-Thr-
Arg-Gln-Arg-Cha-NH$_2$ compound No. 268:
Morpholinocarbonyl-[D-Pro24, Pya(4)26,
Cha27,36, Aib28,31, Lys30]-PYY(23-36)
Morpholinocarbonyl-Ser-D-Pro-Arg-Pya(4)-Cha-Aib-
Asn-Lys-Aib-Thr-Arg-Gln-Arg-Cha-NH$_2$ compound. No. 269:
(cis-2,6-Dimethylmorpholin-4-yl)carbonyl-[D-Pro24,
Pya(4)26, Cha27,36, Aib28,31, Lys30]-PYY(23-36)
(cis-2,6-Dimethylmorpholin-4-yl)carbonyl-Ser-D-
Pro-Arg-Pya(4)-Cha-Aib-Asn-Lys-Aib-Thr-Arg-Gln-
Arg-Cha-NH$_2$ compound No. 270:
Tetrahydro-2H-pyran-4-yl-carbamoyl-[D-Pro24,
Pya(4)26, Cha27,36, Aib28,31, Lys30]-PYY(23-36)
Thp(4)-NHCO-Ser-D-Pro-Arg-Pya(4)-Cha-Aib-Asn-Lys-
Aib-Thr-Arg-Gln-Arg-Cha-NH$_2$ compound No. 271:
[(1S)-1-Carboxy-3-methylbutyl]carbamoyl-[D-Pro24,
Pya(4)26, Cha27,36, Aib28,31, Lys30]-PYY(23-36)
CC(Leu)-Ser-D-Pro-Arg-Pya(4)-Cha-Aib-Asn-Lys-Aib-
Thr-Arg-Gln-Arg-Cha-NH$_2$ compound No. 272:
Ac-[Lys22,30, D-Pro24, Pya(4)26, Cha27,36,
Aib28,31]-PYY(22-36)
Ac-Lys-Ser-D-Pro-Arg-Pya(4)-Cha-Aib-Asn-Lys-Aib-
Thr-Arg-Gln-Arg-Cha-NH$_2$ compound No. 273:
Ac-[Dap22, D-Pro24, Pya(4)26, Cha27,36,
Aib28,31, Lys30]-PYY(22-36)
Ac-Dap-Ser-D-Pro-Arg-Pya(4)-Cha-Aib-Asn-Lys-Aib-
Thr-Arg-Gln-Arg-Cha-NH$_2$ compound No. 274:
Ac-[Leu22, D-Pro24, Pya(4)26, Cha27,36,
Aib28,31, Lys30]-PYY(22-36)
Ac-Leu-Ser-D-Pro-Arg-Pya(4)-Cha-Aib-Asn-Lys-Aib-
Thr-Arg-Gln-Arg-Cha-NH$_2$ compound No. 275:
Ac-[Phe22, D-Pro24, Pya(4)26, Cha27,36,
Aib28,31, Lys30]-PYY(22-36)
Ac-Phe-Ser-D-Pro-Arg-Pya(4)-Cha-Aib-Asn-Lys-Aib-
Thr-Arg-Gln-Arg-Cha-NH$_2$ compound No. 276:
2-Methylbutanoyl-[D-Pro24, Pya(4)26,
Cha27,36, Aib28,31, Lys30]-PYY(23-36)
2-Methylbutanoyl-Ser-D-Pro-Arg-Pya(4)-Cha-Aib-Asn-
Lys-Aib-Thr-Arg-Gln-Arg-Cha-NH$_2$ compound No. 277:
Ac-[D-Pro24, Pya(4)26, Cha27,36, Aib28,31,
Har30]-PYY(23-36)
Ac-Ser-D-Pro-Arg-Pya(4)-Cha-Aib-Asn-Har-Aib-Thr-
Arg-Gln-Arg-Cha-NH$_2$ compound No. 278:
Ac-[D-Pro24, Pya(4)26, Cha27,36, Aib28,31,
Lys(Ac)30]-PYY(23-36)
Ac-Ser-D-Pro-Arg-Pya(4)-Cha-Aib-Asn-Lys(Ac)-Aib-
Thr-Arg-Gln-Arg-Cha-NH$_2$ compound No. 279:
Ac-[D-Pro24, Pya(4)26, Cha27,36, Aib28,31,
Lys(Hexyl)30]-PYY(23-36)
Ac-Ser-D-Pro-Arg-Pya(4)-Cha-Aib-Asn-Lys(Hexyl)-
Aib-Thr-Arg-Gln-Arg-Cha-NH$_2$ compound No. 280:
Ac-[D-Pro24, Lys(Ac)25, Pya(4)26, Cha27,36,
Aib28,31, Lys30]-PYY(23-36)
Ac-Ser-D-Pro-Lys(Ac)-Pya(4)-Cha-Aib-Asn-Lys-Aib-
Thr-Arg-Gln-Arg-Cha-NH$_2$ compound No. 281:
Ac-[D-Pro24, Arg(Me)25, Cha27,36, Aib28,31,
Lys30]-PYY(23-36)
Ac-Ser-D-Pro-Arg(Me)-His-Cha-Aib-Asn-Lys-Aib-Thr-
Arg-Gln-Arg-Cha-NH$_2$ compound No. 282:
Tetrahydro-2H-pyran-4-yl-carbamoyl-[Glu23, D-
Pro24, Pya(4)26, Cha27,36, Aib28,31, Lys30]-
PYY(23-36)
Thp(4)-NHCO-Glu-D-Pro-Arg-Pya(4)-Cha-Aib-Asn-Lys-
Aib-Thr-Arg-Gln-Arg-Cha-NH$_2$ compound No. 283:
[(1S)-1-Carboxy-3-methylbutyl]carbamoyl-[Glu23,
D-Pro24, Pya(4)26, Cha27,36, Aib28,31, Lys30]-
PYY(23-36)
CC(Leu)-Glu-D-Pro-Arg-Pya(4)-Cha-Aib-Asn-Lys-Aib-
Thr-Arg-Gln-Arg-Cha-NH$_2$ compound No. 284:
[(1S)-1-Carboxy-3-methylbutyl]carbamoyl-[Gln23,
D-Pro24, Pya(4)26, Cha27,36, Aib28,31, Lys30]-
PYY(23-36)
CC(Leu)-Glu-D-Pro-Arg-Pya(4)-Cha-Aib-Asn-Lys-Aib-
Thr-Arg-Gln-Arg-Cha-NH$_2$ compound No. 285:
[(1S)-1-Carboxy-2-(4-hydroxyphenyl)ethyl]carb-
amoyl-[D-Pro24, Pya(4)26, Cha27,36, Aib28,31,
Lys30]-PYY(23-36)
CC(Tyr)-Ser-D-Pro-Arg-Pya(4)-Cha-Aib-Asn-Lys-Aib-
Thr-Arg-Gln-Arg-Cha-NH$_2$ compound No. 286:
[(1S)-1-Carboxyethyl]carbamoyl-[D-Pro24,
Pya(4)26, Cha27,36, Aib28,31, Lys30]-PYY(23-36)
CC(β-Ala)-Ser-D-Pro-Arg-Pya(4)-Cha-Aib-Asn-Lys-
Aib-Thr-Arg-Gln-Arg-Cha-NH$_2$ compound No. 287:
(Carboxymethyl)carbamoyl-[D-Pro24, Pya(4)26,
Cha27,36, Aib28,31, Lys30]-PYY(23-36)
CC(Gly)-Ser-D-Pro-Arg-Pya(4)-Cha-Aib-Asn-Lys-Aib-
Thr-Arg-Gln-Arg-Cha-NH$_2$ compound No. 288:
[(1S)-1-carboxy-2-hydroxyethyl]carbamoyl-[D-Pro24,
Pya(4)26, Cha27,36, Aib28,31, Lys30]-PYY(23-36)
CC(Ser)-Ser-D-Pro-Arg-Pya(4)-Cha-Aib-Asn-Lys-Aib-
Thr-Arg-Gln-Arg-Cha-NH$_2$ compound No. 289:
Ac-[D-Pro24, Har25, Pya(4)26, Cha27,36,
Aib28,31, Lys30]-PYY(23-36)
Ac-Ser-D-Pro-Har-Pya(4)-Cha-Aib-Asn-Lys-Aib-Thr-
Arg-Gln-Arg-Cha-NH$_2$ compound No. 290:
Ac-[D-Pro24, Nar25, Pya(4)26, Cha27,36,
Aib28,31, Lys30]-PYY(23-36)
Ac-Ser-D-Pro-Nar-Pya(4)-Cha-Aib-Asn-Lys-Aib-Thr-
Arg-Gln-Arg-Cha-NH$_2$ -continued compound No. 291:
Ac-[D-Pro24, Har25, Cha27,36, Aib28,31, Lys30]-PYY(23-36)
Ac-Ser-D-Pro-Har-His-Cha-Aib-Asn-Lys-Aib-Thr-Arg-Gln-Arg-Cha-NH₂ compound No. 292:
(2-amino-2-oxoethyl)carbamoyl-[D-Pro24, Pya(4)26, Cha27,36, Aib28,31, Lys30]-PYY(23-36)
H2N-CC(Gly)-Ser-D-Pro-Arg-Pya(4)-Cha-Aib-Asn-Lys-Aib-Thr-Arg-Gln-Arg-Cha-NH₂ compound No. 293:
(3-carboxypropyl)carbamoyl-[D-Pro24, Pya(4)26, Cha27,36, Aib28,31, Lys30]-PYY(23-36)
CC(GABA)-Ser-D-Pro-Arg-Pya(4)-Cha-Aib-Asn-Lys-Aib-Thr-Arg-Gln-Arg-Cha-NH₂ compound No. 294:
(5-carboxypentyl)carbamoyl-[D-Pro24, Pya(4)26, Cha27,36, Aib28,31, Lys30]-PYY(23-36)
CC(Acp)-Ser-D-Pro-Arg-Pya(4)-Cha-Aib-Asn-Lys-Aib-Thr-Arg-Gln-Arg-Cha-NH₂ compound No. 295:
Ac-[D-Pro24, Iva25, Pya(4)26, Cha27,36, Leu(Me)28, Lys30, Aib31]-PYY(23-36)
Ac-Ser-D-Pro-Iva-Pya(4)-Cha-Leu(Me)-Asn-Lys-Aib-Thr-Arg-Gln-Arg-Cha-NH₂ compound No. 296:
Ac-[D-Pro24, Iva25,28, Pya(4)26, Cha27,36, Lys30, Aib31]-PYY(23-36)
Ac-Ser-D-Pro-Iva-Pya(4)-Cha-Iva-Asn-Lys-Aib-Thr-Arg-Gln-Arg-Cha-NH₂ compound No. 297:
Ac-[D-Hyp24, Iva25, Pya(4)26, Cha27,36, Aib28,31, Lys30]-PYY(23-36)
Ac-Ser-D-Hyp-Iva-Pya(4)-Cha-Aib-Asn-Lys-Aib-Thr-Arg-Gln-Arg-Cha-NH₂ compound No. 298:
Ac-[D-Hyp24, Iva25,28, Pya(4)26, Cha27,36, Lys30, Aib31]-PYY(23-36)
Ac-Ser-D-Hyp-Iva-Pya(4)-Cha-Iva-Asn-Lys-Aib-Thr-Arg-Gln-Arg-Cha-NH₂ compound No. 299:
4-Imidazolecarbonyl-[D-Hyp24, Iva25, Pya(4)26, Cha27,36, Aib28,31, Lys30]-PYY(23-36)
4-Imidazolecarbonyl-Ser-D-Hyp-Iva-Pya(4)-Cha-Aib-Asn-Lys-Aib-Thr-Arg-Gln-Arg-Cha-NH₂ compound No. 300:
4-Imidazolecarbonyl-[D-Pro24, Iva25, Pya(4)26, Cha27,36, Aib28,31, Lys30]-PYY(23-36)
4-Imidazolecarbonyl-Ser-D-Pro-Iva-Pya(4)-Cha-Aib-Asn-Lys-Aib-Thr-Arg-Gln-Arg-Cha-NH₂ compound No. 301:
4-Pyridinecarbonyl-[D-Pro24, Iva25, Pya(4)26, Cha27,36, Aib28,31, Lys30]-PYY(23-36)
4-Pyridinecarbonyl-Ser-D-Pro-Iva-Pya(4)-Cha-Aib-Asn-Lys-Aib-Thr-Arg-Gln-Arg-Cha-NH₂ compound No. 302:
4-Imidazolecarbonyl-[D-Pro24, Nle25, Pya(4)26, Cha27,36, Aib28,31, Lys30]-PYY(23-36)
4-Imidazolecarbonyl-Ser-D-Pro-Nle-Pya(4)-Cha-Aib-Asn-Lys-Aib-Thr-Arg-Gln-Arg-Cha-NH₂ compound No. 303:
3-Carboxypropionyl-[D-Pro24, Pya(4)26, Cha27,36, Aib28,31, Lys30]-PYY(24-36)
3-Carboxypropionyl-D-Pro-Arg-Pya(4)-Cha-Aib-Asn-Lys-Aib-Thr-Arg-Gln-Arg-Cha-NH₂ compound No. 304:
[Acp23, D-Pro24, Pya(4)26, Cha27,36, Aib28,31, Lys30]-PYY(23-36)
Ac-Acp-D-Pro-Arg-Pya(4)-Cha-Aib-Asn-Lys-Aib-Thr-Arg-Gln-Arg-Cha-NH₂ compound No. 305:
Ac-[D-Pro24, Pya(4)26, Phe(4F)27, Aib28,31, Lys30, Cha36]-PYY(23-36)
Ac-Ser-D-Pro-Arg-Pya(4)-Phe(4F)-Aib-Asn-Lys-Aib-Thr-Arg-Gln-Arg-Cha-NH₂ compound No. 306:
Ac-[D-Pro24, Pya(4)26, Nal(1)27, Aib28,31, Lys30, Cha36]-PYY(23-36)
Ac-Ser-D-Pro-Arg-Pya(4)-Nal(1)-Aib-Asn-Lys-Aib-Thr-Arg-Gln-Arg-Cha-NH₂ compound No. 307:
Ac-[D-Pro24, Pya(4)26, Nal(2)27, Aib28,31, Lys30, Cha36]-PYY(23-36)
Ac-Ser-D-Pro-Arg-Pya(4)-Nal(2)-Aib-Asn-Lys-Aib-Thr-Arg-Gln-Arg-Cha-NH₂ compound No. 308: Ac-[D-Pro24, Pya(4)26, Ala(4Pip)27, Aib28,31, Lys30, Cha36]-PYY(23-36) former peak
Ac-Ser-D-Pro-Arg-Pya(4)-Ala(4Pip)-Aib-Asn-Lys-Aib-Thr-Arg-Gln-Arg-Cha-NH₂ former peak
provided that Ala(4Pip) in peptide of compound No. 308 is any of D-form and L-form.

compound No. 309: Ac-[D-Pro24, Pya(4)26, Ala(4Pip)27, Aib28,31, Lys30, Cha36]-PYY(23-36) later peak
Ac-Ser-D-Pro-Arg-Pya(4)-Ala(4Pip)-Aib-Asn-Lys-Aib-Thr-Arg-Gln-Arg-Cha-NH₂ later peak
provided that Ala(4Pip) in peptide of compound No. 309 is any of D-form and L-form.

compound No. 310: Ac-[D-Pro24, Ala(4Pip)26, Cha27,36, Aib28,31, Lys30]-PYY(23-36)
Ac-Ser-D-Pro-Arg-Ala(4Pip)-Cha-Aib-Asn-Lys-Aib-Thr-Arg-Gln-Arg-Cha-NH₂
provided that Ala(4Pip) in peptide of compound No. 310 is any of D-form and L-form.

compound No. 311: Ac-[D-Pro24, Ala(4Pip)25, Pya(4)26, Cha27,36, Aib28,31, Lys30]-PYY(23-36) former peak
Ac-Ser-D-Pro-Ala(4Pip)-Pya(4)-Cha-Aib-Asn-Lys-Aib-Thr-Arg-Gln-Arg-Cha-NH₂ former peak
provided that Ala(4Pip) in peptide of compound No. 311 is any of D-form and L-form.

compound No. 312: Ac-[D-Pro24, Ala(4Pip)25, Pya(4)26, Cha27,36, Aib28,31, Lys30]-PYY(23-36) later peak
Ac-Ser-D-Pro-Ala(4Pip)-Pya(4)-Cha-Aib-Asn-Lys-Aib-Thr-Arg-Gln-Arg-Cha-NH₂ later peak
provided that Ala(4Pip) in peptide of compound No. 312 is any of D-form and L-form.

compound No. 313: Ac-[D-Pro24, Pya(4)26, Cha27,36, Aib28,31, Ala(4-pip)30]-PYY(23-36)
Ac-Ser-D-Pro-Arg-Pya(4)-Cha-Alb-Asn-Ala(4Pip)-Aib-Thr-Arg-Gln-Arg-Cha-NH₂
provided that Ala(4Pip) in peptide of compound No. 313 is any of D-form and L-form.

compound No. 314:
Ac-[D-Pro24, Pya(4)26, Cha27,36, Aib28,31, Arg(Me)30]-PYY(23-36)
Ac-Ser-D-Pro-Arg-Pya(4)-Cha-Aib-Asn-Arg(Me)-Aib-Thr-Arg-Gln-Arg-Cha-NH₂ compound No. 315:
Ac-[D-Pro24, Arg(Me)25,30, Pya(4)26, Cha27,36, Aib28,31]-PYY(23-36)
Ac-Ser-D-Pro-Arg(Me)-Pya(4)-Cha-Aib-Asn-Arg(Me)-Aib-Thr-Arg-Gln-Arg-Cha-NH₂ compound No. 316:
Ac-[D-Pro24, Iva25, Pya(4)26, Cha27,36,
Aib28,31, Arg(Me)30]-PYY(23-36)
Ac-Ser-D-Pro-Iva-Pya(4)-Cha-Aib-Asn-Arg(Me)-Aib-
Thr-Arg-Gln-Arg-Cha-NH$_2$ compound No. 317:
Ac-[D-Pro24, Iva25, Pya(4)26, Cha27,36,
Aib28,31, Har30]-PYY(23-36)
Ac-Ser-D-Pro-Iva-Pya(4)-Cha-Aib-Asn-Har-Aib-Thr-
Arg-Gln-Arg-Cha-NH$_2$ compound No. 318:
4-Imidazolecarbonyl-[D-Pro24, Iva25,
Pya(4)26, Cha27,30,36, Aib28,31]-PYY(23-36)
4-Imidazolecarbonyl-Ser-D-Pro-Iva-Pya(4)-Cha-Aib-
Asn-Cha-Aib-Thr-Arg-Gln-Arg-Cha-NH$_2$ compound No. 319:
Ac-[D-Pro24, Arg(Me)25, Pya(4)26, Cha27,36,
Aib28,31, Lys30]-PYY(23-36)
Ac-Ser-D-Pro-Arg(Me)-Pya(4)-Cha-Aib-Asn-Lys-Aib-
Thr-Arg-Gln-Arg-Cha-NH$_2$ compound No. 320:
Ac-[D-Pro24, Abu26, Cha27,36, Aib28,31, Lys30]-
PYY(23-36)
Ac-Ser-D-Pro-Arg-Abu-Cha-Aib-Asn-Lys-Aib-Thr-Arg-
Gln-Arg-Cha-NH$_2$ compound No. 321:
Ac-[Arg23, D-Pro24, Iva25, Pya(4)26,
Cha27,36, Aib28,31, Lys30]-PYY(23-36)
Ac-Arg-D-Pro-Iva-Pya(4)-Cha-Aib-Asn-Lys-Aib-Thr-
Arg-Gln-Arg-Cha-NH$_2$ compound No. 322:
Ac-[Glu23, D-Pro24, Iva25, Pya(4)26,
Cha27,36, Aib28,31, Lys30]-PYY(23-36)
Ac-Glu-D-Pro-Iva-Pya(4)-Cha-Aib-Asn-Lys-Aib-Thr-
Arg-Gln-Arg-Cha-NH$_2$ compound No. 323:
[(1S)-5-Amino-1-carboxypentyl]carbamoyl-[D-
Pro24, Cha27,28,36, Aib31]-PYY(23-36)
CC(Acp)-Ser-D-Pro-Arg-His-Cha-Cha-Asn-Leu-Aib-Thr-
Arg-Gln-Arg-Cha-NH$_2$ compound No. 324:
(Tetrahydro-2H-pyran-4-yl)carbonyl-[D-Pro24,
Pya(4)26, Cha27,36, Aib28,31, Lys30]-PYY(23-36)
Thp(4)-CO-Ser-D-Pro-Arg-Pya(4)-Cha-Aib-Asn-Lys-
Aib-Thr-Arg-Gln-Arg-Cha-NH$_2$ compound No. 325:
(Tetrahydro-2H-pyran-4-ylmethyl)carbamoyl-
[D-Pro24, Pya(4)26, Cha27,36, Aib28,31, Lys30]-
PYY(23-36)
Thp(4)-CH$_2$NHCO-Ser-D-Pro-Arg-Pya(4)-Cha-Aib-Asn-
Lys-Aib-Thr-Arg-Gln-Arg-Cha-NH$_2$ compound No. 326:
(2-Carboxyethyl)carbamoyl-[D-Pro24, Pya(4)26,
Cha27,36, Aib28,31, Lys30]-PYY(23-36)
CC(β-Ala)-Ser-D-Pro-Arg-Pya(4)-Cha-Aib-Asn-Lys-
Aib-Thr-Arg-Gln-Arg-Cha-NH$_2$ compound No. 327:
(Carboxymethyl)carbamoyl-[D-Pro24, Iva25,
Pya(4)26, Cha27,36, Aib28,31, Lys30]-PYY(23-36)
CC(Gly)-Ser-D-Pro-Iva-Pya(4)-Cha-Aib-Asn-Lys-Aib-
Thr-Arg-Gln-Arg-Cha-NH$_2$ compound No. 328:
(3-Carboxypropyl)carbamoyl-[D-Pro24, Iva25,
Pya(4)26, Cha27,36, Aib28,31, Lys30]-PYY(23-36)
CC(GABA)-Ser-D-Pro-Iva-Pya(4)-Cha-Aib-Asn-Lys-Aib-
Thr-Arg-Gln-Arg-Cha-NH$_2$ compound No. 329:
Ac-[D-Pro24, Pya(4)26, Cha27,
Aib28,31, Lys30, Phe(2,6-Me$_2$)36]-PYY(23-36)
Ac-Ser-D-Pro-Arg-Pya(4)-Cha-Aib-Asn-Lys-Aib-Thr-
Arg-Gln-Arg-Phe(2,6-Me$_2$)-NH$_2$
provided that Phe(2,6-Me$_2$) in peptide of compound
No. 329 is any of D-form and L-form.

compound No. 330:
(Tetrahydro-2H-pyran-4-yl)
carbamoyl-[D-Pro24, Iva25, Pya(4)26, Cha27,36,
Aib28,31, Lys30]-PYY(23-36)
Thp(4)-NHCO-Ser-D-Pro-Iva-Pya(4)-Cha-Aib-Asn-Lys-
Aib-Thr-Arg-Gln-Arg-Cha-NH$_2$ compound No. 331:
Carbamoylmethylcarbamoyl-[D-
Pro24, Iva25, Pya(4)26, Cha27,36, Aib28,31,
Lys30]-PYY(23-36)
H$_2$N-CC(Gly)-Ser-D-Pro-Iva-Pya(4)-Cha-Aib-Asn-Lys-
Aib-Thr-Arg-Gln-Arg-Cha-NH$_2$ compound No. 332:
[(1S)-1-Carboxy-2-hydroxyethyl]
carbamoyl-[D-Pro24, Iva25, Pya(4)26, Cha27,36,
Aib28,31, Lys30]-PYY(23-36)
CC(Ser)-Ser-D-Pro-Iva-Pya(4)-Cha-Aib-Asn-Lys-Aib-
Thr-Arg-Gln-Arg-Cha-NH$_2$ compound No. 333:
4-Pyridinecarbonyl-[D-Hyp24,
Iva25, Pya(4)26, Cha27,36, Leu(Me)28, Lys30,
Aib31]-PYY(23-36)
4-Pyridinecarbonyl-Ser-D-Hyp-Iva-Pya(4)-Cha-Leu
(Me)-Asn-Lys-Aib-Thr-Arg-Gln-Arg-Cha-NH$_2$ compound No. 334:
4-Pyridinecarbonyl-[D-Hyp24, Iva25,28,
Pya(4)26, Cha27,36, Lys30, Aib31]-PYY (23-36)
4-Pyridinecarbonyl-Ser-D-Hyp-Iva-Pya(4)-Cha-Iva-
Asn-Lys-Aib-Thr-Arg-Gln-Arg-Cha-NH$_2$ compound No. 335:
Ac-[D-Hyp24, Iva25, Pya(4)26,
Cha27,36, Leu(Me)28, Lys30, Aib31]-PYY(23-36)
Ac-Ser-D-Hyp-Iva-Pya(4)-Cha-Leu(Me)-Asn-Lys-Aib-
Thr-Arg-Gln-Arg-Cha-NH$_2$ compound No. 336:
4-Imidazolecarbonyl-[D-Hyp24, Iva25, Pya(4)26,
Cha27,36, Leu(Me)28, Lys30, Aib31]-PYY(23-36)
4-Imidazolecarbonyl-Ser-D-Hyp-Iva-Pya(4)-Cha-Leu
(Me)-Asn-Lys-Aib-Thr-Arg-Gln-Arg-Cha-NH$_2$ compound No. 337:
4-Imidazolecarbonyl-[D-Hyp24, Iva25,28,
Pya(4)26, Cha27,36, Lys30, Adb31]-PYY(23-36)
4-Imidazolecarbonyl-Ser-D-Hyp-Iva-Pya(4)-Cha-Iva-
Asn-Lys-Aib-Thr-Arg-Gln-Arg-Cha-NH$_2$ compound No. 338:
Glycoloyl-[D-Hyp24, Iva25,28, Pya(4)26,
Cha27,36, Leu(Me)28, Lys30, Aib31]-PYY(23-36)
Glycoloyl-Ser-D-Hyp-Iva-Pya(4)-Cha-Iva-Asn-Lys-
Aib-Thr-Arg-Gln-Arg-Cha-NH$_2$ compound No. 339:
[2-Hydroxy-1-(hydroxymethyl)
ethyl]carbamoyl-[D-Pro24, Iva25, Pya(4)26,
Cha27,36, Aib28,31, Lys30]-PYY(23-36)
(HOCH$_2$)$_2$CHNHCO-Ser-D-Pro-Iva-Pya(4)-Cha-Aib-Asn-
Lys-Aib-Thr-Arg-Gln-Arg-Cha-NH$_2$ compound No. 340:
(Tetrahydro-2H-pyran-4-ylmethyl)
carbamoyl-[D-Pro24, Iva25, Pya(4)26, Cha27,36,
Aib28,31, Lys30]-PYY(23-36)
Thp(4)-CH$_2$NHCO-Ser-D-Pro-Iva-Pya(4)-Cha-Aib-Asn-
Lys-Aib-Thr-Arg-Gln-Arg-Cha-NH$_2$ compound No. 341:
(2-Carboxyethyl)carbamoyl-[D-Pro24, Iva25,
Pya(4)26, Cha27,36, Aib28,31, Lys30]-PYY(23-36)
CC(β-Ala)-Ser-D-Pro-Iva-Pya(4)-Cha-Aib-Asn-Lys-
Aib-Thr-Arg-Gln-Arg-Cha-NH₂ compound No. 342:
(Tetrahydro-2H-pyran-4-yl)
carbonyl-[D-Pro24, Iva25, Pya(4)26, Cha27,36,
Aib28,31, Lys30]-PYY(23-36)
Thp(4)-CO-Ser-D-Pro-Iva-Pya(4)-Cha-Aib-Asn-Lys-
Aib-Thr-Arg-Gln-Arg-Cha-NH₂ compound No. 343:
4-Imidazolecarbonyl-[D-Hyp24, Iva25, Pya(4)26,
Cha27,36, αMePhe28, Lys30, Aib31]-PYY(23-36)
4-Imidazolecarbonyl-Ser-D-Hyp-Iva-Pya(4)-Cha-
αMePhe-Asn-Lys-Aib-Thr-Arg-Gln-Arg-Cha-NH₂ compound No. 344:                    (SEQ ID NO: 128)
4-Imidazolecarbonyl-[Aib24,28,
31, Iva25, Pya(4)26, Cha27,36, Lys30]-PYY(23-36)
4-Imidazolecarbonyl-Ser-Aib-Iva-Pya(4)-Cha-Aib-
Asn-Lys-Aib-Thr-Arg-Gln-Arg-Cha-NH₂ compound No. 345:
Ac-[D-Pro24, Phe26, Cha27,36,
Aib28,31, Lys30]-PYY(23-36)
Ac-Ser-D-Pro-Arg-Phe-Cha-Aib-Asn-Lys-Aib-Thr-Arg-
Gln-Arg-Cha-NH₂ compound No. 346:
Ac-[D-Pro24, Tyr26, Cha27,36,
Aib28,31, Lys30]-PYY(23-36)
Ac-Ser-D-Pro-Arg-Tyr-Cha-Aib-Asn-Lys-Aib-Thr-Arg-
Gln-Arg-Cha-NH₂ compound No. 347:
Ac-[D-Pro24, Trp26, Cha27,36,
Aib28,31, Lys30]-PYY(23-36)
Ac-Ser-D-Pro-Arg-Trp-Cha-Aib-Asn-Lys-Aib-Thr-Arg-
Gln-Arg-Cha-NH₂ compound No. 348:
Ac-[D-Pro24, Tyr(Me)26, Cha27,36, Aib28,31,
Lys30]-PYY(23-36)
Ac-Ser-D-Pro-Arg-Tyr(Me)-Cha-Aib-Asn-Lys-Aib-Thr-
Arg-Gln-Arg-Cha-NH₂ compound No. 349:
(3-Carboxypropyl)carbamoyl-[D-
Hyp24, Iva25, Pya(4)26, Cha27,36, Leu(Me)28,
Lys30, Aib31]-PYY(23-36)
CC(GABA)-Ser-D-Hyp-Iva-Pya(4)-Cha-Leu(Me)-Asn-Lys-
Aib-Thr-Arg-Gln-Arg-Cha-NH₂ compound No. 350:
3-Carboxypropionyl-[D-Hyp24, Iva25, Pya(4)26,
Cha27,36, Leu(Me)28, Lys30, Aib31]-PYY(23-36)
3-Carboxypropionyl-Ser-D-Hyp-Iva-Pya(4)-Cha-Leu
(Me)-Asn-Lys-Aib-Thr-Arg-Gln-Arg-Cha-NH₂ compound No. 351:
Ac-[Glu23, D-Hyp24, Iva25, Pya(4)26, Cha27,36,
Leu(Me)28, Lys30, Aib31]-PYY(23-36)
Ac-Glu-D-Hyp-Iva-Pya(4)-Cha-Leu(Me)-Asn-Lys-Aib-
Thr-Arg-Gln-Arg-Cha-NH₂ compound No. 352:
Ac-[D-Pro24, Iva25, Pya(4)26,
Cha27,36, Nva28, Aib31, Lys30]-PYY(23-36)
Ac-Ser-D-Pro-Iva-Pya(4)-Cha-Nva-Asn-Lys-Aib-Thr-
Arg-Gln-Arg-Cha-NH₂ compound No. 353:                    (SEQ ID NO: 129)
[Ile22,28,31, Lys23, Acp24, Ala26]-PYY(22-36)
Ile-Lys-Acp-Arg-Ala-Tyr-Ile-Asn-Leu-Ile-Thr-Arg-
Gln-Arg-Tyr-NH₂ compound No. 354:                    (SEQ ID NO: 130)
4-Aminomethylbenzoyl-[Ala26, ILe28,31,
Abu32]-PYY(25-36)
4-Aminomethylbenzoyl-Arg-Ala-Tyr-Ile-Asn-Leu-Ile-
Abu-Arg-Gln-Arg-Tyr-NH₂ compound No. 355:
Ac-[D-Tyr21, D-Pro24, Cha27,28,
36, Aib31]-PYY(20-36)
Ac-Tyr-D-Tyr-Ala-Ser-D-Pro-Arg-His-Cha-Cha-Asn-
Leu-Aib-Thr-Arg-Gln-Arg-Cha-NH₂ compound No. 356:
CC(Gly)-[D-Hyp24, Iva25, Pya(4)26,
Cha27,36, Leu(Me)28, Lys30, Aib31]-PYY(23-36)
CC(Gly)-Ser-D-Hyp-Iva-Pya(4)-Cha-Leu(Me)-Asn-Lys-
Aib-Thr-Arg-Gln-Arg-Cha-NH₂ compound No. 357:
CC(β-Ala)-[D-Hyp24, Iva25, Pya(4)26, Cha27,36,
Leu(Me)28, Lys30, Aib31]-PYY(23-36)
CC(β-Ala)-Ser-D-Hyp-Iva-Pya(4)-Cha-Leu(Me)-Asn-
Lys-Aib-Thr-Arg-Gln-Arg-Cha-NH₂ compound No. 358:
Thp(4)-NHCO-[D-Hyp24, Iva25, Pya(4)26,
Cha27,36, Leu(Me)28, Lys30, Aib31]-PYY(23-36)
Thp(4)-NHCO-Ser-D-Hyp-Iva-Pya(4)-Cha-Leu(Me)-Asn-
Lys-Aib-Thr-Arg-Gln-Arg-Cha-NH₂ compound No. 359:
Thp(4)-CH₂NHCO-[D-Hyp24, Iva25, Pya(4)26,
Cha27,36, Leu(Me)28, Lys30, Aib31]-PYY(23-36)
Thp(4)-CH₂NHCO-Ser-D-Hyp-Iva-Pya(4)-Cha-Leu(Me)-
Asn-Lys-Aib-Thr-Arg-Gln-Arg-Cha-NH₂ compound No. 360:
4-Imidazolecarbonyl-[D-Hyp24,
Iva25, Pya(4)26, Cha27, Leu(Me)28, Lys30, Aib31,
Phe(2,6-Me2)36]-PYY(23-36)
4-Imidazolecarbonyl-Ser-D-Hyp-Iva-Pya(4)-Cha-
Leu(Me)-Asn-Lys-Aib-Thr-Arg-Gln-Arg-Phe(2,6-Me2)-
NH₂ compound No. 361:
Thp(4)-CO-[D-Hyp24, Iva25, Pya(4)26,
Cha27,36, Leu(Me)28, Lys30, Aib31]-PYY(23-36)
Thp(4)-CO-Ser-D-Hyp-Iva-Pya(4)-Cha-Leu(Me)-Asn-
Lys-Aib-Thr-Arg-Gln-Arg-Cha-NH₂ compound No. 362:
4-Imidazolecarbonyl-[D-Hyp24,
Iva25, Pya(4)26, Cha27,36, Leu(Me)28, Lys(Ac)30,
Aib31]-PYY(23-36)
4-Imidazolecarbonyl-Ser-D-Hyp-Iva-Pya(4)-Cha-Leu
(Me)-Asn-Lys(Ac)-Aib-Thr-Arg-Gln-Arg-Cha-NH₂ compound No. 363:
Ac-[Glu23, D-Pro24, Iva25, Pya(4)26,
Cha27,36, Leu(Me)28, Lys30, Aib31]-PYY(23-36)
Ac-Glu-D-Pro-Iva-Pya(4)-Cha-Leu(Me)-Asn-Lys-Aib-
Thr-Arg-Gln-Arg-Cha-NH₂ compound No. 364:
Carbamoyl-[D-Hyp24, Iva25, Pya(4)26,
Cha27,36, Leu(Me)28, Lys30, Aib31]-PYY(23-36)
Carbamoyl-Ser-D-Hyp-Iva-Pya(4)-Cha-Leu(Me)-Asn-
Lys-Aib-Thr-Arg-Gln-Arg-Cha-NH₂ compound No. 365:
4-Imidazolecarbonyl-[D-Pro24,
Iva25, Pya(4)26, Cha27,36, Leu(Me)28, Lys(Ac)30,
Aib31]-PYY(23-36)
4-Imidazolecarbonyl-Ser-D-Pro-Iva-Pya(4)-Cha-Leu
(Me)-Asn-Lys(Ac)-Aib-Thr-Arg-Gln-Arg-Cha-NH₂

-continued

```
compound No. 366:
4-Imidazolecarbonyl-[D-Pro24, Pya(4)26,
Cha27,36, Iva28, Lys30, Aib31]-PYY(23-36)
4-Imidazolecarbonyl-Ser-D-Pro-Arg-Pya(4)-Cha-Iva-
Asn-Lys-Aib-Thr-Arg-Gln-Arg-Cha-NH2 compound No. 367:
4-Imidazolecarbonyl-[D-Hyp24,
Iva25, Pya(4)26, Cha27,36, Leu(Me)28, Har30,
Aib31]-PYY(23-36)
4-Imidazolecarbonyl-Ser-D-Hyp-Iva-Pya(4)-Cha-Leu
(Me)-Asn-Har-Aib-Thr-Arg-Gln-Arg-Cha-NH2 compound No. 368:
                                      (SEQ ID NO: 174)
4-Imidazolecarbonyl-[Aib24,31, Iva25, Pya(4)26,
Cha27,36, Leu(Me)28, Lys(Ac)30]-PYY(23-36)
4-Imidazolecarbonyl-Ser-Aib-Iva-Pya(4)-Cha-Leu
(Me)-Asn-Lys(Ac)-Aib-Thr-Arg-Gln-Arg-Cha-NH2 compound No. 369:
4-Imidazolecarbonyl-[D-Hyp24,
Iva25, Pya(4)26, Cha27,36, Leu(Me)28, Lys(Ac)30,
D-Iva31]-PYY(23-36)
4-Imidazolecarbonyl-Ser-D-Hyp-Iva-Pya(4)-Cha-Leu
(Me)-Asn-Lys(Ac)-D-Iva-Thr-Arg-Gln-Arg-Cha-NH2 compound No. 370:
4-Imidazolecarbonyl-[D-Hyp24, Pya(4)26,
Cha27,36, Leu(Me)28, Lys30, Aib31]-PYY(23-36)
4-Imidazolecarbonyl-Ser-D-Hyp-Arg-Pya(4)-Cha-Leu
(Me)-Asn-Lys-Aib-Thr-Arg-Gln-Arg-Cha-NH2 compound No. 371:
4-Imidazolecarbonyl-[D-Pro24, Pya(4)26,
Cha27,36, Iva28, Lys(Ac)30, Aib31]-PYY(23-36)
4-Imidazolecarbonyl-Ser-D-Pro-Arg-Pya(4)-Cha-Iva-
Asn-Lys(Ac)-Aib-Thr-Arg-Gln-Arg-Cha-NH2 compound No. 372:
4-Imidazolecarbonyl-[D-Hyp24, Iva25, Pya(4)26,
Cha27,36, Iva28, Lys30, D-Iva31]-PYY(23-36)
4-Imidazolecarbonyl-Ser-D-Hyp-Iva-Pya(4)-Cha-Iva-
Asn-Lys-D-Iva-Thr-Arg-Gln-Arg-Cha-NH2 compound No. 373:
[D-Hyp24, Iva25, Pya(4)26,
Cha27,36, Leu(Me)28, Lys(Ac)30, Aib31]-PYY(23-36)
Ser-D-Hyp-Iva-Pya(4)-Cha-Leu(Me)-Asn-Lys(Ac)-Aib-
Thr-Arg-Gln-Arg-Cha-NH2 compound No. 374:
4-Imidazolecarbonyl-[D-Hyp24, Pya(4)26,
Cha27,36, Iva28, Lys(Ac)30, D-Iva31]-PYY(23-36)
4-Imidazolecarbonyl-Ser-D-Hyp-Arg-Pya(4)-Cha-Iva-
Asn-Lys(Ac)-D-Iva-Thr-Arg-Gln-Arg-Cha-NH2
```

Compound (B) is
a peptide represented by the formula:

$$P^1—X^4-A23-A24-A25-A26-A27-A28-Asn-A30-A31-Thr-Arg-Gln-Arg-A36-NH_2 \text{ (SEQ ID NO: 187)} \quad (II)$$

wherein $P^1$ is acetyl, 3-carboxypropionyl, 4-imidazolecarbonyl, tetrahydro-2H-pyran-4-ylcarbonyl, 3-carboxypropylcarbamoyl, carboxymethylcarbamoyl, [(1S)-1-carboxy-3-methylbutyl]carbamoyl, tetrahydro-2H-pyran-4-ylcarbamoyl, 2-hydroxyethyl, glycoloyl, 2-methylbutanoyl, isobutanoyl, 4-pyridinecarbonyl, morpholinocarbonyl, (cis-2,6-dimethylmorpholin-4-yl)carbonyl, piperidinocarbonyl, 2-carboxyethylcarbamoyl, 1,3-dihydroxypropan-2-ylcarbamoyl, 5-carboxypentylcarbamoyl, tetrahydro-2H-pyran-4-ylmethylcarbamoyl, carbamoylmethylcarbamoyl, [(1S)-1-carboxy-2-hydroxyethyl]carbamoyl, [(1S)-1-carboxy-2-(4-hydroxyphenyl)ethyl]carbamoyl, benzoyl, D-pyroglutamyl, carbamoyl, or amidino(preferably, acetyl, 3-carboxypropionyl, 4-imidazolecarbonyl, Thp(4)-CO, CC(GABA), CC(Gly), CC(Leu), Thp(4)-NHCO, 2-hydroxyethyl, glycoloyl, 2-methylbutanoyl, isobutanoyl, 4-pyridinecarbonyl, morpholinocarbonyl, (cis-2,6-dimethylmorpholin-4-yl)carbonyl, piperidinocarbonyl, CC(β-Ala), 1,3-dihydroxypropan-2-ylcarbamoyl, CC(Acp), Thp(4)-CH$_2$NHCO, NH$_2$—CC(Gly), CC(Ser), or CC(Tyr);

more preferably acetyl, 3-carboxypropionyl, 4-imidazolecarbonyl, Thp(4)-CO, CC(GABA), CC(Gly), CC(Leu), or Thp(4)-NHCO);

$X^4$ shows
(1) a bond, or
(2) any amino acid residue(s) bound continuously or discontinuously to each other from the C-terminal of the 1st-22nd amino acid of the amino acid sequence shown by SEQ ID NO:1 (preferably, a bond);

A23 is Ser, Glu, Gln, Arg, Acp, Thr, or Asp (preferably, Ser, Glu, Gln, Arg, Acp or Thr; more preferably, Ser, or Glu);

A24 is D-Pro, D-Hyp, Aib, D-Iva, Iva, β-Ala, DL-β-HOAla, Aipe, or Ambz(4) (preferably, D-Pro, D-Hyp, Aib, D-Iva, Iva, or β-Ala; more preferably, D-Pro or D-Hyp);

A25 is Iva, Arg, Nle, Arg(Me), Ala(4Pip), Cit, Aib, Nar, Lys(Ac), or Har (preferably, Iva, Arg, Nle, Arg(Me), Ala(4Pip), Cit, or Aib; more preferably, Iva, Arg or Nle);

A26 is Pya(4), His, Abu, Ala(4Pip), Phe, Pya(2), Cha, Gln, or Aib (preferably, Pya(4), His, Abu, Ala(4Pip), Phe, Pya(2), or Cha; more preferably, Pya(4), or His);

A27 is Cha, Nal(2), Phe(4F), Nal(1), or Ala(4Pip) (preferably, Cha);

A28 is Aib, Iva, Leu(Me), Cha, α-MePhe, or D-Iva (preferably, Aib, Iva, or Leu(Me));

A30 is Lys, Har, Arg(Me), Ala(4Pip), Cha, Lys(Me), Orn, Lys(Ac), Arg, Leu, Nle, Cit, Lys(Hexyl), Trp, Hse, or Thr (preferably, Lys, Har, Arg(Me), Ala(4Pip), Cha, Lys(Me), or Orn;

more preferably, Lys, Har, Arg(Me), or Ala(4Pip); further preferably, Lys);

A31 is Aib, D-Iva, or Iva (preferably, Aib); and

A36 is Cha, Phe(2,6-Me$_2$), Phe(3Me), or Phe(2Me) (preferably, Cha), or a salt thereof.

Examples of the "amino acid residue(s) bound continuously or discontinuously to each other from C-terminal of the 1-22nd amino acid of the amino acid sequence shown by SEQ ID NO:1" for $X^4$ include (1) Ala- (2) Tyr-Ala- (3) Tyr-Tyr-Ala- (4) Arg-Tyr-Tyr-Ala- (SEQ ID NO: 131)

(5) Asn-Arg-Tyr-Tyr-Ala- (SEQ ID NO: 132)

(6) Leu-Asn-Arg-Tyr-Tyr-Ala- (SEQ ID NO: 133)

(7) Glu-Leu-Asn-Arg-Tyr-Tyr-Ala- (SEQ ID NO: 134)

(8) Glu-Glu-Leu-Asn-Arg-Tyr-Tyr-Ala- (SEQ ID NO: 135)

(9) Pro-Glu-Glu-Leu-Asn-Arg-Tyr-Tyr-Ala- (SEQ ID NO: 136)

(10) Ser-Pro-Glu-Glu-Leu-Asn-Arg-Tyr-Tyr-Ala- (SEQ ID NO: 137)

(11) Ala-Ser-Pro-Glu-Glu-Leu-Asn-Arg-Tyr-Tyr-Ala- (SEQ ID NO: 138)

-continued

(12) Asp-Ala-Ser-Pro-Glu-Glu-Leu-Asn-Arg-Tyr-Tyr-Ala- (SEQ ID NO: 139)

(13) Glu-Asp-Ala-Ser-Pro-Glu-Glu-Leu-Asn-Arg-Tyr-Tyr-Ala- (SEQ ID NO: 140)

(14) Gly-Glu-Asp-Ala-Ser-Pro-Glu-Glu-Leu-Asn-Arg-Tyr-Tyr-Ala- (SEQ ID NO: 141)

(15) Pro-Gly-Glu-Asp-Ala-Ser-Pro-Glu-Glu-Leu-Asn-Arg-Tyr-Tyr-Ala- (SEQ ID NO: 142)

(16) Ala-Pro-Gly-Glu-Asp-Ala-Ser-Pro-Glu-Glu-Leu-Asn-Arg-Tyr-Tyr-Ala- (SEQ ID NO: 143)

(17) Glu-Ala-Pro-Gly-Glu-Asp-Ala-Ser-Pro-Glu-Glu-Leu-Asn-Arg-Tyr-Tyr-Ala- (SEQ ID NO: 144)

(18) Pro-Glu-Ala-Pro-Gly-Glu-Asp-Ala-Ser-Pro-Glu-Glu-Leu-Asn-Arg-Tyr-Tyr-Ala- (SEQ ID NO: 145)

(19) Lys-Pro-Glu-Ala-Pro-Gly-Glu-Asp-Ala-Ser-Pro-Glu-Glu-Leu-Asn-Arg-Tyr-Tyr-Ala- (SEQ ID NO: 146)

(20) Ile-Lys-Pro-Glu-Ala-Pro-Gly-Glu-Asp-Ala-Ser-Pro-Glu-Glu-Leu-Asn-Arg-Tyr-Tyr-Ala- (SEQ ID NO: 147)

(21) Pro-Ile-Lys-Pro-Glu-Ala-Pro-Gly-Glu-Asp-Ala-Ser-Pro-Glu-Glu-Leu-Asn-Arg-Tyr-Tyr-Ala- (SEQ ID NO: 148)

(22) Tyr-Pro-Ile-Lys-Pro-Glu-Ala-Pro-Gly-Glu-Asp-Ala-Ser-Pro-Glu-Glu-Leu-Asn-Arg-Tyr-Tyr-Ala- (SEQ ID NO: 149)

and the like.

Preferable examples of compound (B) include the following peptides and salts thereof.

[Compound (B)-1]

A peptide represented by the formula:

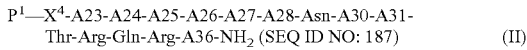
$P^1$—$X^4$-A23-A24-A25-A26-A27-A28-Asn-A30-A31-Thr-Arg-Gln-Arg-A36-NH$_2$ (SEQ ID NO: 187) (II)

wherein
$P^1$ is acetyl, 3-carboxypropionyl, 4-imidazolecarbonyl, Thp(4)-CO, CC(GABA), CC(Gly), CC(Leu), Thp(4)-NHCO, 2-hydroxyethyl, glycoloyl, 2-methylbutanoyl, isobutanoyl, 4-pyridinecarbonyl, morpholinocarbonyl, (cis-2,6-dimethyl-morpholin-4-yl)carbonyl, piperidinocarbonyl, CC(β-Ala), 1,3-dihydroxypropan-2-ylcarbamoyl, CC(Acp), Thp(4)-CH$_2$NHCO, NH$_2$—CC(Gly), CC(Ser), or CC(Tyr);
$X^4$ is a bond;
A23 is Ser, Glu, Gln, Arg, Acp, or Thr;
A24 is D-Pro, D-Hyp, Aib, D-Iva, Iva, or β-Ala;
A25 is Iva, Arg, Nle, Arg(Me), Ala(4Pip), Cit, or Aib;
A26 is Pya(4), His, Abu, Ala(4Pip), Phe, Pya(2), or Cha;
A27 is Cha, Nal(2), Phe(4F), Nal(1), or Ala(4Pip);
A28 is Aib, Iva, Leu(Me), Cha, α-MePhe, or D-Iva;
A30 is Lys, Har, Arg(Me), Ala(4Pip), Cha, Lys(Me), or Orn;
A31 is Aib, D-Iva, or Iva; and
A36 is Cha, Phe(2,6-Me$_2$), Phe(3Me), or Phe(2Me), or a salt thereof.

[Compound (B)-2]

A peptide represented by the formula:

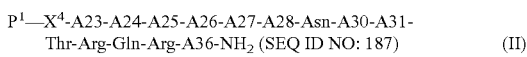
$P^1$—$X^4$-A23-A24-A25-A26-A27-A28-Asn-A30-A31-Thr-Arg-Gln-Arg-A36-NH$_2$ (SEQ ID NO: 187) (II)

wherein
$P^1$ is acetyl, 3-carboxypropionyl, 4-imidazolecarbonyl, Thp(4)-CO, CC(GABA), CC(Gly), CC(Leu), Thp(4)-NHCO, 2-hydroxyethyl, glycoloyl, 2-methylbutanoyl, isobutanoyl, 4-pyridinecarbonyl, morpholinocarbonyl, (cis-2,6-dimethyl-morpholin-4-yl)carbonyl, piperidinocarbonyl, CC(β-Ala), 1,3-dihydroxypropan-2-ylcarbamoyl, CC(Acp), Thp(4)-CH$_2$NHCO, NH$_2$—CC(Gly), CC(Ser), or CC(Tyr);
$X^4$ is a bond;
A23 is Ser, Glu, Gln, Arg, Acp, or Thr;
A24 is D-Pro, D-Hyp, Aib, D-Iva, Iva, or β-Ala;
A25 is Iva, Arg, Nle, Arg(Me), Ala(4Pip), Cit, or Aib;
A26 is Pya(4), His, Abu, Ala(4Pip), Phe, Pya(2), or Cha;
A27 is Cha, Nal(2), Phe(4F), Nal(1), or Ala(4Pip);
A28 is Aib, Iva, Leu(Me), Cha, α-MePhe, or D-Iva;
A30 is Lys, Har, Arg(Me), or Ala(4Pip);
A31 is Aib, D-Iva, or Iva; and
A36 is Cha, Phe(2,6-Me$_2$), Phe(3Me), or Phe(2Me), or a salt thereof.

[Compound (B)-3]

A peptide represented by the formula:

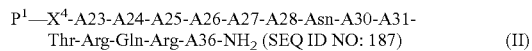
$P^1$—$X^4$-A23-A24-A25-A26-A27-A28-Asn-A30-A31-Thr-Arg-Gln-Arg-A36-NH$_2$ (SEQ ID NO: 187) (II)

wherein $P^1$ is acetyl, 3-carboxypropionyl, 4-imidazolecarbonyl, Thp(4)-CO, CC(GABA), CC(Gly), CC(Leu), or Thp(4)-NHCO;
$X^4$ is a bond;
A23 is Ser, or Glu;
A24 is D-Pro, or D-Hyp;
A25 is Iva, Arg, or Nle;
A26 is Pya(4), or His;
A27 is Cha;
A28 is Aib, Iva, or Leu(Me);
A30 is Lys;
A31 is Aib; and
A36 is Cha,
or a salt thereof.

[Compound (B)-4]

Ac-Ser-D-Pro-Arg-Pya(4)-Cha-Aib-Asn-Lys-Aib-Thr-Arg-Gln-Arg-Cha-NH$_2$ (compound No. 138),
Ac-Glu-D-Pro-Arg-Pya(4)-Cha-Leu(Me)-Asn-Lys-Aib-Thr-Arg-Gln-Arg-Cha-NH$_2$ (compound No. 169),
Ac-Ser-D-Hyp-Arg-Pya(4)-Cha-Aib-Asn-Lys-Aib-Thr-Arg-Gln-Arg-Cha-NH$_2$ (compound No. 207),
3-Carboxypropionyl-Ser-D-Pro-Arg-Pya(4)-Cha-Aib-Asn-Lys-Aib-Thr-Arg-Gln-Arg-Cha-NH$_2$ (compound No. 217),
Ac-Ser-D-Pro-Nle-Pya(4)-Cha-Aib-Asn-Lys-Aib-Thr-Arg-Gln-Arg-Cha-NH$_2$ (compound No. 224),
Thp(4)-NHCO-Ser-D-Pro-Arg-His-Cha-Leu(Me)-Asn-Lys-Aib-Thr-Arg-Gln-Arg-Cha-NH$_2$ (compound No. 229),
Thp(4)-NHCO-Glu-D-Pro-Arg-His-Cha-Cha-Asn-Lys-Aib-Thr-Arg-Gln-Arg-Cha-NH$_2$ (compound No. 230),
Ac-Ser-D-Pro-Arg-Pya(4)-Cha-Iva-Asn-Lys-Aib-Thr-Arg-Gln-Arg-Cha-NH$_2$ (compound No. 233),
Ac-Ser-D-Pro-Iva-Pya(4)-Cha-Aib-Asn-Lys-Aib-Thr-Arg-Gln-Arg-Cha-NH$_2$ (compound No. 237),
CC(Leu)-Ser-D-Pro-Arg-His-Cha-Leu(Me)-Asn-Lys-Aib-Thr-Arg-Gln-Arg-Cha-NH$_2$ (compound No. 253),
Ac-Ser-D-Pro-Arg-Pya(4)-Cha-Aib-Asn-Nle-Aib-Thr-Arg-Gln-Arg-Cha-NH$_2$ (compound No. 267),
Thp(4)-NHCO-Ser-D-Pro-Arg-Pya(4)-Cha-Aib-Asn-Lys-Aib-Thr-Arg-Gln-Arg-Cha-NH$_2$ (compound No. 270),
CC(Leu)-Ser-D-Pro-Arg-Pya(4)-Cha-Aib-Asn-Lys-Aib-Thr-Arg-Gln-Arg-Cha-NH$_2$ (compound No. 271),
Thp(4)-NHCO-Glu-D-Pro-Arg-Pya(4)-Cha-Aib-Asn-Lys-Aib-Thr-Arg-Gln-Arg-Cha-NH$_2$ (compound No. 292),
CC(Gly)-Ser-D-Pro-Arg-Pya(4)-Cha-Aib-Asn-Lys-Aib-Thr-Arg-Gln-Arg-Cha-NH$_2$ (compound No. 287),
CC(GABA)-Ser-D-Pro-Arg-Pya(4)-Cha-Aib-Asn-Lys-Aib-Thr-Arg-Gln-Arg-Cha-NH$_2$ (compound No. 293),
Ac-Ser-D-Pro-Iva-Pya(4)-Cha-Leu(Me)-Asn-Lys-Aib-Thr-Arg-Gln-Arg-Cha-NH$_2$ (compound No. 295), Ac-Ser-D-Hyp-Iva-Pya(4)-Cha-Aib-Asn-Lys-Aib-Thr-Arg-Gln-Arg-Cha-NH$_2$ (compound No. 297),
Ac-Ser-D-Hyp-Iva-Pya(4)-Cha-Iva-Asn-Lys-Aib-Thr-Arg-Gln-Arg-Cha-NH$_2$ (compound No. 298),
4-Imidazolecarbonyl-Ser-D-Hyp-Iva-Pya(4)-Cha-Aib-Asn-Lys-Aib-Thr-Arg-Gln-Arg-Cha-NH$_2$ (compound No. 299),
Thp(4)-CO-Ser-D-Pro-Arg-Pya(4)-Cha-Aib-Asn-Lys-Aib-Thr-Arg-Gln-Arg-Cha-NH$_2$ (compound No. 324),
CC(GABA)-Ser-D-Pro-Iva-Pya(4)-Cha-Aib-Asn-Lys-Aib-Thr-Arg-Gln-Arg-Cha-NH$_2$ (compound No. 328),
Thp(4)-NHCO-Ser-D-Pro-Iva-Pya(4)-Cha-Aib-Asn-Lys-Aib-Thr-Arg-Gln-Arg-Cha-NH$_2$ (compound No. 330),
4-Imidazolecarbonyl-Ser-D-Hyp-Iva-Pya(4)-Cha-Leu(Me)-Asn-Lys-Aib-Thr-Arg-Gln-Arg-Cha-NH$_2$ (compound No. 336),
Thp(4)-CO-Ser-D-Pro-Iva-Pya(4)-Cha-Aib-Asn-Lys-Aib-Thr-Arg-Gln-Arg-Cha-NH$_2$ (compound No. 342),
CC(GABA)-Ser-D-Hyp-Iva-Pya(4)-Cha-Leu(Me)-Asn-Lys-Aib-Thr-Arg-Gln-Arg-Cha-NH$_2$ (compound No. 349),
3-Carboxypropionyl-Ser-D-Hyp-Iva-Pya(4)-Cha-Leu(Me)-Asn-Lys-Aib-Thr-Arg-Gln-Arg-Cha-NH$_2$ (compound No. 350) or a salt thereof.
[Compound (B)-5]
Ac-Ser-D-Pro-Arg-Pya(4)-Cha-Iva-Asn-Lys-Aib-Thr-Arg-Gln-Arg-Cha-NH$_2$ (compound No. 233) or a salt thereof.
Thp(4)-NHCO-Ser-D-Pro-Arg-Pya(4)-Cha-Aib-Asn-Lys-Aib-Thr-Arg-Gln-Arg-Cha-NH$_2$ (compound No. 270) or a salt thereof.
Thp(4)-NHCO-Glu-D-Pro-Arg-Pya(4)-Cha-Aib-Asn-Lys-Aib-Thr-Arg-Gln-Arg-Cha-NH$_2$ (compound No. 282) or a salt thereof.
CC(Gly)-Ser-D-Pro-Arg-Pya(4)-Cha-Aib-Asn-Lys-Aib-Thr-Arg-Gln-Arg-Cha-NH$_2$ (compound No. 287) or a salt thereof.
Ac-Ser-D-Hyp-Iva-Pya(4)-Cha-Iva-Asn-Lys-Aib-Thr-Arg-Gln-Arg-Cha-NH$_2$ (compound No. 298) or a salt thereof.
4-Imidazolecarbonyl-Ser-D-Hyp-Iva-Pya(4)-Cha-Leu(Me)-Asn-Lys-Aib-Thr-Arg-Gln-Arg-Cha-NH$_2$ (compound No. 336) or a salt thereof.
Thp(4)-CO-Ser-D-Pro-Iva-Pya(4)-Cha-Aib-Asn-Lys-Aib-Thr-Arg-Gln-Arg-Cha-NH$_2$ (compound No. 342) or a salt thereof.
CC(GABA)-Ser-D-Hyp-Iva-Pya(4)-Cha-Leu(Me)-Asn-Lys-Aib-Thr-Arg-Gln-Arg-Cha-NH$_2$ (compound No. 349) or a salt thereof.
[Compound (B)-6]
Thp(4)-NHCO-Ser-D-Pro-Arg-Pya(4)-Cha-Aib-Asn-Lys-Aib-Thr-Arg-Gln-Arg-Cha-NH$_2$ (compound No. 270) or a salt thereof.
Ac-Ser-D-Hyp-Iva-Pya(4)-Cha-Iva-Asn-Lys-Aib-Thr-Arg-Gln-Arg-Cha-NH$_2$ (compound No. 298) or a salt thereof.
4-Imidazolecarbonyl-Ser-D-Hyp-Iva-Pya(4)-Cha-Leu(Me)-Asn-Lys-Aib-Thr-Arg-Gln-Arg-Cha-NH$_2$ (compound No. 336) or a salt thereof.
CC(GABA)-Ser-D-Hyp-Iva-Pya(4)-Cha-Leu(Me)-Asn-Lys-Aib-Thr-Arg-Gln-Arg-Cha-NH$_2$ (compound No. 349) or a salt thereof.

Compound (A) and compound (B) (hereinafter to be sometimes abbreviated as compound (I)) can be produced according to a peptide synthesis method known per se. The method of peptide synthesis may be any of, for example, a solid phase synthesis process and a liquid phase synthesis process. That is, the object peptide can be produced by repeating condensation of a partial peptide or amino acid capable of constituting compound (I) and the remaining portion according to a desired sequence. When a product having the desirable sequence has a protecting group, the object peptide can be produced by eliminating a protecting group. Examples of the condensing method and eliminating method of a protecting group to be known include methods described in the following (1)-(5).
(1) M. Bodanszky and M. A. Ondetti: Peptide Synthesis, Interscience Publishers, New York (1966)
(2) Schroeder and Luebke: The Peptide, Academic Press, New York (1965)
(3) Nobuo Izumiya, et al.: Peptide Gosei-no-Kiso to Jikken (Basics and experiments of peptide synthesis), published by Maruzen Co. (1975)
(4) Haruaki Yajima and Shunpei Sakakibara: Seikagaku Jikken Koza (Biochemical Experiment) 1, Tanpakushitsu no Kagaku (Chemistry of Proteins) IV, 205 (1977)
(5) Haruaki Yajima, ed.: Zoku Iyakuhin no Kaihatsu (A sequel to Development of Pharmaceuticals), Vol. 14, Peptide Synthesis, published by Hirokawa Shoten.

After the reaction, the peptide of the present invention can be purified and isolated using conventional methods of purification, such as solvent extraction, distillation, column chromatography, liquid chromatography, recrystallization, etc., in combination thereof. When the peptide obtained by the above-mentioned method is in a free form, it can be converted to a suitable salt by a known method; conversely, when the peptide is obtained in the form of a salt, the salt can be converted to a free form or other salt by a known method.

The starting compound may also be a salt. Examples of such salt include those exemplified as salts of compound (I) mentioned below.

For condensation of protected amino acid or peptide, various activation reagents usable for peptide synthesis can be used, which are particularly preferably trisphosphonium salts, tetramethyluronium salts, carbodiimides and the like. Examples of the trisphosphonium salt include benzotriazol-1-yloxytris(pyrrolizino)phosphoniumhexafluorophosphate (PyBOP), bromotris(pyrrolizino)phosphoniumhexafluorophosphate (PyBroP), 7-azabenzotriazol-1-yloxytris(pyrrolizino)phosphoniumhexafluorophosphate (PyAOP), examples of the tetramethyluronium salt include 2-(1H-benzotriazol-1-yl)-1,1,3,3-hexafluorophosphate (HBTU), 2-(7-azabenzotriazol-1-yl)-1,1,3,3-hexafluorophosphate (HATU), 2-(1H-benzotriazol-1-yl)-1,1,3,3-tetramethyluroniumtetrafluoroborate (TBTU), 2-(5-norbornane-2,3-dicarboxylmide)-1,1,3,3-tetramethyluroniumtetrafluoroborate (TNTU), O—(N-succimidyl)-1,1,3,3-tetramethyluroniumtetrafluoroborate (TSTU), and examples of the carbodiimide include DCC, N,N'-diisopropylcarbodiimide (DIPCDI), N-ethyl-N'-(3-dimethylaminopropyl)carbodiimide hydrochloride (EDCI.HCl) and the like. For condensation using these, addition of a racemization inhibitor (e.g., HONB, HOBt, HOAt, HOOBt etc.) is preferable. A solvent to be used for the condensation can be appropriately selected from those known to be usable for peptide condensation reaction. For example, acid amides such as anhydrous or water-containing N,N-dimethylformamide, N,N-dimethylacetamide, N-methylpyrrolidone and the like, halogenated hydrocarbons such as methylene chloride, chloroform and the like, alcohols such as trifluoroethanol, phenol and the like, sulfoxides such as dimethylsulfoxide and the like, tertiary amines such as pyridine and the like, ethers such as dioxane, tetrahydrofuran and the like, nitriles such as acetonitrile, propionitrile and the like, esters such as methyl acetate, ethyl acetate and the like, an appropriate mixture of these and the like can be used. Reaction temperature is appropriately selected from the range known to be usable for peptide binding reactions, and is normally selected from the range of about −20° C. to 50° C. An activated amino acid derivative is normally used from 1.5 to 6 times in excess. In phase synthesis, when a test using the ninhydrin reaction reveals that the condensation is insufficient, sufficient condensation can be conducted by repeating the condensation reaction without elimination of protecting groups. If the condensation is yet insufficient even after repeating the reaction, unreacted amino acids can be acylated with acetic anhydride, acetylimidazole or the like so that an influence on the subsequent reactions can be avoided.

Examples of the protecting groups for the amino groups of the starting amino acid include Z, Boc, tert-pentyloxycarbonyl, isobornyloxycarbonyl, 4-methoxybenzyloxycarbonyl, Cl—Z, Br—Z, adamantyloxycarbonyl, trifluoroacetyl, phthaloyl, formyl, 2-nitrophenylsulphenyl, diphenylphosphinothioyl, Fmoc, trityl and the like.

Examples of the carboxyl-protecting group for the starting amino acid include allyl, 2-adamantyl, 4-nitrobenzyl, 4-methoxybenzyl, 4-chlorobenzyl, phenacyl and benzyloxycarbonylhydrazide, tert-butoxycarbonylhydrazide, tritylhydrazide and the like, in addition to the above-mentioned $C_{1-6}$ alkyl group, $C_{3-10}$ cycloalkyl group, $C_{7-14}$ aralkyl group.

The hydroxyl group of serine or threonine can be protected, for example, by esterification or etherification. Examples of the group suitable for the esterification include lower ($C_{2-4}$) alkanoyl groups such as an acetyl group and the like, aroyl groups such as a benzoyl group and the like, and the like, and a group derived from an organic acid and the like. In addition, examples of the group suitable for etherification include benzyl, tetrahydropyranyl, tert-butyl($Bu^t$), trityl(Trt) and the like.

Examples of the protecting group for the phenolic hydroxyl group of tyrosine include Bzl, 2,6-dichlorobenzyl, 2-nitrobenzyl, Br—Z, tert-butyl and the like.

Examples of the protecting group for the imidazole of histidine include Tos, 4-methoxy-2,3,6-trimethylbenzenesulfonyl (Mtr), DNP, Bom, Bum, Boc, Trt, Fmoc and the like.

Examples of the protecting group for the guanidino group of arginine include Tos, Z, 4-methoxy-2,3,6-trimethylbenzenesulfonyl (Mtr), p-methoxybenzenesulfonyl (MBS), 2,2,5,7,8-pentamethylchromane-6-sulfonyl (Pmc), mesitylene-2-sulfonyl (Mts), 2,2,4,6,7-pentamethyldihydrobenzofuran-5-sulfonyl (Pbf), Boc, Z, $NO_2$ and the like.

Examples of the protecting group for a side chain amino group of lysine include Z, Cl—Z, trifluoroacetyl, Boc, Fmoc, Trt, Mtr, 4,4-dimethyl-2,6-dioxocyclohexylideneyl (Dde) and the like.

Examples of the protecting group for indolyl of tryptophan include formyl (For), Z, Boc, Mts, Mtr and the like.

Examples of the protecting group for asparagine and glutamine include Trt, xanthyl (Xan), 4,4'-dimethoxybenzhydryl (Mbh), 2,4,6-trimethoxybenzyl (Tmob) and the like.

Examples of activated carboxyl groups in the starting material include corresponding acid anhydride, azide, active esters [ester with alcohol (e.g., pentachlorophenol, 2,4,5-trichlorophenol, 2,4-dinitrophenol, cyanomethylalcohol, paranitrophenol, HONB, N-hydroxysuccimide, 1-hydroxybenzotriazole (HOBt), 1-hydroxy-7-azabenzotriazole (HOAt))] and the like. Examples of the activated amino group in the starting material include corresponding phosphorous amide.

Examples of the method for removing (eliminating) a protecting group include a catalytic reduction in a hydrogen stream in the presence of a catalyst such as Pd-black or Pd-carbon; an acid treatment using anhydrous hydrogen fluoride, methanesulfonic acid, trifluoromethanesulfonic acid, trifluoroacetate, trimesylsilyl bromide (TMSBr), trimethylsilyl trifluoromethanesulfonate, tetrafluoroboric acid, tris(trifluoro)boric acid, boron tribromide, or a mixture solution thereof; a base treatment using diisopropylethylamine, triethylamine, piperidine, piperazine or the like; and reduction with sodium in liquid ammonia, and the like. The elimination reaction by the above-described acid treatment is generally carried out at a temperature of −20° C. to 40° C.; the acid treatment is efficiently conducted by adding a cation scavenger such as anisole, phenol, thioanisole, metacresol and paracresol; dimethylsulfide, 1,4-butanedithiol, 1,2-ethanedithiol and the like. Also, a 2,4-dinitrophenyl group used as a protecting group of the imidazole of histidine is removed by thiophenol treatment; a formyl group used as a protecting group of the indole of tryptophan is removed by deprotection by acid treatment in the presence of 1,2-ethanedithiol, 1,4-butanedithiol, or the like, as well as by alkali treatment with dilute sodium hydroxide, dilute ammonia, or the like.

Protection of a functional group that should not be involved in the reaction of a starting material and a protecting group, elimination of the protecting group, activation of a functional group involved in the reaction and the like can be appropriately selected from known protecting groups and known means.

In a method of preparing an amide of the peptide, it is formed by a solid phase synthesis using a resin for amide synthesis, or the α-carboxyl group of the carboxy terminal amino acid is amidated, and a peptide chain is elongated to a desired chain length toward the amino group side, thereafter a peptide wherein the protecting group for the N terminal α-amino group of the peptide chain only removed and a peptide wherein the protecting group for the C terminal carboxyl group only removed of the peptide chain are prepared, and the both peptides are condensed in a mixed solvent described above. For details about the condensation reaction, the same as above applies. After the protected peptide obtained by the condensation is purified, all protecting groups can be removed by the above-described method to yield a desired crude polypeptide. By purifying this crude peptide using various publicly known means of purification, and freeze-drying the main fraction, a desired amide of the peptide can be prepared.

Compound (I) can be chemically modified according to a method known per se and using polyethylene glycol, alkyl chain and the like. For example, chemically modified compound (I) can be produced by conjugatedly binding polyethylene glycol, alkyl chain and the like to Cys residue, Asp residue, Glu residue, Lys residue and the like of compound (I).

Examples of polyethylene glycol usable for chemical modification of compound (I) include polyethylene glycol having a molecular weight of 1-1000 kDa. Examples of the alkyl chain usable for chemical modification of compound (I) include alkyl chain with a carbon number of 1-50.

Compound (I) and polyethylene glycol or alkyl chain may be bonded via a linker.

When the compound (I) is present as a configurational isomer such as enantiomer, diastereomer etc., a conformer or the like, they are also encompassed in compound (I) and each can be isolated by a means known per se or the above separation and purification methods on demand. In addition, when the compound (I) is in the form of a racemate, it can be separated into S- and R-forms by conventional optical resolution.

When the compound (I) includes stereoisomers, both the isomers alone and mixtures of each isomers are also encompassed in compound (I).

In addition, the compound (I) may be a solvate (e.g., hydrate) or a non-solvate (e.g., non-hydrate).

The compound (I) may be labeled with an isotope (e.g., $^3$H, $^{14}$C, $^{35}$S, $^{125}$I) or the like.

Furthermore, compound (I) may be a deuterium conversion form wherein $^1H$ is converted to $^2H(D)$.

For the peptides mentioned herein, the left end is the N terminal (amino terminal) and the right end is the C teiminal (carboxyl terminal) in accordance with the conventional peptide marking. The C terminal of peptide may be any of an amide (—CONH$_2$), a carboxyl group (—COOH), a carboxylate (—COO$^-$), an alkylamide (—CONHR$^a$), and an ester (—COOR$^a$). Particularly, amide (—CONH$_2$) is preferable. Here, as R$^a$ in the ester or alkylamide, a C$_{1-6}$ alkyl group such as methyl, ethyl, n-propyl, isopropyl, n-butyl etc.; a C$_{3-10}$ cycloalkyl group such as cyclopentyl, cyclohexyl etc.; a C$_{6-12}$ aryl group such as phenyl, α-naphthyl etc.; a phenyl-C$_{1-2}$ alkyl group such as benzyl, phenethyl, benzhydryl, etc.; a C$_{7-14}$ aralkyl group such as an α-naphthyl-C$_{1-2}$ alkyl group such as α-naphthylmethyl etc.; a pivaloyloxymethyl group widely used as oral ester; and the like are used.

Compound (I) may be in a salt form. Examples of such salt include metal salts, ammonium salts, salts with organic base, salts with inorganic acid, salts with organic acid, salts with basic or acidic amino acid, and the like. Preferable examples of the metal salt include alkali metal salts such as sodium salt, potassium salt and the like; alkaline earth metal salts such as calcium salt, magnesium salt, barium salt and the like; aluminum salt and the like. Preferable examples of the salt with organic base include salts with trimethylamine, triethylamine, pyridine, picoline, 2,6-lutidine, ethanolamine, diethanolamine, triethanolamine, cyclohexylamine, dicyclohexylamine, N,N-dibenzylethylenediamine and the like. Preferable examples of the salt with inorganic acid include salts with hydrochloric acid, hydrobromic acid, nitric acid, sulfuric acid, phosphoric acid and the like. Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salt with basic amino acid include salts with arginine, lysine, ornithine and the like. Preferable examples of the salt with acidic amino acid include salts with aspartic acid, glutamic acid and the like.

Of these, a pharmaceutically acceptable salt is preferable. For example, when a compound has an acidic functional group, an inorganic salt such as alkali metal salt (e.g., sodium salt, potassium salt etc.), alkaline earth metal salt (e.g., calcium salt, magnesium salt, barium salt etc.) and the like, ammonium salt etc., and when a compound has a basic functional group, for example, a salt with inorganic acid such as hydrochloric acid, hydrobromic acid, nitric acid, sulfuric acid, phosphoric acid and the like, or a salt with organic acid such as acetic acid, phthalic acid, fumaric acid, oxalic acid, tartaric acid, maleic acid, citric acid, succinic acid, methanesulfonic acid, p-toluenesulfonic acid and the like are preferable.

A prodrug of compound (I) means a compound which is converted to compound (I) with a reaction due to an enzyme, gastric acid, etc. under the physiological condition in the living body, that is, a compound which is converted to compound (I) with oxidation, reduction, hydrolysis, etc. according to an enzyme; a compound which is converted to compound (I) by hydrolysis etc. due to gastric acid, etc.

Examples of a prodrug of compound (I) include a compound wherein an amino group of compound (I) is acylated, alkylated or phosphorylated (e.g., compound wherein amino group of compound (I) is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated or tert-butylated, and the like); a compound wherein a hydroxy group of compound (I) is acylated, alkylated, phosphorylated or berated (e.g., a compound wherein a hydroxy group of compound (I) is acetylated, palmitoylated, propanoylated, pivaloylated, succinylated, fumarylated, alanylated or dimethylaminomethylcarbonylated, and the like); a compound wherein a carboxy group of compound (I) is esterified or amidated (e.g., a compound wherein a carboxy group of compound (I) is ethyl esterified, phenyl esterified, carboxymethyl esterified, dimethylaminomethyl esterified, pivaloyloxymethyl esterified, ethoxycarbonyloxyethyl esterified, phthalidyl esterified, (5-methyl-2-exo-1,3-dioxolen-4-yl) methyl esterified, cyclohexyloxycarbonylethyl esterified or methylamidated, and the like) and the like. These compounds can be produced from compound (I) by a method known per se.

A prodrug of compound (I) may also be one which is converted into compound (I) under a physiological condition, such as those described in IYAKUHIN no KAIHATSU (Development of Pharmaceuticals), Vol. 7, Design of Molecules, p. 163-198, Published by HIROKAWA SHOTEN (1990).

Compound (I) may be a crystal, and the crystal form of the crystal may be singular or plural. Crystals can be produced by a crystallization method known per se.

Compound (I) may be a pharmaceutically acceptable cocrystal or cocrystal salt. Here, the cocrystal or cocrystal salt means a crystalline substance consisting of two or more particular substances which are solids at room temperature, each having different physical properties (e.g., structure, melting point, heat of melting, hygroscopicity, solubility, stability etc.). The cocrystal and cocrystal salt can be produced by cocrystallization known per se.

The crystal of compound (I) is superior in physicochemical properties (e.g., melting point, solubility, stability) and biological properties (e.g., pharmacokinetics (absorption, distribution, metabolism, excretion), efficacy expression), and thus it is extremely useful as a medicament.

Compound (I) and a prodrug thereof (hereinafter to be sometimes abbreviated as the compound of the present invention) have a superior Y2 receptor agonist action.

Y2 receptor agonist transmits satiety signals to the hypothalamus via Y2 receptors. Therefore, the compound of the present invention has a feeding suppressive action, weight increase inhibitory action and the like.

In addition, Y2 receptor forms a Y receptor family together with Y1 receptor, Y4 receptor and the like. The compound of the present invention shows low affinity for Y1 receptor, Y4 receptor and the like, and shows high affinity for Y2 receptor. That is, the compound of the present invention shows a selective agonist action on Y2 receptor.

Furthermore, the compound of the present invention shows superior stability in blood.

The compound of the present invention has low toxicity (e.g., acute toxicity, chronic toxicity, genetic toxicity, reproductive toxicity, cardiac toxicity, carcinogenicity), shows a few side effects, and can be safely administered to a mammal (e.g., human, bovine, horse, dog, cat, monkey, mouse, rat) as an agent for the prophylaxis or treatment of various diseases mentioned below and the like.

The compound of the present invention can be used as a Y2 receptor agonist.

The compound of the present invention can be used as an agent for the prophylaxis or treatment of obesity.

The compound of the present invention can be used as an agent for the prophylaxis or treatment of symptomatic obesity, obesity based on simple obesity, disease state or disease associated with obesity, eating disorder and the like.

Examples of the symptomatic obesity include endocrine obesity (e.g., Cushing syndrome, hypothyroidism, insulinoma, obese type II diabetes, pseudohypoparathyroidism, hypogonadism), central obesity (e.g., hypothalamic obesity, frontal lobe syndrome, Kleine-Levin syndrome), hereditary obesity (e.g., Prader-Willi syndrome, Laurence-Moon-Biedl syndrome), drug-induced obesity (e.g., steroid, phenothiazine, insulin, sulfonylurea (SU) agent, β-blocker-induced obesity) and the like.

Examples of the disease state or disease associated with obesity include glucose tolerance disorders, diabetes (particularly type 2 diabetes, obese diabetes), lipid metabolism abnormality (hypercholesterolemia, high LDL-cholesterolemia, low HDL-cholesterolemia, postprandial hyperlipemia, hypertriglyceridemia), hypertension, cardiac failure, hyperuricemia-gout, fatty liver (including non-alchoholic steato-hepatitis), coronary heart disease (myocardial infarction, angina pectoris), cerebral infarction (brain thrombosis, transient cerebral ischemic attack), bone-articular disease (knee osteoarthritis, hip osteoarthritis, spondylitis deformans, lumbago), sleep apnea syndrome-Pickwick syndrome, menstrual disorder (abnormal menstrual cycle, abnormality of menstrual flow and cycle, amenorrhea, abnormal catamenial symptom), metabolic syndrome (disease states having 3 or more selected from hypertriglycerid(TG)emia, low HDL cholesterol(HDL-C)emia, hypertension, abdominal obesity and impaired glucose tolerance) and the like.

The compound of the present invention can also be used for secondary prevention or suppression of progression of the above-mentioned various diseases (e.g., cardiovascular events such as myocardial infarction and the like).

In addition, the compound of the present invention is also useful as a feeding suppressant and a weight increase inhibitor.

The compound of the present invention can also be used in combination with a diet therapy (e.g., diet therapy for diabetes), and an exercise therapy.

The compound of the present invention can also be used as an agent for improving or the prophylaxis or treatment of borderline type diabetes, impaired glucose tolerance, IFG (Impaired Fasting Glucose) and IFG (Impaired Fasting Glycemia). Moreover, the compound of the present invention can prevent progress of borderline type, impaired glucose tolerance, IFG (Impaired Fasting Glucose) or (IFG (Impaired Fasting Glycemia) into diabetes.

In addition, the compound of the present invention can also be used as an agent for the prophylaxis or treatment of diabetic complications [e.g., neuropathy, nephropathy, retinopathy, diabetic cardiomyopathy, cataract, macroangiopathy, osteopenia, hyperosmolar diabetic coma, infectious disease (e.g., respiratory infection, urinary tract infection, gastrointestinal infection, dermal soft tissue infections, inferior limb infection), diabetic gangrene, xerostomia, hypacusis, cerebrovascular disorder, peripheral blood circulation disorder] and the like.

A medicament containing the compound of the present invention shows low toxicity and is obtained using the compound of the present invention alone or in admixture with a pharmacologically acceptable carrier according to a method known per se generally used for production methods of pharmaceutical preparations, and safely administered orally or parenterally (e.g., topically, rectally, intravenously administered) as a pharmaceutical preparation, for example, tablets (inclusive of sugar-coated tablets, film-coated tablets, sublingual tablets, orally disintegrating tablets), powders, granules, capsules (inclusive of soft capsules, microcapsules), liquids, troches, syrups, emulsions, suspensions, injections (e.g., subcutaneous injections, intravenous injections, intramuscular injections, intraperitoneal injections etc.), external preparations (e.g., transnasal preparations, dermal preparations, ointments), suppository (e.g., rectal suppositories, vaginal suppositories), pellets, nasal preparations, pulmonary preparations (inhalants), transfusions and the like.

These preparations may be controlled release preparations such as a rapid release preparation, a sustained release preparation and the like (e.g., a sustained release microcapsule).

The content of the compound of the present invention in a pharmaceutical preparation is about 0.01-about 100 wt % of the whole preparation.

The dosage of the compound of the present invention is appropriately determined according to the subject of administration, symptom, administration method and the like. For example, when the compound of the present invention is administered orally, the daily dose for an obesity patient (body weight 60 kg) is about 0.1-100 mg, preferably about 1.0-50 mg, more preferably about 1.0-20 mg. When the compound of the present invention is administered parenterally, the daily dose for an obesity patient (body weight 60 kg) is about 0.01-30 mg, preferably about 0.1-20 mg, more preferably about 0.5-10 mg. These amounts can be administered in about 1 to several portions a day.

The compound of the present invention is formulated alone or along with a pharmacologically acceptable carrier into a preparation according to a method known per se, for example, the method described in the Japanese Pharmacopoeia, and used as a medicament.

The pharmaceutically acceptable carrier which may be used for the production of the pharmaceutical drug of the present invention may be exemplified by various organic or inorganic carrier materials that are conventionally used as preparation materials, for example, excipient, lubricant, binding agent and disintegrant for solid preparations; or solvent, solubilizing agent, suspending agent, isotonic agent, buffering agent, soothing agent and the like for liquid preparations. Further, if necessary, general additives such as preservative, antioxidant, colorant, sweetening agent, adsorbing agent, wetting agent and the like can be also used appropriately in a suitable amount.

Examples of the excipient include lactose, sucrose, D-mannitol, starch, corn starch, crystalline cellulose, light anhydrous silicic acid and the like.

Examples of the lubricant include magnesium stearate, calcium stearate, talc, colloidal silica and the like.

Examples of the binding agent include crystalline cellulose, sucrose, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, carboxymethylstarch sodium, L-hydroxypropylcellulose and the like.

Examples of the solvent include water for injection, alcohol, propylene glycol, Macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerin, D-mannitol and the like.

Examples of the buffering agent include buffer solutions such as phosphates, acetates, carbonates, citrates and the like.

Examples of the soothing agent include benzyl alcohol and the like.

Examples of the preservative include parahydroxybenzoic acid esters, chlorobutanol, benzyl alcohol, phenethyl alcohol, dehydroacetic acid, sorbic acid and the like.

Examples of the antioxidant include sulfites, ascorbic acid, α-tocopherol and the like.

Examples of the colorant include water-soluble Food coal tar dyes (e.g., Food dyes such as Food Red No. 2 and No. 3, Food Yellow No. 4 and No. 5, Food Blue No. 1 and No. 2, and the like), water-insoluble lake dyes (e.g., aluminum salts of the aforementioned water-soluble Food coal tar dyes), natural dyes (e.g., β-carotene, chlorophyll, ferric oxide red) and the like.

Examples of the sweetening agent include saccharin sodium, dipotassium glycyrrhizinate, aspartame, stevia and the like.

Examples of the adsorbent include porous starch, calcium silicate (trade name: Florite RE), magnesium alumino metasilicate (trade name: Neusilin) and light anhydrous silicic acid (trade name: Sylysia).

Examples of the wetting agent include propylene glycol monostearate, sorbitan monooleate, diethylene glycol monolaurate and polyoxyethylenelauryl ether.

During production of an oral preparation, coating may be applied as necessary for the purpose of masking of taste, enteric property or durability.

Examples of the coating base to be used for coating include sugar coating base, aqueous film coating base, enteric film coating base and sustained-release film coating base.

As the sugar coating base, sucrose is used. Moreover, one or more kinds selected from talc, precipitated calcium carbonate, gelatin, gum arabic, pullulan, carnauba wax and the like may be used in combination.

Examples of the aqueous film coating base include cellulose polymers such as hydroxypropyl cellulose, hydroxypropylmethyl cellulose, hydroxyethyl cellulose, methylhydroxyethyl cellulose etc.; synthetic polymers such as polyvinylacetal diethylaminoacetate, aminoalkyl methacrylate copolymer E [Eudragit E (trade name)], polyvinylpyrrolidone etc.; and polysaccharides such as pullulan etc.

Examples of the enteric film coating base include cellulose polymers such as hydroxypropylmethyl cellulose phthalate, hydroxypropylmethyl cellulose acetate succinate, carboxymethylethyl cellulose, cellulose acetate phthalate etc.; acrylic polymers such as methacrylic acid copolymer L [Eudragit L (trade name)], methacrylic acid copolymer LD [Eudragit L-30D55 (trade name)], methacrylic acid copolymer S [Eudragit S (trade name)] etc.; and naturally occurring substances such as shellac etc.

Examples of the sustained-release film coating base include cellulose polymers such as ethyl cellulose etc.; and acrylic polymers such as aminoalkyl methacrylate copolymer RS [Eudragit RS (trade name)], ethyl acrylate-methyl methacrylate copolymer suspension [Eudragit NE (trade name)] etc.

The above-mentioned coating bases may be used after mixing with two or more kinds thereof at appropriate ratios.

For coating, for example, a light shielding agent such as titanium oxide, red ferric oxide and the like can be used.

The compound of the present invention can be used in combination with a concomitant drug that does not adversely influence the compound of the present invention, for the purpose of, for example, promoting the action (treatment of effect for obesity, diabetes and the like) of the compound of the present invention, reducing the dose of the compound of the present invention, and the like. Examples of such concomitant drug include "antiobesity drug", "therapeutic drug for diabetes", "therapeutic agents for diabetic complications", "therapeutic agents for hypertension", "therapeutic agents for hyperlipidemia", "diuretic", "antithrombotic agent" and the like.

The time of administration of the compound of the present invention and that of the concomitant drug are not limited, and they may be administered simultaneously or in a staggered manner to the administration subject.

Examples of such administration mode include the following:
(1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The dose of the concomitant drug can be appropriately determined based on the dose employed in clinical situations. The mixing ratio of the compound of the present invention and a concomitant drug can be appropriately determined depending on the administration subject, symptom, administration method, target disease, combination and the like. When the subject of administration is human, for example, a concomitant drug can be used in 0.01-100 parts by weight relative to 1 part by weight of the compound of the present invention.

Examples of the above-mentioned "antiobesity agent" include monoamine uptake inhibitors (e.g., phentermine, sibutramine, mazindol, fluoxetine, tesofensine), serotonin 2C receptor agonists (e.g., lorcaserin), serotonin 6 receptor antagonists, histamine H3 receptor GABA modulator (e.g., topiramate), neuropeptide Y antagonists (e.g., velneperit), cannabinoid receptor antagonists (e.g., rimonabant, taranabant), ghrelin antagonists, ghrelin receptor antagonists, ghrelinacylation enzyme inhibitors, opioid receptor antagonists (e.g., GSK-1521498), orexin receptor antagonists, melanocortin 4 receptor agonists, 11β-hydroxysteroid dehydrogenase inhibitors (e.g., AZD-4017), pancreatic lipase inhibitors (e.g., orlistat, cetilistat), β3 agonists (e.g., N-5984), diacylglycerol acyltransferase 1 (DGAT1) inhibitors, acetyl-CoA carboxylase (ACC) inhibitors, stearoyl-CoA desaturated enzyme inhibitors, microsomal triglyceride transfer protein inhibitors (e.g., R-256918), Na-glucose cotransporter inhibitors (e.g., JNJ-28431754, remogliflozin), NFx inhibitory (e.g., HE-3286), PPAR agonists (e.g., GFT-505, DRF-11605), phosphotyrosine phosphatase inhibitors (e.g., sodium vanadate, Trodusquemin), GPR119 agonists (e.g., PSN-821), glucokinase activators (e.g., AZD-1656), leptin, leptin derivatives (e.g., metreleptin), CNTF (ciliary neurotrophic factor), BDNF (brain-derived neurotrophic factor), cholecystokinin agonists, glucagon-like peptide-1 (GLP-1) preparations (e.g., animal GLP-1 preparations extracted from the pancreas of bovine or swine; human GLP-1 preparations genetically synthesized using Escherichia coli or yeast; fragments or derivatives of GLP-1 (e.g., exenatide, liraglutide)), amylin preparations (e.g., pramlintide, AC-2307), neuropeptide Y agonists (e.g., PYY3-36, derivatives of PYY3-36, obineptide, TM-30339, TM-30335), oxyntomodulin preparations: FGF21 preparations (e.g., animal FGF21 preparations extracted from the pancreas of bovine or swine; human FGF21 preparations genetically synthesized using Escherichia coli or yeast; fragments or derivatives of FGF21)), anorexigenic agents (e.g., P-57) and the like.

Here, as the above-mentioned "therapeutic drug for diabetes", for example, insulin preparations (e.g., animal insulin preparations extracted from the pancreas of bovine or swine; human insulin preparations genetically synthesized using Escherichia coli or yeast; zinc insulin; protamine zinc insulin; fragment or derivative of insulin (e.g., INS-1), oral insulin preparation), insulin sensitizers (e.g., pioglitazone or a salt thereof (preferably, hydrochloride), rosiglitazone or a salt thereof (preferably, maleate), Metaglidasen, AMG-131, Balaglitazone, MBX-2044, Rivoglitazone, Aleglitazar, Chiglitazar, Lobeglitazone, PLX-204, PN-2034, GFT-505, THR-0921, compound described in WO2007/013694, WO2007/018314, WO2008/093639 or WO2008/099794), α-glucosidase inhibitors (e.g., voglibose, acarbose, miglitol, emiglitate), biguanides (e.g., metformin, buformin or a salt thereof (e.g., hydrochloride, fumarate, succinate)), insulin secretagogues (e.g., sulfonylurea (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or calcium salt hydrate thereof), dipeptidyl peptidase IV inhibitors (e.g., Alogliptin or a salt thereof (preferably, benzoate), Vildagliptin, Sitagliptin, Saxagliptin, BI1356, GRC8200, MP-513, PF-00734200, PHX1149, SK-0403, ALS2-0426, TA-6666, TS-021, KRP-104, 2-[[6-[(3R)-3-amino-1-piperidinyl]-3,4-dihydro-3-methyl-2,4-dioxo-1(2H)-pyrimidinyl]methyl]-4-fluorobenzonitrile or a salt thereof), β3 agonists (e.g., N-5984), GPR40 agonists (e.g., compound described in WO2004/041266, WO2004/106276, WO2005/063729, WO2005/063725, WO2005/087710, WO2005/095338, WO2007/013689 or WO2008/001931), GLP-1 receptor agonists (e.g., GLP-1, GLP-1MR agent, Liraglutide, Exenatide, AVE-0010, BIM-51077, Aib(8,35)hGLP-1(7,37)NH2, CJC-1131, Albiglutide), amylin agonists (e.g., pramlintide), phosphotyrosine phosphatase inhibitors (e.g., sodium vanadate), gluconeogenesis inhibitors (e.g., glycogen phosphorylase inhibitors, glucose-6-phosphatase inhibitors, glucagon antagonists, FBPase inhibitors), SGLT2 (sodium-glucose cotransporter 2) inhibitors (e.g., Depagliflozin, AVE2268, TS-033, YM543, TA-7284, Remogliflozin, ASP1941), SGLT1 inhibitors, 11β-hydroxysteroid dehydrogenase inhibitors (e.g., BVT-3498, INCB-13739), adiponectin or agonist thereof, IKK inhibitors (e.g., AS-2868), leptin resistance improving drugs, somatostatin receptor agonists, glucokinase activators (e.g., Piragliatin, AZD1656, AZD6370, TTP-355, compound described in WO2006/112549, WO2007/028135, WO2008/047821, WO2008/050821, WO2008/136428 or WO2008/156757), GIP (Glucose-dependent insulinotropic peptide), GPR119 agonists (e.g., PSN821), FGF21, FGF analogue and the like can be mentioned.

As the above-mentioned "therapeutic agent for diabetic complications", aldose reductase inhibitors (e.g., tolrestat, epalrestat, zopolrestat, fidarestat, CT-112, ranirestat (AS-3201), lidorestat), neurotrophic factor and increasing agents thereof (e.g., NGF, NT-3, BDNF, neurotrophic production/secretion promoting agent described in WO01/14372 (e.g., 4-(4-chlorophenyl)-2-(2-methyl-1-imidazolyl)-5-[3-(2-methylphenoxy)propyl]oxazole), compound described in WO2004/039365), PKC inhibitors (e.g., ruboxistaurin mesylate), AGE inhibitors (e.g., ALT946, N-phenacylthiazolium bromide (ALT766), EXO-226, Pyridorin, pyridoxamine), GABA receptor agonists (e.g., gabapentin, pregabalin), serotonin and noradrenalin reuptake inhibitors (e.g., duloxetine), sodium channel inhibitors (e.g., lacosamide), active oxygen scavengers (e.g., thioctic acid), cerebral vasodilators (e.g., tiapuride, mexiletine), somatostatin receptor agonists (e.g., BIM23190), apoptosis signal regulating kinase-1 (ASK-1) inhibitors and the like can be mentioned.

Examples of the above-mentioned "therapeutic agent for hypertension" include angiotensin converting enzyme inhibitors (e.g., captopril, enalapril, delapril etc.), angiotensin II antagonists (e.g., candesartan cilexetil, candesartan, losartan, losartan potassium, eprosartan, valsartan, telmisartan, irbesartan, tasosartan, olmesartan, olmesartan medoxomil, azilsartan, azilsartan medoxomil etc.), calcium antagonists (e.g., manidipine, nifedipine, amlodipine, efonidipine, nicardipine, amlodipine, cilnidipine and the like), β blockers (e.g., metoprolol, atenolol, propranolol, carvedilol, pindolol etc.), clonidine and the like.

As the above-mentioned "therapeutic agent for hyperlipidemia", HMG-CoA reductase inhibitors (e.g., pravastatin, simvastatin, lovastatin, atorvastatin, fluvastatin, rosuvastatin, pitavastatin or a salt thereof (e.g., sodium salt, calcium salt)), squalene synthase inhibitors (e.g., compound described in WO97/10224, for example, N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidin-4-acetic acid), fibrate compounds (e.g., bezafibrate, clofibrate, simfibrate, clinofibrate), anion exchange resin (e.g., colestyramine), probucol, nicotinic acid drugs (e.g., nicomol, niceritrol, niaspan), ethyl icosapentate, phytosterol (e.g., soysterol, gamma oryzanol (γ-oryzanol)), cholesterol absorption inhibitors (e.g., zechia), CETP inhibitors (e.g., dalcetrapib, anacetrapib), ω-3 fatty acid preparations (e.g., ω-3-acid ethyl esters 90) and the like can be mentioned.

As the above-mentioned "diuretic", for example, xanthine derivatives (e.g., theobromine sodium salicylate, theobromine calcium salicylate and the like), thiazide preparations (e.g., ethiazide, cyclopenthiazide, trichloromethiazide, hydrochlorothiazide, hydroflumethiazide, benzylhydrochlorothiazide, penfluthiazide, poly5thiazide, methyclothiazide and the like), antialdosterone preparations (e.g., spironolactone, triamterene and the like), carbonic anhydrase inhibitors (e.g., acetazolamide and the like), chlorobenzenesulfonamide agents (e.g., chlortalidone, mefruside, indapamide and the like), azosemide, isosorbide, ethacrynic acid, piretanide, bumetanide, furosemide and the like can be mentioned.

As the above-mentioned "antithrombotic agent", for example, heparin (e.g., heparin sodium, heparin calcium, enoxaparin sodium, dalteparin sodium), warfarin (e.g., warfarin potassium), anti-thrombin drugs (e.g., aragatroban, dabigatran), FXa inhibitors (e.g., rivaroxaban, apixaban, edoxaban, YM150, compound described in WO02/06234, WO2004/048363, WO2005/030740, WO2005/058823 or WO2005/113504), thrombolytic agents (e.g., urokinase, tisokinase, alteplase, nateplase, monteplase, pamiteplase), platelet aggregation inhibitors (e.g., ticlopidine hydrochloride, clopidogrel, prasugrel, E5555, SHC530348, cilostazol, ethyl icosapentate, beraprost sodium, sarpogrelate hydrochloride) and the like can be mentioned.

By combining the compound of the present invention and concomitant drug:
(1) the dose of the compound of the present invention or a concomitant drug can be reduced as compared to single administration of the compound of the present invention or a concomitant drug,
(2) the drug to be used in combination with the compound of the present invention can be selected depending on the condition of patients (mild, severe and the like),
(3) the period of treatment can be set longer by selecting a concomitant drug having different action and mechanism from those of the compound of the present invention,
(4) a sustained treatment effect can be designed by selecting a concomitant drug having different action and mechanism from those of the compound of the present invention,
(5) a synergistic effect can be afforded by a combined use of the compound of the present invention and a concomitant drug, and the like, can be achieved.

In the following, a combined use of the compound of the present invention with a concomitant drug is referred to as "the combination agent of the present invention".

The combination agent of the present invention has low toxicity, and can be safely administered orally or parenterally (e.g., topical; rectal, intravenous administration etc.) by, for example, mixing the compound of the present invention or(and) the above-mentioned concomitant drug with a pharmacologically acceptable carrier according to a method known per se to give the aforementioned pharmaceutical preparation.

The mixing ratio of the compound of the present invention m to the concomitant drug in the combination agent of the present invention can be appropriately selected depending on an administration subject, administration method, diseases and the like.

For example, the content of the compound of the present invention in the combination agent of the present invention differs depending on the form of a preparation, and usually from about 0.01 to 100 wt %, preferably from about 0.1 to 50 wt %, further preferably from about 0.5 to 20 wt %, based on the whole of the preparation.

The content of the concomitant drug in the combination agent of the present invention differs depending on the form of a preparation, and usually from about 0.01 to 100 wt %, preferably from about 0.1 to 50 wt %, further preferably from about 0.5 to 20 wt %, based on the whole preparation.

The content of additives such as a carrier and the like in the combination agent of the present invention differs depending on the form of a preparation, and usually from about 1 to 99.99 wt %, preferably from about 10 to 90 wt %, based on the whole preparation.

In addition, when the compound of the present invention and a concomitant drug are separately formulated, the contents thereof may be similar.

As mentioned above, the compound of the present invention shows superior stability in blood, and may be formed into a conjugate with a normeutralizing antibody to the compound of the present invention, for the purpose of further enhancing the stability in blood. Such normeutralizing antibody can be produced according to, for example, the method described in WO2005/094881. The compound of the present invention can be bound to the antibody according to a method known per se and via a linker containing, for example, a substituted or unsubstituted aliphatic alkylene chain and having, on both terminals thereof, a group capable of binding to the compound of the present invention or a functional group of the antibody, such as N-hydroxysuccinimide group, ester group, thiol group, imidocarbonate group, aldehyde group and the like.

The abbreviations used in the present specification mean the following (Table 1-1-Table 1-3).

TABLE 1

| abbreviation | name (explanation) |
| --- | --- |
| Aad | 2-aminoadipic acid |
| Abu | 2-aminobutyric acid |
| Abz(2) | 2-aminobenzoic acid |
| Ac | acetyl |
| Acp | 6-aminocaproic acid |
| Acpc | 1-aminocyclopropanecarboxylic acid |
| Adc(12) | 12-aminododecanic acid |
| Aib | α-aminoisobutyric acid |
| Aipe | 3-aminobutyric acid |
| Ala(4Pip) | 4-piperidinylalanine |
| Ala(cPr) | cyclopropylalanine |
| Alb | Albizziin, 2-amino-3-ureidopropionic acid |
| Ambz(4) | 4-aminomethylbenzoyl |
| Aoc(8) | 8-aminocaprylic acid |
| Arg(Me) | $N^{\omega}$-methylarginine |
| Asn(Me) | $N^{\omega}$-methylasparagine |
| Aze(2) | azetidine-2-carboxylic acid |
| Aze(3) | azetidine-3-carboxylic acid |
| CC(Acp) | 5-carboxypentylcarbamoyl |
| CC(GABA) | 3-carboxypropylcarbamoyl |
| CC(Gly) | carboxymethylcarbamoyl |
| CC(Leu) | [(1S)-1-carboxy-3-methylbutyl]carbamoyl |
| CC(Ser) | [(1S)-1-carboxy-2-hydroxyethyl]carbamoyl |
| CC(Tyr) | [(1S)-1-carboxy-2-(4-hydroxyphenyl)ethyl]carbamoyl |
| CC(β-Ala) | 2-carboxyethylcarbamoyl |
| Cha | cyclohexylalanine |
| cisHyp | cis-4-hydroxyproline |
| Cit | citrulline |
| Dab | 2,4-diaminobutyric acid |
| Dap | 2,3-diaminopropionic acid |

TABLE 1-continued

| abbreviation | name (explanation) |
| --- | --- |
| GABA | γ-aminobutyric acid |
| Gly(cPr) | cyclopropylglycine |
| Gly-ψ[(E)CH=CH]-Leu | —CONH— bond between Gly and Leu is substituted by (E) type alkene |
| Har | homoarginine |
| homoLeu | homoleucine |
| Hse | homoserine |
| Hyp | trans-4-hydroxyproline |
| Ile-Thr($^{\gamma Me,Me}$Pro) | [structure] |
| Iva | isovaline |
| Leu(Me) | γ-methylleucine |
| Lys(Ac) | N$^\varepsilon$-acetyllysine |
| Lys(Hexyl) | N$^\varepsilon$-hexyllysine |
| Lys(Me) | N$^\varepsilon$-methyllysine |
| Lys(Me$_2$) | N$^{\varepsilon,\varepsilon}$-dimethyllysine |
| Lys[Hexadecanoyl-(PEG2)] | [structure] |
| MPA | β-maleimidopropionyl |
| N(2-hydroxyethyl)Gly | N-(2-hydroxyethyl)glycine |
| N(iBu)Gly | N-isobutylglycine |
| Nal(1) | 1-naphthylalanine |
| Nal(2) | 2-naphthylalanine |
| Nar | norarginine |
| Nle | norleucine |
| NMeAla | N$^\alpha$-methylalanine |
| NMeSer | N$^\alpha$-methylserine |
| NMePhe | N$^\alpha$-methylphenylalanine |
| Nva | norvaline |
| Orn | ornithine |
| PEG2 | [structure] |
| Phe(2,6-Me$_2$) | 2,6-dimethylphenylalanine |
| Phe(2F) | 2-fluorophenylalanine |
| Phe(2Me) | 2-methylphenylalanine |
| Phe(3F) | 3-fluorophenylalanine |
| Phe(3Me) | 3-methylphenylalanine |
| Phe(4Cl) | 4-chlorophenylalanine |
| Phe(4F) | 4-fluorophenylalanine |
| Phe(4Me) | 4-methylphenylalanine |
| Phe(4NH$_2$) | 4-aminophenylalanine |
| Phg | phenylglycine |
| Pic(2) | 2-piperidinecarboxylic acid |
| Pic(4) | 4-piperidinecarboxylic acid |
| Pya(2) | 2-pyridylalanine |
| Pya(3) | 3-pyridylalanine |
| Pya(4) | 4-pyridylalanine |
| Sar | sarcosine |
| Ser(Me) | O-methylserine |
| Thp(4) | tetrahydro-2H-pyran-4-yl |
| Thr(Me) | O-methylthreonine |
| threo-PhSer | threo-3-phenylSerine |
| Tic | 1,2,3,4-tetrahydroisoquinoline-3-carboxylic acid |
| Tyr(2F) | 2-fluorotyrosine |
| Tyr(3F) | 3-fluorotyrosine |
| Tyr(Me) | O-methyltyrosine |
| Z | benzyloxycarbonyl |
| α-MePhe | α-methylphenylalanine |
| α-MePro | α-methylproline |

| abbreviation | name (explanation) |
|---|---|
| β-Ala | β-alanine |
| β-HOAla | β-homoalanine |

In the specification and drawings, where bases, amino acids, etc. are denoted by their codes, they are based on conventional codes in accordance with the IUPAC-IUB Commission on Biochemical Nomenclature or by the common codes in the art, examples of which are shown below. For amino acids that may have an optical isomer, L-form is presented unless otherwise indicated (e.g., "Ala" is L-form of Ala). In addition, "D-" means a D-form (e.g., "D-Ala" is D-form of Ala), and "DL-" means a racemate of a D-form and an L-form (e.g., "DL-Ala" is DL racemate of Ala).

DNA: deoxyribonucleic acid
cDNA: complementary deoxyribonucleic acid
A: adenine
T: thymine
G: guanine
C: cytosine
Y: thymine or cytosine
N: thymine, cytosine, adenine or guanine
R: adenine or guanine
M: cytosine or adenine
W: thymine or adenine
S: cytosine or guanine
RNA: ribonucleic acid
mRNA: messenger ribonucleic acid
dATP: deoxyadenosine triphosphate
dTTP: deoxythymidine triphosphate
dGTP: deoxyguanosine triphosphate
dCTP: deoxycytidine triphosphate
ATP: adenosine triphosphate
EDTA: ethylenediaminetetraacetic acid
SDS: sodium dodecyl sulfate
TFA: trifluoroacetic acid
EIA: enzyme immunoassay
Gly or G: glycine
Ala or A: alanine
Val or V: valine
Leu or L: leucine
Ile or I: isoleucine
Ser or S: serine
Thr or T: threonine
Cys or C: cysteine
Met or M: methionine
Glu or E: glutamic acid
Asp or D: aspartic acid
Lys or K: lysine
Arg or R: arginine
His or H: histidine
Phe or F: phenylalanine
Tyr or Y: tyrosine
Trp or W: tryptophan
Pro or P: proline
Asn or N: asparagine
Gln or Q: glutamine
pGlu: pyroglutamic acid The present invention is explained in detail in the following by referring to the following Examples, Experimental Examples and Formulation Examples, which are mere embodiments and not to be construed as limitative. In addition, the present invention may be modified without departing from the scope of invention.

The term "room temperature" in the following Examples indicates the range of generally from about 10° C. to about 35° C. As for "%", the yield is in mol/mol %, the solvent used for chromatography is in % by volume and other "%" is in % by weight. OH proton, NH proton etc. on proton NMR spectrum that could not be confirmed due to broad peak are not included in the data.

Example 1

(Synthesis Method A): Production of [Ala$^{26}$, Ile$^{28,31}$]-PYY(19-36) (Compound No. 2)

(1) Synthesis of Fmoc-Tyr(Bu$^t$)-Rink Amide MBHA resin

Commercially available Rink Amide MBHA resin (0.55 mmol/g, 3.64 g) was swollen with DMF, and treated with 20% piperidine/DMF solution (30 mL)) for 20 min to remove Fmoc group. The obtained resin was washed with DMF, and treated with Fmoc-Tyr(Bu$^t$)-OH (689 mg, 1.5 mmol), DIPCDI (845 μL, 6 mmol), 0.5 M HOAt/DMF solution (12 mL, 6 mmol) at room temperature for 18 hr. The resin was washed with DMF, acetic anhydride (945 μL, 10 mmol), DIEA (697 μL, 4 mmol), DMF (20 mL) were added, and the mixture was shaken for 1 hr to give Fmoc-Tyr(Bu$^t$)-Rink Amide MBHA resin (4.3495 g, 0.302 mmol/g).

(2) Synthesis of [Ala$^{26}$, Ile$^{28,31}$]-PYY(19-36)

Using Fmoc-Tyr(Bu$^t$)-Rink Amide MBHA resin (0.219 mmol/g, 1.142 g, 0.25 mmol) obtained in (1) above as a starting material, the peptide chain was elongated by an ABI433A solid phase synthesizer. As the protocol for solid phase synthesis, FastMoc 0.25 mmol was used and 0.45 M HATU/DMF solution was prepared and used instead of 0.45 M HBTU-0.5 M HOBt/DMF solution used as the standard. Amino acids were repeatedly condensed from the 36-position toward the N-terminal to elongate the peptide chain up to the 25-position to give Fmoc-Arg(Pbf)-Ala-Tyr(Bu$^t$)-Ile-Asn(Trt)-Leu-Ile-Thr(Bu$^t$)-Arg(Pbf)-Gln(Trt)-Arg(Pbf)-Tyr(Bu$^t$)-Rink Amide MBHA resin (SEQ ID NO:150). Furthermore, the peptide chain was elongated up to the 19-position by a similar protocol using an ABI433A solid phase synthesizer, at which the synthesizer was stopped. A ¼ amount of the resin was extracted to give Arg(Pbf)-Tyr(Bu$^t$)-Tyr(Bu$^t$)-Ala-Ser(Bu$^t$)-Leu-Arg(Pbf)-Ala-Tyr(Bu$^t$)-Ile-Asn(Trt)-Leu-Ile-Thr(Bu$^t$)-Arg(Pbf)-Gln(Trt)-Arg(Pbf)-Tyr(Bu$^t$)-Rink Amide MBHA resin (SEQ ID NO:151) (0.0625 mmol). To the half amount (158.8 mg) thereof was added TFA:thioanisole:m-cresol:H$_2$O:EDT:TIS (80:5:5:5:2.5:2.5) (1.5 ml), and the mixture was stirred for 90 min. Diethyl ether was added to the reaction solution to allow precipitation of a white powder. An operation to remove ether by decantation after centrifugation was repeated twice to remove acid and scavenger. The residue was extracted with aqueous acetic acid solution, and applied to preparative HPLC using Daisopak-SP100-5-ODS-P column (20×250 mm) [Solution A: 0.1% TFA-water, Solution B: 0.1% TFA-containing acetonitrile, flow rate 8 mL/min, A/B: 76/24-66/34 linear concentration gradient elution (60 min)]. The fractions containing the object product were collected and freeze-dried to give 6.8 mg of a white powder.

MALDI-TOF-MS analysis, (M+H)$^+$ 2319.5 (Calculated: 2319.3) HPLC elution time: 12.1 min
elution condition (HPLC mode a):
  column: YMC-AM301 (4.6×100 mm)
  eluent: using Solution A: 0.1% TFA-water, Solution B: 0.1% TFA-containing acetonitrile, A/B: 80/20-30/70 linear concentration gradient elution (25 min)
  flow rate: 1.0 mL/min Example 2

(Synthesis Method B): Production of 4-Guanidinomethylbenzoyl-[Ala$^{26}$, Ile$^{28,31}$]-PYY(25-36) (Compound No. 4)

Synthesis of 4-Guanidinomethylbenzoyl-[Ala$^{26}$, Ile$^{28,31}$]-PYY(25-36)

Fmoc-Arg(Pbf)-Ala-Tyr(Bu$^t$)-Ile-Asn(Trt)-Leu-Ile-Thr(Bu$^t$)-Arg(Pbf)-Gln(Trt)-Arg(Pbf)-Tyr(Bu$^t$)-Rink Amide MBHA resin (SEQ ID NO:150) (109.5 mg, 0.015 mmol) obtained in Example 1 was washed with DMF and, after swelling, Fmoc group was removed. Then, after treatment with Fmoc-4-aminomethylbenzoic acid (33.7 mg, 0.1 mmol), 0.5 M HOAt/DMF (0.2 ml, 0.1 mmol), DIPCDI (15.9 µL, 0.1 mmol) in DMF at room temperature for 90 min, and the mixture was washed. N-terminal Fmoc group was removed and, after a treatment with N,N'-Bis-Boc-1-guanylpyrazole (31.0 mg, 0.1 mmol), DIEA (17.4 µL, 0.1 mmol) in DMF at room temperature for 20 hr, and the mixture was washed and dried. The obtained N,N'-bis-Boc-Guanidinomethylbenzoyl-Arg(Pbf)-Ala-Tyr(Bu$^t$)-Ile-Asn(Trt)-Leu-Ile-Thr(Bu$^t$)-Arg(Pbf)-Gln(Trt)-Arg(Pbf)-Tyr(Bu$^t$)-Rink Amide MBHA resin (SEQ ID NO:153) (111.5 mg) was deprotected with TFA:thioanisole:m-cresol:H$_2$O:EDT:TIS (80:5:5:5:2.5:2.5) (0.75 mL) to give a crude peptide. Then, HPLC preparative purification by A/B: 78/22-68/32 linear concentration gradient elution (60 min) was performed to give 4.4 mg of a white powder. MALDI-TOF-MS analysis, (M+H)$^+$1740.8 (Calculated: 1741.0)
HPLC elution time: 9.4 min
elution condition (HPLC mode a):
  column: YMC-AM301 (4.6×100 mm)
  eluent: using Solution A: 0.1% TFA-water, Solution B: 0.1% TFA-containing acetonitrile, A/B: 80/20-30/70 linear concentration gradient elution (25 min)
  flow rate: 1.0 mL/min Example 3

(Synthesis Method C): Production of 4-aminomethylbenzoyl-[Ala$^{26}$, Ile$^{28,31}$, Phe$^{36}$]-PYY(25-36) (Compound No. 6)

(1) Synthesis of Fmoc-Ile-Thr($^{\gamma Me,Me}$Pro)-O-2-chlorotrityl resin

Fmoc-Ile-Thr($^{\gamma Me,Me}$Pro)-OH (296.8 mg, 0.6 mmol) was dissolved in DMF (5 mL, and DIEA (0.209 mL) was added. The obtained solution was added to 2-chlorotritylchloide resin (1 g, 1.2 mmol), and the mixture was stirred at room temperature overnight. The solution was removed by filtration, and the resin was washed with DMF, then the resin was washed 5 times with MeOH-DIEA-DMF (1:1:18), washed with DMF, MeOH and the resin was dried. The replacement rate of the obtained resin was calculated by the method shown below.
yield: 1.1779 g, 0.324 mmol/g, (2) Resin Replacement Rate Measurement Method Based on Quantification of Fmoc Group A resin (about 1-2 mg) was accurately measured and placed in a 20 mL measuring flask, piperidine (0.8 ml) and DMF (0.8 mL) were added. The measuring flask was gently shaken and stood still for 30 min. Then MeOH (3.2 mL) was added, and the mixture was measured up with DMF and blended by upside-down mixing the measuring flask. In a measuring flask free of the resin, a similar operation was performed and used as a blank solution. The absorbance of each solution at 301 nm was measured, and the resin replacement rate was calculated by the following formula.

$$\text{replacement rate (mmol/g)} = \frac{(Abs_{sample} - Abs_{blank}) \times 20 \text{ (mL)}}{7800 \times \text{resin amount (g)}}$$

(3) Synthesis of Fmoc-Arg(Pbf)-Ala-Tyr(Bu$^t$)-Ile-Asn(Trt)-Leu-Ile-Thr($^{\gamma Me,Me}$Pro)-OH(SEQ ID NO:154)

Using Fmoc-Ile-Thr($^{\gamma Me,Me}$Pro)-O-2-chlorotrityl resin (3.226 g, 1.5 mmol) as a starting material, the peptide chain was elongated up to the 25-position by manual solid phase synthesis and the resin was divided into ⅓. Into the amount of 0.5 mmol of the resin was introduced Fmoc-Ambz(4)-OH by manual solid phase synthesis to give Fmoc-Ambz(4)-Arg(Pbf)-Ala-Tyr (Bu$^t$)-Ile-Asn(Trt)-Leu-Ile-Thr($^{\gamma Me,Me}$Pro)-O-2-chlorotrityl resin (SEQ ID NO:155). The obtained resin was treated with 50 mL of AcOH-TFE-toluene (1:4:5) for 1 hr and the solution was collected by removing the resin by filtration. The resin was washed several times with AcOH-TFE-toluene (1:4:5). The filtrates were combined and concentrated. Diethyl ether was added to the obtained residue and the precipitated solid was collected by filtration to give Fmoc-Ambz(4)-Arg(Pbf)-Ala-Tyr(Bu$^t$)-Ile-Asn(Trt)-Leu-Ile-Thr($^{\gamma Me,Me}$Pro)-OH as a white powder.

(4) Synthesis of 4-Aminomethylbenzoyl-[Ala$^{26}$, Ile$^{28,31}$,Phe$^{36}$]-PYY (25-36)

Commercially available Sieber Amide resin (60.3 mg, 0.025 mmol) was measured and placed in a reaction vessel and swollen with DMF. By a manual solid phase synthesis operation, the 36-33-position amino acids were introduced to give Emoc-Arg(Pbf)-Gln(Trt)-Arg(Pbf)-Phe-Sieber Amide resin (SEQ ID NO:156). Fmoc was removed from the obtained resin, and the resin was treated with Emoc-Ambz(4)-Arg(Pbf)-Ala-Tyr(Bu$^t$)-Ile-Asn(Trt)-Leu-Ile-Thr($^{\gamma Me,Me}$Pro)-OH (28.4 mg, 0.015 mmol) obtained in the above section, PyAOP (27.1 mg, 0.05 mmol), 0.5 M HOAt/DMF (0.2 ml, 0.1 mmol), and DIEA (34.8 µL, 0.2 mmol) in DMF at room temperature overnight. After removal of Fmoc, the obtained resin was washed with MeOH, diethyl ether and dried. The obtained resin was treated with TFA:thioanisole:

m-cresol:H₂O:EDT:TIS (80:5:5:5:2.5:2.5) (0.5 mL) for 90 min, and diethyl ether was added to the reaction solution to allow precipitation of a white powder. An operation to remove ether by decantation after centrifugation was repeated twice to remove acid and scavenger. The residue was extracted with aqueous acetic acid solution, and purified by preparative HPLC using Daisopak-SP100-5-ODS-P 2×25 cm to give 1.9 mg of a white powder.

MALDI-TOF-MS analysis, (M+H)⁺1682.6 (Calculated: 1683.0)

HPLC elution time: 8.1 min elution condition (HPLC mode a):
    column: YMC-AM301 (4.6×100 mm)
    eluent: using Solution A: 0.1% TFA-water, Solution B: 0.1% TFA-containing acetonitrile, A/B: 80/20-30/70 linear concentration gradient elution (25 min)
    flow rate: 1.0 mL/min Example 4

(Synthesis Method D): Production of 4-aminomethylbenzoyl-[Ala²⁶, Ile²⁸,³¹, Har³³]-PYY(25-36) (Compound No. 11)

Synthesis of 4-aminomethylbenzoyl-[Ala²⁶, Ile²⁸,³¹, Har³³]-PYY(25-36)

Commercially available Rink Amide MBHA resin (1 g, 0.45 mmol) was measured and placed in a reaction vessel and swollen with DMF. By a manual solid phase synthesis operation, Tyr(Buᵗ), Arg(Pbf) were successively condensed, and Fmoc was removed. The resin was washed with DMF, MeOH, and dried to give H-Arg(Pbf)-Tyr(Buᵗ)-Rink Amide MBHA resin (1.162 g). From the obtained resin, 65.6 mg, 0.025 mmol was measured and placed in a reaction vessel. Gln(Trt), Lys(Mtt) were introduced thereto by manual solid phase synthesis process to give Fmoc-Lys(Mtt)-Gln(Trt)-Arg(Pbf)-Tyr(Buᵗ)-Rink Amide MBHA resin (SEQ ID NO:175) (Mtt: methyltrityl). The obtained resin was washed with toluene, then TFA-TIS-TFE-toluene (1:5:47:47) was added and the mixture was shaken in the reaction vessel for 10 min. The processing was repeated until the solution was no longer colored with free trityl group to remove Mtt group. The resin was neutralized with 5% DIEA/toluene solution, suspended in toluene:TFE (4:1), N,N-bis-Boc-1-guanylpyrazole (31.0 mg, 0.1 mmol) was added, and the mixture was adjusted to pH 10 with DIEA, and treated overnight at room temperature. After removal of Fmoc from the obtained Fmoc-Har(Boc₂)-Gln(Trt)-Arg(Pbf)-Tyr(Buᵗ)-Rink Amide MBHA resin (SEQ ID NO:157), the resin was treated with Fmoc-Ambz(4)-Arg(Pbf)-Ala-Tyr(Buᵗ)-Ile-Asn (Trt)-Leu-Ile-Thr ($^{iMe,Me}$Pro)-OH (28.4 mg, 0.015 mmol) obtained in Example 3, PyAOP (27.1 mg, 0.05 mmol), 0.5 M HOAt/DMF (0.2 mL, 0.1 mmol), DIEA (34.8 μL, 0.2 mmol) at room temperature overnight. The obtained resin (92.0 mg) was treated with TFA:thioanisole:m-cresol:H₂O:EDT:TIS (80:5:5:5:2.5:2.5) (0.6 mL) for 90 min, and diethyl ether was added to the reaction solution to allow precipitation of a white powder. An operation to remove ether by decantation after centrifugation was repeated twice to remove acid and scavenger. The residue was extracted with aqueous acetic acid solution, and purified by preparative HPLC using Daisopak-SP100-5-ODS-P 2×25 cm to give 2.2 mg of a white powder.

MALDI-TOF-MS analysis, (M+H)⁺1713.4 (Calculated: 1713.0)

HPLC elution time: 8.6 min elution condition (HPLC mode a):
    column: YMC-AM301 (4.6×100 mm)
    eluent: using Solution A: 0.1% TFA-water, Solution B: 0.1% TFA-containing acetonitrile, A/B: 80/20-30/70 linear concentration gradient elution (25 min).
    flow rate: 1.0 mL/min Example 5

(Synthesis Method E): Production of 4-({[Imino(octylamino)methyl]amino}methyl)benzoyl-[Ala²⁶, Ile²⁸,³¹]-PYY(25-36) (Compound No. 28)

(1) Synthesis of N-Boc-N'-n-octyl-1-guanylpyrazole

Under ice-cooling and under nitrogen atmosphere, to a suspension of NaH (60% in oil, 283 mg, 7.08 mmol) in DMF (10 mL)) was added N,N'-bis-Boc-1-guanylpyrazole (2 g, 6.44 mmol) by small portions. After stirring at the same temperature for 15 min, 1-iodooctane (2.33 mL, 12.9 mmol) was added dropwise, and the mixture was stirred overnight while raising the temperature to room temperature. Under ice-cooling, water was added to discontinue the reaction, and the whole mixture was extracted with AcOEt. The organic layer was washed with saturated aqueous NaCl solution, and dried over MgSO₄ and concentrated under reduced pressure. The residue was purified by silica gel chromatography using n-hexane:AcOEt=8:1 as an eluate to give the object product as an oil (yield: 1.8 g, 66.1%).

¹H NMR (300 MHz, CHLOROFORM-d) δppm 0.78-0.92 (3H, m), 1.19-1.36 (10H, m), 1.27 (9H, s), 1.50 (9H, s), 1.65-1.81 (2H, m), 3.61-3.69 (2H, m), 6.41 (1H, dd, J=2.7, 1.6 Hz), 7.69 (1H, d, J=1.1 Hz), 7.93 (1H, br. s.)

(2) Synthesis of 4-({[imino(octylamino)methyl]amino}methyl)benzoyl-[Ala²⁶, Ile²⁸,³¹]-PYY(25-36)

H-Arg(Pbf)-Ala-Tyr(Buᵗ)-Ile-Asn(Trt)-Leu-Ile-Thr (Buᵗ)-Arg(Pbf)-Gln(Trt)-Arg(Pbf)-Tyr(Buᵗ)-Rink Amide MBHA Resin (SEQ ID NO:158) (194 mg, 0.03 mmol) synthesized using ABI433A peptide synthesizer DCC/HOBt 0.25 mmol protocol was washed with DMF and, after swelling, treated with Fmoc-Ambz(4)-OH (29.9 mg, 0.08 mmol), DIPCDI (0.00127 mL, 0.08 mmol), 0.5 M HOAt/DMF solution (0.16 mL, 0.08 mmol) at room temperature for 3 hr, after which treated with 20% piperidine/DMF solution for 20 min to give H-Ambz(4)-Arg(Pbf)-Ala-Tyr(Buᵗ)-Ile-Asn(Trt)-Leu-Ile-Thr(Buᵗ)-Arg(Pbf)-Gln(Trt)-Arg(Pbf)-Tyr(Buᵗ)-Rink amide MBHA resin (SEQ ID NO:159) (0.03 mmol). The obtained resin was treated with N-Boc-N'-n-octyl-1-guanylpyrazole (127 mg, 0.3% mmol) obtained in the above section, DIEPA (0.0523 ml, 0.3 mmol) in DMF at room temperature for 3 days, washed successively with DMF, MeOH and dried under reduced pressure to give (4-N-Boc-N'-n-octyl-1-guanidinomethyl)benzoyl-Arg(Pbf)-Ala-Tyr(Buᵗ)-Ile-Asn(Trt)-Leu-Ile-Thr(Buᵗ)-Arg(Pbf)-Gln(Trt)-Arg(Pbf)-Tyr(Buᵗ)-Rink amide MBHA resin (SEQ ID NO:160). To the total amount of the obtained resin was added TFA:thioanisole:m-cresol:H₂O:EDT:TIS (80:5:5:5:2.5:2.5) (2 mL), and the mixture was stirred at ambient temperature for 90 min, and diethyl ether was added to the reaction solution to allow precipitation of a white powder. An operation to remove ether by decantation after centrifugation of the suspension was repeated twice to remove acid and scavenger. The residue was extracted with aqueous acetic acid solution, and purified by preparative HPLC using Daisopak-SP100-5-ODS-P 2×25 cm to give 9.3 mg of a white powder.

MALDI-TOF-MS analysis, $(M+H)^+$ 1852.1 (Calculated: 1853.1)

HPLC elution time: 13.0 min elution condition (HPLC mode a):
  column: YMC-AM301 (4.6×100 mm)
  eluent: using Solution A: 0.1% TFA-water, Solution B: 0.1% TFA-containing acetonitrile, A/B: 80/20-30/70 linear concentration gradient elution (25 min).
  flow rate: 1.0 mL/min Example 6

(Synthesis Method F): Production of 4-aminomethylbenzoyl-[Ala$^{26,28}$, Ile$^{31}$]-PYY(25-36) (Compound No. 31)

(1) Synthesis of Boc-Ambz(4)-Arg(Pbf)-Ala-Tyr(Bu$^t$)-OH

Commercially available 2-chlorotrityl resin (Clt resin) (5 g, 7 mmol) was measured and placed in a reaction vessel, a solution of Fmoc-Tyr(Bu$^t$)—OH (3.861 g, 8.4 mmol) and DIEA (1.463 mL, 8.4 mmol) in DMF was added, and the mixture was stirred at room temperature for 3 hr. The reaction solution was removed by filtration, and the resin was washed 5 times with DMF, 5 times with MeOH:DIEA:DMF (2:1:18) solution, and 10 times each with DMF and MeOH and dried. The obtained resin was treated with piperidine, and the replacement rate was determined by a method of measuring a free Fmoc group by absorbance (0.607 mmol/g). The peptide chain was elongated on the obtained resin by manual solid phase synthesis process using DIPCDI/HOOBt to give Boc-Ambz(4)-Arg(Pbf)-Ala-Tyr(Bu$^t$)-O-Clt resin (8.247 g). The obtained resin was treated with 30 mL of AcOH-TFE-toluene (1:2:7) for 1 hr and the solution was collected while removing the resin by filtration. The resin was washed several times with AcOH-TFE-toluene (1:2:7), and the filtrates were combined and concentrated. Diethyl ether was added to the obtained residue and the precipitated solid was collected by filtration to give Boc-Ambz(4)-Arg(Pbf)-Ala-Tyr(Bu$^t$)—OH (2.8684 g).

(2) Synthesis of 4-Aminomethylbenzoyl-[Ala$^{26,28}$, Ile$^{31}$]-PYY(25-36)

Using commercially available Sieber Amide resin (as a starting material, and ABI433A solid phase synthesizer DCC/HOBt 0.25 mmol protocol, Tyr(Bu$^t$), Arg(Pbf), Gln(Trt), Arg(Pbf) were successively condensed to construct the 33-36-position of the peptide chain. 52.1 mg (0.02 mmol) of the obtained H-Arg(Pbf)-Gln(Trt)-Arg(Pbf)-Tyr(Bu$^t$)-Sieber Amide resin (SEQ ID NO:161) was weighed and placed in a reaction vessel, amino acids of the 32-position to the 28-position were successively introduced thereinto by manual solid phase synthesis to give H-Ala-Asn(Trt)-Leu-Ile-Thr(Bu$^t$)-Arg(Pbf)-Gln(Trt)-Arg(Pbf)-Tyr(Bu$^t$)-Sieber Amide resin (SEQ ID NO:162), which was treated with Boc-Ambz(4)-Arg(Pbf)-Ala-Tyr(Bu$^t$)-OH (57.0 mg, 0.06 mmol) obtained in the above, DIPCDI (9.5 µL, 0.06 mmol), HOOBt (16.3 mg, 0.1 mmol) at room temperature for 15 hr, washed with DMF, MeOH, and dried to give Boc-Ambz(4)-Arg(Pbf)-Ala-Tyr(Bu$^t$)-Ala-Asn(Trt)-Leu-Ile-Thr(Bu$^t$)-Arg(Pbf)-Gln(Trt)-Arg(Pbf)-Tyr(Bu$^t$)-Sieber Amide resin, (SEQ ID NO:163). The obtained resin (72.1 mg) was treated with TFA:thioanisole:m-cresol:H$_2$O:EDT:TIS (80:5:5:5:2.5:2.5) (0.6 mL) for 90 min, and diethyl ether was added to the reaction solution to allow precipitation of a white powder. An operation to remove ether by decantation after centrifugation was repeated twice to remove acid and scavenger. The residue was extracted with aqueous acetic acid solution, and purified by preparative HPLC using Daisopak-SP100-5-ODS-P 2×25 cm to give 9.2 mg of a white powder.

MALDI-TOF-MS analysis, $(M+H)^+$ 1657.0 (Calculated: 1656.9)

HPLC elution time: 4.1 min elution condition (HPLC mode a):
  column: YMC-AM301 (4.6×100 mm)
  eluent: using Solution A: 0.1% TFA-water, Solution B: 0.1% TFA-containing acetonitrile, A/B: 80/20-30/70 linear concentration gradient elution (25 min).
  flow rate: 1.0 mL/min Example 7

(Synthesis Method G): Production of Benzoyl-[Cha$^{27,28,36}$,Aib$^{31}$]-PYY (25-36) (Compound No. 64)

Synthesis of Benzoyl-[Cha$^{27,28,36}$,Aib$^{31}$]-PYY(25-36)

Using commercially available Sieber Amide resin (347 mg, 0.25 mmol) as a starting material, and ABI433A peptide synthesizer DCC/HOBt 0.25 mmol protocol, amino acids were successively condensed to give H-Arg(Pbf)-His(Trt)-Cha-Cha-Asn(Trt)-Leu-Aib-Thr(Bu$^t$)-Arg(Pbf)-Gln(Trt)-Arg(Pbf)-Cha-Sieber Amide Resin (SEQ ID NO:164) (1.1292 g, 0.232 mmol/g). 401.6 mg (0.1 mmol) of the obtained resin was weighed, washed with DMF and, after swelling, treated with benzoic acid (48.8 mg, 0.4 mmol), DIPCDI (63.6 µL, 0.4 mmol), 0.5 M HOAt/DMF (0.8 mL, 0.4 mmol) in DMF for 90 min to benzoylate the N-terminal. The resin was washed with DMF, MeOH, and dried to give Benzoyl-Arg(Pbf)-His(Trt)-Cha-Cha-Asn(Trt)-Leu-Aib-Thr(Bu$^t$)-Arg(Pbf)-Gln(Trt)-Arg(Pbf)-Cha-Sieber Amide Resin (SEQ ID NO:165) (452.0 mg, 0.1 mmol). To the entire amount of the obtained resin was added TFA:thioanisole:m-cresol:H$_2$O:EDT:TIS (80:5:5:5:2.5:2.5) (3 ml), and the mixture was stirred at ambient temperature for 90 min, and diethyl ether was added to the reaction solution to allow precipitation of a white powder. An operation to remove ether by decantation after centrifugation of the suspension was repeated twice to remove acid and scavenger. The residue was extracted with aqueous acetic acid solution, and purified by preparative HPLC using Daisopak-SP100-5-ODS-P 2×25 cm to give 84.1 mg of a white powder.

MALDI-TOF-MS analysis, $(M+H)^+$ 1728.0 (Calculated: 1728.1)

HPLC elution time: 14.3 min elution condition (HPLC mode d):
  column: Merck Chromolith Performance RP-18e (4.6×100 mm I.D.)
  eluent: using Solution A: 0.1% TFA-water, Solution B: 0.1% TFA-containing acetonitrile, A/B: 80/20-30/70 linear concentration gradient elution (25 min).
  flow rate: 1.0 mL/min

Example 8

(Synthesis Method H): Production of 4-Guanidinomethylbenzoyl-[Nle$^{25}$, Cha$^{27,28,31,36}$,Arg$^{30}$]-PYY(25-36) (Compound No. 76)

Synthesis of 4-Guanidinomethylbenzoyl-[Nle$^{25}$, Cha$^{27,28,31,36}$,Arg$^{30}$]-PYY(25-36)

Using commercially available Sieber Amide resin (2.777 g, 2 mmol) as a starting material, and by a manual solid phase synthesis operation, Cha, Arg(Pbf), Gln(Trt), Arg(Pbf) were successively condensed, and the 33-36-position of the peptide chain was constructed to give H-Arg(Pbf)-Gln(Trt)-Arg (Pbf)-Cha-Sieber Amide resin (SEQ ID NO:166) (4.6409 g). 37.6 mg (0.015 mmol) of the obtained resin was weighed and placed in a reaction vessel and amino acids of the 32-position to the 25-position were successively introduced thereinto by manual solid phase synthesis to give H-Nle-His(Trt)-Cha-Cha-Asn(Trt)-Arg(Pbf)-Cha-Thr(Bu$^t$)-Arg(Pbf)-Gln(Trt)-Arg(Pbf)-Cha-Sieber Amide resin (SEQ ID NO:167). Then, after treatment with Fmoc-4-aminomethylbenzoic acid (33.7 mg, 0.1 mmol), 0.5 M HOAt/DMF (0.2 mL, 0.1 mmol), DIPCDI (15.9 μL, 0.1 mmol) in DMF at room temperature for 90 min, and the mixture was washed. N-terminal Fmoc group was removed and, after a treatment with N,N'-Bis-Boc-1-guanylpyrazole (31.0 mg, 0.1 mmol), DIEA (17.4 μL, 0.1 mmol) in DMF at room temperature for 90 min, and the mixture was washed and dried to give 4-(N,N'-bis-Boc-guanidinomethyl)benzoyl-Nle-His(Trt)-Cha-Cha-Asn(Trt)-Arg(Pbf)-Cha-Thr(Bu$^t$)-Arg(Pbf)-Gln(Trt)-Arg(Pbf)-Cha-Sieber Amide resin (SEQ ID NO:168) (54.1 mg). To the entire amount of the obtained resin was added TFA:thioanisole:m-cresol:H$_2$O:EDT:TIS (80:5:5:5:2.5:2.5) (0.5 ml), and the mixture was stirred at ambient temperature for 90 min, and diethyl ether was added to the reaction solution to allow precipitation of a white powder. An operation to remove ether by decantation after centrifugation of the suspension was repeated twice to remove acid and scavenger. The residue was extracted with aqueous acetic acid solution, and purified by preparative HPLC using Daisopak-SP100-5-ODS-P 2×25 cm to give 12.9 mg of a white powder.
MALDI-TOF-MS analysis, (M+H)$^+$1867.0 (Calculated: 1867.2)
HPLC elution time: 13.4 min
elution condition (HPLC mode d):
  column: Merck Chromolith Performance RP-18e(4.6×100 mm I.D.)
  eluent: using Solution A: 0.1% TFA-water, Solution B: 0.1% TFA-containing acetonitrile, A/B: 80/20-30/70 linear concentration gradient elution (25 min).
  flow rate: 1.0 mL/min

Example 9

(Synthesis Method I): Production of Ac-[D-Cha$^{24}$, Abu$^{26}$,Cha$^{27,28,36}$,Aib$^{31}$]-PYY(24-36) (Compound No. 84)

Synthesis of Ac-[D-Cha$^{24}$,Abu$^{26}$,Cha$^{27,28,36}$,Aib$^{31}$]-PYY(24-36)

Using commercially available Sieber Amide resin (347 mg, 0.25 mmol) as a starting material, an operation to successively condensing amino acids using ABI433A peptide synthesizer DCC/HOBt 0.25 mmol protocol was repeated twice, and the obtained resins were combined and washed with MeOH and dried to give H-Arg(Pbf)-Abu-Cha-Cha-Asn(Trt)-Leu-Aib-Thr(Bu$^t$)-Arg(Pbf)-Gln(Trt)-Arg(Pbf)-Cha-Sieber Amide resin (SEQ ID NO:169) (1.971 g, 0.249 mmol/g). 40.1 mg (0.01 mmol) of the obtained resin was washed with DMF and, after swelling, treated with Fmoc-D-Cha-OH (19.7 mg, 0.05 mmol), DIPCDI (8.0 μL, 0.05 mmol), 0.5 M HOAt/DMF (0.1 mL, 0.05 mmol) in DMF for 90 min to introduce D-Cha. Then, Fmoc was removed, the resin was washed, and treated with acetic anhydride (4.7 μL, 0.05 mmol), DIEA (8.7 μL, 0.05 mmol) in DMF for 20 min to acetylate the N-terminal. The resin was washed with DMF, MeOH, and dried to give Ac-D-Cha-Arg(Pbf)-Abu-Cha-Cha-Asn(Trt)-Leu-Aib-Thr(Bu$^t$)-Arg(Pbf)-Gln(Trt)-Arg(Pbf)-Cha-Sieber Amide resin (43.3 mg). To the entire amount of the obtained resin was added TFA:thioanisole:m-cresol:H$_2$O:EDT:TIS (80:5:5:5:2.5:2.5) (0.5 ml), and the mixture was stirred at ambient temperature for 90 min, and diethyl ether was added to the reaction solution to allow precipitation of a white powder. An operation to remove ether by decantation after centrifugation of the suspension was repeated twice to remove acid and scavenger. The residue was extracted with aqueous acetic acid solution, and purified by preparative HPLC using Daisopak-SP100-5-ODS-P 2×25 cm to give 15.1 mg of a white powder.
MALDI-TOF-MS analysis, (M+H)$^+$1766.8 (Calculated: 1767.1)
HPLC elution time: 18.1 min
elution condition (HPLC mode d):
  column: Merck Chromolith Performance RP-18e(4.6×100 mm I.D.)
  eluent: using Solution A: 0.1% TFA-water, Solution B: 0.1% TFA-containing acetonitrile, A/B: 80/20-30/70 linear concentration gradient elution (25 min)
  flow rate: 1.0 mL/min

Example 10

(Synthesis Method J): Production of Ac—[N(iBu)Gly$^{24}$,Cha$^{27,28,36}$,Aib$^{31}$]-PYY(23-36) (Compound No. 108)

Synthesis of Ac—[N(iBu)Gly$^{24}$,Cha$^{27,28,36}$,Aib$^{31}$]-PYY(23-36)

Using commercially available Sieber Amide resin (391 mg, 0.25 mmol) as a starting material, amino acids were condensed in the order of Cha, Arg(Pbf), Gln(Trt), Arg(Pbf), Thr(Bu$^t$), Aib, Leu, Asn(Trt), Cha, Cha, His(Trt), Arg(Pbf) using ABI433A peptide synthesizer DCC/HOBt 0.25 mmol protocol to give H-Arg(Pbf)-His-Cha-Cha-Asn(Trt)-Leu-Aib-Thr(Bu$^t$)-Arg(Pbf)-Gln(Trt)-Arg(Pbf)-Cha-Sieber Amide Resin(SEQ ID NO:170) (1.303 g, 0.232 mmol/g). The obtained resin (43.1 mg, 0.01 mmol) was washed with DMF and, after swelling, bromoacetic acid (13.8 mg, 0.01 mmol) was dissolved in DMF (0.4 ml) in another reaction vessel, DIPCDI (8.0 μL, 0.05 mmol) was added, and the mixture was stirred for 10 min. The obtained bromoacetic acid anhydride solution was added to the resin, and the mixture was stirred at room temperature for 1 hr. The resin was washed with DMF, suspended in a small amount of DMF, isobutylamine (10.1 μL, 0.1 mmol) was added, and the mixture was stirred at room temperature for 15 hr. The resin was washed with DMF, Fmoc was removed with 20% piperidine/DMF and the obtained resin was treated with Fmoc-Ser(Bu$^t$)—OH (38.3 mg), DIPCDI (15.9 μL), 0.5 M HOAt/DMF solution (0.2 mL) for 90 min, Ser(Bu$^t$) was introduced and Fmoc group was removed. Then, the resin was treated with Ac$_2$O (4.7 μL), DIEA (8.7 μL) in DMF for 30 min to allow acetylation, and the obtained resin was washed with MeOH and dried. The obtained resin (42.4 mg) was treated with TFA:thioanisole:m-cresol:$H_2O$:EDT:TIS (80:5:5:2.5:2.5) (0.5 mL) for 90 min, an operation to add diethyl ether to the reaction solution, precipitate a white powder by centrifugation, and remove diethyl ether by decantation was repeated twice. The residue was dissolved in aqueous acetic acid solution, passed through a disc filter with a pore diameter 0.45 μm to remove fine granules, and purified by preparative HPLC using Daisopak-SP100-5-ODS-P 2×25 cm, and Solution A: 0.1% TFA-water, Solution B: 0.1% TFA-containing acetonitrile, flow rate 8 mL/min, A/B: 68/32-58/42 linear concentration gradient elution (60 min) was performed. The eluted object product was fractionated in test tubes, and each fraction was analyzed by HPLC to specify fractions containing only the object product. These fractions were combined and freeze-dried to give 10.9 mg of a white powder.

MALDI-TOF-MS analysis, $(M+H)^+$ 1866.1 (Calculated 1866.2)

HPLC elution time: 13.0 min elution condition (HPLC mode d):
 column: Merck Chromolith Performance RP-18e(4.6×100 mm I.D.)
 eluent: using Solution A: 0.1% TFA-water, Solution B: 0.1% TFA-containing acetonitrile, A/B: 80/20-30/70 linear concentration gradient elution (25 min)
 flow rate: 1.0 mL/min Example 11

(Synthesis Method K): Production of [N(iBu)Gly$^{23}$, D-Pro$^{24}$,Cha$^{27,28,36}$,Aib$^{31}$]-PYY(23-36)(Compound No. 133)

Synthesis of [N(iBu)Gly$^{23}$, D-Pro$^{24}$,Cha$^{27,28,36}$, Aib$^{31}$]-PYY(23-36)

H-Arg (Pbf)-His (Trt)-Cha-Cha-Asn (Trt)-Leu-Aib-Thr(Bu$^t$)-Arg(Pbf)-Gln(Trt)-Arg(Pbf)-Cha-Sieber Amide resin (SEQ ID NO:164)(0.223 mmol/g, 44.8 mg, 0.01 mmol) obtained in Example 7 was swollen with DMF, Fmoc-D-Pro was condensed by manual solid phase synthesis using 4 equivalents each of Fmoc-amino acid/HOAt/DIPCDI. Fmoc group was removed with 20% piperidine in DMF, the resin was treated with BrCH$_2$CO$_2$H (6.94 mg, 0.05 mmol), HOAt in DMF (0.5 M, 100 μL, 0.05 mmol), DIPCDI (7.95 μL, 0.05 mmol) in DMF for 1 hr. The resin was washed with DMF, and treated with isobutylamine (9.94 μL, 0.1 mmol) in DMF for 2 days, washed successively with DMF, MeOH, dried under reduced pressure and the obtained resin (49 mg) was suspended in TFA:thioanisole:m-cresol:$H_2O$:EDT:TIS (80:5:5:5:2.5:2.5) (1 mL), and the suspension was stirred at room temperature for 4 hr. An operation to add diethyl ether to the reaction solution to allow precipitation and remove the supernatant after centrifugation was repeated 3 times and washed. The residue was extracted with 50% aqueous acetic acid solution, the resin was removed by filtration, applied to preparative HPLC using YMC Pack R&D-ODS-5-B S-5, 120A column (30×250 mm), Solution A: 0.1% TFA-water, Solution B: 0.1% TFA-containing acetonitrile, flow rate 15 ml/min, A/B: 73.5/26.5-63.5/36.5 linear concentration gradient elution (60 min). The fractions containing the object product were collected and freeze-dried to give 7.7 mg of a white powder.

MALDI-TOF-MS analysis, $(M+H)^+$ 1833.5 (Calculated 1834.2)

HPLC elution time: 11.4 min elution condition (HPLC mode g):
 column: SHISEIDO CAPCELL PAK C18 MGII(4.6×100 mm)
 eluent: using Solution A: 0.1% TFA-water, Solution B: 0.1% TFA-containing acetonitrile, A/B: 80/20-30/70 linear concentration gradient elution (25 min)
 flow rate: 1.0 mL/min Example 12

(Synthesis Method L): Production of Ac-[D-Pro$^{24}$, Pya(4)$^{26}$,Cha$^{27,36}$,Aib$^{28,31}$,Lys$^{30}$]-PYY(23-36) (Compound No. 138)

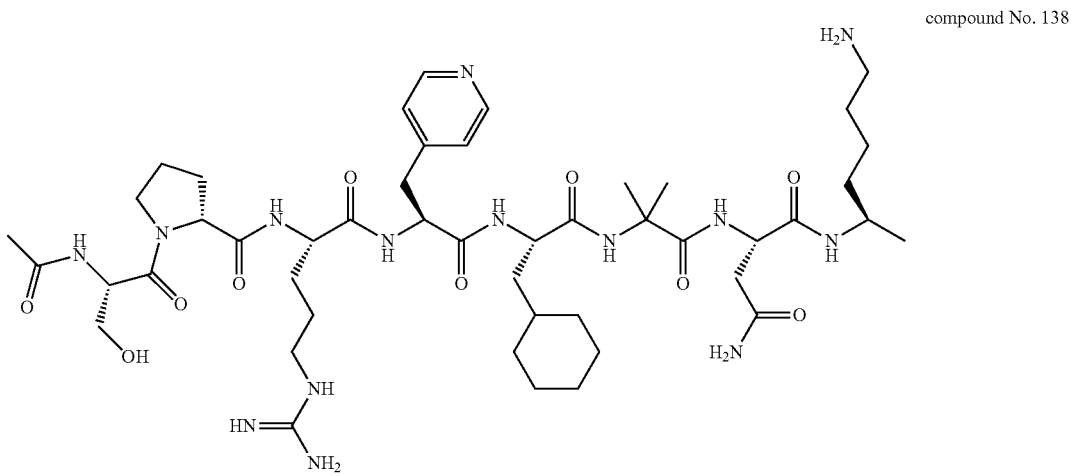

compound No. 138

-continued

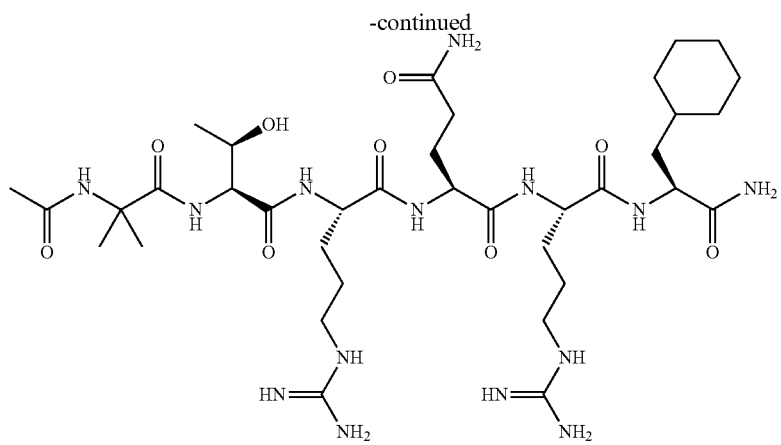

Synthesis of Ac-[D-Pro$^{24}$,Pya(4)$^{26}$,Cha$^{27,36}$,Aib$^{28,31}$, Lys$^{30}$]-PYY(23-36)

Using commercially available Sieber Amide resin (391 mg, 0.25 mmol) as a starting material, amino acids were condensed to in the order of Cha, Arg(Pbf), Gln(Trt), Arg (Pbf), Thr(Bu$^t$), Aib using ABI433A peptide synthesizer DCC/HOBt 0.25 mmol protocol to give H-Aib-Thr(Bu$^t$)-Arg (Pbf)-Gln(Trt)-Arg(Pbf)-Cha-Sieber Amide resin (SEQ ID NO:172). The obtained resin was washed with DMF, stirred in DMF for 20 min to swell the resin. Then, the resin was treated with Fmoc-Lys(Boc)-OH (468.5 mg, 1 mmol), 0.5 M HOAt/DMF solution (2 mL, 1 mmol), DIPCDI (0.159 ml, 1 mmol) for 100 min to introduce Lys(Boc) residue. Then, the resin was treated with decanoic anhydride (0.921 mL, 2.5 mmol), DIEA (0.436 ml, 2.5 mmol) in DMF for 30 min for capping. Using the obtained resin and ABI433A peptide synthesizer DCC/HOBt 0.25 mmol protocol, the amino acids were condensed in the order of Asn(Trt), Aib, Cha to convert to Fmoc-Cha-Aib-Asn (Trt)-Lys (Boc)-Aib-Thr (Bu$^t$)-Arg (Pbf)-Gln(Trt)-Arg(Pbf)-Cha-Sieber Amide resin (SEQ ID NO:173). The 27-position Cha condensation was performed by double coupling. The obtained resin was washed with DMF, stirred in DMF for 20 min to swell the resin. The N-terminal Fmoc group was removed by 20% piperidine/ DMF treatment, the resin was treated with Fmoc-Pya(4)-OH (388.4 mg, 1 mmol), 0.5 M HOAt/DMF solution (2 mL, 1 mmol), DIPCDI (0.159 mL, 1 mmol) for 6 hr to introduce Pya(4) residue. In this case, DIEA (0.174 mL, 1 mmol) was added to the reaction solution during condensation. In the obtained resin, the amino acids were condensed in the order of Arg(Pbf), D-Pro, Ser(Bu$^t$) using ABI433A peptide synthesizer DCC/HOBt 0.25 mmol protocol to convert to Ac-Ser (Bu$^t$)-D-Pro-Arg(Pbf)-Pya(4)-Cha-Aib-Asn(Trt)-Lys(Boc)-Aib-Thr(Bu$^t$)-Arg(Pbf)-Gln(Trt)-Arg(Pbf)-Cha-Sieber Amide resin. In this case, the protocol was partly modified, and capping protocol using acetic anhydride was incorporated after completion of condensation of Ser(Bu$^t$). Washing with MeOH and post-drying gave a resin (1.0606 g, 0.236 mmol/g). The obtained resin was treated with TFA:thioanisole:m-cresol:H$_2$O:EDT:TIS (80:5:5:5:2.5:2.5) (10 mL) for 100 min, an operation to add diethyl ether to the reaction solution, precipitate a white powder by centrifugation, and remove diethyl ether by decantation was repeated twice. The residue was dissolved in aqueous acetic acid solution, passed through a disc filter with a pore diameter 0.45 µm to remove fine granules, and concentrated in an evaporator to give a crude peptide (486.6 mg). A similar operation was repeated twice to give a crude peptide corresponding to 0.75 mmol. After confirmation of the purity of the obtained crude peptide solution by HPLC, the peptide was purified in 28 portions by preparative HPLC using Daisopak-SP100-5-ODS-P 2×25 cm, and Solution A: 0.1% TFA-water, Solution B: 0.1% TFA-containing acetonitrile, flow rate 8 mL/min, A/B: 82/18-72/28 linear concentration gradient elution (60 min) was performed. The eluted object product was fractionated in test tubes, and each fraction was analyzed by HPLC to specify fractions containing only the object product. These fractions were combined and freeze-dried to give 744 mg of a white powder. The obtained purified sample (744 mg, 410.6 µmol) was dissolved in a small amount of water, and AG 1×8 AcO$^-$ resin (6.84 mL, 8.21 mmol equivalents) was added. The solution was stood for 1 hr while occasionally stirring with hand, passed through a disc filter with a pore diameter 0.45 µm to remove fine granules, concentrated in an evaporator to reduce the liquid amount to about 5 mL, and the solution was freeze-dried by cooling in a dry ice bath to give 610 mg of a white powder.

MALDI-TOF-MS analysis, (M+H)$^+$ 1808.4 (Calculated 1808.1)

HPLC elution time: 6.6 min
elution condition (HPLC mode d):
    column: Merck Chromolith Performance RP-18e(4.6×100 mmI.D.)
    eluent: using Solution A: 0.1% TFA-water, Solution B: 0.1% TFA-containing acetonitrile, A/B: 80/20-30/70 linear concentration gradient elution (25 min)
    flow rate: 1.0 mL/min Example 13

(Synthesis Method M): Production of Ac-[D-Pro$^{24}$, Cha$^{27,28}$,Aib$^{31}$]-PYY(23-36) (Compound No. 142)

(1) Synthesis of Ac-Ser (Bu$^t$)-D-Pro-Arg(Pbf)-His-Cha-Cha-Asn(Trt)-Leu-Aib-Thr (Bu$^t$)-OH Commercially available 2-Chlorotrityl chloride resin (2 g, 2.8 mmol) was weighed and placed in a reaction vessel, and treated with Fmoc-Thr(Bu$^t$)—OH (1391 mg, 3.5 mmol), DIEA (0.6097 ml, 3.5 mmol), DMF (20 mL) for 18 hr to introduce Thr(Bu$^t$) residue into 2-chlorotrityl chloride resin. Then, N-terminal Fmoc group was removed by 20% piperidine/DMF treatment. The obtained resin was dissolved in a small amount of DMF and treated with Fmoc-Aib-OH (1952 mg, 6 mmol), HOOBt (978.8 mg, 6 mmol), DIPCDI (0.954 mL, 6 mmol) for 90 min, and Fmoc group was removed with 20% piperidine/DMF. By a similar procedure, Leu, Asn(Trt), Cha, Cha, His(Trt), Arg(Pbf), D-Pro, Ser(Bu$^t$) were introduced. Capping with acetic anhydride was performed after completion of condensation of Leu, Arg(Pbf). After removal of Fmoc from the obtained Fmoc-Ser(Bu$^t$)-D-Pro-Arg(Pbf)-His-Cha-Cha-Asn(Trt)-Leu-Aib-Thr(Bu$^t$)-O-2-chlorotrityl resin, the resin was treated with Ac$_2$O (1.887 mL, 20 mmol), DIEA (3.484 mL, 20 mmol) in DMF for 50 min, and the resin was washed with MeOH and dried. The obtained resin was stirred in AcOH/trifluoroethanol/toluene (=1/4.5/4.5) mixed solvent for 90 min, the resin was filtered off by filtration through a disc filter with a pore diameter 0.45 μm, and washed with the same mixed solvent. The filtrate was concentrated under reduced pressure, diethyl ether was added to the residue and the mixture was left standing overnight at −4° C. The precipitated white precipitate was collected by suction filtration, washed with diethyl ether, and dried to give 2142 mg of Ac-Ser(Bu$^t$)-D-Pro-Arg(Pbf)-His-Cha-Cha-Asn(Trt)-Leu-Aib-Thr(Bu$^t$)-OH.

(2) Synthesis of Ac-[D-Pro$^{24}$,Cha$^{27,28}$,Aib$^{31}$]-PYY (23-36)

Commercially available Sieber amide resin (31.25 mg, 0.02 mmol) was weighed and placed in a reaction vessel, washed with DMF, and stirred in DMF for 20 min to swell the resin. Then, the resin was treated with 20% piperidine/DMF for 20 min. Fmoc group was removed, and the resin was treated with Fmoc-Tyr(Bu$^t$)—OH (36.77 mg, 0.08 mmol), 0.5 M HOAt/DMF (160 μL, 0.08 mmol), DIPCDI (12.71 μL, 0.08 mmol) for 16 hr to introduce Tyr(Bu$^t$). By a similar procedure, Arg(Pbf), Gln(Trt) were introduced, and N-terminal Fmoc group was removed. Then, the obtained resin was treated with Ac-Ser(Bu$^t$)-D-Pro-Arg(Pbf)-His-Cha-Cha-Asn(Trt)-Leu-Aib-Thr(Bu$^t$)—OH (84.25 mg, 0.04 mmol), HOOBt (9.787 mg, 0.06 mmol), DIPCDI (6.36 μL, 0.04 mmol) dissolved in a small amount of DMF overnight, washed with MeOH, and dried to give Ac-Ser(Bu$^t$)-D-Pro-Arg(Pbf)-His-Cha-Cha-Asn(Trt)-Leu-Aib-Thr(Bu$^t$)-Arg(Pbf)-Gln(Trt)-Arg(Pbf)-Tyr(Bu$^t$)-Sieber amide resin (67.0 mg).

The obtained resin was treated with TFA:thioanisole:m-cresol:H$_2$O:EDT:TIS (80:5:5:5:2.5:2.5) (0.700 mL) for 90 min, an operation to add diethyl ether to the reaction solution, precipitate a white powder by centrifugation, and remove ether by decantation was repeated twice. The residue was dissolved in aqueous acetic acid solution, passed through a disc filter with a pore diameter 0.45 μm to remove fine granules, and concentrated in an evaporator. After confirmation of the purity of the obtained crude peptide solution by HPLC, the peptide was purified by preparative HPLC using Daiso-pak-SP100-5-ODS-P 2×25 cm, and Solution A: 0.1% TFA-water, Solution B: 0.1% TFA-containing acetonitrile, flow rate 8 mL/min, A/B: 73/27-63/37 linear concentration gradient elution (60 min) was performed. The eluted object product was fractionated in test tubes, and each fraction was analyzed by HPLC to specify fractions containing only the object product. These fractions were combined and freeze-dried to give 1.6 mg of a white powder.
MALDI-TOF-MS analysis, (M+H)$^+$ 1860.2 (Calculated 1860.1)
HPLC elution time: 9.9 min
elution condition (HPLC mode d):
  column: Merck Chromolith Performance RP-18e(4.6×100 mm I.D.)
  eluent: using Solution A: 0.1% TFA-water, Solution B: 0.1% TFA-containing acetonitrile, A/B: 80/20-30/70 linear concentration gradient elution (25 min)
  flow rate: 1.0 mL/min Example 14

(Synthesis Method N): Production of carbamoyl-[Asp$^{23}$,D-Pro$^{24}$,Cha$^{27,28,36}$,Aib$^{31}$]-PYY (23-36) (Compound No. 161)

Synthesis of carbamoyl-[Asp$^{23}$,D-Pro$^{24}$,Cha$^{27,28,36}$, Aib$^{31}$]-PYY(23-36)

H-Arg(Pbf)-His(Trt)-Cha-Cha-Asn(Trt)-Leu-Aib-Thr(Bu$^t$)-Arg(Pbf)-Gln(Trt)-Arg(Pbf)-Cha-Sieber Amide resin (SEQ ID NO:164)(0.223 mmol/g, 44.8 mg, 0.01 mmol) obtained in Example 7 was swollen with DMF, and D-Pro, Asp(OBu$^t$) were successively condensed by manual solid phase synthesis using 4 equivalents each of Fmoc-amino acid/HOAt/DIPCDI. The obtained H-Asp(OBu$^t$)-D-Pro-Arg(Pbf)-His(Trt)-Cha-Cha-Asn(Trt)-Leu-Aib-Thr(Bu$^t$)-Arg(Pbf)-Gln(Trt)-Arg(Pbf)-Cha-Sieber Amide resin was treated with trimethylsilyl isocyanate (85%, 15.6 μL, 0.1 mmol) in DMF for 2 days, washed successively with DMF, MeOH, dried under reduced pressure. The obtained resin (49 mg) was suspended in TFA:thioanisole:m-cresol:H$_2$O:EDT:TIS (80:5:5:5:2.5:2.5) (1 mL), and the mixture was stirred at room temperature for 4 hr. An operation to add diethyl ether to the reaction solution to allow precipitation and remove the supernatant after centrifugation was repeated 3 times. The residue was extracted with 50% aqueous acetic acid solution, the resin was removed by filtration, and applied to preparative HPLC using YMC Pack R&D-ODS-5-B S-5 120A column (30×250 mm), Solution A: 0.1% TFA-water, Solution B: 0.1% TFA-containing acetonitrile, flow rate 15 mL/min, A/B: 72.0/28.0-62.0/38.0 linear concentration gradient elution (60 min). The fractions containing the object product were collected and freeze-dried to give 6.8 mg of a white powder.
MALDI-TOF-MS analysis, (M+H)$^+$1879.6 (Calculated 1879.1)
HPLC elution time: 11.5 min
elution condition (HPLC mode g):
  column: SHISEIDO CAPCELL PAK C18 MGII(4.6×100 mm)
  eluent: using Solution A: 0.1% TFA-water, Solution B: 0.1% TFA-containing acetonitrile, A/B: 80/20-30/70 linear concentration gradient elution (25 min)
  flow rate: 1.0 mL/min Example 15

(Synthesis Method O): Production of 3-Carboxypropionyl-[D-Pro$^{24}$,Cha$^{27,28,36}$,Lys$^{30}$,Aib$^{31}$]-PYY(23-36) (Compound No. 167)

Synthesis of 3-Carboxypropionyl-[D-Pro$^{24}$, Cha$^{27,28,36}$,Lys$^{30}$,Aib$^{31}$]-PYY(23-36)

Using commercially available Sieber Amide resin (391 mg, 0.25 mmol) as a starting material, amino acids were condensed in the order of Cha, Arg(Pbf), Gln(Trt), Arg(Pbf), Thr(Bu$^t$), Aib using ABI433A peptide synthesizer DCC/HOBt 0.25 mmol protocol to give H-Aib-Thr(Bu$^t$)-Arg(Pbf)-Gln(Trt)-Arg(Pbf)-Cha-Sieber Amide resin (SEQ ID NO: 176) (0.912 g, 0.342 mmol/g). The obtained resin (29.2 mg, 0.01 mmol) was washed with DMF and, after swelling, treated with Fmoc-Lys(Boc)-OH (23.3 mg, 0.05 mmol), 0.5 M HOAt/DMF solution (0.1 mL, 0.05 mmol), DIPCDI (8.0 µL, 0.05 mmol) for 120 min to introduce Lys(Boc) residue. After completion of the reaction, the resin was washed, and N-terminal Fmoc group was removed by 20% piperidine/DMF treatment. By a similar procedure, Asn(Trt) was introduced. Removal of Fmoc group and condensation were repeated to introduce Cha, Cha, His(Trt), Arg(Pbf), D-Pro, Ser(Bu$^t$). The obtained Fmoc-Ser(Bu$^t$)-D-Pro-Arg(Pbf)-Arg(Pbf)-His-Cha-Cha-Asn(Trt)-Lys(Boc)-Aib-Thr(Bu$^t$)-Arg(Pbf)-Gln(Trt)-Arg(Pbf)-Cha-Sieber Amide resin was treated with succinic anhydride (5.0 mg, 0.05 mmol), DIEA (8.7 µL, 0.05 mmol) in DMF for 60 min after removal of Fmoc to succinylate the N-terminal, and the resin was washed with MeOH, and dried to give 3-Carboxypropionyl-Ser(Bu$^t$)-D-Pro-Arg(Pbf)-Arg(Pbf)-His-Cha-Cha-Asn(Trt)-Lys(Boc)-Aib-Thr(Bu$^t$)-Arg(Pbf)-Gln(Trt)-Arg(Pbf)-Cha-Sieber Amide resin. The obtained resin (87.1 mg) was treated with TFA:thioanisole:m-cresol:H$_2$O:EDT:TIS (80:5:5:5:2.5:2.5) (0.6 mL) for 90 min, an operation to add diethyl ether to the reaction solution, precipitate a white powder by centrifugation, and remove ether by decantation was repeated twice. The residue was dissolved in aqueous acetic acid solution, passed through a disc filter with a pore diameter 0.45 µm to remove fine granules, and purified by preparative HPLC using Daisopak-SP100-5-ODS-P 2×25 cm, and Solution A: 0.1% TFA-water, Solution B: 0.1% TFA-containing acetonitrile, flow rate 8 mL/min, A/B: 73/27-63/37 linear concentration gradient elution (60 min) was performed. The eluted object product was fractionated in test tubes, and each fraction was analyzed by HPLC to specify fractions containing only the object product. They were combined and freeze-dried to give 4.2 mg of a white powder.
MALDI-TOF-MS analysis, (M+H)$^+$1923.3 (Calculated 1923.1)
HPLC elution time: 9.7 min
elution condition (HPLC mode d):
  column: Merck Chromolith Performance RP-18e (4.6×100 mm I.D.)
  eluent: using Solution A: 0.1% TFA-water, Solution B: 0.1% TFA-containing acetonitrile, A/B: 80/20-30/70 linear concentration gradient elution (25 min)
  flow rate: 1.0 mL/min Example 16

(Synthesis Method P): Production of 3-Carboxypropionyl-[Acp$^{22}$,D-Pro$^{24}$,Cha$^{27,36}$,Leu(Me)$^{28}$,Lys$^{30}$, Aib$^{31}$]-PYY (22-36) (compound No. 185)

Synthesis of Succinyl-[Acp$^{22}$, D-Pro$^{24}$, Cha$^{27,36}$, Leu(Me)$^{28}$,Lys$^{30}$,Aib$^{31}$]-PYY(22-36)

H-Ser(Bu$^t$)-D-Pro-Arg(Pbf)-His(Trt)-Cha-Leu(Me)-Asn(Trt)-Lys(Boc)-Aib-Thr(Bu$^t$)-Arg(Pbf)-Gln(Trt)-Arg(Pbf)-Cha-Sieber Amide resin (0.207 mmol/g, 48.3 mg, 0.01 mmol) obtained by condensation of amino acids in the same manner as in Example 12 and using commercially available Sieber Amide resin as a starting material and ABI433A peptide synthesizer DCC/HOBt 0.25 mmol protocol was swollen with DMF, treated overnight with Fmoc-Acp-OH (21.2 mmol, 0.06 mmol), HOAt in DMF (0.5 M, 120 µL, 0.06 mmol), DIPCDI (9.54 µL, 0.06 mmol) in DMF, washed with DMF, treated with 20% piperidine in DMF for 20 min to cleavage the Fmoc group. The resin was washed with DMF, treated with succinic anhydride (6.0 mg, 0.06 mmol), DIPEA (10.5 µL, 0.06 mmol) in DMF for 3 hr, washed successively with DMF, MeOH, and dried under reduced pressure. The obtained resin (50.7 mg) was suspended in TFA:thioanisole:m-cresol:H$_2$O:EDT:TIS (80:5:5:5:2.5:2.5) (1 mL), and the suspension was stirred at room temperature for 3 hr. An operation to add diethyl ether to the reaction solution to allow precipitation and remove the supernatant after centrifugation was repeated 3 times. The residue was extracted with 50% aqueous acetic acid solution, the resin was removed by filtration, and applied to preparative HPLC using YMC Pack R&D-ODS-5-B S-5 120A column (30×250 mm), Solution A: 0.1% TFA-water, Solution B: 0.1% TFA-containing acetonitrile, flow rate 15 mL/min, A/B: 73.0/27.0-63.0/37.0 linear concentration gradient elution (60 min). The fractions containing the object product were collected and freeze-dried to give 11.8 mg of a white powder.
MALDI-TOF-MS analysis, (M+H)$^+$2009.6 (Calculated 2010.2)
HPLC elution time: 8.8 min
elution condition (HPLC mode g):
  column: SHISEIDO CAPCELL PAK C18 MGII(4.6×100 mm)
  eluent: using Solution A: 0.1% TFA-water, Solution B: 0.1% TFA-containing acetonitrile, A/B: 80/20-30/70 linear concentration gradient elution (25 min)
  flow rate: 1.0 mL/min Example 17

(Synthesis Method Q): Production of Amidino-[D-Pro$^{24}$,Cha$^{27,36}$, Leu(Me)$^{28}$,Lys$^{30}$,Aib$^{31}$]-PYY(23-36) (Compound No. 186)

Synthesis of Amidino-[D-Pro$^{24}$,Cha$^{27,36}$,Leu(Me)$^{28}$, Lys$^{30}$,Aib$^{31}$]-PYY(23-36)

H-Ser(Bu$^t$)-D-Pro-Arg(Pbf)-His(Trt)-Cha-Leu(Me)-Asn(Trt)-Lys(Boc)-Aib-Thr(Bu$^t$)-Arg(Pbf)-Gln(Trt)-Arg(Pbf)-Cha-Sieber Amide resin (0.207 mmol/g, 48.3 mg, 0.01 mmol) obtained in Example 16 was swollen with DMF, treated overnight with N,N'-bis-Boc-1-guanylpyrazole (31.0 mg, 0.1 mmol), DIPEA (17.4 µL, 0.1 mmol) in toluene/2,2,2-trifluoroethanol (4:1), washed with DMF, and further stirred with the similar reagent in DMF overnight, washed successively with DMF, MeOH, and dried under reduced pressure. The obtained resin (54 mg) was suspended in TFA:thioanisole:m-cresol:H$_2$O:EDT:TIS (80:5:5:5:2.5:2.5) (1 mL), and the suspension was stirred at room temperature for 3 hr. An operation to add diethyl ether to the reaction solution to allow precipitation and remove the supernatant after centrifugation was repeated 3 times. The residue was extracted with 50% aqueous acetic acid solution, the resin was removed by filtration, and applied to preparative HPLC using YMC Pack R&D-ODS-5-B S-5 120A column (30×250 mm), Solution A: 0.1% TFA-water, Solution B: 0.1% TFA-containing acetonitrile, flow rate 15 mL/min, A/B: 74.5/25.5-64.5/35.5 linear concentration gradient elution (60 min). The fractions containing the object product were collected and freeze-dried to give 5.5 mg of a white powder.
MALDI-TOF-MS analysis, (M+H)$^+$ 1839.4 (Calculated 1839.1)
HPLC elution time: 7.9 min
elution condition (HPLC mode g):
  column: SHISEIDO CAPCELL PAK C18 MGII(4.6×100 mm)
  eluent: using Solution A: 0.1% TFA-water, Solution B: 0.1% TFA-containing acetonitrile, A/B: 80/20-30/70 linear concentration gradient elution (25 min)
  flow rate: 1.0 mL/min

Example 180

(Synthesis Method R): Production of Morpholinocarbonyl-[D-Pro$^{24}$, Cha$^{27,36}$,Leu(Me)$^{28}$,Lys$^{30}$, Aib$^{31}$]-PYY (23-36) (Compound No. 187)

Synthesis of Morpholinocarbonyl-[D-Pro$^{24}$,Cha$^{27,36}$, Leu (Me)$^{28}$,Lys$^{30}$,Aib$^{31}$]-PYY (23-36)

H-Ser(Bu$^t$)-D-Pro-Arg(Pbf)-His(Trt)-Cha-Leu(Me)-Asn (Trt)-Lys(Boc)-Aib-Thr(Bu$^t$)-Arg(Pbf)-Gln(Trt)-Arg(Pbf)-Cha-Sieber Amide resin (0.207 mmol/g, 48.3 mg, 0.01 mmol) obtained in Example 16 was swollen with DMF, treated overnight with CDI (16.2 mg, 0.1 mmol), DIPEA (17.4 µL, 0.1 mmol) in DMF, and washed with DMF. The resin was treated overnight with morpholine (8.75 µL, 0.1 mmol) in DMF, washed successively with DMF, MeOH, dried under reduced pressure. The obtained resin (53 mg) was suspended in TFA:thioanisole:m-cresol:H$_2$O:EDT:TIS (80:5:5:5:2.5:2.5) (1 mL), and the mixture was stirred at room temperature for 3 hr. An operation to add diethyl ether to the reaction solution to allow precipitation and remove the supernatant after centrifugation was repeated 3 times. The residue was extracted with 50% aqueous acetic acid solution, the resin was removed by filtration, and applied to preparative HPLC using YMC Pack R&D-ODS-5-B S-5 120A column (30×250 mm), Solution A: 0.1% TFA-water, Solution B: 0.1% TFA-containing acetonitrile, flow rate 15 mL/min, A/B: 74.5/25.5-64.5/35.5 linear concentration gradient elution (60 min). The fractions containing the object product were collected and freeze-dried to give 3.9 mg of a white powder.

MALDI-TOF-MS analysis, (M+H)$^+$1909.9 (Calculated 1910.2)

HPLC elution time: 9.0 min elution condition (HPLC mode g):
 column: SHISEIDO CAPCELL PAK C18 MGII (4.6×100 mm)
 eluent: using Solution A: 0.1% TFA-water, Solution B: 0.1% TFA-containing acetonitrile, A/B: 80/20-30/70 linear concentration gradient elution (25 min)
 flow rate: 1.0 mL/min

Example 19

(Synthesis Method S): Production of Tetrahydro-2H-pyran-4-yl-carbamoyl-[D-Pro$^{24}$, Cha$^{27,36}$, Leu (Me)$^{28}$,Lys$^{30}$,Aib$^{31}$]-PYY (23-36) (Compound No. 229)

Synthesis of Tetrahydro-2H-pyran-4-yl-carbamoyl-[D-Pro$^{24}$, Cha$^{27,36}$,Leu(Me)$^{28}$,Lys$^{30}$,Aib$^{31}$]-PYY (23-36)

H-Ser(Bu$^t$)-D-Pro-Arg(Pbf)-His(Trt)-Cha-Leu(Me)-Asn (Trt)-Lys(Boc)-Aib-Thr(Bu$^t$)-Arg(Pbf)-Gln(Trt)-Arg(Pbf)-Cha-Sieber Amide resin (0.207 mmol/g, 48.3 mg, 0.01 mmol) obtained in Example 16 was swollen with DMF, treated for 8 hr with CDI (16.2 mg, 0.1 mmol), DIPEA (17.4 µL, 0.1 mmol) in DMF, and washed with DMF. The resin was treated overnight with 4-aminotetrahydropyran (10.1 mg, 0.1 mmol) in DMF, washed successively with DMF, MeOH, dried under reduced pressure. The obtained resin (53 mg) was suspended in TFA:thioanisole:m-cresol:H$_2$O:EDT:TIS (80:5:5:5:2.5:2.5) (1 mL), and the mixture was stirred at room temperature for 4 hr. An operation to add diethyl ether to the reaction solution to allow precipitation remove the supernatant after centrifugation was repeated 3 times. The residue was extracted with 50% aqueous acetic acid solution, the resin was removed by filtration, and applied to preparative HPLC using YMC Pack R&D-ODS-5-B S-5 120A column (30×250 mm), Solution A: 0.1% TFA-water, Solution B: 0.1% TFA-containing acetonitrile, flow rate 15 mL/min, A/B: 73.5/26.5-63.5/36.5 linear concentration gradient elution (60 min). The fractions containing the object product were collected and freeze-dried to give 11.1 mg of a white powder.

MALDI-TOF-MS analysis, (M+H)$^+$1924.7 (Calculated 1924.2)

HPLC elution time: 9.2 min elution condition (HPLC mode g):
 column: SHISEIDO CAPCELL PAK C18 MGII(4.6×100 mm)
 eluent: using Solution A: 0.1% TFA-water, Solution B: 0.1% TFA-containing acetonitrile, A/B: 80/20-30/70 linear concentration gradient elution (25 min)
 flow rate: 1.0 mL/min

Example 20

(Synthesis Method T): Production of Ac-[D-Pro$^{24}$, Pya(4)$^{26}$,Cha$^{27,36}$,Iva$^{28}$,Lys$^{30}$,Aib$^{31}$]-PYY (23-36) (Compound No. 233)

Compound No. 233

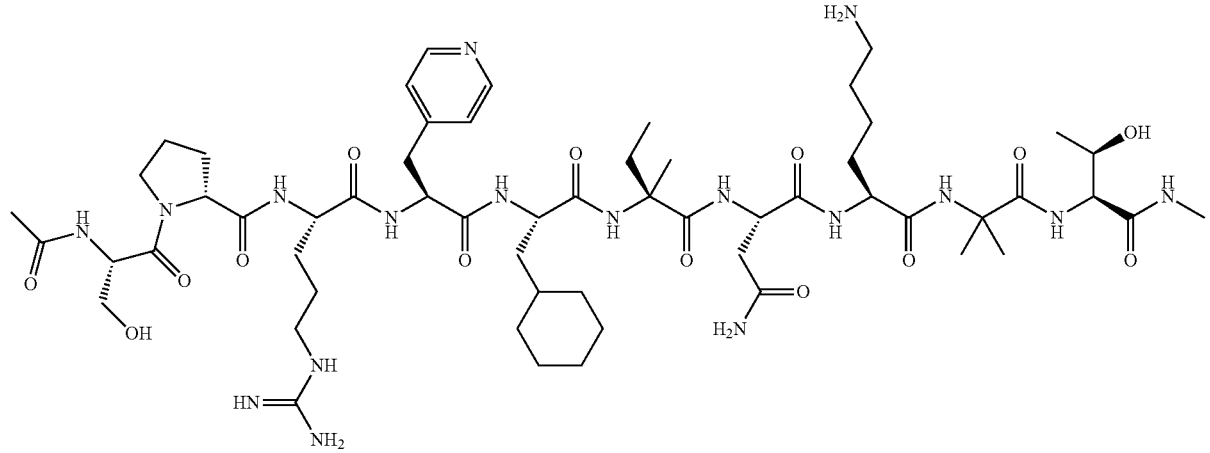

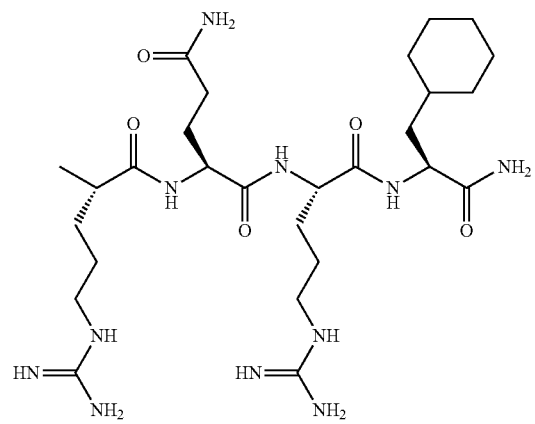

(1) Synthesis of H-Asn(Trt)-Lys(Boc)-Aib-Thr(Bu$^t$)-Arg(Pbf)-Gln(Trt)-Arg(Pbf)-Cha-NH-Sieber amide resin (SEQ ID NO:177)

Using commercially available Sieber Amide resin (391 mg, 0.25 mmol) as a starting material, amino acids were condensed in the order of Cha, Arg(Pbf), Gln(Trt), Arg(Pbf), Thr(Bu$^t$), Aib, Lys(Boc), Asn(Trt) using ABI433A peptide synthesizer DCC/HOBt 0.25 mmol protocol to give H-Asn(Trt)-Lys(Boc)-Aib-Thr(Bu$^t$)-Arg(Pbf)-Gln(Trt)-Arg(Pbf)-Cha-Sieber Amide resin. In this case, the protocol was partly modified, and capping protocol with acetic anhydride was incorporated after every condensation procedure. In addition, the 30-position Lys(Boc) condensation was performed by double coupling. The obtained resin was washed with MeOH and dried any amino acid residue(s) bound continuously or discontinuously to each other to give a resin (881.7 mg, 0.289 mmol/g). A similar operation was repeated 11 times to give a resin corresponding to 2.75 mmol.

(2) Synthesis of Ac-[D-Pro$^{24}$,Pya (4)$^{26}$, Cha$^{27,36}$, Iva$^{28}$,Lys$^{30}$,Aib$^{31}$]-PYY(23-36)

H-Asn(Trt)-Lys(Boc)-Aib-Thr(Bu$^t$)-Arg(Pbf)-Gln(Trt)-Arg(Pbf)-Cha-Sieber Amide resin (891.0 mg, 0.25 mmol) obtained in (1) above was weighed and placed in a reaction vessel, washed with DMF, and stirred in DMF for 20 min to swell the resin. Then, the resin was treated with Fmoc-Iva-OH (339.4 mg, 1 mmol), 0.5 M HOAt/DMF solution (2 mL, 1 mmol), DIPCDI (159 µL, 1 mmol) for 120 min, and washed with DMF. The N-terminal Fmoc group was removed by 20% piperidine/DMF treatment. By a similar procedure, Cha was introduced. In the same manner, removal of Fmoc group and condensation were repeated to introduce Pya(4). During introduction of Pya(4), DIEA (174 µL, 1 mmol) was also added. Using the obtained resin as a starting material, amino acids were condensed in the order of Arg(Pbf), D-Pro, Ser(Bu$^t$) using ABI433A peptide synthesizer DCC/HOBt 0.25 mmol protocol. In this case, the protocol was partly modified, and capping protocol with acetic anhydride was incorporated after every condensation procedure. In addition, a protocol for acetylation of N-terminal with Ac$_2$O was designed, and N-terminal acetylation was performed after completion of the 23-position condensation. The obtained resin was washed with MeOH and dry to give Ac-Ser(Bu$^t$)-D-Pro-Arg(Pbf)-Pya(4)-Cha-Iva-Asn(Trt)-Lys(Boc)-Aib-Thr(Bu$^t$)-Arg(Pbf)-Gln(Trt)-Arg(Pbf)-Cha-Sieber Amide resin. The obtained resin (1.2067 g) was treated with TFA:thioanisole:m-cresol: H$_2$O:EDT:TIS (80:5:5:5:2.5:2.5) (6 mL) for 120 min. An operation to add diethyl ether to the reaction solution, precipitate a white powder by centrifugation, and remove ether by decantation was repeated twice. The residue was dissolved in aqueous acetic acid solution, passed through a disc filter with a pore diameter 0.45 µm to remove fine granules, and concentrated in an evaporator. After confirmation of the purity of the obtained crude peptide solution by HPLC, the peptide was purified in 6 portions by preparative HPLC using Daisopak-SP100-5-ODS-P 2×25 cm, and Solution A: 0.1% TFA-water, Solution B: 0.1% TFA-containing acetonitrile, flow rate 8 mL/min, A/B: 77/23-67/33 linear concentration gradient elution (60 min) was performed. The eluted object product was fractionated in test tubes, and each fraction was analyzed by HPLC to specify fractions containing only the object product. These fractions were combined and freeze-dried to give 174.8 mg of a white powder.

The obtained purified sample (174.8 mg, 95.93 gmol) was dissolved in water (20 mL), and AG 1×8 AcO$^-$ resin (2.00 mL, 2.40 mmol equivalents) was added. The solution was stood for 1 hr while occasionally stirring with hand, passed through a disc filter with a pore diameter 0.45 µm to remove fine granules, concentrated in an evaporator to reduce the liquid amount to about 5 mL, and the solution was freeze-dried by cooling in a dry ice bath to give 159.6 mg of a white powder. MALDI-TOF-MS analysis, (M+H)$^+$1821.8 (Calculated 1822.1)

HPLC elution time: 7.7 min
elution condition (HPLC mode d):
  column: Merck Chromolith Performance RP-18e(4.6×100 mm I.D.)
  eluent: using Solution A: 0.1% TFA-water, Solution B: 0.1% TFA-containing acetonitrile, A/B: 80/20-30/70 linear density gradient elution (25 min)
  flow rate: 1.0 mL/min

Example 21

(Synthesis Method U): Production of [(1S)-1-carboxy-3-methylbutyl] carbamoyl-[D-Pro$^{24}$, Cha$^{27,38}$, Leu(Me)$^{28}$, Lys$^{30}$,Aib$^{31}$]-PYY(23-36) (Compound No. 253)

Synthesis of [(1S)-1-carboxy-3-methylbutyl]carbamoyl-[D-Pro$^{24}$, Cha$^{27,38}$,Leu(Me))$^{28}$,Lys$^{30}$,Aib$^{31}$]-PYY (23-36)

H-Ser(Bu$^t$)-D-Pro-Arg(Pbf)-His(Trt)-Cha-Leu(Me)-Asn(Trt)-Lys(Boc)-Aib-Thr(Bu$^t$)-Arg(Pbf)-Gln(Trt)-Arg(Pbf)-

Cha-Sieber Amide resin (0.207 mmol/g, 48.3 mg, 0.01 mmol) obtained in Example 16 was swollen with DMF, treated with CDI (16.2 mg, 0.1 mmol), DIPEA (17.4 μL, 0.1 mmol) in DMF for 4 hr, and washed with DMF. The resin was treated with H-Leu-OBu$^t$.HCl (22.4 mg, 0.1 mmol), DIEA (34.8 μL, 0.2 mmol) in DMF for 18 hr, washed successively with DMF, MeOH, and dried under reduced pressure. The obtained resin (total amount) was suspended in TFA:thioanisole:m-cresol:H$_2$O:EDT:TIS (80:5:5:5:2.5:2.5), (1.5 mL), and the mixture was stirred at room temperature for 4 hr. An operation to add diethyl ether to the reaction solution to allow precipitation and remove the supernatant after centrifugation was repeated 3 times. The residue was extracted with 50% aqueous acetic acid solution, and the resin was removed by filtration and applied to preparative HPLC using YMC Pack R&D-ODS-5-B S-5 120A column (30×250 mm), Solution A: 0.1% TFA-water, Solution B: 0.1% TFA-containing acetonitrile, flow rate 15 mL/min, A/B: 72/28-62/38 linear concentration gradient elution (60 min). The fractions containing the object product were collected and freeze-dried to give 9.6 mg of a white powder.

MALDI-TOF-MS analysis, (M+H)$^+$1954.7 (Calculated 1954.2)

HPLC elution time: 9.8 min elution condition (HPLC mode g):

column: SHISEIDO CAPCELL PAK C18 MGII(4.6×100 mm)

eluent: using Solution A: 0.1% TFA-water, Solution B: 0.1% TFA-containing acetonitrile, A/B: 80/20-30/70 linear concentration gradient elution (25 min)

flow rate: 1.0 mL/min

Example 22

(Synthesis Method V): Production of tetrahydro-2H-pyran-4-ylcarbamoyl-[D-Pro$^{24}$,Pya(4)$^{26}$,Cha$^{27,36}$, Aib$^{28,31}$,Lys$^{30}$]-PYY (23-36) (Compound No. 270)

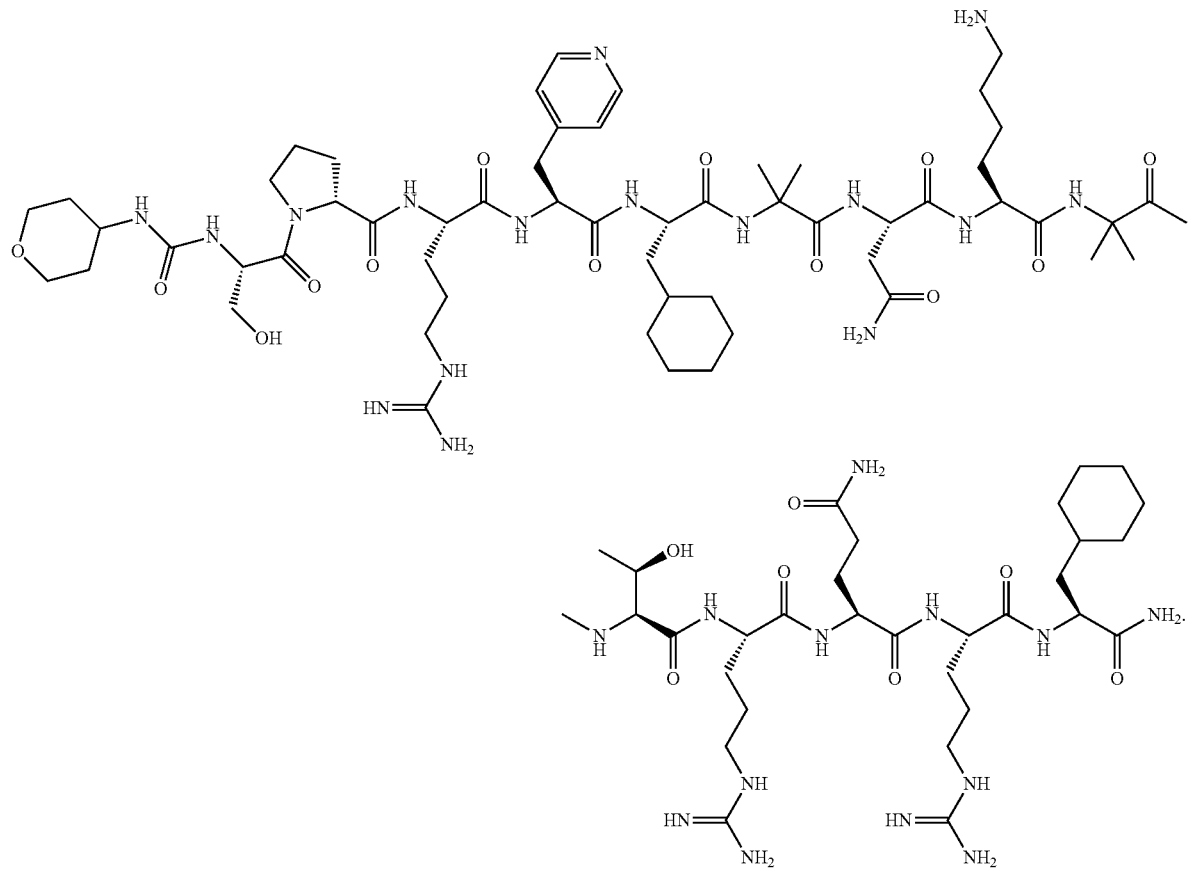

Compound No. 270

Synthesis of tetrahydro-2H-pyran-4-ylcarbamoyl-[D-Pro$^{24}$,Pya(4)$^{26}$,Cha$^{27,36}$,Aib$^{28,31}$,Lys$^{30}$]-PYY (23-36)

H-Asn(Trt)-Lys(Boc)-Aib-Thr(Bu$^t$)-Arg(Pbf)-Gln(Trt)-Arg(Pbf)-Cha-Sieber Amide resin (0.289 mmol/g, 1.73 g, 0.5 mmol) obtained by condensing amino acids in the same manner as in Example 12 and using Sieber Amide resin as a starting material, ABI433A peptide synthesizer DCC/HOBt 0.25 mmol protocol was swollen with DMF. Then, the resin was treated with Fmoc-Aib-OH (651 mg, 2.0 mmol), HOAt in DMF (0.5 M, 4.0 mL, 2.0 mmol), DIPCDI (318 μL, 2.0 mmol) for 1.5 hr. Fmoc group was removed with 20% piperidine in DMF, and the resin was treated with Fmoc-Cha-OH (787 mg, 2.0 mmol), HOAt in DMF (0.5 M, 4.0 mL, 2.0 mmol), DIPCDI (318 μL, 2.0 mmol) for 1.5 hr. The resin was washed, and further treated overnight with Fmoc-Cha-OH (787 mg, 2.0 mmol), HOAt in DMF (0.5 M, 4.0 ml, 2.0 mmol), DIPCDI (318 μL, 2.0 mmol). The resin was washed, and subjected to a capping treatment with decanoic anhydride (737 µL, 2.0 mmol), DIEA (348 µL, 2.0 mmol) in DMF for 30 min. Fmoc group was removed with 20% piperidine in DMF, and the resin was treated with Fmoc-Pya(4)-OH (767 mg, 2.0 mmol), HOAt in DMF (0.5 M, 4.0 mL, 2.0 mmol), DIEA (348 µL, 2.0 mmol), DIPCDI (318 µL, 2.0 mmol) for 2.5 hr. The resin was washed with DMF, Fmoc group was removed with 20% piperidine in DMF, and the resin was treated with Fmoc-Arg(Pbf)-OH (1.30 g, 2.0 mmol), HOAt in DMF (0.5 M, 4.0 ml, 2.0 mmol), DIPCDI (318 µL, 2.0 mmol) for 2 hr. The resin was washed, and subjected to a capping treatment with decanoic anhydride (737 µL, 2.0 mmol), DIEA (348 µL, 2.0 mmol) in DMF for 30 min. Fmoc group was removed with 20% piperidine in DMF, and the resin was treated with Fmoc-D-Pro-OH (674 mg, 2.0 mmol), HOAt in DMF (0.5 M, 4.0 mL, 2.0 mmol), DIPCDI (318 µL, 2.0 mmol) for 12 hr. The resin was washed, and further treated overnight with Fmoc-D-Pro-OH (674 mg, 2.0 mmol), HOAt in DMF (0.5 M, 4.0 mL, 2.0 mmol), DIPCDI (318 µL, 2.0 mmol). The resin was washed, and subjected to a capping treatment with decanoic anhydride (737 µL, 2.0 mmol), DIEA (348; IL, 2.0 mmol) in DMF for 30 min. The resin was washed with DMF, Fmoc group was removed with 20% piperidine in DMF, and the resin was treated with Fmoc-Ser(Bu$^t$)—OH (767 mg, 2.0 mmol), HOAt in DMF (0.5 M, 4.0 mL, 2.0 mmol), DIPCDI (318 µL, 2.0 mmol) for 2 hr. The resin was washed successively with DMF, MeOH, and dried under reduced pressure. The total amount of the obtained H-Ser(Bu$^t$)-D-Pro-Arg(Pbf)-Pya(4)-Cha-Aib-Asn(Trt)-Lys(Boc)-Aib-Thr(Bu$^t$)-Arg(Pbf)-Gln(Trt)-Arg(Pbf)-Cha-Sieber Amide resin was swollen again with DMF, and treated with CDI (405 mg, 2.5 mmol), DIEA (436 µL, 2.5 mmol) in DMF for 2 hr. The resin was washed with DMF, and treated overnight with 4-aminotetrahydropyrane (404 mg, 4.0 mmol) in DMF. The resin was washed successively with DMF, MeOH, dried under reduced pressure and the total amount of the obtained resin was suspended in TFA:thioanisole:m-cresol:H$_2$O:EDT:TIS (80:5:5:5:2.5:2.5) (15 mL), and the mixture was stirred at room temperature for 4 hr. The reaction solution was added to stirring diethyl ether under ice-cooling while removing the resin by a filter to obtain precipitation, and an operation to remove the supernatant after centrifugation was repeated 3 times. The residue was extracted with 50% aqueous acetic acid solution, passed through a disc filter with a pore diameter 0.45 µm to remove fine granules, and purified in 9 portions by HPLC. The HPLC conditions were YMC Pack R&D-ODS-5-B S-5 120A column (30×250 mm), Solution A: 0.1% TFA-water, Solution B: 0.1% TFA-containing acetonitrile, flow rate 15 mL/min, A/B: 77/23-67/33 linear concentration gradient elution (60 min). Each fraction was analyzed by HPLC to specify fractions containing only the object product. The fractions with low purity obtained by the first purification were concentrated, and subjected to HPLC separation in 2 portions under the same conditions. All the fractions containing only the object product were combined and freeze-dried to give 685 mg of a white powder.

The obtained purified sample (685 mg) was dissolved in CH$_3$CN/H$_2$O (15/30 mL), and AG 1×8 AcO$^-$ resin (7.54 mL, 9.05 mmol equivalents) was added. The solution was stood for 1 hr while occasionally stirring with hand, passed through a disc filter with a pore diameter 0.45 µm to remove fine granules, concentrated in an evaporator to reduce the liquid amount to about 5 ml, and the solution was freeze-dried to give 515 mg of a white powder.

MALDI-TOF-MS analysis, (M+H)$^+$1893.2 (Calculated 1893.1)
HPLC elution time: 7.5 min
elution condition (HPLC mode g):
  column: SHISEIDO CAPCELL PAK C18 MGII(4.6×100 mm)
  eluent: using Solution A: 0.1% TFA-water, Solution B: 0.1% TFA-containing acetonitrile, A/B: 80/20-30/70 linear concentration gradient elution (25 min)
  flow rate: 1.0 mL/min Example 23

(Synthesis Method W): Production of Ac-[D-Pro$^{24}$, Pya(4)$^{26}$,Cha$^{27,36}$,Aib$^{28,31}$, Har$^{30}$]-PYY(23-36) (Compound No. 277)

Synthesis of Ac-[D-Pro$^{24}$,Pya(4)$^{26}$,Cha$^{27,36}$,Aib$^{28,31}$, Har$^{30}$]-PYY(23-36)

Commercially available Rink Amide LL Resin (1.176 g, 0.4 mmol) was weighed and placed in a reaction vessel, washed with DMF, and stirred in DMF for 20 min to swell the resin. Then, N-terminal Fmoc group was removed by a treatment with 20% piperidine/DMF for 20 min, and the resin was treated with Fmoc-Cha-OH (787 mg, 2 mmol), HOBt (306 mg, 2 mmol), DIPCDI is (318 µL, 2 mmol) in DMF for 90 min. The N-terminal Fmoc group was removed by 20% piperidine/DMF treatment. By a similar procedure, Arg(Pbf) was introduced, and similarly, removal of Fmoc group and condensation were repeated to introduce Gln(Trt), Arg(Pbf), Thr(Bu$^t$), Aib. After removal of Fmoc, the obtained resin was washed with MeOH, and dried to give H-Aib-Thr(Bu$^t$)-Arg(Pbf)-Gln(Trt)-Arg(Pbf)-Cha-Rink Amide resin (SEQ ID NO:178) (1.771 g, 0.223 mmol/g).

The obtained resin (89.7 mg, 0.02 mmol) was weighed and placed in a reaction vessel, washed with DMF and, after swelling, treated with Fmoc-Lys(Mtt)-OH (125.0 mg, 0.2 mmol), 0.5 M HOAt/DMF solution (0.4 mL, 0.2 mmol), DIPCDI (31.8 µL, 0.2 mmol) for 15 hr to introduce Lys(Mtt) residue. The obtained resin was washed with toluene, treated with TFA-triisopropylsilane-trifluoroethanol-toluene (1:5:47:47) for 10 min, and an operation to remove the reaction solution was repeated until the solution was no longer colored. The resin was washed with toluene, neutralized by washing with 5% DIEA-toluene solution, washed again with toluene. To the obtained resin was added N,N-bis-Boc-1-guanylpyrazole (31.0 mg, 0.1 mmol), DIEA (17.4 µL, 0.1 mmol), in toluene:TFE (3:1), and treated at room temperature overnight. The progress of the reaction was confirmed by Kaiser test, and Asn(Trt), Aib, Cha, Pya(4), Arg(Pbf), D-Pro, Ser(Bu$^t$) were successively introduced by manual solid phase synthesis process including repeats of removal of Fmoc by 20% piperidine/DMF treatment and condensation by a treatment with Fmoc-amino acid (0.1 mmol), 0.5 M HOAt/DMF (0.2 mL, 0.1 mmol), DIPCDI (16 µL, 0.1 mmol). Then, after removal of Fmoc, the resin was treated with Ac$_2$O (9.4 µL), DIEA (17.4 µL) in DMF for 30 min for acetylation, and the obtained resin was washed with MeOH and dried. The obtained resin (87.1 mg) was treated with TFA:thioanisole: m-cresol:H$_2$O:EDT:TIS (80:5:5:5:2.5:2.5) (1 mL) for 90 min, an operation to add diethyl ether to the reaction solution, precipitate a white powder by centrifugation, and remove ether by decantation was repeated twice. The residue was dissolved in aqueous acetic acid solution, passed through a disc filter with a pore diameter 0.45 µm to remove fine granules, and purified by preparative HPLC using Daisopak- SP100-5-ODS-P 2×25 cm, and Solution A: 0.1% TFA-water, Solution B: 0.1% TFA-containing acetonitrile, flow rate 8 mL/min, A/B: 78/22-68/32 linear concentration gradient elution (60 min) was performed. The eluted object product was fractionated in test tubes, and each fraction was analyzed by HPLC to specify fractions containing only the object product. They were combined and freeze-dried to give 4.1 mg of a white powder.

MALDI-TOF-MS analysis, $(M+H)^+$ 1850.3 (Calculated 1850.1)

HPLC elution time: 7.4 min elution condition (HPLC mode d):
  column: Merck Chromolith Performance RP-18e(4.6×100 mm I.D.)
  eluent: using Solution A: 0.1% TFA-water, Solution B: 0.1% TFA-containing acetonitrile, A/B: 80/20-30/70 linear concentration gradient elution (25 min)
  flow rate: 1.0 mL/min Example 24

(Synthesis Method X): Production of Ac-[D-Pro$^{24}$, Pya(4)$^{26}$,Cha$^{27,36}$,Aib$^{28,31}$,Lys(Ac)$^{30}$]-PYY(23-36) (Compound No. 278)

Synthesis of Ac-[D-Pro$^{24}$,Pya(4)$^{26}$,Cha$^{27,36}$,Aib$^{28,31}$, Lys(Ac)$^{30}$]—PYY (23-36)

H-Aib-Thr(Bu$^t$)-Arg(Pbf)-Gln(Trt)-Arg(Pbf)-Cha-Rink Amide resin (89.7 mg, 0.02 mmol) synthesized in Example 23 was weighed and placed in a reaction vessel, washed with DMF and, after swelling, treated with Fmoc-Lys(Mtt)-OH (125.0 mg, 0.2 mmol), 0.5 M HOAt/DMF solution (0.4 mL, 0.2 mmol), DIPCDI (31.8 μL, 0.2 mmol) for 15 hr to introduce Lys(Mtt) residue. The obtained resin was washed with toluene, treated with TFA-triisopropylsilane-trifluoroethanol-toluene (1:5:47:47) for 10 min, and an operation to remove the reaction solution was repeated until the solution was no longer colored. The resin was washed with toluene, neutralized by washing with 5% DIEA-toluene solution, washed with DMF, and the obtained resin was treated overnight with Ac$_2$O (9.4 μL), DIEA (17.4 μL) in DMF at room temperature. The progress of the reaction was confirmed by Kaiser test, and Asn(Trt), Aib, Cha, Pya(4), Arg(Pbf), D-Pro, Ser(Bu$^t$) were successively introduced by manual solid phase synthesis process including repeats of removal of Fmoc by 20% piperidine/DMF treatment and condensation by a treatment with Fmoc-amino acid (0.1 mmol), 0.5 M HOAt/DMF (0.2 mL, 0.1 mmol), DIPCDI (16 μL, 0.1 mmol). Then, after removal of Fmoc, the resin was treated with Ac$_2$O (9.4 μL), DIEA (17.4 μL) in DMF for 30 min for acetylation, and the obtained resin was washed with MeOH and dried. The obtained resin (102.8 mg) was treated with TFA:thioanisole:m-cresol:H$_2$O:EDT:TIS (80:5:5:5:2.5:2.5) (1 mL) for 90 min, an operation to add diethyl ether to the reaction solution, precipitate a white powder by centrifugation, and remove ether by decantation was repeated twice. The residue was dissolved in aqueous acetic acid solution, passed through a disc filter with a pore diameter 0.45 μm to remove fine granules, and purified by preparative HPLC using Daisopak-SP100-5-ODS-P 2×25 cm, and Solution A: 0.1% TFA-water, Solution B: 0.1% TFA-containing acetonitrile, flow rate 8 mL/min, A/B: 77/23-67/33 linear concentration gradient elution (60 min) was performed. The eluted object product was fractionated in test tubes, and each fraction was analyzed by HPLC to specify fractions containing only the object product. They were combined and freeze-dried to give 5.1 mg of a white powder.

MALDI-TOF-MS analysis, $(M+H)^+$ 1850.2 (Calculated 1850.1)

HPLC elution time: 8.0 min elution condition (HPLC mode d):
  column: Merck Chromolith Performance RP-18e(4.6×100 mm I.D.)
  eluent: using Solution A: 0.1% TFA-water, Solution B: 0.1% TFA-containing acetonitrile, A/B: 80/20-30/70 linear concentration gradient elution (25 min)
  flow rate: 1.0 ml/min Example 25

(Synthesis Method Y): Production of Ac-[D-Pro$^{24}$, Pya(4)$^{26}$,Cha$^{27,36}$,Aib$^{28,31}$,Lys(Hexyl)$^{30}$]-PYY(23-36) (compound No. 279)

Synthesis of Ac-[D-Pro$^{24}$,Pya (4)$^{26}$,Cha$^{27,36}$, Aib$^{28,31}$,Lys(Hexyl)$^{30}$]-PYY(23-36)

H-Aib-Thr(Bu$^t$)-Arg(Pbf)-Gln(Trt)-Arg(Pbf)-Cha-Rink Amide resin (89.7 mg, 0.02 mmol) synthesized in Example 23 was weighed and placed in a reaction vessel, washed with DMF and, after swelling, treated with Fmoc-Lys(Mtt)-OH (125.0 mg, 0.2 mmol), 0.5 M HOAt/DMF solution (0.4 mL, 0.2 mmol), DIPCDI (31.8 μL, 0.2 mmol) for 15 hr to introduce Lys(Mtt) residue. The obtained resin was washed with toluene, treated with TFA-triisopropylsilane-trifluoroethanol-toluene (1:5:47:47) for 10 min, and an operation to remove the reaction solution was repeated until the solution was no longer colored. The resin was washed with toluene, neutralized by washing with 5% DIEA-toluene solution, and washed with DMF. The obtained resin was suspended in DMF, 1-hexanal (2.5 μL, 0.04 mmol) was added in the presence of acetic acid (50 μL) and the mixture was stirred for 15 min. NaBH$_3$CN (6.2 mg, 0.1 mmol) was added, and the mixture was further stirred for 15 hr. The resin was washed with DMF, and treated with Boc$_2$O (24.4 mg, 0.2 mmol), DIEA (34.8 μL, 0.2 mmol) in DMF at room temperature for 3 hr. The progress of the reaction was confirmed by Kaiser test, and Asn(Trt), Aib, Cha, Pya(4), Arg(Pbf), D-Pro, Ser(Bu$^t$) were successively introduced by manual solid phase synthesis process including repeats of removal of Fmoc by 20% piperidine/DMF treatment and condensation by a treatment with Fmoc-amino acid (0.1 mmol), 0.5 M HOAt/DMF (0.2 mL, 0.1 mmol), DIPCDI (16 μL, 0.1 mmol). Then, after removal of Fmoc, the resin was treated with Ac$_2$O (9.4 μL), DIEA (17.4 μL) in DMF for 30 min for acetylation, and the obtained resin was washed with MeOH and dried.

The obtained resin (103.9 mg) was treated with TFA:thioanisole:m-cresol:H$_2$O:EDT:TIS (80:5:5:5:2.5:2.5) (1 mL) for 90 min, an operation to add diethyl ether to the reaction solution, precipitate a white powder by centrifugation, and remove diethyl ether by decantation was repeated twice. The residue was dissolved in aqueous acetic acid solution, passed through a disc filter with a pore diameter 0.45 μm to remove fine granules, and purified by preparative HPLC using Daisopak-SP100-5-ODS-P 2×25 cm, and Solution A: 0.1% TFA-water, Solution B: 0.1% TFA-containing acetonitrile, flow rate 8 mL/min, A/B: 73/27-63/37 linear density gradient elution (60 min) was performed. The eluted object product was fractionated in test tubes, and each fraction was analyzed by HPLC to specify fractions containing only the object product. They were combined and freeze-dried to give 2.7 mg of a white powder.

MALDI-TOF-MS analysis, (M+H)$^+$1891.9 (Calculated 1892.2)

HPLC elution time: 9.6 min elution condition (HPLC mode d):

column: Merck Chromolith Performance RP-18e(4.6×100 mm I.D.)

eluent: using Solution A: 0.1% TFA-water, Solution B: 0.1% TFA-containing acetonitrile, A/B: 80/20-30/70 linear concentration gradient elution (25 min)

flow rate: 1.0 mL/min

Example 26

(Synthesis Method Z): Production of (Tetrahydro-2H-pyran-4-yl)carbamoyl-[Glu$^{23}$,D-Pro$^{24}$,Pya(4)$^{26}$, Cha$^{27,36}$,Aib$^{28,31}$,Lys$^{30}$]-PYY(23-36) (Compound No. 282)

able Sieber Amide resin as a starting material, and ABI433A peptide synthesizer DCC/HOBt 0.25 mmol protocol was weighed and placed in a reaction vessel, washed with DMF, and stirred in DMF for 20 min to swell the resin. Then, the resin was treated with Fmoc-Pya(4)-OH (1165.3 mg, 3 mmol), 0.5 M HOAt/DMF solution (3 mL, 4 mmol), DIPCDI (0.477 mL, 3 mmol) for 75 min to introduce Pya(4) residue. In this case, DIEA (0.5226 mL, 3 mmol) was added to the reaction solution during condensation. The N-terminal Fmoc group was removed by 20% piperidine/DMF treatment. By a similar procedure, Arg(Pbf) was introduced. In the same manner, removal of Fmoc group and condensation were repeated to introduce D-Pro, Glu(OBu$^t$), and the obtained resin was washed with MeOH and dried to give H-Glu(OBu$^t$)-D-Pro-Arg(Pbf)-Pya(4)-Cha-Aib-Asn(Trt)-Lys(Boc)-Aib-Thr(Bu$^t$)-Arg(Pbf)-Gln(Trt)-Arg(Pbf)-Cha-NH-Sieber Amide resin. The obtained resin was washed with DMF and, after swelling, treated with CDI (304.0 mg, 1.88 mmol), DIEA (0.327 mL, 1.88 mmol), DMF (3 mL) for 60 min. The resin was washed, and further treated for 60 min under similar Compound No. 282

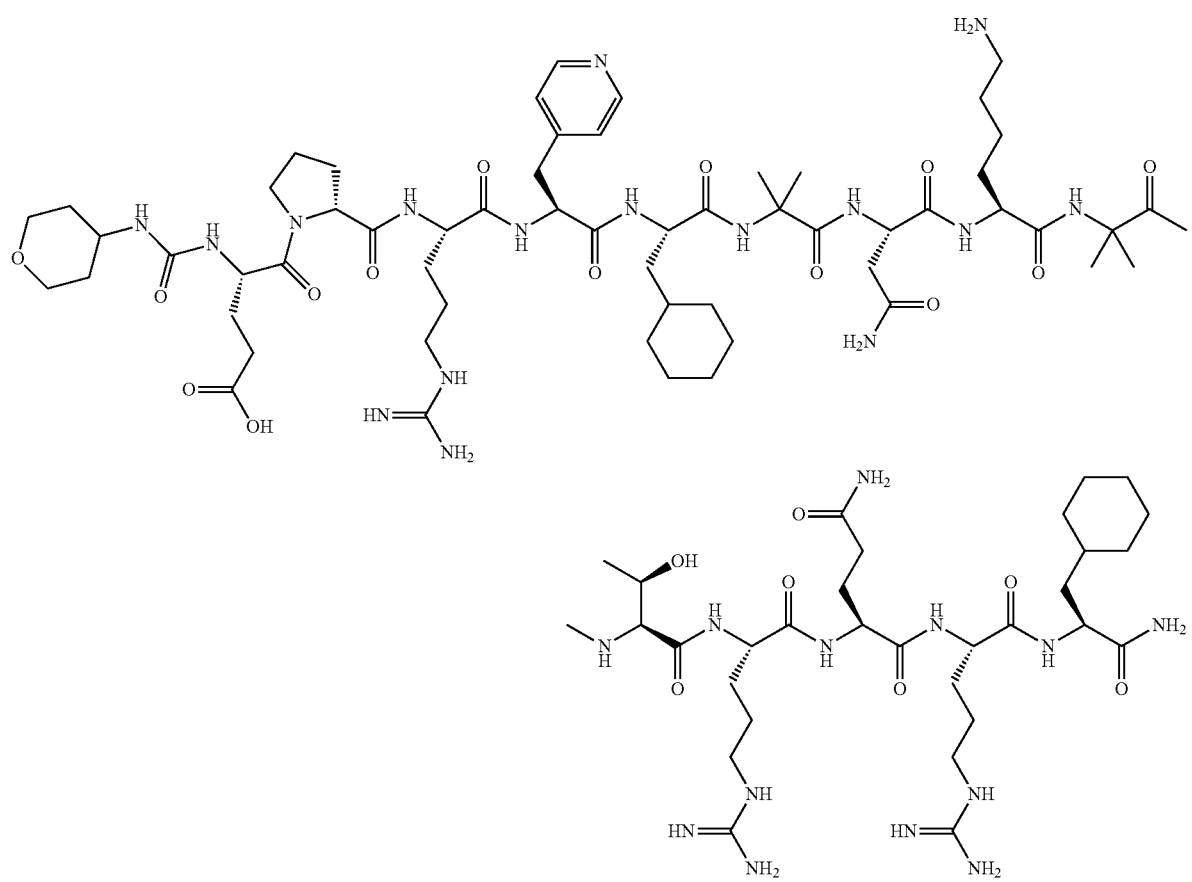

Synthesis of (Tetrahydro-2H-pyran-4-yl)carbamoyl-[Glu$^{23}$,D-Pro$^{24}$, Pya(4)$^{26}$,Cha$^{27,36}$,Aib$^{28,31}$, Lys$^{30}$]-PYY(23-36)

Cha-Aib-Asn(Trt)-Lys(Boc)-Aib-Thr(Bu$^t$)-Arg(Pbf)-Gln(Trt)-Arg(Pbf)-Cha-Sieber Amide resin (SEQ ID NO:179) (0.375 mmol) obtained by condensing amino acids in the same manner as in Example 12 and using commercially availconditions. The resin was washed with DMF, treated with 4-aminotetrahydropyrane (303.0 mg, 3 mmol), DMF (3 mL) for 4 hr, and washed successively with DMF, MeOH and dried. The obtained resin (1.63 g) was treated with TFA: thioanisole:m-cresol:H$_2$O:EDT:TIS (80:5:5:5:2.5:2.5) (20 mL) for 4 hr, an operation to add diethyl ether to the reaction solution, precipitate a white powder by centrifugation, and remove ether by decantation was repeated twice. The residue was dissolved in aqueous acetic acid solution, passed through a disc filter with a pore diameter 0.45 μm to remove fine granules, and concentrated in an evaporator. After confirmation of the purity of the obtained crude peptide solution by HPLC, it was purified in 10 portions by preparative HPLC using Daisopak-SP100-5-ODS-P 2×25 cm (Solution A: 0.1% TFA-water, Solution B: 0.1% TFA-containing acetonitrile, flow rate 8 mL/min, A/B: 80/20-70/30 linear concentration gradient elution (60 min)). The eluted object product was fractionated in test tubes, and each fraction was analyzed by HPLC to specify fractions containing only the object product. They were combined and freeze-dried to give 316 mg of a white powder.

The obtained purified sample (316 mg) was dissolved in $H_2O$ (40 mL), and AG 1×8 $AcO^-$ resin (2.85 mL, 3.42 mmol equivalents) was added. The solution was stood for 1 hr while occasionally stirring with hand, passed through a disc filter with a pore diameter 0.45 μm to remove fine granules, concentrated in an evaporator to reduce the liquid amount to about 5 mL, and the solution was freeze-dried to give 173 mg of a white powder.

MALDI-TOF-MS analysis, $(M+H)^+$ 1935.5 (Calculated 1935.1)

HPLC elution time: 7.6 min elution condition (HPLC mode g):

column: SHISEIDO CAPCELL PAK C18 MGII(4.6×100 mm)

eluent: using Solution A: 0.1% TFA-water, Solution B: 0.1% TFA-containing acetonitrile, A/B: 80/20-30/70 linear concentration gradient elution (25 min)

flow rate: 1.0 mL/min

Example 27

(Synthesis method AA): Production of (carboxymethyl)carbamoyl-[D-Pro$^{24}$,Pya(4)$^{26}$,Cha$^{27,36}$,Aib$^{28,31}$,Lys$^{30}$]-PYY(23-36) (Compound No. 287)

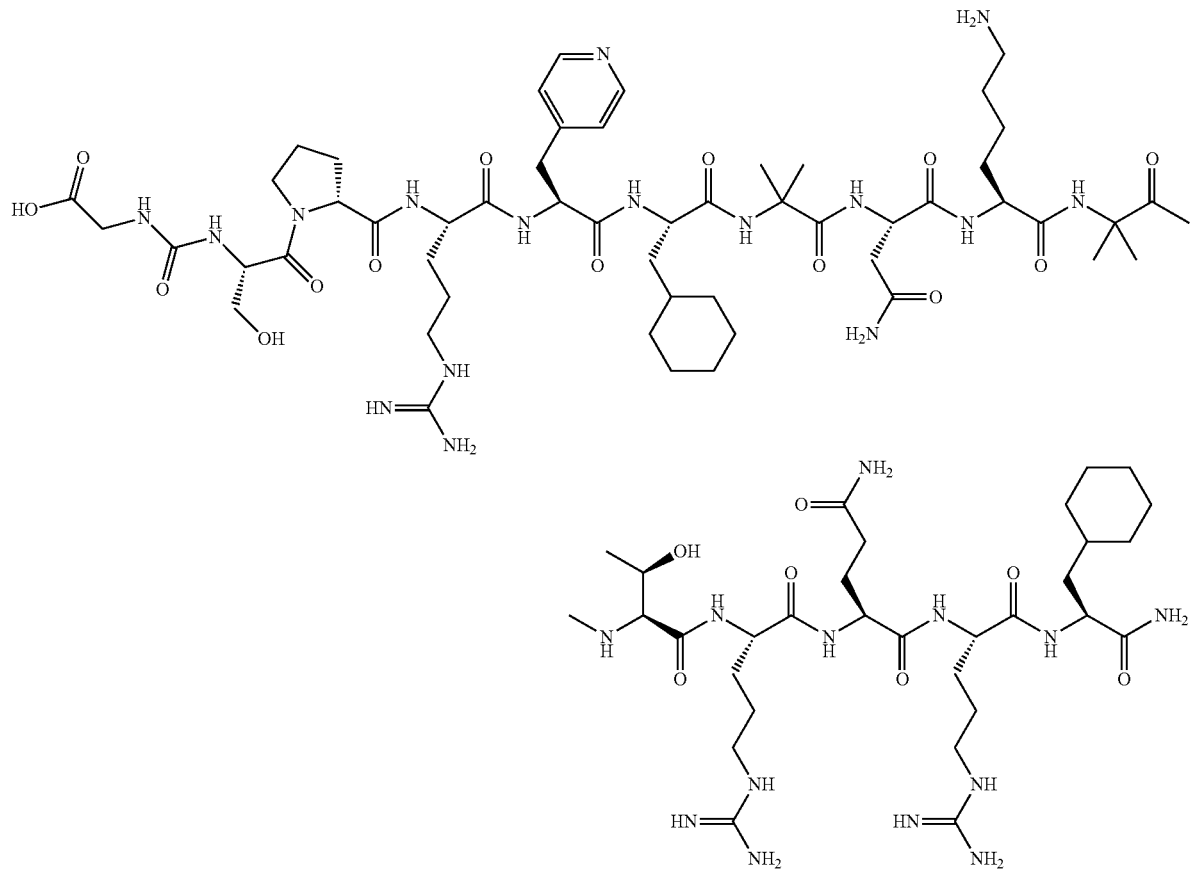

Compound No. 287

Synthesis of (Carboxymethyl)carbamoyl-[D-Pro$^{24}$, Pya(4)$^{26}$,Cha$^{27,36}$,Aib$^{28,31}$,Lys$^{30}$]-PYY (23-36)

Cha-Aib-Asn(Trt)-Lys(Boc)-Aib-Thr(Bu$^t$)-Arg(Pbf)-Gln(Trt)-Arg(Pbf)-Cha-Sieber Amide resin (0.375 mmol) obtained in Example 26 was weighed and placed in a reaction vessel, washed with DMF, and stirred in DMF for 20 min to swell the resin. Then, the resin was treated with Fmoc-Pya(4)-OH (1165.3 mg, 3 mmol), 0.5 M HOAt/DMF solution (3 ml, 4 mmol), DIPCDI (0.477 mL, 3 mmol) for 75 min to introduce Pya(4) residue. In this case, DIEA (0.5226 mL, 3 mmol) was added to the reaction solution during condensation. The N-terminal Fmoc group was removed by 20% piperidine/DMF treatment. By a similar procedure, Arg(Pbf) was introduced. In the same manner, removal of Fmoc group and condensation were repeated to introduce D-Pro, Ser(Bu$^t$), and the obtained resin was washed with MeOH and dried to give H-Ser(Bu$^t$)-D-Pro-Arg(Pbf)-Pya(4)-Cha-Aib-Asn(Trt)-Lys(Boc)-Aib-Thr(Bu$^t$)-Arg(Pbf)-Gln(Trt)-Arg(Pbf)-Cha-Sieber Amide resin. The obtained resin was washed with DMF and, after swelling, treated with CDI (304.0 mg, 1.88 mmol), DIEA (0.327 ml, 1.88 mmol), DMF (3 mL) for 60 min. The resin was washed, and further treated for 60 min under similar conditions. After washing, the resin was treated with H-Gly-OBu$^t$ hydrochloride (503 mg, 3 mmol), DIEA (0.523 mL, 3 mmol), DMF (3 mL) for 4 hr, and washed and dried.

The obtained resin (1.69 g) was treated with TFA:thioanisole:m-cresol:H$_2$O:EDT:TIS (80:5:5:5:2.5:2.5) (20 mL) for 4 hr, the reaction solution was added to diethyl ether under ice-cooling while removing the resin with a filter to give precipitate, and an operation to remove the supernatant after centrifugation was repeated 3 times. The residue was dissolved in aqueous acetic acid solution, passed through a disc filter with a pore diameter 0.45 μm to remove fine granules, and concentrated in an evaporator. After confirmation of the purity of the obtained crude peptide solution by HPLC, it was purified in 7 portions by preparative HPLC using YMC Pack R&D-ODS-5-B S-5 120A column (30×250 mm) (Solution A: 0.1% TFA-water, Solution B: 0.1% TFA-containing acetonitrile, flow rate 15 mL/min, A/B: 78/22-68/32 linear concentration gradient elution (60 min)). The eluted object product was fractionated in test tubes, and each fraction was analyzed by HPLC to specify fractions containing only the object product. They were combined and freeze-dried to give 233 mg of a white powder.

The obtained purified sample (233 mg) was dissolved in CH$_3$CN/H$_2$O (10/20 mL), and AG 1×8 AcO$^-$ resin (2.60 mL, 3.125 mmol equivalents) was added. The solution was stood for 1 hr while occasionally stirring with hand, passed through a disc filter with a pore diameter 0.45 μm to remove fine granules, concentrated in an evaporator to reduce the liquid amount to about 5 mL, and the solution was freeze-dried to give 184 mg of a white powder.

MALDI-TOF-MS analysis, (M+H)$^+$1867.1 (Calculated 1867.1)

HPLC elution time: 7.1 min elution condition (HPLC mode g):

column: SHISEIDO CAPCELL PAK C18 MGII(4.6×100 mm)

eluent: using Solution A: 0.1% TFA-water, Solution B: 0.1% TFA-containing acetonitrile, A/B: 80/20-30/70 linear concentration gradient elution (25 min)

flow rate: 1.0 mL/min

Example 28

(Synthesis Method AB): Production of Ac-[D-Pro$^{24}$, Iva$^{25}$,Pya(4)$^{26}$,Cha$^{27,36}$,Leu(Me)$^{28}$,Lys$^{30}$,Aib$^{31}$]-PYY(23-36) (Compound No. 295)

Compound No. 295

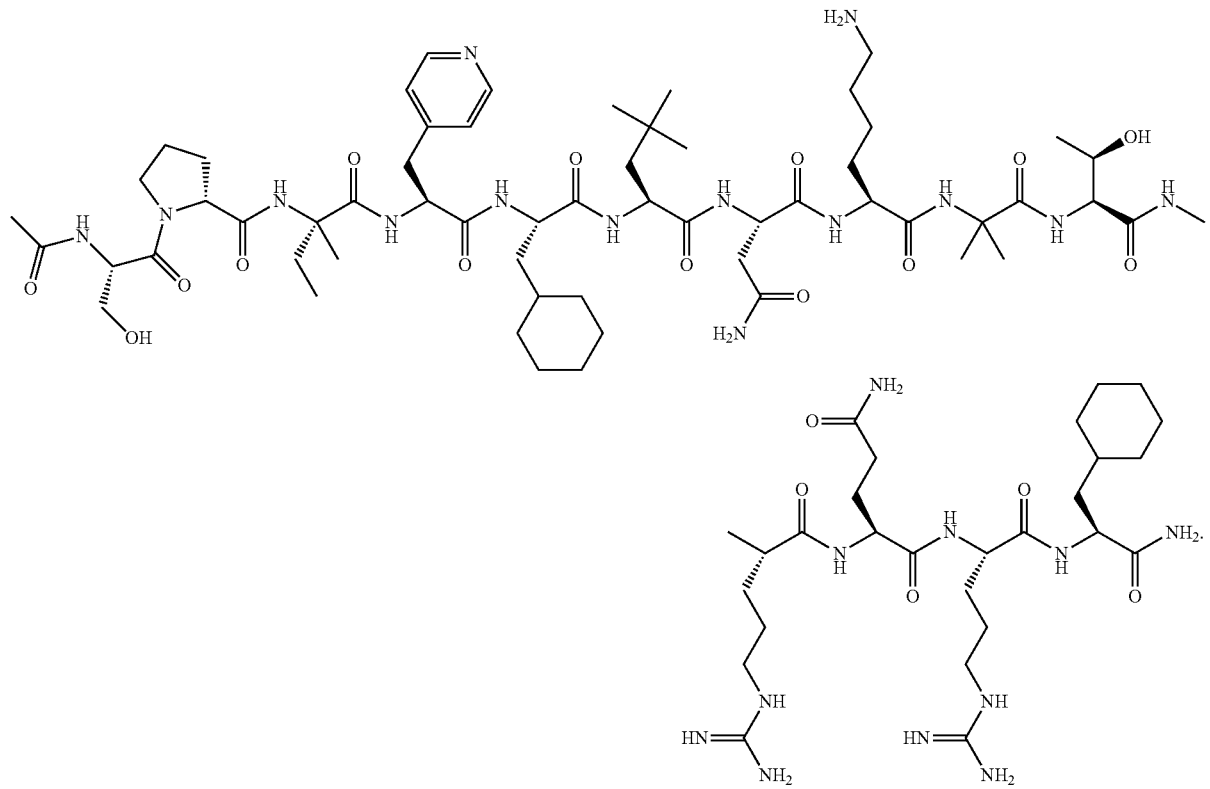

Synthesis of Ac-[D-Pro$^{24}$,Iva$^{25}$,Pya(4)$^{26}$,Cha$^{27,36}$, Leu(Me)$^{28}$,Lys$^{30}$,Aib$^{31}$]-PYY (23-36)

Iva-Pya(4)-Cha-Leu(Me)-Asn(Trt)-Lys(Boc)-Aib-Thr(Bu$^t$)-Arg(Pbf)-Gln(Trt)-Arg(Pbf)-Cha-Sieber Amide resin (SEQ ID NO:180) (840.8 mg, 0.21 mmol) obtained by condensing amino acids in the same manner as in Example 12 and using commercially available Sieber Amide resin as a starting material, and ABI433A peptide synthesizer DCC/HOBt 0.25 mmol protocol was weighed and placed in a reaction vessel, washed with DMF, and stirred in DMF for 20 min to swell the resin. Then, the resin was treated with Fmoc-D-Pro-OH (337.4 mg, 1 mmol), 0.5 M HOAt/DMF solution (2 mL, 1 mmol), DIPCDI (159 µL, 1 mmol) for 15 hr to introduce D-Pro. Fmoc group was removed, and Ser(Bu$^t$) was introduced in the same manner. After removal of Fmoc, the obtained resin was treated with Ac$_2$O (94.3 µL), DIEA (174.2 µL, 1 mmol) in DMF for 20 min, and the resin was washed and dried. The obtained Ac-Ser(Bu$^t$)-D-Pro-Iva-Pya(4)-Cha-Leu(Me)-Asn(Trt)-Lys(Boc)-Aib-Thr(Bu$^t$)-Arg(Pbf)-Gln(Trt)-Arg(Pbf)-Cha-Sieber Amide resin (0.941 g) was treated with TFA:thioanisole:m-cresol:H$_2$O:EDT:TIS (80:5:5:5:2.5:2.5) (5 mL) for 120 min. An operation to add diethyl ether to the reaction solution, precipitate a white powder by centrifugation, and remove ether by decantation was repeated twice. The residue was dissolved in aqueous acetic acid solution, passed through a disc filter with a pore diameter 0.45 µm to remove fine granules, and concentrated in an evaporator. After confirmation of the purity of the obtained crude peptide solution by HPLC, the peptide was purified in 6 portions by preparative HPLC using Daisopak-SP100-5-ODS-P 2×25 cm. Solution A: 0.1% TFA-water, Solution B: 0.1% TFA-containing acetonitrile, flow rate 8 mL/min, A/B: 71/29-61/39 linear concentration gradient elution (60 min) was performed, the eluted object product was fractionated in test tubes, and each fraction was analyzed by HPLC to specify fractions containing only the object product. They were combined and freeze-dried to give 279.8 mg of a white powder.

The obtained purified sample (279.8 mg, 156.04 mmol) was dissolved in water (20 ml), and AG 1×8 AcO$^-$ resin (2.60 mL, 3.12 mmol equivalents) was added. The solution was stood for 1 hr while occasionally stirring with hand, passed through a disc filter with a pore diameter 0.45 µm to remove fine granules, concentrated in an evaporator to reduce the liquid amount to about 5 mL, and the solution was freeze-dried by cooling in a dry ice bath to give 213.7 mg of a white powder.

MALDI-TOF-MS analysis, (M+H)$^+$1792.8 (Calculated 1793.1)
HPLC elution time: 11.9 min
elution condition (HPLC mode d):
  column: Merck Chromolith Performance RP-18e(4.6×100 mm I.D.)
  eluent: using Solution A: 0.1% TFA-water, Solution B: 0.1% TFA-containing acetonitrile, A/B: 80/20-30/70 linear concentration gradient elution (25 min)
  flow rate: 1.0 mL/min Example 29

(Synthesis Method AC): Production of Ac-[D-Hyp$^{24}$, Iva$^{25,28}$,Pya(4)$^{26}$,Cha$^{27,36}$,Lys$^{30}$,Aib$^{31}$]-PYY (23-36)
(Compound No. 298)

Compound No. 298

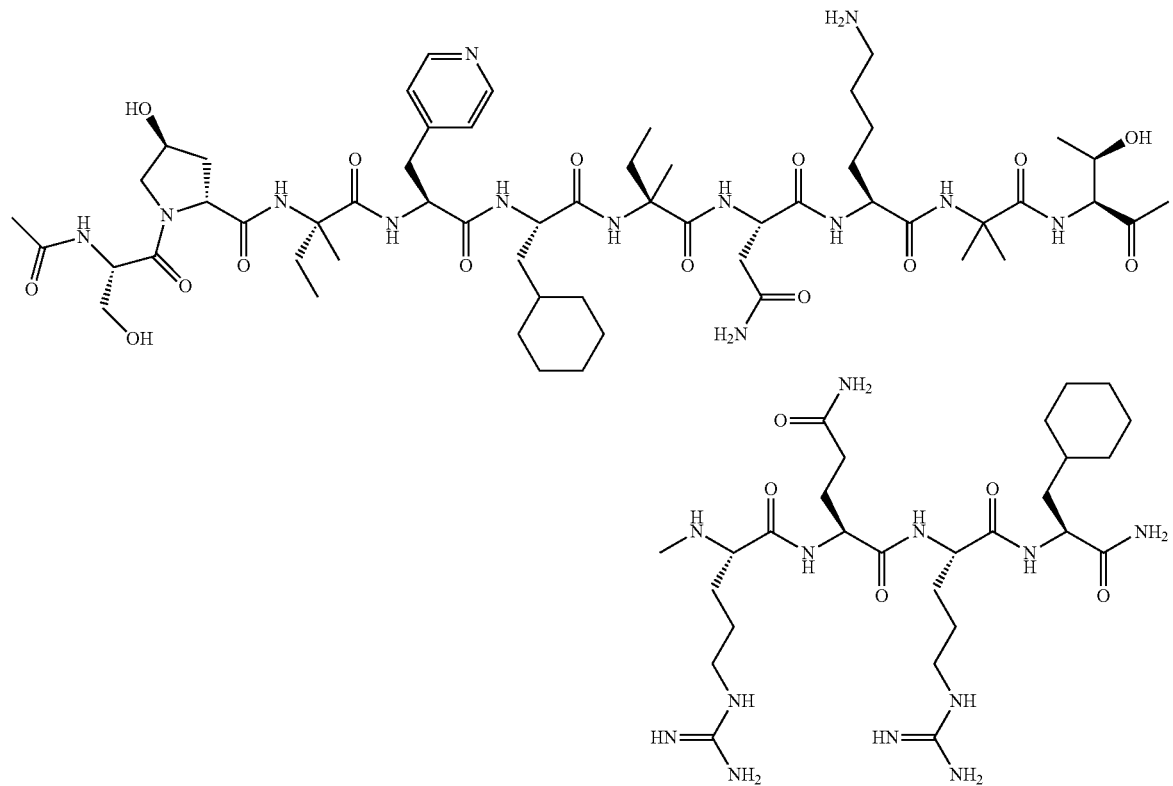

Synthesis of Ac-[D-Hyp$^{24}$,Iva$^{25,28}$,Pya(4)$^{26}$,Cha$^{27,36}$, Lys$^{30}$,Aib$^{31}$]-PYY(23-36)

H-Asn(Trt)-Lys(Boc)-Aib-Thr(Bu$^t$)-Arg(Pbf)-Gln(Trt)-Arg(Pbf)-Cha-Sieber Amide resin (SEQ ID NO:177) (952.8 mg, 0.25 mmol) obtained in Example 20 was weighed and placed in a reaction vessel, washed with DMF, and stirred in DMF for 20 min to swell the resin. Then, the resin was treated with Fmoc-Iva-OH (339.4 mg, 1 mmol), 0.5 M HOAt/DMF solution (2 mL, 1 mmol), DIPCDI (159 µL, 1 mmol) for 120 min. The N-terminal Fmoc group was removed by 20% piperidine/DMF treatment. By a similar procedure, Cha was introduced. In the same manner, removal of Fmoc group and condensation were repeated to introduce Pya(4), Iva, D-Hyp, Ser(Bu$^t$). After removal of Fmoc, the obtained resin was treated with AcOSu (157.1 mg, 1 mmol), DIEA (174.2 μL, 1 mmol) in DMF for 60 min, and washed with NeOH and dried to give Ac-Ser(Bu$^t$)-D-Hyp-Iva-Pya(4)-Cha-Iva-Asn(Trt)-Lys(Boc)-Aib-Thr(Bu$^t$)-Arg(Pbf)-Gln(Trt)-Arg(Pbf)-Cha-Sieber Amide resin (1.1162 g). The obtained resin (1.1162 g) was treated with TFA:thioanisole:m-cresol:H$_2$O:EDT:TIS (80:5:5:5:2.5:2.5) (6 mL) for 120 min, an operation to add diethyl ether to the reaction solution, precipitate a white powder by centrifugation, and remove diethyl ether by decantation was repeated twice. The residue was dissolved in aqueous acetic acid solution, passed through a disc filter with a pore diameter 0.45 μm to remove fine granules, and concentrated in an evaporator. After confirmation of the purity of the obtained crude peptide solution by HPLC, the peptide was purified by preparative HPLC in 6 portions using Daisopak-SP100-5-ODS-P 2×25 cm, and Solution A: 0.1% TFA-water, Solution B: 0.1% TFA-containing acetonitrile, flow rate 8 mL/min, A/B: 75/25-65/35 linear concentration gradient elution (60 min) was performed. The eluted object product was fractionated in test tubes, and each fraction was analyzed by HPLC to specify fractions containing only the object product. They were combined and freeze-dried to give 250.2 mg of a white powder.

The obtained purified sample (250.2 mg, 140.47 μmol) was dissolved in water (20 mL), and AG 1×8 AcO$^-$ resin (2.34 ml, 2.81 mmol equivalents) was added. The solution was stood for 1 hr while occasionally stirring with hand, passed through a disc filter with a pore diameter 0.45 μm to remove fine granules, concentrated in an evaporator to reduce the liquid amount to about 5 mL, and the solution was freeze-dried by cooling in a dry ice bath to give 186.1 mg of a white powder.
MALDI-TOF-MS analysis, (M+H)$^+$1780.6 (Calculated 1781.1)
HPLC elution time: 9.2 min
elution condition (HPLC mode d):
 column: Merck Chromolith Performance RP-18e(4.6×100 mm I.D.)
 eluent: using Solution A: 0.1% TFA-water, Solution B: 0.1% TFA-containing acetonitrile, A/B: 80/20-30/70 linear concentration gradient elution (25 min)
 flow rate: 1.0 mL/min Example 30

(Synthesis Method AD): Production of (tetrahydro-2H-pyran-4-yl) carbonyl-[D-Pro$^{24}$,Pya(4)$^{26}$,Cha$^{27,36}$, Aib$^{28,31}$,Lys$^{30}$]-PYY (23-36) (Compound No. 324)

Synthesis of (tetrahydro-2H-pyran-4-yl)carbonyl-[D-Pro$^{24}$,Pya(4)$^{26}$,Cha$^{27,36}$,Aib$^{28,31}$,Lys$^{30}$]-PYY (23-36)

H-Pya(4)-Cha-Aib-Asn(Trt)-Lys(Boc)-Aib-Thr(Bu$^t$)-Arg(Pbf)-Gln(Trt)-Arg(Pbf)-Cha-Sieber Amide resin (SEQ ID NO:182) (0.251 mmol/g, 39.8 mg, 0.01 mmol) obtained by condensing amino acids in the same manner as in Example 12 and using Sieber Amide resin as a starting material, and ABI433A peptide synthesizer DCC/HOBt 0.25 mmol protocol was swollen with DMF. Arg(Pbf), D-Pro, Ser(Bu$^t$) were successively condensed by manual solid phase synthesis using 4 equivalents or 6 equivalents each of Fmoc-amino acid/HOAt/DIPCDI. The obtained H-Ser(Bu$^t$)-D-Pro-Arg(Pbf)-Pya(4)-Cha-Aib-Asn(Trt)-Lys(Boc)-Aib-Thr(Bu$^t$)-Arg(Pbf)-Gln(Trt)-Arg(Pbf)-Cha-Sieber Amide resin was treated with tetrahydropyran-4-yl carboxylic acid (7.81 mg, 0.06 mmol), HOAt in DMF (0.5 M, 120 μL, 0.06 mmol), DIPCDI (9.54 μL, 0.06 mmol) in DMF for 4 hr, washed successively with DMF, MeOH, and dried under reduced pressure. The obtained resin (47 mg) was suspended in TFA:thioanisole:m-cresol:H$_2$O:EDT:TIS (80:5:5:5:2.5:2.5) (1 mL), and the mixture was stirred at room temperature for 4 hr. An operation to add diethyl ether to the reaction solution to allow precipitation and remove the supernatant after centrifugation was repeated 3 times. The residue was extracted with 50% aqueous acetic acid solution, the resin was removed by filtration, and applied to preparative HPLC using YMC Pack R&D-ODS-5-B S-5 120A column (30×250 mm), Solution A: 0.1% TFA-water, Solution B: 0.1% TFA-containing acetonitrile, flow rate 15 mL/min, A/B: 77/23-67/33 linear concentration gradient elution (60 min). The fractions containing the object product were collected and freeze-dried to give 6.6 mg of a white powder.

MALDI-TOF-MS analysis, (M+H)$^+$1877.9 (Calculated 1878.1)

HPLC elution time: 7.6 min elution condition (HPLC mode g):
 column: SHISEIDO CAPCELL PAK C18 MGII(4.6×100 mm)
 eluent: using Solution A: 0.1% TFA-water, Solution B: 0.1% TFA-containing acetonitrile, A/B: 80/20-30/70 linear concentration gradient elution (25 min)
 flow rate: 1.0 mL/min Example 31

(Synthesis Method AE): Production of 4-Imidazole-carbonyl-[D-Hyp$^{24}$,Iva$^{25}$,Pya(4)$^{26}$,Cha$^{27,38}$, Leu(Me)$^{28}$,Lys$^{30}$,Aib$^{31}$]-PYY (23-36) (Compound No. 336)

Compound No. 336

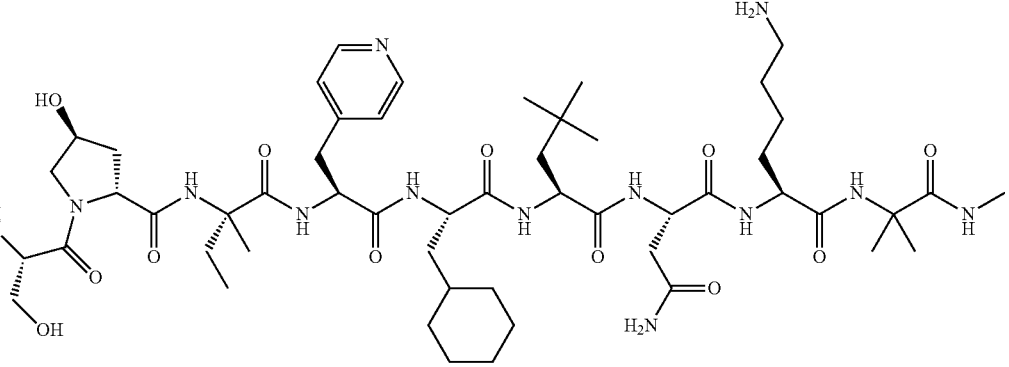

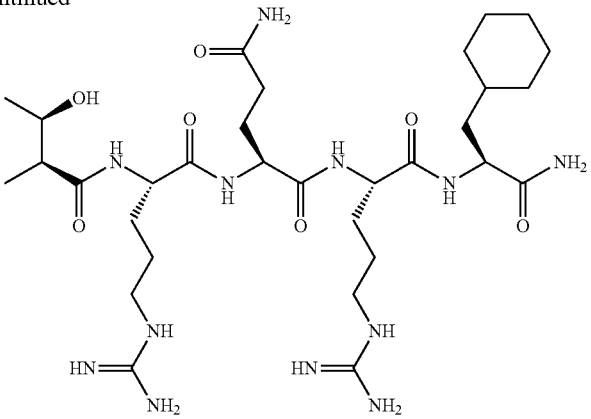

Synthesis of 4-imidazolecarbonyl-[D-Hyp$^{24}$,Iva$^{25}$, Pya(4)$^{26}$,Cha$^{27,36}$,Leu(Me)$^{28}$,Lys$^{30}$,Aib$^{31}$]-PYY (23-36)

H-Asn(Trt)-Lys(Boc)-Aib-Thr(Bu$^t$)-Arg(Pbf)-Gln(Trt)-Arg(Pbf)-Cha-Sieber Amide resin (1.795 g, 0.5 mmol) obtained in Example 20 was weighed and placed in a reaction vessel, washed with DMF, and stirred in DMF for 20 min to swell the resin. Then, the resin was treated with Fmoc-Leu(Me)-OH (734.8 mg, 2 mmol), 0.5 M HOAt/DMF solution (4 ml, 2 mmol), DIPCDI (0.318 mL, 2 mmol) for 120 min to introduce Leu(Me) residue. The N-terminal Fmoc group was removed by 20% piperidine/DMF treatment. By a similar procedure, Cha was introduced. In the same manner, removal of Fmoc group and condensation were repeated to introduce Pya(4), Iva. The obtained resin was washed with MeOH and dried to give H-Iva-Pya(4)-Cha-Leu(Me)-Asn(Trt)-Lys(Boc)-Aib-Thr(Bu$^t$)-Arg(Pbf)-Gln(Trt)-Arg(Pbf)-Cha-Sieber Amide resin (SEQ ID NO:181) (2.1612 g). In this case, for introduction of Pya(4) residue, DIEA (348.4 µL, 2 mmol) was added to the reaction solution during condensation. The obtained resin (1.0806 g, 0.25 mmol) was washed with DMF and, after swelling, treated with Fmoc-D-Hyp-OH (353.4 mg, 1 mmol), 0.5 M HOAt/DMF solution (2 mL, 1 mmol), DIPCDI (159 µL, 1 mmol) for 15 hr to introduce D-Hyp. Fmoc group was removed, and Ser(Bu$^t$) was similarly introduced. After removal of Fmoc from the obtained Fmoc-Ser(Bu$^t$)-D-Hyp-Iva-Pya(4)-Cha-Leu(Me)-Asn(Trt)-Lys(Boc)-Aib-Thr(Bu$^t$)-Arg(Pbf)-Gln(Trt)-Arg(Pbf)-Cha-Sieber amide resin, the resin was treated with 1-trityl-1H-imidazole-4-carboxylic acid (354.4 mg, 1 mmol), DIPCDI (159 µL, 1 mmol) in DMSO (1 mL), 0.5 M HOAt/DMF solution (2 mL, 1 mmol) for 120 min, and the resin was washed and dried. The obtained resin (1.2067 g) was treated with TFA:thioanisole:m-cresol:H$_2$O:EDT:TIS (80:5:5:5:2.5:2.5) (6 mL) for 120 min, an operation to add diethyl ether to the reaction solution, precipitate a white powder by centrifugation, and remove diethyl ether by decantation was repeated twice. The residue was dissolved in aqueous acetic acid solution, passed through a disc filter with a pore diameter 0.45 µm to remove fine granules, and concentrated in an evaporator. After confirmation of the purity of the obtained crude peptide solution by HPLC, the peptide was purified by preparative HPLC in 6 portions using Daisopak-SP100-5-ODS-P 2×25 cm, and Solution A: 0.1% TFA-water, Solution B: 0.1% TFA-containing acetonitrile, flow rate 8 mL/min, A/B: 74/26-64/36 linear concentration gradient elution (60 min) was performed. The eluted object product was fractionated in test tubes, and each fraction was analyzed by HPLC to specify fractions containing only the object product. They were combined and freeze-dried to give 365.5 mg of a white powder.

The obtained purified sample (365.5 mg, 196.38 gmol) was dissolved in water (30 mL), and AG 1×8 AcO$^-$ resin (4.09 mL, 4.91 mmol equivalents) was added. The solution was stood for 1 hr while occasionally stirring with hand, passed through a disc filter with a pore diameter 0.45 µm to remove fine granules, concentrated in an evaporator to reduce the liquid amount to about 5 mL, and the solution was freeze-dried by cooling in a dry ice bath to give 303.2 mg of a white powder.

MALDI-TOF-MS analysis, (M+H)$^+$1860.9 (Calculated 1861.1)

HPLC elution time: 9.9 min elution condition (HPLC mode d):

column: Merck Chromolith Performance RP-18e(4.6×100 mm I.D.)

eluent: using Solution A: 0.1% TFA-water, Solution B: 0.1% TFA-containing acetonitrile, A/B: 80/20-30/70 linear concentration gradient elution (25 min)

flow rate: 1.0 mL/min

Example 32

(Synthesis Method AF): Production of (3-carboxypropyl)carbamoyl-[D-Hyp$^{24}$,Iva$^{25}$,Pya(4)$^{26}$, Cha$^{27,36}$,Leu (Me)$^{28}$, Lys$^{30}$,Aib$^{31}$]-PYY(23-36) (Compound No. 349)

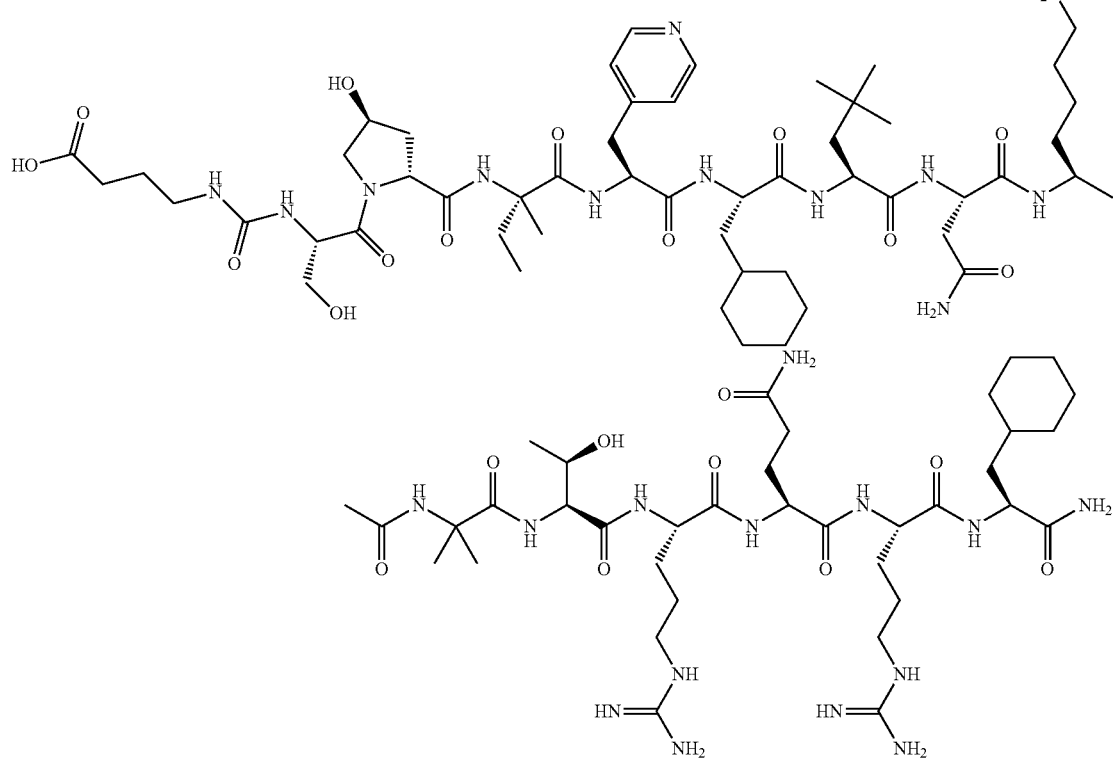

Compound No. 349

Synthesis of (3-carboxypropyl)carbamoyl-[D-Hyp$^{24}$, Iva$^{25}$,Pya(4)$^{26}$,Cha$^{27,36}$,Leu(Me)$^{28}$,Lys$^{30}$,Aib$^{31}$]-PYY (23-36)

Using commercially available Sieber Amide resin (391 mg, 0.25 mmol) as a starting material, and ABI433A peptide synthesizer DCC/HOBt 0.25 mmol protocol, amino acids were condensed in the order of Cha, Arg(Pbf), Gln(Trt), Arg (Pbf), Thr(Bu$^t$), Aib, Lys(Boc), Asn(Trt), Leu(Me), Cha to give H-Cha-Leu(Me)-Asn(Trt)-Lys(Boc)-Aib-Thr(Bu$^t$)-Arg (Pbf)-Gln(Trt)-Arg(Pbf)-Cha-Sieber Amide Resin (SEQ ID NO:183). In this case, the protocol was partly modified, and capping protocol with acetic anhydride was incorporated after every condensation procedure. In addition, the 30-position Lys(Boc) condensation was performed by double coupling. The obtained resin was swollen with DMF, and treated with Fmoc-Pya(4)-OH (388 mg, 1.0 mmol), HOAt in DMF (0.5 M, 2.0 mL, 1.0 mmol), DIPEA (174 μL, 1.0 mmol), DIPCDI (159 μL, 1.0 mmol) for 3 hr. Fmoc group was removed with 20% piperidine in DMF and the resin was treated with Fmoc-Iva-OH (339 mg, 1.0 mmol), HOAt in DMF (0.5 M, 2.0 mL, 1.0 mmol), DIPCDI (159 μL, 1.0 mmol) for 2 hr. The resin was washed with DMF, and further treated overnight with Fmoc-Iva-OH (339 mg, 1.0 mmol), HOAt in DMF (0.5 M, 2.0 mL, 1.0 mmol), DIPCDI (159 μL, 1.0 mmol). The resin was washed and subjected to a capping treatment with decanoic anhydride (368 μL, 1.0 mmol), DIEA (174 μL, 1.0 mmol) in DMF for 20 min. Fmoc group was removed with 20% piperidine in DMF and the resin was treated with Fmoc-D-Hyp-OH (409 mg, 1.0 mmol), HOAt in DMF (0.5 M, 2.0 mL, 1.0 mmol), DIPCDI (159 μL, 1.0 mmol) for 6 hr. The resin was washed, and the resin was subjected to a capping treatment with decanoic anhydride (368 μL, 1.0 mmol), DIEA (174 μL, 1.0 mmol) in DMF for 30 min. Fmoc group was removed with 20% piperidine in DMF and the resin was treated with Fmoc-Ser(Bu$^t$)-OH (383 mg, 1.0 mmol), HOAt in DMF (0.5 M, 2.0 mL, 1.0 mmol), DIPCDI (159 μL, 1.0 mmol) for 2 hr. The resin was washed, and the resin was subjected to a capping treatment with decanoic anhydride (368 μL, 1.0 mmol), DIEA (174 μL, 1.0 mmol) in DMF for 30 min. Fmoc group was removed with 20% piperidine in DMF and the resin was washed successively with DMF, MeOH and dried under reduced pressure. The total amount of the obtained H-Ser(Bu$^t$)-D-Hyp(Bu$^t$)-Iva-Pya(4)-Cha-Leu(Me)-Asn(Trt)-Lys(Boc)-Aib-Thr(Bu$^t$)-Arg(Pbf)-Gln(Trt)-Arg(Pbf)-Cha-Sieber Amide resin was swollen again with DMF, and treated with CDI (203 mg, 1.25 mmol), DIEA (218 μL, 1.25 mmol) in DMF for 2 hr. The resin was washed with DMF, and treated with 4-aminobutyric acid (206 mg, 2.0 mmol), DIEA (523 μL, 3.0 mmol) in DMF for 24 hr. The resin was washed successively with DMF, MeOH, dried under reduced pressure and the obtained resin (1.13 g) was suspended in TFA:thioanisole:m-cresol:H$_2$O:EDT:TIS (80:5:5:2.5:2.5) (10 mL) and the suspension was stirred at room temperature for 7 hr. The reaction solution was added to stirring diethyl ether under ice-cooling while removing the resin by a filter to obtain precipitation, and an operation to remove the supernatant after centrifugation was repeated 3 times. The residue was extracted with 50% aqueous acetic acid solution, passed through a disc filter with a pore diameter 0.45 μm to remove fine granules, and purified in 4 portions by HPLC. The HPLC conditions were YMC Pack R&D-ODS-5-B S-5 120A column (30×250 mm), Solution A: 0.1% TFA-water, Solution B: 0.1% TFA-containing acetonitrile, flow rate 15 mL/min, A/B: 74.5/25.5-64.5/35.5 or 74/26-64/36 linear concentration gradient elution (60 min). Each fraction was analyzed by HPLC to specify fractions containing only the object product. The fractions with low purity obtained by the first purification were concentrated, and subjected to HPLC purification again under the same conditions. All the fractions containing only the object product were combined and freeze-dried to give 345 mg of a white powder.

The obtained purified sample (345 mg) was dissolved in $CH_3CN/H_2O$ (10/20 mL), and AG 1×8 AcO$^-$ resin (3.03 ml, 3.64 mmol equivalents) was added. The solution was stood for 1 hr while occasionally stirring with hand, passed through a disc filter with a pore diameter 0.45 μm to remove fine granules, concentrated in an evaporator to reduce the liquid amount to about 5 mL, and the solution was freeze-dried to give 222 mg of a white powder.

MALDI-TOF-MS analysis, (M+H)$^+$1896.3 (Calculated 1896.1)

HPLC elution time: 10.4 min elution condition (HPLC mode g):

column: SHISEIDO CAPCELL PAK C18 MGII(4.6×100 mm)

eluent: using Solution A: 0.1% TFA-water, Solution B: 0.1% TFA-containing acetonitrile, A/B: 80/20-30/70 linear concentration gradient elution (25 min)

flow rate: 1.0 mL/min

Example 33

(Synthesis Method AG): Production of 3-carboxypropionyl-[D-Hyp$^{24}$,Iva$^{25}$,Pya(4)$^{26}$,Cha$^{27,36}$,Leu(Me)$^{28}$,Lys$^{30}$,Aib$^{31}$]-PYY (23-36) (Compound No. 350)

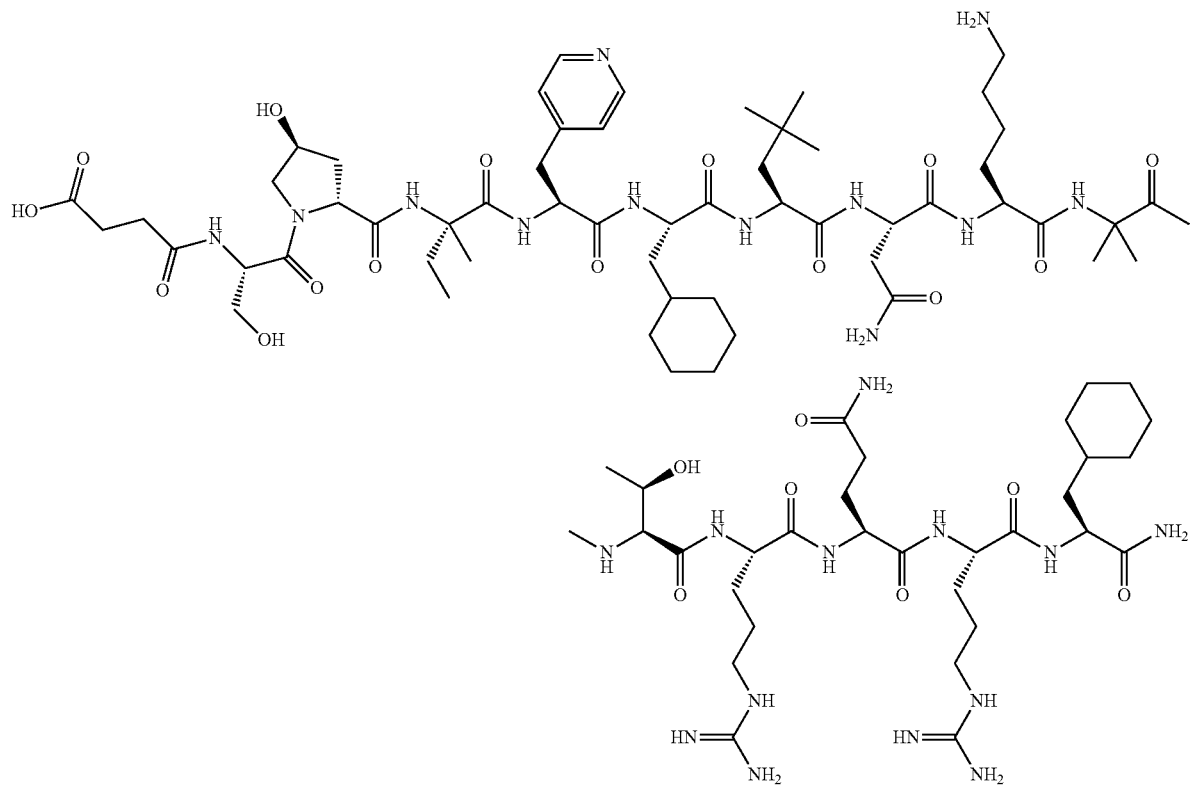

Compound No. 350

Synthesis of 3-Carboxypropionyl-[D-Hyp$^{24}$,Iva$^{25}$, Pya(4)$^{26}$,Cha$^{27,36}$,Leu(Me)$^{28}$,Lys$^{30}$,Aib$^{31}$]-PYY (23-36)

Using commercially available Sieber Amide resin (391 mg, 0.25 mmol) as a starting material, amino acids were condensed in the order of Cha, Arg(Pbf), Gln(Trt), Arg(Pbf), Thr(Bu$^t$), Aib, Lys(Boc), Asn(Trt), Leu(Me), Cha using ABI433A peptide synthesizer DCC/HOBt 0.25 mmol protocol to give H-Cha-Leu(Me)-Asn(Trt)-Lys(Boc)-Aib-Thr(Bu$^t$)-Arg(Pbf)-Gln(Trt)-Arg(Pbf)-Cha-Sieber Amide resin (SEQ ID NO:186). In this case, the protocol was partly modified, and capping protocol with acetic anhydride was incorporated after every condensation procedure. In addition, the 30-position Lys(Boc) condensation was performed by double coupling. The obtained resin was washed with MeOH and dried to give a resin (972.8 mg, 0.264 mmol/g).

The total amount of the obtained resin was placed in a reaction vessel, washed with DMF, and stirred in DMF for 20 min to swell the resin. Then, the resin was treated with Fmoc- D-Pya(4)-OH (776.8 mg, 2 mmol), 0.5 M HOAt/DMF solution (2 ml, 1 mmol), DIPCDI (318 µL, 2 mmol) for 1.5 hr to introduce Pya(4). Fmoc group was removed by 20% piperidine/DMF treatment, and the resin was treated with Fmoc-Iva-OH (339.4 mg, 1 mmol), 0.5 M HOAt/DMF solution (2 mL, 1 mmol), DIPCDI (159 µL, 1 mmol) for 3 hr to introduce Iva. Similarly, removal of Fmoc group and condensation were repeated to introduce D-Hyp, Ser(Bu$^t$). After removal of Fmoc from the obtained resin, the resin was treated with mono-tert-butylsuccinate (174.2 mg, 1 mmol), HOOBt (179.4 mg, 1.1 mmol), DIPCDI (159 µL, 1 mmol) in DMF for 8 hr, and washed and dried. The obtained mono-tert-butyl-succinyl-Ser(Bu$^t$)-D-Hyp(Bu$^t$)-Iva-Pya(4)-Cha-Leu(Me)-Asn(Trt)-Lys(Boc)-Aib-Thr(Bu$^t$)-Arg(Pbf)-Gln(Trt)-Arg(Pbf)-Cha-Sieber Amide resin (1.1636 g) was treated with TFA:thioanisole:m-cresol:H$_2$O:EDT:TIS (80:5:5:5:2.5:2.5) (6 mL) for 120 min, an operation to add diethyl ether to the reaction solution, precipitate a white powder by centrifugation, and remove diethyl ether by decantation was repeated twice. The residue was dissolved in aqueous acetic acid solution, passed through a disc filter with a pore diameter 0.45 µm to remove fine granules, and concentrated in an evaporator. After confirmation of the purity of the obtained crude peptide solution by HPLC, the peptide was purified by preparative HPLC in 6 portions using Daisopak-SP100-5-ODS-P 2×25 cm, and Solution A: 0.1% TFA-water, Solution B: 0.1% TFA-containing acetonitrile, flow rate 8 mL/min, A/B: 73/27-63/37 linear concentration gradient elution (60 min) was performed. The eluted object product was fractionated in test tubes, and each fraction was analyzed by HPLC to specify fractions containing only the object product. They were combined and freeze-dried to give 217.2 mg of a white powder.

The obtained purified sample (217.2 mg, 116.32 µmol) was dissolved in water (20 ml), and AG 1×8 AcO$^-$ resin (1.45 mL, 1.74 mmol equivalents) was added. The solution was stood for 1 hr while occasionally stirring with hand, passed through a disc filter with a pore diameter 0.45 µm to remove fine granules, concentrated in an evaporator to reduce the liquid amount to about 5 mL, and the solution was freeze-dried by cooling in a dry ice bath to give 159.1 mg of a white powder.

MALDI-TOF-MS analysis, (M+H)$^+$1867.3 (Calculated 1867.1)

HPLC elution time: 10.4 min elution condition (HPLC mode d):

column: Merck Chromolith Performance RP-18e(4.6×100 mm I.D.)

eluent: using Solution A: 0.1% TFA-water, Solution B: 0.1% TFA-containing acetonitrile, A/B: 80/20-30/70 linear concentration gradient elution (25 min)

flow rate: 1.0 mL/min

The structures (abbreviations) and physicochemical properties of the compounds synthesized in the same manner as in Examples 1-33 are shown in the following Table 2 (Table 2-1 to Table 2-12) and Table 3 (Table 3-1 to Table 3-11). In the Tables, M+H+ (obs.) means MALDI-TOF-MS analysis, (M+H)$^+$, M+H+ (cal.) means (M+H)$^+$ Calculated, and HPLC (min.) means HPLC elution time (min).

HPLC modes (a-h) means that the elution time was measured under respective conditions shown in Table 4 and using Solution A: 0.1% TFA-water, Solution B: 0.1% TFA-containing acetonitrile as eluents.

TABLE 2

| compound No. | structure |
|---|---|
| 1 | Ac-[Ala26,Ile28,31,Arg(Me)35]-PYY(22-36) |
| 2 | [Ala26,Ile28,31]-PYY(19-36) |
| 3 | [D-Ala22,Ala26,Ile28,31,Arg(Me)35]-PYY(22-36) |
| 4 | 4-Guanidinomethylbenzoyl-[Ala26,Ile28,31]-PYY(25-36) |
| 5 | Ac-[Ala26,Ile28,31]-PYY(20-36) |
| 6 | 4-Aminomethylbenzoyl-[Ala26,Ile28,31,Phe36]-PYY(25-36) |
| 7 | 4-Aminomethylbenzoyl-[Ala26,Ile28,31,Tyr(Me)36]-PYY(25-36) |
| 8 | 4-Aminomethylbenzoyl-[Ala26,Ile28,31,Phe(4Cl)36]-PYY(25-36) |
| 9 | 4-Aminomethylbenzoyl-[D-Arg25,Ala26,Ile28,31]-PYY(25-36) |
| 10 | 4-Aminomethylbenzoyl-[Orn25,Ala26,Ile28,31]-PYY(25-36) |
| 11 | 4-Aminomethylbenzoyl-[Ala26,Ile28,31,Har33]-PYY(25-36) |
| 12 | 4-Aminomethylbenzoyl-[Ala26,Ile28,31,Phe(4NH2)36]-PYY(25-36) |
| 13 | 4-Aminomethylbenzoyl-[Ala26,Ile28,31,Nal(1)36]-PYY(25-36) |
| 14 | 4-Aminomethylbenzoyl-[Ala26,Ile28,31,Nal(2)36]-PYY(25-36) |
| 15 | 4-Aminomethylbenzoyl-[Ala26,Ile28,31,Phe(4Me)36)-PYY(25-36) |
| 16 | 4-Aminomethylbenzoyl-[Ala26,Ile28,31,NMePhe36]-PYY(25-36) |
| 17 | 4-Aminomethylbenzoyl-[Ala26,Ile28,31,Tic36]-PYY(25-36) |
| 18 | 4-Aminomethylbenzoyl-[Arg26,Ile28,31]-PYY(25-36) |
| 19 | 4-Aminomethylbenzoyl-[Pro26,Ile28,31]-PYY(25-36) |
| 20 | 4-Aminomethylbenzoyl-[Ala26,Ile31]-PYY(25-36) |
| 21 | 4-Aminomethylbenzoyl-[Ala26,Nle28,Ile31]-PYY(25-36) |
| 22 | 4-Aminomethylbenzoyl-[Ala26Phe28,Ile31]-PYY(25-36) |
| 23 | 4-Aminomethylbenzoyl-[Ala26,Trp28,Ile31]-PYY(25-36) |
| 24 | [D-Leu24, Ala26,Ile28,31]-PYY(24-36) |
| 25 | cyclo(27-31)-4-Aminomethylbenzoyl-[Glu27,Ile28,Lys31]-PYY(25-36) |
| 26 | cyclo(28-32)-4-Aminomethylbenzoyl-[Lys28,Ile31,Glu32]-PYY(25-36) |
| 27 | [D-Arg23,Ala26,Ile28,31]-PYY(23-36) |
| 28 | 4-([[imino(octylamino)methyl]amino]methyl)benzoyl-[Ala26,Ile28,31]-PYY(25-36) |
| 29 | 4-Aminomethylbenzoyl-[Ala26,Arg27,Ile28,31]-PYY(25-36) |
| 30 | 4-Aminomethylbenzoyl-[Ala26,Gln27,Ile26,31]-PYY(25-36) |
| 31 | 4-Aminomethylbenzoyl-[Ala26,28,Ile31]-PYY(25-36) |
| 32 | 4-Aminomethylbenzoyl-[Ala26,30,Ile28,31]-PYY(25-36) |
| 33 | 4-Aminomethylbenzoyl-[Ala26,31,Ile28]-PYY(25-36) |
| 34 | Ac-[Phe24,Ala26,Ile28,31]-PYY(24-36) |
| 35 | Ac-[D-Phe24,Ala26,Ile28,31]-PYY(24-36) |
| 36 | Ac-[Cha24,Ala26,Ile28,31]-PYY(24-36) |
| 37 | Ac-[D-Cha24,Ala26,Ile28,31]-PYY(24-36) |
| 38 | Ac-[Pro24,Ala26,Ile28,31]-PYY(24-36) |
| 39 | 4-Aminomethylbenzoyl-[Ala26,Ile28,Val31]-PYY(25-36) |
| 40 | 4-Aminomethylbenzoyl-[Ala26,Ile28,Phg31]-PYY(25-36) |
| 41 | 4-Aminomethylbenzoyl-[Ala26,Ile28,Cha31]-PYY(25-36) |
| 42 | 4-Aminomethylbenzoyl-[Ala26,Ile28,Nle31]-PYY(25-36) |
| 43 | 4-Aminomethylbenzoyl-[Ala26,Nle27,Ile28,31]-PYY(25-36) |
| 44 | 4-Aminomethylbenzoyl-[Ala26,Pya(4)27,Ile28,31]-PYY(25-36) |
| 45 | 4-Aminomethylbenzoyl-[Ala26,Ile28,31,Gly30]-PYY(25-36) |
| 46 | 4-Aminomethylbenzoyl-[Ala26,Ile28,31,Aib29]-PYY(25-36) |
| 47 | 4-Aminomethylbenzoyl-[Ala26,Ile28,31,Aib30]-PYY(25-36) |
| 48 | 4-Aminomethylbenzoyl-[Ala(cPr)26,Ile28,32)-PYY(25-36) |
| 49 | 4-Aminomethylbenzoyl-[Lys25,Ala26,Ile28,31]-PYY(25-36) |
| 50 | 4-Aminomethylbenzoyl-[Gly26,Ile28,31]-PYY(25-36) |
| 51 | 4-Aminomethylbenzoyl-[Ala26,Trp27,Ile28,31]-PYY(25-36) |
| 52 | 4-Aminomethylbenzoyl-[Ala26,Phe(4NH2)27,Ile28,31]-PYY(25-36) |
| 53 | 4-Aminomethylbenzoyl-[Ala26,Aib27,Ile28,31]-PYY(25-36) |
| 54 | 4-Aminomethylbenzoyl-[Ala26,Ile28,31,Phe30]-PYY(25-36) |
| 55 | 4-Aminomethylbenzoyl-[Ala26,Ile28,31,Nal(1)30]-PYY(25-36) |
| 56 | 4-Aminomethylbenzoyl-[Ala26,Ile28,31,Nal(2)30]-PYY(25-36) |
| 57 | 4-Aminomethylbenzoyl-[Ala26,Ile28,31,Tyr30]-PYY(25-36) |
| 58 | 4-Aminomethylbenzoyl-[Ala26,Ile28,31,Phe(4F)30]-PYY(25-36) |
| 59 | 4-Aminomethylbenzoyl-[Ala26,Ile28,Phe31]-PYY(25-36) |
| 60 | 4-Aminomethylbenzoyl-[Ala26,Ile28,31,Ser32]-PYY(25-36) |
| 61 | 4-Aminomethylbenzoy]-[Ala26,Ile28,31,Nva32]-PYY(25-36) |
| 62 | 4-Aminomethylbenzoyl-[Ala26,Ile28,31,Leu32]-PYY(25-36) |
| 63 | Benzoyl-[Cha27,36,Nal(1)28,Aib31]-PYY(25-36) |
| 64 | Benzoyl-[Cha27,28,36,Aib31]-PYY(25-36) |
| 65 | Benzoyl-[Cha27,36,Ile28,Arg31]-PYY(25-36) |
| 66 | Benzoyl-[Ala(4Pip)27,Ile28,31,Trp30,Cha36]-PYY(25-36) later peak |
| 67 | Benzoyl-[Dap27,Ile28,31,Trp30,Cha36]-PYY(25-36) |
| 68 | [Abz(2)24,Cha27,36,Ile28,31,Trp30]-PYY(24-36) |
| 69 | Benzoyl-[Cha27,36,Ile28,Dap31]-PYY(25-36) |
| 70 | Benzoyl-[Cha27,36,Ile28,Arg(M)31]-PYY(25-36) |
| 71 | Benzoyl-[Cha27,36,Ile28,Pya(4)31]-PYY(25-36) |
| 72 | Benzoyl-[Cha27,36,Ile28,Phe(4NH2)31]-PYY(25-36) |
| 73 | Benzoyl-[Cha27,36,Ile28,31,Phe(4NH2)30]-PYY(25-36) |

TABLE 2-continued

| compound No. | structure |
|---|---|
| 74 | 4-Aminomethylbenzoyl-[Ala28,Ile28,31,Thr(Me)32]-PYY(25-36) |
| 75 | Cyclohexanecarbonyl-[Cha27,36,Ile28,31,Asn(Me)29]-PYY(25-36) |
| 76 | 4-Guanidinomethylbenzoyl-[Nle25,Cha27,28,31,36,Arg30]-PYY(25-36) |
| 77 | Cyclohexanecarbonyl-[Nle26,Cha27,28,36,Aib31]-PYY(25-36) |
| 78 | Cyclohexanecarbonyl-[Cha27,36,Ala(cPr)28,Aib31]-PYY(25-36) |
| 79 | Isobutanoyl-[Abu26,Cha27,36,Phe(4F)28,Aib31]-PYY(25-36) |
| 80 | Isobutanoyl-[Abu26,Cha27,28,36,Ala(cP)30,Aib31]-PYY(25-36) |
| 81 | Isobutanoyl-[Abu26,Cha27,28,36,Leu(Me)30,Aib31]-PYY(25-36) |
| 82 | Isobutanoyl-[Abu26,Cha27,36,Pya(3)31]-PYY(25-36) |
| 83 | Isobutanoyl-[Abu26,Cha27,36,Pya(4)28,Aib31]-PYY(25-36) |
| 84 | Ac-[D-Cha24,Abu26,Cha27,28,36,Aib31]-PYY(24-36) |
| 85 | [D-Ser23,Abu26,Cha27,28,36,Aib31]-PYY(23-36) |
| 86 | Isobutanoyl-[Abu26,Cha27,28,Aib31,Tyr(2F)36]-PYY(25-36) |
| 87 | Isobutanoyl-[Abu26,Cha27,28,Aib31,Tyr(3F)36]-PYY(25-36) |
| 88 | Isobutanoyl-[Abu26,Cha27,28,36,Gly(cPr)31]-PYY(25-36) |
| 89 | Isobutanoyl-[Abu26,Cha27,28,36,Ser30,Aib31]-PYY(25-36) |
| 90 | Isobutanoyl-[Abu26,Cha27,28,36,Gln30,Aib31]-PYY(25-36) |
| 91 | Isobutanoyl-[Abu26,Cha27,28,36,Abu30,Aib31]-PYY(25-36) |
| 92 | Isobutanoyl-[Abu26,Cha27,28,36,His30,Aib31]-PYY(25-36) |
| 93 | Isobutanoyl-[Abu26,Cha27,36,Gly(cPr)28,Aib31]-PYY(25-36) |
| 94 | Isobutanoyl-[Abu26,27,Cha28,36,Aib31]-PYY(25-36) |
| 95 | Isobutanoyl-[Abu26,Gly27,Cha28,36,Aib31]-PYY(25-36) |
| 96 | Amidino-[Gly23,Pic(4)24,Cha27,36,Ile28,31,Trp30]-PYY(23-36) |
| 97 | Benzoyl-[Ser26,Cha27,28,36,Aib31]-PYY(25-36) |
| 98 | Benzoyl-[Ser(Me)26,Cha27,28,36,Aib31]-PYY(25-36) |
| 99 | Benzoyl-[Asn26,Cha27,28,36,Aib31]-PYY(25-36) |
| 100 | Isobutanoyl-[Abu26,Cha27,36,Gln28,Aib31]-PYY(25-36) |
| 101 | Isobutanoyl-[Abu26,Cha27,36,His28,Aib31]-PYY(25-36) |
| 102 | Isobutanoyl-[Abu26,Cha27,36,Ser28,Aib31]-PYY(25-36) |
| 103 | Benzoyl-[Nva27,Cha28,36,Aib31]-PYY(25-36) |
| 104 | Benzoyl-[His27,Cha28,36,Aib31]-PYY(25-36) |
| 105 | Ac-[Abu23, D-Pro24,Abu26,Cha27,28,36,Aib31]-PYY(23-36) |
| 106 | Ac-[Ser(Me)23, D-Pro24,Abu26,Cha27,28,36,Aib31]-PYY(23-36) |
| 107 | Ac-[Phe23, D-Pro24,Abu26,Cha27,28,36,Aib31]-PYY(23-36) |
| 108 | Ac-[N (iBu) Gly24,Cha27,28,36,Aib31]-PYY(23-36) |
| 109 | Ac-[D-Ser23,MeAla24,Cha27,28,36,Aib31]-PYY(23-36) |
| 110 | Ac-[D-MeAla24,Cha27,28,36,Aib31]-PYY(23-36) |
| 111 | Ac-[D-Ser23,Sar24,Cha27,28,36,Aib31]-PYY(23-36) |
| 112 | Ac-[Gly24,Cha27,28,36,Aib31]-PYY(23-36) |
| 113 | Ac-[Aze(3)24,Cha27,28,36,Aib31]-PYY(23-36) |
| 114 | Ac-[D-Hyp24,Cha27,28,36,Aib31]-PYY(23-36) |
| 115 | Ac-[Asn23,D-Pro24,Cha27,28,36,Aib31]-PYY(23-36) |
| 116 | [β Ala23,D-Pro24,Cha27,28,36,Aib31]-PYY(23-36) |
| 117 | [Aoc(8)23,D-Pro24,Cha27,28,36,Aib31]-PYY(23-36) |
| 118 | [(PEG2)23,D-Pro24,Cha27,28,36,Aib31]-PYY(23-36) |
| 119 | Ac-[D-Pic(2)24,Cha27,28,36,Aib31]-PYY(23-36) |
| 120 | Ac-[Glu23,D-Pic(2)24,Cha27,28,36,Aib31]-PYY(23-36) |
| 121 | Ac-[D-Tyr21,D-Pro24,Cha27,28,36,Aib31]-PYY(21-36) |
| 122 | Ac-[Gly23-y[(E)-CH=CH]-Leu24,Cha27,28,36,Aib31]-PYY(23-36) |
| 123 | [MeAla22,D-Pro24,Cha27,28,36,Aib31]-PYY(22-36) |
| 124 | Ac-[D-MeAla22,D-Pro24,Cha27,28,36,Aib31]-PYY(22-36) |
| 125 | N-4-Pyridiniyl-[Pic(4)23,DPro24,Cha27,28,36,Aib31]-PYY(23-36) |
| 126 | Ac-[Hyp23,D-Pro24,Cha27,28,36,Aib31]-PYY(23-36) |
| 127 | Isobutanoyl-[Asp23, D-Hyp24,Cha27,28,36,Aib31]-PYY(23-36) |
| 128 | Ac-[D-Pro24,Hse26,Cha27,36,Aib28,36]-PYY(23-36) |
| 129 | Ac-[MeSer23,D-Pro24,Cha27,28,36,Aib31]-PYY(22-36) |
| 130 | Ureido-[D-Pro24,Cha27,28,36,Aib31]-PYY(23-36) |
| 131 | Ac-[D-Pro24,Cha27,28,36,Acpc31]-PYY(23-36) |
| 132 | Ac-[D-Pro24,Cha27,28,36,Thr30,Aib31)-PYY(23-36) |
| 133 | [N(iBu)Gly23,D-Pro24,Cha27,28,36,Aib31]-PYY(23-36) |
| 134 | [N(2-hydroxyethyl)Gly23,D-Pro24,Cha27,28,36,Aib31]-PYY(23-36) |
| 135 | Ac-[D-Pro24,Cha27,36,Aib28,Lys30,Aib31]-PYY(23-36) |
| 136 | Ac-[D-Pro24,Cha27,36,Leu(Me)28,Lys30,Aib31]-PYY(23-36) |
| 137 | Ac-[Glu23,D-Pro24,Cha27,36,Lys30,Aib31]-PYY(23-36) |
| 138 | Ac-[D-Pro24,Pya(4)26,Cha27,36,Aib28,31,Lys30]-PYY(23-36) |
| 139 | Ac-[Glu23,D-Pro24,Pya(4)26,Cha27,36,Tyr28,Lys30,Aib31]-PYY(23-36) |
| 140 | Ac-[D-Pro24,Nle25,Pya(4)26,Cha27,36,Aib31]-PYY(23-36) |
| 141 | Ac-[Glu23,D-Pro24,Pya(4)26,Cha27,36,Aib31]-PYY(23-36) |
| 142 | Ac-[D-Pro24,Cha27,28,36,Aib31]-PYY(23-36) |
| 143 | Ac-[D-Pro24,Cha27,28,Aib31,Phe36]-PYY(23-36) |
| 144 | Ac-[D-Pro24,Cha27,36,Hse28,Aib31]-PYY(23-36) |
| 145 | Ac-[D-Pro24,Cha27,36,Acpc28,Aib31]-PYY(23-36) |
| 146 | Ac-[D-Pro24,Cit27,Cha28,36,Aib31]-PYY(23-36) |
| 147 | Ac-[D-Pro24,Thr26,Cha27,28,36,Aib31]-PYY(23-36) |
| 148 | Ac-[D-Pro24,Pya(3)26,Cha27,28,36,Aib31]-PYY(23-36) |
| 149 | Ac-[D-Pro24,Alb26,Cha27,28,36,Aib31]-PYY(23-36) |
| 150 | Ac-[D-Pro24,Orn26,Cha27,28,36,Aib31]-PYY(23-36) |
| 151 | Ac-[D-Pro24,Glu26,Cha27,28,36,Aib31]-PYY(23-36) |
| 152 | Ac-[D-Pro24,Cit26,Cha27,28,36,Aib31]-PYY(23-36) |
| 153 | Ac-[D-Aze(2)24,Cha27,28,36,Aib31]-PYY(23-36) |
| 154 | Ac-[α MePro24,Cha27,28,36,Aib31]-PYY(23-36) |
| 155 | Ac-[D-α MePro24,Cha27,28,36,Aib31]-PYY(23-36) |
| 156 | Ac-[GABA24,Cha27,28,36,Aib31]-PYY(23-36) |
| 157 | Ac-[Hse23,D-Pro24,Cha27,28,36,Aib31)-PYY(23-36) |
| 158 | Ac-[D-Thr23,D-Pro24,Cha27,28,36,Aib31)-PYY(23-36) |
| 159 | Ac-[Aad23,D-Pro24,Cha27,28,36,Aib31]-PYY(23-36) |
| 160 | Ac-[Lys(Me)223,D-Pro24,Cha27,28,36,Aib31]-PYY(23-36) |
| 161 | ureido-[Asp23,D-Pro24,Cha27,28,36,Aib31]-PYY(23-36) |
| 162 | Ac-[Tyr23,D-Pro24,Cha27,28,36,Aib31]-PYY(23-36) |
| 163 | [Lys(Ac)23,D-Pro24,Cha27,28,36,Aib31]-PYY(23-36) |
| 164 | Ac-[Arg20,D-Tyr21,D-Pro24,Cha27,28,36,Aib31]-PYY(20-36) |
| 165 | Ac-[D-Pro24,Cha27,28,36,Dab30,Aib31]-PYY(23-36) |
| 166 | Ac-[D-Pro24,Cha27,28,36,Lys(Me2)30,Aib31]-PYY(23-36) |
| 167 | 3-Carboxypropionyl-[D-Pro24,Cha27,28,36,Lys30,Aib31]-PYY(23-36) |
| 168 | Ac-[Glu23,D-Pro24,Cha27,36,Leu(Me)28,Lys30,Aib31]-PYY(23-36) |
| 169 | Ac-[Glu23,D-Pro24,Pya(4)26,Cha27,36,Leu(Me)28,Lys30,Aib31]-PYY(23-36) |
| 170 | Isobutanoyl-[Glu23,D-Pro24,Pya(4)26,Cha27,36,Leu(Me)28,Lys30,Aib31]-PYY(23-36) |
| 171 | Ac-[Glu23,D-Pro24,Cha27,36,Aib28,31,Lys30]-PYY(23-36) |
| 172 | Ac-[Glu23,D-Pro24,Nle25,Pya(4)26,Cha27,28,36,Lys30,Aib31]-PYY(23-36) |
| 173 | Morpholinocarbonyl-[Asp23,D-Pro24,Cha27,28,36,Aib31]-PYY(23-36) |
| 174 | Morpholinocarbonyl-[Glu23,D-Pro24,Cha27,28,36,Aib31]-PYY(23-36) |
| 175 | Ac-[D-Pro24,Iva27,Cha28,36,Aib31]-PYY(23-36) |
| 176 | Ac-[D-Pro24,Iva26,Cha27,28,36,Aib31]-PYY(23-36) |
| 177 | Ac-[D-Pro24,Iva25,Cha27,28,36,Aib31]-PYY(23-36) |
| 178 | Ac-[Iva23,D-Pro24,Cha27,28,36,Aib31]-PYY(23-36) |
| 179 | Ac-[D-Pro24,Cha27,28,36,D-Iva29,Aib31]-PYY(23-36) |
| 180 | Ac-[D-Pro24,D-Iva27,Cha28,36,Aib31]-PYY(23-36) |
| 181 | Ac-[D-Pro24,D-Iva26,Cha27,28,36,Aib31]-PYY(23-36) |
| 182 | Ac-[D-Pro24,D-Iva25,Cha27,28,36,Aib31]-PYY(23-36) |
| 183 | Ac-[D-Iva23,D-Pro24,Cha27,28,36,Aib31]-PYY(23-36) |
| 184 | [(1S)-1-carboxy-3-methylbutyl]carbamoyl-[D-Pro24,Cha27,28,36,Aib31]-PYY(23-36) |
| 185 | 3-Carboxypropionyl-[Acp22,D-Pro24,Cha27,36,Leu(Me)28,Lys30,Aib31]-PYY(22-36) |
| 186 | amidino-[D-Pro24,Cha27,36,Leu(Me)28,Lys30,Aib31]-PYY(23-36) |
| 187 | morpholinocarbonyl-[D-Pro24,Cha27,36,Leu(Me)28,Lys30,Aib31]-PYY(23-36) |
| 188 | 2-hydroxyethylcarbamoyl-[D-Pro24,Cha27,36,Leu(Me)28,Lys30,Aib31]-PYY(23-36) |
| 189 | Ac-[Acp22,Glu23,D-Pro24,Cha27,28,36,Lys30,Aib31]-PYY(22-36) |
| 190 | amidino-[Glu23,D-Pro24,Cha27,28,36,Lys30,Aib31]-PYY(23-36) |
| 191 | morpholinocarbonyl-[Glu23,D-Pro24,Cha27,28,36,Lys30,Aib31]-PYY(23-36) |
| 192 | 2-hydroxyethylcarbamoyl-[Glu23,D-Pro24,Cha27,28,36,Lys30,Aib31]-PYY(23-36) |
| 193 | piperidinocarbonyl-[Glu23,D-Pro24,Pya(4)26,Cha27,36,Aib28,31,Lys30]-PYY(23-36) |
| 194 | Ac-[D-Pro24,Cha27,28,Aib31,Phe(2F)36]-PYY(23-36) |
| 195 | Ac-[D-Pro24,Cha27,28,Aib31,Phe(3F)36]-PYY(23-36) |
| 196 | Ac-[D-Pro24,Cha27,28,Aib31,Phe(2Me)36]-PYY(23-36) |
| 197 | Ac-[D-Pro24,Cha27,28,Aib31,Phe(3Me)36]-PYY(23-36) |
| 198 | Ac-[D-Pro24,Cha27,28,Aib31,Leu(Me)36]-PYY(23-36) |
| 199 | Ac-[D-Pro24,Cha27,28,Aib31,hLeu36]-PYY(23-36) |
| 200 | Ac-[D-Pro24,Cha27,28,Aib31,threo-PhSer36]-PYY(23-36) |
| 201 | Ac-[D-Pro24,Cha27,28,Aib31,DL-Phe(2,6Me2)36]-PYY(23-36) |
| 202 | Ac-[D-Pro24,Cha27,28,36,Iva30,Aib31]-PYY(23-36) |
| 203 | Ac-[D-Hyp24,Cha27,36,Leu(Me)28,Lys30,Aib31]-PYY(23-36) |
| 204 | Ac-[Glu23,D-Hyp24,Cha27,28,36,Lys30,Aib31]-PYY(23-36) |
| 205 | Ac-[D-Pro24,Pya(4)26,Cha27,36,Aib28,31,Trp30]-PYY(23-36) |
| 206 | Ac-[D-Pro24,Pya(4)26,Cha27,36,Aib28,31,Orn30]-PYY(23-36) |
| 207 | Ac-[D-Hyp24,Pya(4)26,Cha27,36,Aib28,31,Lys30]-PYY(23-36) |
| 208 | Ac-[Glu23,D-Hyp24,Pya(4)26,Cha27,36,Aib28,31,Lys30]-PYY(23-36) |

TABLE 2-continued

| compound No. | structure |
|---|---|
| 209 | Ac-[Glu23,D-Pro24,Pya(4)26,Cha27,36,Aib28,31,Lys30]-PYY(23-36) |
| 210 | Ac-[Gln23,D-Pro24,Pya(4)26,Cha27,36,Aib28,31,Lys30]-PYY(23-36) |
| 211 | Ac-[Thr23,D-Pro24,Pya(4)26,Cha27,36,Aib28,31,Lys30]-PYY(23-36) |
| 212 | Isobutanoyl-[D-Pro24,Pya(4)26,Cha27,36,Aib28,31,Lys30]-PYY(23-36) |
| 213 | 4-Imidazolecarbonyl-[D-Pro24,Pya(4)26,Cha27,36,Aib28,31,Lys30]-PYY(23-36) |
| 214 | Isobutanoyl-[Glu23,D-Pro24,Pya(4)26,Cha27,36,Aib28,31,Lys30]-PYY(23-36) |
| 215 | 4-Pyridinecarbonyl-[Glu23,D-Pro24,Pya(4)26,Cha27,36,Aib28,31,Lys30]-PYY(23-36) |
| 216 | 4-Imidazolecarbonyl-[Glu23,D-Pro24,Pya(4)26,Cha27,36,Aib28,31,Lys30]-PYY(23-36) |
| 217 | 3-Carboxypropionyl-[D-Pro24,Pya(4)26,Cha27,36,Aib28,31,Lys30]-PYY(23-36) |
| 218 | 3-Carboxypropionyl-[Gln23,D-Pro24,Pya(4)26,Cha27,36,Aib28,31,Lys30]-PYY(23-36) |
| 219 | Ac-[D-Pro24,Pya(4)26,Cha27,36,Aib28,31,Lys30]-PYY(22-36) |
| 220 | Ac-[Glu23,D-Pro24,Pya(4)26,Cha27,36,Aib28,31,Lys30]-PYY(22-36) |
| 221 | Ac-[D-Pro24,Gln26,Cha27,36,Aib28,31,Lys30]-PYY(23-36) |
| 222 | Ac-[β Ala24,Pya(4)26,Cha27,36,Aib28,31,Lys30]-PYY(23-36) |
| 223 | Ac-[Glu23, β Ala24,Pya(4)26,Cha27,36,Aib28,31,Lys30]-PYY(23-36) |
| 224 | Ac-[D-Pro24,Nle25,Pya(4)26,Cha27,36,Aib28,31,Lys30]-PYY(23-36) |
| 225 | Ac-[D-Pro24,Cit25,Pya(4)26,Cha27,36,Aib28,31,Lys30]-PYY(23-36) |
| 226 | Ac-[D-Pro24,Cit25,Cha27,36,Aib28,31,Lys30]-PYY(23-36) |
| 227 | Ac-[Glu23,D-Pro24,Nle25,Pya(4)26,Cha27,36,Aib28,31,Lys30]-PYY(23-36) |
| 228 | 4-Pyridinecarbonyl-[Glu23,D-Pro24,Nle25,Pya(4)26,Cha27,36,Aib28,31,Lys30]-PYY(23-36) |
| 229 | tetrahydro-2H-pyran-4-yl-carbamoyl-[D-Pro24,Cha27,36,Leu(Me)28,Lys30,Aib31]-PYY(23-36) |
| 230 | tetrahydro-2H-pyran-4-yl-carbamoyl-[Glu23,D-Pro24,Cha27,28,36,Lys30,Aib31]-PYY(23-36) |
| 231 | Ac-[D-Pro24,Pya(4)26,Cha27,36,Aib28,Lys30,Iva31]-PYY(23-36) |
| 232 | Ac-[D-Pro24,Pya(4)26,Cha27,36,Aib28,Lys30,D-Iva31]-PYY(23-36) |
| 233 | Ac-[D-Pro24,Pya(4)26,Cha27,36,Iva28,Lys30,Aib31]-PYY(23-36) |
| 234 | Ac-[D-Pro24,Pya(4)26,Cha27,36,D-Iva28,Lys30,Aib31]-PYY(23-36) |
| 235 | Ac-[D-Pro24,Aib26,28,31Cha27,36,Lys30]-PYY(23-36) |
| 236 | Ac-[D-Pro24,Aib25,28,31,Pya(4)26,Cha27,36,Lys30]-PYY(23-36) |
| 237 | Ac-[D-Pro24,Iva25,Pya(4)26,Cha27,36,Aib28,31,Lys30]-PYY(23-36) |
| 238 | Ac-[D-Pro24,Aib25,28,31,Cha27,36,Lys30]-PYY(23-36) |
| 239 | Ac-[D-Pro24,Iva25,Cha27,36,Aib28,31,Lys30]-PYY(23-36) |
| 240 | Ac-[Aib24,28,31,Pya(4)26,Cha27,36,Lys30]-PYY(23-36) |
| 241 | Ac-[Iva24,Pya(4)26,Cha27,36,Aib28,31,Lys30]-PYY(23-36) |
| 242 | Ac-[D-Iva24,Pya(4)26,Cha27,36,Aib28,31,Lys30]-PYY(23-36) |
| 243 | Ac-[Aipe24,Pya(4)26,Cha27,36,Aib28,31,Lys30]-PYY(23-36) |
| 244 | Ac-[β HomoAla24,Pya(4)26,Cha27,36,Aib28,31,Lys30]-PYY(23-36) former peak |
| 245 | Ac-[β HomoAla24,Pya(4)26,Cha27,36,Aib28,31,Lys30]-PYY(23-36) later peak |
| 246 | Ac-[D-Pro24,Pya(4)26,Cha27,36,Iva28,31,Lys30]-PYY(23-36) |
| 247 | Ac-[D-Pro24,Pya(4)26,Cha27,36,D-Iva28,31,Lys30]-PYY(23-36) |
| 248 | Ac-[D-Pro24,Pya(4)26,Cha27,36,D-Iva28,Lys30,Iva31]-PYY(23-36) |
| 249 | Ac-[D-Pro24,Pya(4)26,Cha27,36,Iva28,Lys30,D-Iva31]-PYY(23-36) |
| 250 | [D-pGlu24,Pya(4)26,Cha27,36,Aib28,31,Lys30]-PYY(24-36) |
| 251 | Ac-[D-Pro24,Pya(4)26,Cha27,36,Aib28,31,Lys30]-PYY(24-36) |
| 252 | 4-Guanidinomethylbenzoyl-[Iva25,Cha27,36,Aib28,31,Lys30]-PYY(25-36) |
| 253 | [(1S)-1-carboxy-3-methylbutyl]carbamoyl-[D-Pro24,Cha27,36,Leu(Me)28,Lys30,Aib31]-PYY(23-36) |
| 254 | [(1S)-1-carboxy-3-methylbutyl]carbamoyl-[Glu23,D-Pro24,Cha27,28,36,Lys30,Aib31]-PYY(23-36) |
| 255 | Ac-[D-Pro24,Cha27,Leu(Me)28,Lys30,Aib31,Phe(2Me)36]-PYY(23-36) |
| 256 | Ac-[Glu23,D-Pro24,Cha27,28,Lys30,Aib31,Phe(2Me)36]-PYY(23-36) |
| 257 | Ac-[D-Pro24,Pya(4)26,Cha27,Aib28,31,Lys30,Phe(2Me)36]-PYY(23-36) |
| 258 | Ac-[D-Pro24,Cha27,Leu(Me)28,Lys30,Aib31,Phe(3Me)36]-PYY(23-36) |
| 259 | Ac-[Glu23,D-Pro24,Cha27,28,Lys30,Aib31,Phe(3Me)36]-PYY(23-36) |
| 260 | Ac-[D-Pro24,Pya(4)26,Cha27,36,Aib28,31,Lys30,Phe(3Me)36]-PYY(23-36) |
| 261 | Ac-[Arg20,D-Tyr21,D-Pro24,Pya(4)26,Cha27,36,Aib28,31,Lys30,Phe(2Me)36]-PYY(20-36) |
| 262 | Ac-[Arg20,D-Tyr21,D-Pro24,Pya(4)26,Cha27,36,Aib28,31,Lys30,Phe(3Me)36]-PYY(20-36) |
| 263 | Ac-[D-Pro24,Pya(4)26,Cha27,36,Aib28,31,Arg30]-PYY(23-36) |
| 264 | Ac-[D-Pro24,Pya(4)26,Cha27,36,Aib28,31,Lys(Me2)30]-PYY(23-36) |
| 265 | Ac-[D-Pro24,Pya(4)26,Cha27,36,Aib28,31,Hse30]-PYY(23-36) |
| 266 | Ac-[D-Pro24,Pya(4)26,Cha27,36,Aib28,31,Cit30]-PYY(23-36) |
| 267 | Ac-[D-Pro24,Pya(4)26,Cha27,36,Aib28,31,Nle30]-PYY(23-36) |
| 268 | morpholinocarbonyl-[D-Pro24,Pya(4)26,Cha27,36,Aib28,31,Lye30]-PYY(23-36) |
| 269 | (cis-2,6-dimethylmorpholin-4-yl)carbonyl-[D-Pro24,Pya(4)26,Cha27,36,Aib28,31,Lys30]-PYY(23-36) |
| 270 | tetrahydro-2H-pyran-4-yl-carbamoyl-[D-Pro24,Pya(4)26,Cha27,36,Aib28,31,Lys30]-PYY(23-36) |
| 271 | [(1S)-1-carboxy-3-methylbutyl]carbamoyl-[D-Pro24,Pya(4)26,Cha27,36,Aib28,31,Lys30]-PYY(23-36) |
| 272 | Ac-[Lys22,30,D-Pro24,Pya(4)26,Cha27,36,Aib28,31]-PYY(22-36) |
| 273 | Ac-[Dap22,D-Pro24,Pya(4)26,Cha27,36,Aib28,31,Lys30]-PYY(22-36) |
| 274 | Ac-[Leu22,D-Pro24,Pya(4)26,Cha27,36,Aib28,31,Lys30]-PYY(22-36) |
| 275 | Ac-[Phe22,D-Pro24,Pya(4)26,Cha27,36,Aib28,31,Lys30]-PYY(22-36) |
| 276 | 2-Methylbutanoyl-[D-Pro24,Pya(4)26,Cha27,36,Aib28,31,Lys30]-PYY(23-36) |
| 277 | Ac-[D-Pro24,Pya(4)26,Cha27,36,Aib28,31,Har30]-PYY(23-36) |
| 278 | Ac-[D-Pro24,Pya(4)26,Cha27,36,Aib28,31,Lys(Ac)30]-PYY(23-36) |
| 279 | Ac-[D-Pro24,Pya(4)26,Cha27,36,Aib28,31,Lys(Hexyl)30]-PYY(23-36) |
| 280 | Ac-[D-Pro24,Lys(Ac)25,Pya(4)26,Cha27,36,Aib28,31,Lys30]-PYY(23-36) |
| 281 | Ac-[D-Pro24,Arg(Me)25,Cha27,36,Aib28,31,Lys30]-PYY(23-36) |
| 282 | (tetrahydro-2H-pyran-4-yl)carbamoyl-[Glu23,D-Pro24,Pya(4)26,Cha27,36,Aib28,31,Lys30]-PYY(23-36) |
| 283 | [(1S)-1-carboxy-3-methylbutyl]carbamoyl-[Glu23,D-Pro24,Pya(4)26,Cha27,36,Aib28,31,Lys30]-PYY(23-36) |
| 284 | [(1S)-1-carboxy-3-methylbutyl]carbamoyl-[Gln23,D-Pro24,Pya(4)26,Cha27,36,Aib28,31,Lys30]-PYY(23-36) |
| 285 | [(1S)-1-carboxy-2-(4-hydroxyphenyl)ethyl]carbamoyl-[D-Pro24,Pya(4)26,Cha27,36,Aib28,31,Lys30]-PYY(23-36) |
| 286 | [(1S)-1-carboxyethyl]carbamoyl-[D-Pro24,Pya(4)26,Cha27,36,Aib28,31,Lys30]-PYY(23-36) |
| 287 | (carboxymethyl)carbamoyl-[D-Pro24,Pya(4)26,Cha27,36,Aib28,31,Lys30]-PYY(23-36) |
| 288 | [(1S)-1-carboxy-2-hydroxyethyl]carbamoyl-[D-Pro24,Pya(4)26,Cha27,36,Aib28,31,Lys30]-PYY(23-36) |
| 289 | Ac-[D-Pro24,Har25,Pya(4)26,Cha27,36,Aib28,31,Lys30]-PYY(23-36) |
| 290 | Ac-[D-Pro24,Nar25,Pya(4)26,Cha27,36,Aib28,31,Lys30]-PYY(23-36) |
| 291 | Ac-[D-Pro24,Har25,Cha27,36,Aib28,31,Lys30]-PYY(23-36) |
| 292 | (2-amino-2-oxoethyl)carbamoyl-[D-Pro24,Pya(4)26,Cha27,36,Aib28,31,Lys30]-PYY(23-36) |
| 293 | (3-carboxypropyl)carbamoyl-[D-Pro24,Pya(4)26,Cha27,36,Aib28,31,Lys30]-PYY(23-36) |
| 294 | (5-carboxypentyl)carbamoyl-[D-Pro24,Pya(4)26,Cha27,36,Aib28,31,Lys30]-PYY(23-36) |
| 295 | Ac-[D-Pro24,Iva25,Pya(4)26,Cha27,36,Leu(Me)28,Lys30, Aib31]-PYY(23-36) |
| 296 | Ac-[D-Pro24,Iva25,28,Pya(4)26,Cha27,36,Lys30,Aib31]-PYY(23-36) |
| 297 | Ac-[D-Hyp24,Iva25,Pya(4)26,Cha27,36,Aib28,31,Lys30]-PYY(23-36) |
| 298 | Ac-[D-Hyp24,Iva25,28,Pya(4)26,Cha27,36,Lys30,Aib31]-PYY(23-36) |

TABLE 2-continued

| compound No. | structure |
|---|---|
| 299 | 4-Imidazolecarbonyl-[D-Hyp24,Iva25,Pya(4)26,Cha27,36,Aib28,31,Lys30]-PYY(23-36) |
| 300 | 4-Imidazolecarbonyl-[D-Pro24,Iva25,Pya(4)26,Cha27,36,Aib28,31,Lys30]-PYY(23-36) |
| 301 | 4-Pyridinecarbonyl-[D-Pro24,Iva25,Pya(4)26,Cha27,36,Aib28,31,Lys30]-PYY(23-36) |
| 302 | 4-Imidazolecarbonyl-[D-Pro24,Nle25,Pya(4)26,Cha27,36,Aib28,31,Lys30]-PYY(23-36) |
| 303 | 3-Carboxypropionyl-[D-Pro24,Pya(4)26,Cha27,36,Aib28,31,Lys30]-PYY(24-36) |
| 304 | [Acp23,D-Pro24,Pya(4)26,Cha27,36,Aib28,31,Lys30]-PYY(23-36) |
| 305 | Ac-[D-Pro24,Pya(4)26,Phe(4F)27,Aib28,31,Lys30,Ch36]-PYY(23-36) |
| 306 | Ac-[D-Pro24,Pya(4)26,Nal(1)27,Aib28,31,Lys30,Ch36]-PYY(23-36) |
| 307 | Ac-[D-Pro24,Pya(4)26,Nal(2)27,Aib28,31,Lys30,Ch36]-PYY(23-36) |
| 308 | Ac-[D-Pro24,Pya(4)26,Ala(4Pip)27,Aib28,31,Lys30,Ch36]-PYY(23-36) former peak |
| 309 | Ac-[D-Pro24,Pya(4)26,Ala(4Pip)27,Aib28,31,Lys30,Ch36]-PYY(23-36) later peak |
| 310 | Ac-[D-Pro24,Ala(4Pip)26,Cha27,36,Aib28,31,Lys30]-PYY(23-36) later peak |
| 311 | Ac-[D-Pro24,Ala(4Pip)25,Pya(4)26,Cha27,36,Aib28,31,Lys30]-PYY(23-36) former peak |
| 312 | Ac-[D-Pro24,Ala(4Pip)25,Pya(4)26,Cha27,36,Aib28,31,Lys30]-PYY(23-36) later peak |
| 313 | Ac-[D-Pro24,Pya(4)26,Cha27,36,Aib28,31,Ala(4pip)30]-PYY(23-36) later peak |
| 314 | Ac-[D-Pro24,Pya(4)26,Cha27,36,Aib28,31,Arg(Me)30]-PYY(23-38) |
| 315 | Ac-[D-Pro24,Arg(Me)25,30,Pya(4)26,Cha27,36,Aib28,31]-PYY(23-36) |
| 316 | Ac-[D-Pro24,Iva25,Pya(4)26,Cha27,36,Aib28,31,Arg(Me)30]-PYY(23-36) |
| 317 | Ac-[D-Pro24,Iva25,Pya(4)26,Cha27,36,Aib38,31,Har30]-PYY(23-36) |
| 318 | 4-Imidazolecarbonyl-[D-Pro24,Iva25,Pya(4)26,Cha27,30,36,Aib28,31]-PYY(23-36) |
| 319 | Ac-[D-Pro24,Arg(Me)25,Pya(4)26,Cha27,36,Aib28,31,Lys30]-PYY(23-36) |
| 320 | Ac-[D-Pro24,Abu26,Cha27,36,Aib28,31,Lys30]-PYY(23-36) |
| 321 | Ac-[Arg23,D-Pro24,Iva25,Pya(4)26,Cha27,36,Aib28,31,Lys30]-PYY(23-36) |
| 322 | Ac-[Glu23,D-Pro24,Iva25,Pya(4)26,Cha27,36,Aib28,31,Lys30]-PYY(23-36) |
| 323 | [(1S)-5-amino-1-carboxypentyl]carbamoyl-[D-Pro24,Cha27,28,36,Aib31]-PYY(23-36) |
| 324 | (tetrahydro-2H-pyran-4-yl)carbonyl-[D-Pro24,Pya(4)26,Cha27,36,Aib28,31,Lys30]-PYY(23-36) |
| 325 | (tetrahydro-2H-pyran-4-ylmethyl)carbamoyl-[D-Pro24,Pya(4)26,Cha27,36,Aib28,31,Lys30]-PYY(23-36) |
| 326 | (2-carboxyethyl)carbamoyl-[D-Pro24,Pya(4)26,Cha27,36,Aib28,31,Lys30]-PYY(23-36) |
| 327 | (carboxymethyl)carbamoyl-[D-Pro24,Iva25,Pya(4)26,Cha27,36,Aib28,31,Lys30]-PYY(23-36) |
| 328 | (3-carboxypropyl)carbamoyl-[D-Pro24,Iva25,Pya(4)26,Cha27,38,Aib28,31,Lys30]-PYY(23-36) |
| 329 | Ac-[D-Pro24,Pya(4)26,Cha27,Aib28,31,Lys30,Phe(2,6-Me2)36]-PYY(23-36) later peak |
| 330 | (tetrahydro-2H-pyran-4-yl)carbamoyl-[D-Pro24,Iva25,Pya(4)26,Cha27,36,Aib28,31,Lys30]-PYY(23-36) |
| 331 | (2-amino-2-oxoethyl)carbamoyl-[D-Pro24,Iva25,Pya(4)26,Cha27,36,Aib28,31,Lys30]-PYY(23-36) |
| 332 | [(1S)-1-carboxy-2-hydroxyethyl]carbamoyl-[D-Pro24,Iva25,Pya(4)26,Cha27,38,Aib28,31,Lys30]-PYY(23-36) |
| 333 | 4-Pyridinecarbonyl-[D-Hyp24,Iva25,Pya(4)26,Cha27,38,Leu(Me)28,Lys30,Aib31]-PYY(23-36) |
| 334 | 4-Pyridinecarbonyl-[D-Hyp24,Iva25,28,Pya(4)26,Cha27,36,Lys30,Aib31]-PYY(23-36) |
| 335 | Ac-[D-Hyp24,Iva25,Pya(4)26,Cha27,36,Leu(Me)28,Lys30,Aib31]-PYY(23-36) |
| 336 | 4-Imidazolecarbonyl-[D-Hyp24,Iva25,Pya(4)26,Cha27,36,Leu(Me)28,Lys30,Aib31]-PYY(23-36) |
| 337 | 4-Imidazolecarbonyl-[D-Hyp24,Iva25,28,Pya(4)26,Cha27,36,Lys30,Aib31]-PYY(23-36) |
| 338 | Glycoloyl-[D-Hyp24,Iva25,28Pya(4)26,Cha27,36,Lys30,Aib31]-PYY(23-36) |
| 339 | [2-hydroxy-1-(hydroxymethyl)ethyl]carbamoyl-[D-Pro24,Iva25,Pya(4)26,Cha27,36,Aib28,31,Lys30]-PYY(23-36) |
| 340 | (tetrahydro-2H-pyran-4-ylmethyl)carbamoyl-[D-Pro24,Iva25,Pya(4)26,Cha27,36,Aib28,31,Lys30]-PYY(23-36) |
| 341 | (2-carboxyethyl)carbamoyl-[D-Pro24,Iva25,Pya(4)26,Cha27,36,Aib28,31,Lys30]-PYY(23-36) |
| 342 | (tetrahydro-2H-pyran-4-yl)carbonyl-[D-Pro24,Iva25,Pya(4)26,Cha27,36,Aib28,31,Lys30]-PYY(23-36) |
| 343 | 4-Imidazolecarbonyl-[D-Hyp24,Iva25,Pya(4)26,Cha27,36, α MePhe28,Lys30,Aib31]-PYY(23-36) |
| 344 | 4-Imidazolecarbonyl-[D-Aib24,28,31,Iva25,Pya(4)26,Cha27,36,Lys30]-PYY(23-36) |
| 345 | Ac-[D-Pro24,Phe26,Cha27,36,Aib28,31,Lys30]-PYY(23-36) |
| 346 | Ac-[D-Pro24,Tyr26,Cha27,36,Aib28,31,Lys30]-PYY(23-36) |
| 347 | Ac-[D-Pro24,Trp26,Cha27,36,Aib28,31,Lys30]-PYY(23-36) |
| 348 | Ac-[D-Pro24,Tyr(Me)26,Cha27,36,Aib28,31,Lys30]-PYY(23-36) |
| 349 | (3-carboxyproply)carbamoyl-[D-Hyp24,Iva25,Pya(4)26,Cha27,36,Leu(Me)28,Lys30,Aib31]PYY(23-36) |
| 350 | 3-Carboxypropionyl-[D-Hyp24,Iva25,Pya(4)26,Cha27,36,Leu(Me)28,Lys30,Aib31]PYY(23-36) |
| 351 | Ac-[Glu23,D-Hyp24,Iva25,Pya(4)26,Cha27,36,Leu(Me)28,Lys30,Aib31]-PYY(23-36) |
| 352 | Ac-[D-Pro24,Iva25,Pya(4)26,Cha27,36,Nva28,Aib31,Lys30]-PYY(23-36) |
| 353 | [Ile22,28,31,Lys23,Acp24,Ala26]-PYY(22-36) |
| 354 | 4-Aminomethylbenzoyl-[Ala26,Ile28,31,Abu32]-PYY(25-36) |
| 355 | Ac-[D-Tyr21,D-Pro24,Cha27,28,36,Aib31]-PYY(20-36) |
| 356 | CC(Gly)-[D-Hyp24,Iva25,Pya(4)26,Cha27,36,Leu(Me)28,Lys30,Aib31]-PYY(23-36) |
| 357 | CC(β-Ala)-[D-Hyp24,Iva25,Pya(4)26,Cha27,36,Leu(Me)28,Lys30,Aib31]-PYY(23-36) |
| 358 | Thp(4)-NHCO-[D-Hyp24,Iva25,Pya(4)26,Cha27,36,Leu(Me)28,Lys30,Aib31]-PYY(23-36) |
| 359 | Thp(4)-CH₂NHCO-[D-Hyp24,Iva25,Pya(4)26,Cha27,36,Leu(Me)28,Lys30,Aib31]-PYY(23-36) |
| 360 | 4-Imidazolecarbonyl-[D-Hyp24,Iva25,Pya(4)26,Cha27,Leu(Me)28,Lys30,Aib31,Phe(2,6-Me)36]-PYY(23-36) |
| 361 | Thp(4)-CO-[D-Hyp24,Iva25,Pya(4)26,Cha27,36,Leu(Me)28,Lys30,Aib31]-PYY(23-36) |
| 362 | 4-Imidazolecarbonyl-[D-Hyp24,Iva25,Pya(4)26,Cha27,36,Leu(Me)28,Lys(Ac)30,Aib31]-PYY(23-36) |
| 363 | Ac-[Glu23,D-Pro24,Iva25,Pya(4)26,Cha27,36,Leu(Me)28,Lys30,Aib31]-PYY(23-36) |
| 364 | Carbamoyl-[D-Hyp24,Iva25,Pya(4)26,Cha27,36,Leu(Me)28,Lys30,Aib31]-PYY(23-36) |
| 365 | 4-Imidazolecarbonyl-[D-Pro24,Iva25,Pya(4)26,Cha27,36,Leu(Me)28,Lys(Ac)30,Aib31]-PYY(23-36) |
| 366 | 4-Imidazolecarbonyl-[D-Pro24,Pya(4)26,Cha27,36,Iva28,Lys30,Aib31]-PYY(23-36) |
| 367 | 4-Imidazolecarbonyl-[D-Hyp24,Iva25,Pya(4)26,Cha27,36,Leu(Me)28,Har30,Aib31]-PYY(23-36) |
| 368 | 4-Imidazolecarbonyl-[Aib24,31,Iva25,Pya(4)26,Cha27,36,Leu(Me)28,Lys(Ac)30]-PYY(23-36) |
| 369 | 4-Imidazolecarbonyl-[D-Hyp24,Iva25,Pya(4)26,Cha27,36,Leu(Me)28,Lys(Ac)30,D-Iva31]-PYY(23-36) |
| 370 | 4-Imidazolecarbonyl-[D-Hyp24,Pya(4)26,Cha27,36,Leu(Me)28,Lys30,Aib31]-PYY(23-36) |

TABLE 2-continued

| compound No. | structure |
|---|---|
| 371 | 4-Imidazolecarbonyl-[D-Pro24,Pya(4)26,Cha27,36,Iva28,Lys(Ac)30,Aib31]-PYY(23-36) |
| 372 | 4-Imidazolecarbonyl-[D-Hyp24,Iva25,Pya(4)26,Cha27,36,Iva28,Lys30,D-Iva31]-PYY(23-36) |
| 373 | [D-Hyp24,Iva25,Pya(4)26,Cha27,36,Leu(Me)28,Lys(Ac)30,Aib31]-PYY(23-36) |
| 374 | 4-Imidazolecarbonyl-[D-Hyp24,Pya(4)26,Cha27,36,Iva28,Lys(Ac)30,D-Iva31]-PYY(23-36) |

TABLE 3

| compound No. | M + H+ (obs.) | M + H+ (cal.) | HPLC (min.) | HPLC mode | synthesis method |
|---|---|---|---|---|---|
| 1 | 1893.2 | 1893.1 | 20.7 | b | W |
| 2 | 2319.5 | 2319.3 | 12.1 | a | A |
| 3 | 1850.5 | 1851.1 | 18.4 | b | W |
| 4 | 1740.8 | 1671.0 | 9.4 | a | B |
| 5 | 2205.3 | 2205.2 | 21.1 | b | A |
| 6 | 1682.6 | 1683.0 | 8.1 | a | C |
| 7 | 1712.7 | 1713.0 | 8.2 | a | C |
| 8 | 1716.9 | 1716.9 | 8.2 | a | C |
| 9 | 1698.9 | 1699.0 | 14.7 | b | F |
| 10 | 1656.9 | 1656.9 | 14.8 | b | F |
| 11 | 1713.4 | 1713.0 | 8.6 | a | D |
| 12 | 1698.2 | 1698.0 | 6.0 | a | F |
| 13 | 1732.7 | 1733.0 | 9.2 | a | F |
| 14 | 1732.8 | 1733.0 | 9.3 | a | F |
| 15 | 1696.9 | 1697.0 | 8.5 | a | F |
| 16 | 1697.3 | 1697.0 | 8.3 | a | F |
| 17 | 1695.5 | 1695.0 | 8.2 | a | F |
| 18 | 1783.9 | 1784.0 | 14.0 | b | F |
| 19 | 1725.3 | 1725.0 | 14.7 | b | F |
| 20 | 1699.1 | 1699.0 | 15.3 | b | F |
| 21 | 1699.1 | 1699.0 | 15.4 | b | F |
| 22 | 1732.9 | 1732.9 | 15.5 | b | F |
| 23 | 1772.2 | 1772.0 | 15.5 | b | F |
| 24 | 1679.4 | 1679.0 | 6.6 | a | F |
| 25 | 1727.7 | 1728.0 | 11.6 | b | F |
| 26 | 1790.1 | 1790.0 | 12.7 | b | F |
| 27 | 1835.6 | 1835.1 | 8.6 | a | F |
| 28 | 1852.1 | 1853.1 | 13.0 | a | E |
| 29 | 1692.0 | 1692.0 | 12.3 | b | F |
| 30 | 1663.9 | 1664.0 | 13.1 | b | F |
| 31 | 1657.0 | 1656.9 | 4.1 | a | F |
| 32 | 1657.3 | 1656.9 | 5.4 | a | F |
| 33 | 1657.3 | 1656.9 | 3.8 | a | F |
| 34 | 1754.3 | 1755.0 | 11.1 | a | I |
| 35 | 1754.6 | 1755.0 | 10.5 | a | I |
| 36 | 1761.1 | 1761.0 | 13.2 | a | I |
| 37 | 1761.2 | 1761.0 | 12.3 | a | I |
| 38 | 1704.8 | 1705.0 | 9.3 | a | I |
| 39 | 1685.2 | 1684.9 | 6.0 | a | F |
| 40 | 1718.9 | 1718.9 | 6.2 | a | F |
| 41 | 1738.6 | 1739.0 | 9.0 | a | F |
| 42 | 1698.8 | 1699.0 | 7.3 | a | F |
| 43 | 1649.0 | 1649.0 | 16.9 | b | F |
| 44 | 1684.1 | 1684.0 | 12.4 | b | F |
| 45 | 1643.2 | 1642.9 | 3.0 | a | F |
| 46 | 1670.4 | 1670.0 | 8.0 | a | F |
| 47 | 1671.3 | 1670.9 | 6.0 | a | F |
| 48 | 1739.4 | 1739.0 | 8.6 | a | F |
| 49 | 1671.5 | 1670.9 | 6.7 | a | F |
| 50 | 1685.3 | 1684.9 | 6.5 | a | F |
| 51 | 1721.9 | 1722.0 | 8.9 | a | F |
| 52 | 1697.7 | 1698.0 | 3.3 | a | F |
| 53 | 1620.6 | 1620.9 | 7.4 | a | F |
| 54 | 1732.2 | 1732.9 | 7.2 | a | F |
| 55 | 1782.6 | 1783.0 | 8.4 | a | F |
| 56 | 1782.7 | 1783.0 | 8.6 | a | F |
| 57 | 1748.9 | 1748.9 | 6.2 | a | F |
| 58 | 1751.2 | 1750.9 | 7.4 | a | F |
| 59 | 1733.2 | 1732.9 | 7.5 | a | F |
| 60 | 1685.1 | 1684.9 | 6.4 | a | F |
| 61 | 1697.3 | 1697.0 | 8.1 | a | F |
| 62 | 1711.2 | 1711.0 | 8.3 | d | F |
| 63 | 1772.0 | 1772.0 | 14.1 | d | G |
| 64 | 1728.0 | 1728.1 | 14.3 | d | G |
| 65 | 1758.8 | 1759.1 | 9.6 | d | G |
| 66 | 1790.0 | 1790.0 | 8.1 | d | G |
| 67 | 1721.8 | 1722.0 | 7.8 | d | G |
| 68 | 1804.1 | 1804.1 | 13.1 | d | F |
| 69 | 1688.6 | 1689.0 | 9.7 | d | G |
| 70 | 1773.0 | 1773.1 | 9.8 | d | G |
| 71 | 1750.9 | 1751.0 | 9.6 | d | G |
| 72 | 1764.4 | 1765.1 | 9.6 | d | G |
| 73 | 1765.1 | 1765.1 | 11.8 | d | G |
| 74 | 1713.2 | 1713.0 | 7.4 | d | F |
| 75 | 1736.1 | 1736.1 | 15.3 | d | G |
| 76 | 1867.0 | 1867.2 | 13.4 | d | H |
| 77 | 1709.7 | 1710.1 | 20.0 | d | G |
| 78 | 1692.0 | 1692.1 | 13.2 | d | G |
| 79 | 1654.0 | 1654.0 | 15.4 | d | G |
| 80 | 1640.1 | 1640.0 | 16.5 | d | G |
| 81 | 1656.3 | 1656.1 | 17.2 | d | G |
| 82 | 1704.9 | 1705.1 | 13.2 | d | G |
| 83 | 1637.2 | 1637.0 | 11.2 | d | G |
| 84 | 1766.8 | 1767.1 | 18.1 | d | I |
| 85 | 1772.1 | 1772.1 | 14.3 | d | I |
| 86 | 1670.1 | 1670.0 | 15.6 | d | G |
| 87 | 1669.7 | 1670.0 | 15.5 | d | G |
| 88 | 1653.8 | 1654.1 | 16.6 | d | G |
| 89 | 1616.0 | 1616.0 | 14.0 | d | G |
| 90 | 1657.1 | 1657.0 | 14.2 | d | G |
| 91 | 1614.2 | 1614.0 | 15.7 | d | G |
| 92 | 1666.1 | 1666.0 | 13.2 | d | G |
| 93 | 1585.7 | 1586.0 | 13.6 | d | G |
| 94 | 1574.1 | 1574.0 | 12.8 | d | G |
| 95 | 1596.0 | 1546.0 | 9.6 | d | G |
| 96 | 1895.2 | 1895.1 | 10.6 | g | H |
| 97 | 1678.5 | 1678.0 | 15.8 | d | G |
| 98 | 1692.3 | 1692.0 | 16.6 | d | G |
| 99 | 1705.3 | 1705.0 | 15.6 | d | G |
| 100 | 1616.8 | 1617.0 | 11.9 | d | G |
| 101 | 1625.7 | 1626.0 | 10.8 | d | G |
| 102 | 1575.9 | 1576.0 | 11.4 | d | G |
| 103 | 1674.2 | 1674.0 | 11.6 | d | G |
| 104 | 1712.2 | 1712.0 | 7.7 | d | G |
| 105 | 1795.9 | 1796.1 | 14.5 | d | I |
| 106 | 1811.6 | 1812.1 | 13.9 | d | I |
| 107 | 1857.5 | 1858.2 | 16.3 | d | I |
| 108 | 1866.1 | 1866.2 | 13.0 | d | J |
| 109 | 1838.3 | 1838.1 | 11.7 | d | I |
| 110 | 1838.0 | 1838.1 | 12.6 | d | I |
| 111 | 1823.7 | 1824.1 | 10.7 | d | I |
| 112 | 1810.4 | 1810.1 | 10.9 | d | I |
| 113 | 1836.4 | 1836.1 | 10.1 | d | I |
| 114 | 1866.4 | 1866.1 | 10.0 | d | 1 |
| 115 | 1877.6 | 1877.1 | 11.0 | d | I |
| 116 | 1791.6 | 1792.1 | 18.4 | b | F |
| 117 | 1861.7 | 1862.2 | 21.0 | b | F |
| 118 | 2038.7 | 2039.3 | 19.6 | b | F |
| 119 | 1864.6 | 1864.1 | 12.7 | d | I |
| 120 | 1906.7 | 1906.2 | 12.8 | d | I |
| 121 | 2084.1 | 2084.2 | 11.9 | d | I |
| 122 | 1819.7 | 1819.2 | 14.5 | d | G |
| 123 | 1893.1 | 1893.2 | 10.6 | d | F |
| 124 | 1935.7 | 1935.2 | 11.9 | d | I |
| 125 | 1909.7 | 1909.2 | 12.3 | g | G |
| 126 | 1876.4 | 1876.1 | 11.6 | g | I |
| 127 | 1922.3 | 1922.1 | 11.4 | d | G |
| 128 | 1746.6 | 1746.1 | 10.1 | d | I |
| 129 | 1935.4 | 1935.2 | 10.9 | d | I |
| 130 | 1850.6 | 1851.1 | 11.5 | g | N |
| 131 | 1848.1 | 1848.1 | 10.8 | d | I |
| 132 | 1837.8 | 1838.1 | 10.2 | d | I |
| 133 | 1833.5 | 1834.2 | 11.4 | g | K |
| 134 | 1822.0 | 1822.1 | 10.7 | g | K |
| 135 | 1796.5 | 1797.1 | 6.8 | d | I |
| 136 | 1838.5 | 1839.1 | 7.3 | d | I |

TABLE 3-continued

| compound No. | M + H+ (obs.) | M + H+ (cal.) | HPLC (min.) | HPLC mode | synthesis method |
|---|---|---|---|---|---|
| 137 | 1907.1 | 1907.1 | 9.6 | d | I |
| 138 | 1808.4 | 1808.1 | 6.6 | d | L |
| 139 | 1928.0 | 1928.1 | 6.1 | d | I |
| 140 | 1818.3 | 1818.1 | 9.5 | d | I |
| 141 | 1903.3 | 1903.1 | 9.6 | d | I |
| 142 | 1860.2 | 1860.1 | 9.9 | d | M |
| 143 | 1844.0 | 1844.1 | 10.6 | d | M |
| 144 | 1798.1 | 1798.1 | 7.0 | d | I |
| 145 | 1780.0 | 1780.0 | 8.4 | d | I |
| 146 | 1854.2 | 1854.1 | 6.7 | d | I |
| 147 | 1814.4 | 1814.1 | 12.7 | d | I |
| 148 | 1861.4 | 1861.1 | 11.2 | d | I |
| 149 | 1842.3 | 1842.1 | 12.4 | d | I |
| 150 | 1827.3 | 1827.1 | 11.3 | d | I |
| 151 | 1842.3 | 1842.1 | 12.7 | d | I |
| 152 | 1870.0 | 1870.2 | 12.5 | d | I |
| 153 | 1836.3 | 1836.1 | 11.0 | d | I |
| 154 | 1864.2 | 1864.1 | 14.1 | d | I |
| 155 | 1864.1 | 1864.1 | 11.6 | d | I |
| 156 | 1837.6 | 1838.1 | 11.2 | d | I |
| 157 | 1863.8 | 1864.1 | 11.5 | d | I |
| 158 | 1864.2 | 1864.1 | 11.7 | d | I |
| 159 | 1906.3 | 1906.2 | 12.0 | d | I |
| 160 | 1919.4 | 1919.2 | 10.8 | d | I |
| 161 | 1879.6 | 1879.1 | 11.5 | g | N |
| 162 | 1926.3 | 1926.2 | 12.2 | d | I |
| 163 | 1891.3 | 1891.2 | 10.2 | d | F |
| 164 | 2241.0 | 2240.3 | 11.1 | d | I |
| 165 | 1837.0 | 1837.1 | 9.5 | d | I |
| 166 | 1893.2 | 1893.2 | 9.6 | d | I |
| 167 | 1923.3 | 1923.1 | 9.7 | d | O |
| 168 | 1881.3 | 1881.1 | 8.9 | d | I |
| 169 | 1892.3 | 1892.1 | 8.9 | d | I |
| 170 | 1920.5 | 1920.2 | 9.6 | d | G |
| 171 | 1839.3 | 1839.1 | 7.2 | d | I |
| 172 | 1875.1 | 1875.1 | 13.0 | d | I |
| 173 | 1949.3 | 1949.2 | 12.1 | g | R |
| 174 | 1963.4 | 1963.2 | 12.5 | g | R |
| 175 | 1796.3 | 1796.1 | 9.9 | d | I |
| 176 | 1812.4 | 1812.1 | 13.6 | d | I |
| 177 | 1793.3 | 1793.1 | 14.8 | d | I |
| 178 | 1862.3 | 1862.2 | 12.3 | d | I |
| 179 | 1835.4 | 1835.1 | 12.5 | d | I |
| 180 | 1796.3 | 1796.1 | 9.2 | d | I |
| 181 | 1811.8 | 1812.1 | 13.1 | d | I |
| 182 | 1793.0 | 1793.1 | 14.1 | d | I |
| 183 | 1862.2 | 1862.2 | 12.3 | d | I |
| 184 | 1965.1 | 1965.2 | 13.2 | g | U |
| 185 | 2009.6 | 2010.2 | 8.8 | g | P |
| 186 | 1839.4 | 1839.1 | 7.9 | g | Q |
| 187 | 1909.9 | 1910.2 | 9.0 | g | R |
| 188 | 1884.2 | 1884.1 | 8.6 | g | R |
| 189 | 2020.4 | 2020.2 | 10.1 | g | R |
| 190 | 1907.1 | 1907.2 | 8.8 | g | I |
| 191 | 1977.8 | 1978.2 | 10.3 | g | R |
| 192 | 1952.4 | 1952.2 | 9.9 | g | R |
| 193 | 1918.9 | 1919.1 | 8.5 | g | R |
| 194 | 1862.4 | 1862.1 | 11.0 | d | I |
| 195 | 1862.3 | 1862.1 | 11.1 | d | I |
| 196 | 1858.3 | 1858.1 | 11.2 | d | I |
| 197 | 1858.4 | 1858.1 | 11.4 | d | I |
| 198 | 1824.5 | 1824.1 | 10.2 | d | I |
| 199 | 1824.6 | 1824.1 | 11.2 | d | I |
| 200 | 1860.2 | 1860.1 | 10.4 | d | I |
| 201 | 1872.1 | 1872.1 | 11.6 | d | I |
| 202 | 1836.1 | 1836.1 | 10.9 | d | I |
| 203 | 1855.2 | 1855.1 | 7.8 | d | I |
| 204 | 1923.3 | 1923.1 | 8.7 | d | I |
| 205 | 1866.2 | 1866.1 | 9.2 | d | I |
| 206 | 1794.2 | 1794.1 | 6.7 | d | I |
| 207 | 1824.3 | 1824.1 | 5.8 | d | I |
| 208 | 1866.2 | 1866.1 | 6.3 | d | I |
| 209 | 1850.2 | 1850.1 | 7.3 | d | I |
| 210 | 1849.4 | 1852.1 | 6.9 | d | I |
| 211 | 1822.5 | 1822.1 | 7.5 | d | I |
| 212 | 1836.3 | 1836.1 | 7.5 | d | G |
| 213 | 1860.2 | 1860.1 | 6.5 | d | G |
| 214 | 1878.1 | 1878.1 | 8.0 | d | G |
| 215 | 1912.9 | 1913.1 | 7.2 | d | G |
| 216 | 1902.2 | 1902.2 | 6.6 | d | G |
| 217 | 1865.8 | 1866.1 | 7.0 | d | O |
| 218 | 1907.1 | 1907.1 | 6.8 | d | O |
| 219 | 1879.3 | 1879.1 | 7.2 | d | I |
| 220 | 1921.2 | 1921.1 | 7.4 | d | I |
| 221 | 1788.3 | 1788.1 | 8.0 | d | I |
| 222 | 1782.3 | 1782.1 | 6.2 | d | I |
| 223 | 1824.3 | 1824.1 | 6.7 | d | I |
| 224 | 1765.3 | 1765.1 | 9.6 | d | I |
| 225 | 1809.3 | 1809.1 | 7.8 | d | I |
| 226 | 1798.3 | 1798.1 | 7.6 | d | I |
| 227 | 1807.3 | 1807.1 | 9.9 | d | I |
| 228 | 1870.5 | 1870.1 | 9.5 | d | G |
| 229 | 1924.7 | 1924.2 | 9.2 | g | S |
| 230 | 1992.7 | 1992.2 | 10.4 | g | S |
| 231 | 1822.2 | 1822.1 | 7.6 | d | I |
| 232 | 1822.0 | 1822.1 | 7.7 | d | I |
| 233 | 1821.8 | 1822.1 | 7.7 | d | T |
| 234 | 1822.4 | 1822.1 | 7.6 | d | I |
| 235 | 1745.3 | 1745.1 | 8.2 | d | I |
| 236 | 1737.4 | 1737.0 | 8.9 | d | I |
| 237 | 1751.3 | 1751.0 | 9.3 | d | I |
| 238 | 1726.2 | 1726.0 | 8.9 | d | I |
| 239 | 1740.2 | 1740.0 | 9.3 | d | I |
| 240 | 1796.3 | 1796.1 | 8.2 | d | I |
| 241 | 1810.3 | 1810.1 | 8.9 | d | I |
| 242 | 1810.2 | 1810.1 | 8.7 | d | I |
| 243 | 1810.0 | 1810.1 | 7.0 | d | I |
| 244 | 1795.7 | 1796.1 | 5.8 | d | I |
| 245 | 1795.7 | 1796.1 | 7.2 | d | I |
| 246 | 1836.4 | 1836.1 | 8.5 | d | I |
| 247 | 1835.9 | 1836.1 | 8.0 | d | I |
| 248 | 1836.1 | 1836.1 | 8.0 | d | I |
| 249 | 1836.4 | 1836.1 | 8.5 | d | I |
| 250 | 1693.2 | 1693.0 | 5.8 | d | G |
| 251 | 1721.2 | 1721.0 | 8.5 | d | I |
| 252 | 1689.1 | 1689.0 | 7.7 | d | N |
| 253 | 1954.7 | 1954.2 | 9.8 | g | U |
| 254 | 2022.7 | 2022.2 | 10.9 | g | U |
| 255 | 1847.1 | 1847.1 | 7.9 | d | I |
| 256 | 1915.0 | 1915.1 | 9.1 | d | I |
| 257 | 1815.8 | 1816.0 | 6.0 | d | I |
| 258 | 1846.5 | 1847.1 | 8.1 | d | I |
| 259 | 1914.7 | 1915.1 | 9.2 | d | I |
| 260 | 1815.8 | 1816.0 | 6.2 | d | I |
| 261 | 2206.1 | 2206.2 | 6.0 | d | I |
| 262 | 2206.1 | 2206.2 | 6.3 | d | I |
| 263 | 1835.9 | 1836.1 | 7.1 | d | I |
| 264 | 1836.1 | 1836.1 | 7.1 | d | I |
| 265 | 1781.2 | 1781.0 | 7.6 | d | I |
| 266 | 1837.1 | 1837.1 | 7.6 | d | I |
| 267 | 1793.2 | 1793.1 | 9.5 | d | I |
| 268 | 1879.1 | 1879.1 | 7.4 | g | R |
| 269 | 1906.8 | 1907.1 | 8.0 | g | R |
| 270 | 1893.2 | 1893.1 | 7.5 | g | V |
| 271 | 1923.0 | 1923.1 | 8.5 | g | U |
| 272 | 1936.1 | 1936.2 | 5.3 | d | I |
| 273 | 1893.9 | 1894.1 | 5.3 | d | I |
| 274 | 1921.2 | 1921.2 | 8.1 | d | I |
| 275 | 1955.3 | 1955.1 | 8.3 | d | I |
| 276 | 1850.5 | 1850.1 | 7.66/7.75 (racemate) | d | G |
| 277 | 1850.3 | 1850.1 | 7.4 | d | W |
| 278 | 1850.2 | 1850.1 | 8.0 | d | X |
| 279 | 1891.9 | 1892.2 | 9.6 | d | Y |
| 280 | 1822.3 | 1822.1 | 8.2 | d | X |
| 281 | 1811.3 | 1811.1 | 7.0 | d | W |
| 282 | 1935.5 | 1935.1 | 7.6 | g | Z |
| 283 | 1964.7 | 1965.2 | 8.7 | g | U |
| 284 | 1963.9 | 1964.2 | 8.3 | g | U |
| 285 | 1972.9 | 1973.1 | 8.1 | g | U |
| 286 | 1880.8 | 1881.1 | 7.5 | g | U |
| 287 | 1867.1 | 1867.1 | 7.1 | g | AA |
| 288 | 1896.6 | 1897.1 | 7.1 | g | U |
| 289 | 1822.2 | 1822.1 | 7.2 | d | W |

TABLE 3-continued

| compound No. | M + H+ (obs.) | M + H+ (cal.) | HPLC (min.) | HPLC mode | synthesis method |
|---|---|---|---|---|---|
| 290 | 1793.9 | 1794.1 | 6.6 | d | W |
| 291 | 1810.9 | 1811.1 | 7.2 | d | W |
| 292 | 1865.5 | 1866.1 | 6.9 | g | U |
| 293 | 1894.8 | 1895.1 | 7.3 | g | U |
| 294 | 1922.8 | 1923.1 | 7.8 | g | U |
| 295 | 1792.8 | 1793.1 | 11.9 | d | AB |
| 296 | 1765.0 | 1765.1 | 10.1 | d | I |
| 297 | 1766.9 | 1767.0 | 8.2 | d | I |
| 298 | 1780.6 | 1781.1 | 9.2 | d | AC |
| 299 | 1819.1 | 1819.0 | 7.1 | d | G |
| 300 | 1803.0 | 1803.1 | 8.3 | d | G |
| 301 | 1814.3 | 1814.1 | 9.1 | d | G |
| 302 | 1817.3 | 1817.1 | 8.8 | d | G |
| 303 | 1779.2 | 1779.1 | 8.5 | d | O |
| 304 | 1792.1 | 1792.1 | 7.4 | d | F |
| 305 | 1819.8 | 1820.0 | 5.3 | f | I |
| 306 | 1851.9 | 1852.0 | 7.1 | f | I |
| 307 | 1852.2 | 1852.0 | 7.3 | f | I |
| 308 | 1809.2 | 1809.1 | 10.6 | f | I |
| 309 | 1809.2 | 1809.1 | 10.8 | f | I |
| 310 | 1814.2 | 1814.1 | 7.3 | d | I |
| 311 | 1806.2 | 1806.1 | 5.8 | d | I |
| 312 | 1806.2 | 1806.1 | 6.4 | d | I |
| 313 | 1834.2 | 1834.1 | 7.2 | d | I |
| 314 | 1850.2 | 1850.1 | 7.2 | d | I |
| 315 | 1863.8 | 1864.1 | 7.3 | d | I |
| 316 | 1792.6 | 1793.1 | 9.6 | d | I |
| 317 | 1793.0 | 1793.1 | 9.9 | d | I |
| 318 | 1827.8 | 1828.1 | 12.1 | d | G |
| 319 | 1821.9 | 1822.1 | 6.9 | d | I |
| 320 | 1745.1 | 1745.1 | 8.1 | d | I |
| 321 | 1820.3 | 1820.2 | 9.0 | d | I |
| 322 | 1793.2 | 1793.1 | 9.9 | d | I |
| 323 | 1979.9 | 1980.2 | 10.5 | g | U |
| 324 | 1877.9 | 1878.1 | 7.6 | g | AD |
| 325 | 1906.8 | 1907.1 | 7.6 | g | S |
| 326 | 1880.9 | 1881.1 | 7.4 | g | U |
| 327 | 1809.9 | 1810.0 | 9.5 | g | U |
| 328 | 1838.0 | 1838.1 | 9.5 | g | U |
| 329 | 1830.0 | 1830.1 | 6.4 | d | I |
| 330 | 1835.8 | 1836.1 | 9.5 | g | S |
| 331 | 1808.8 | 1809.1 | 9.1 | g | U |
| 332 | 1839.8 | 1840.1 | 9.4 | g | U |
| 333 | 1872.2 | 1872.1 | 10.3 | d | G |
| 334 | 1844.1 | 1844.1 | 8.6 | d | G |
| 335 | 1809.2 | 1809.1 | 10.5 | d | I |
| 336 | 1860.9 | 1861.1 | 9.9 | d | AE |
| 337 | 1833.3 | 1833.1 | 8.2 | d | G |
| 338 | 1797.1 | 1797.0 | 8.9 | d | G |
| 339 | 1826.1 | 1826.1 | 9.0 | g | R |
| 340 | 1850.0 | 1850.1 | 9.6 | g | S |
| 341 | 1823.9 | 1824.1 | 9.6 | g | U |
| 342 | 1820.8 | 1821.1 | 9.8 | g | G |
| 343 | 1895.0 | 1895.1 | 9.7 | d | G |
| 344 | 1790.9 | 1791.1 | 9.0 | d | G |
| 345 | 1807.3 | 1807.1 | 8.5 | d | I |
| 346 | 1823.3 | 1823.1 | 7.9 | d | I |
| 347 | 1846.4 | 1846.1 | 8.8 | d | I |
| 348 | 1837.6 | 1837.1 | 8.3 | d | I |
| 349 | 1896.3 | 1896.1 | 10.4 | g | AF |
| 350 | 1867.3 | 1867.1 | 10.4 | d | AG |
| 351 | 1851.2 | 1851.1 | 10.7 | d | I |
| 352 | 1765.0 | 1765.1 | 10.2 | d | I |
| 353 | 1920.3 | 1920.2 | 15.6 | b | A |
| 354 | 1683.1 | 1683.0 | 7.4 | a | F |
| 355 | 2247.8 | 2247.3 | 12.1 | d | I |
| 356 | 1868.1 | 1868.1 | 10.6 | g | U |
| 357 | 1882.1 | 1882.1 | 10.6 | g | U |
| 358 | 1894.1 | 1894.1 | 10.3 | g | S |
| 359 | 1908.1 | 1908.2 | 10.8 | g | S |
| 360 | 1884.0 | 1883.1 | 9.1 | d | G |
| 361 | 1879.4 | 1879.1 | 10.8 | g | G |
| 362 | 1903.3 | 1903.1 | 10.5 | g | G |
| 363 | 1835.9 | 1835.1 | 11.7 | d | I |
| 364 | 1809.3 | 1810.1 | 9.8 | d | N |
| 365 | 1887.3 | 1887.1 | 12.0 | d | G |
| 366 | 1874.4 | 1874.1 | 6.7 | d | G |
| 367 | 1903.5 | 1903.1 | 9.4 | d | G |
| 368 | 1875.7 | 1875.1 | 12.6 | d | G |
| 369 | 1916.9 | 1917.1 | 10.9 | d | G |
| 370 | 1918.8 | 1918.1 | 6.8 | d | G |
| 371 | 1916.0 | 1916.1 | 7.9 | d | G |
| 372 | 1847.1 | 1847.1 | 8.3 | d | G |
| 373 | 1809.0 | 1809.1 | 9.4 | d | F |
| 374 | 1946.1 | 1946.1 | 7.4 | d | G |

TABLE 4

| HPLC mode | measurement condition |
|---|---|
| a | 20-70% AUN/25 min, flow1 ml/min, YMC ODS AM-301 (4.6 × 100 mm) |
| b | 0-50% AUN/25 min, flow1 ml/min, Wakosil-II 5C18 HG (4.6 × 100 mm) |
| c | 0-50% AUN/25 min, flow1 ml/min, YMC ODS AM-301 (4.6 × 100 mm) |
| d | 20-70% AUN/25 min, flow1 ml/min, Merck Chromolith Performance RP-18e (4.6 × 100 mmI. D.) |
| e | 20-100% AUN/40 min, flow1 ml/min, Merck Chromolith Performance RP-18e(4.6 × 100 mmI.D.) |
| f | 5-55% AUN/25 min, flow1 ml/min, Merck Chromolith Performance RP-18e(4.6 × 100 mmI.D.) |
| g | 20-70% AUN/25 min flow1 ml/min SHISEIDO CAPCELL PAK C18 MGII (4.6 × 100 mm) |
| h | 5-55% AUN/25 min flow1 ml/min SHISEIDO CAPCELL PAK C18 MGII (4.6 × 100 mm) |

Test Example

Evaluation of Biological Activity (1) Construction of Expression Plasmid for the Human Y2 Receptor (Y2R) Gene PCR was performed by a reaction using Pfu DNA polymerase (STRATAGENE), with a human brain cDNA (PT3158-1, Clontech) as the template, wherein synthetic DNAs with the following sequences were used as a combination of 5' and 3' primers, whereby the human Y2R gene was cloned. Primer 1 was prepared on the basis of base sequence information on the human Y2R gene (Refseq ID No. NM_000910) with the addition of Kozak's consensus sequence. Primer 2 was prepared on the basis of base sequence information on the human Y2R gene.

```
Primer 1:
                            (SEQ ID NO: 184)
5'-CCACCATGGGTCCAATAGGTGCAGAGGCTGATG-3'

Primer 2:
                            (SEQ ID NO: 185)
5'-TTAGACATTGGTAGCCTCTGTGAAAGAGTC-3'
```

The PCR product obtained was cloned into pCR4-Blunt-TOPO (Invitrogen), and the plasmid was extracted according to a conventional method (QIAwell 8 Plus, QIAGEN). After confirming the base sequence, the human Y2R gene was re-cloned by a PCR reaction with the plasmid DNA as the template, using Primer 1 as the 5' primer and Primer 2 as the 3' primer. The PCR was performed using the Pyrobest DNA polymerase (TaKaRa). The PCR product obtained was re-cloned into pCR-Blunt II-TOPO (Invitrogen), and the plasmid was extracted according to a conventional method (QIAGEN). An Xho I restriction enzyme digestion site and an Spe I restriction enzyme digestion site are present in the cloning site of the pCR-Blunt II-TOPO; a plasmid clone was selected wherein the human Y2R gene was inserted in the orientation such that the Xho I restriction enzyme digestion site was positioned upstream of Primer 1, and the Spe I restriction enzyme digestion site was positioned downstream of Primer 2. After confirming the base sequence, the plasmid clone was digested with the restriction enzymes Xho I and Spe I to yield a DNA fragment. The DNA fragment was inserted into the animal cell expression vector pAKKO-111H (the same plasmid as pAKKO-1.111H described in Biochem. Biophys. Acta, Hinuma, S. et al., 1219, 251-259 (1994)), which was enzymatically digested with Sal I and Spe I, to yield the expression plasmid pAK-hY2R (pAKKO-111H/Y2R).

(2) Test Method: Receptor Binding Assay (RBA) for Human Y2

A human NPY2R (hY2R) stable expression cell line was acquired by transducing the animal cell expression plasmid pAK-hY2R into CHO/dhfr-cells using the CellPhect Transfection kit (Amersham Pharmacia Biotech Co.). First, 240 µl of Buffer A (attached to the CellPhect Transfection kit) was added to 9.6 µg of the plasmid DNA dissolved in 240 µl of distilled water; this mixture was stirred and allowed to stand for 10 minutes, after which 480 µL of Buffer B (attached to the CellPhect Transfection kit) was added, and the mixture was vigorously stirred to form a liposome containing the DNA. $2.5 \times 10^5$ or $4 \times 10^5$ CHO/dhfr– cells (obtained from ATCC) were seeded to 60 mm petri dishes, and cultured in Ham's F-12 medium (Sigma Co.) containing 10% fetal bovine serum (BioWest Co.) at 37° C. in 5% gaseous carbon dioxide for 1 day, after which 480 µL of the liposome was added drop by drop on to the cells in each petri dish. This was cultured at 37° C. in 5% gaseous carbon dioxide for 6 hours, after which the cells were twice washed with serum-free Ham's F-12 medium; 3 mL of 15% glycerol was added onto the cells in the petri dish and treated for 2 minutes. This was again washed 3 times with serum-free Ham's F-12 medium, after which the cells were cultured in Ham's F-12 medium containing 10% fetal bovine serum at 37° C. in 5% gaseous carbon dioxide. The cells were dispersed by trypsinization and recovered from the petri dishes, and seeded to a 6-well plate at $2.5 \times 10^4$ or $4 \times 10^4$ cells per well; cultivation was begun in Dulbecco's modified Eagle medium <DMEM> medium (Sigma Co.) containing dialyzed 10% fetal bovine serum (Invitrogen Co.) at 37° C. in 5% gaseous carbon dioxide. Since plasmid-introduced transformant CHO cells grow in the medium, whereas cells without plasmid introduction die gradually, about 20 colonies of transformed CHO cell that had grown 9-13 days after the start of the cultivation were isolated. RNA was extracted from the cells of these colonies, and cells exhibiting high expression of the RNA of hY2R were sorted by the QPCR (quantify TaqMan PCR) method. Furthermore, cells exhibiting high reactivity to the peptide YY, which is a ligand peptide (hereinafter abbreviated to hY2R/CHO) were sorted and used for the subsequent experiments.

The affinity of the compound of the present invention for the human Y2 receptor was measured by the method described below.

Cultured in 10 trays of the Single Tray (Nunc) using Dulbecco's modified Eagle's medium (containing 10% dialyzed fetal bovine serum, MEM non-essential amino acids, 50 units/mL penicillin, and 50 µg/mL streptomycin), hY2R/CHO was detached using PBS-EDTA, after which they were centrifuged at 1000 rpm for 10 minutes, and the cells were recovered and frozen at −80° C. 50 ml of a disrupting buffer (10 mM NaHCO$_3$, 5 mM EDTA, 0.5 mM phenylmethylsulfonylfluoride, 10 µg/mL pepstatin A, 20 µg/mL leupeptin, 10 µg/mL E-64) was added to the cell precipitate, and pipetting was performed, after which disruption was performed using a polytron homogenizer for 3 minutes. The cell disruption liquid was centrifuged at 2500 rpm for 10 minutes; the supernatant obtained was centrifuged at 30000 rpm for 60 minutes. The precipitate obtained was suspended by the addition of a suspending buffer (50 mM Tris, 5 mM MgCl$_2$, 150 mM NaCl, 0.5 mM phenylmethylsulfonylfluoride, 10 µg/mL pepstatin A, 20 µg/mL leupeptin, 10 µg/mL E-64, 0.03% NaN$_3$, pH 7.4) (20 mL), and the protein concentration was measured using the Coomassie Plus Protein Assay Reagent (PIERCE). This suspension was dispensed, after which it was stored at −80° C. until use as a membrane fraction in the subsequent experiments.

2 µL of the test compound, serially diluted with DMSO from 100 µM to 1 nM, was dispensed to a 96-well plate, and 100 µL of the membrane fraction, previously diluted with an assay buffer (50 mM Tris, 5 mM MgCl$_2$, 150 mM NaCl, 0.03% NaN$_3$, pH 7.4) to 0.5 µg protein/mL, was dispensed thereto; subsequently, 100 µL of a [$^{125}$I]-PYY solution (NEX341, PerkinElmer, previously diluted with the assay buffer to 400 pM) was added, and they were mixed by pipetting. After incubation at room temperature for 60 minutes, the mixture was filtered through the cell harvester FilterMate (PerkinElmer) using UniFilter-96 GF/C treated with polyethylenimine (PEI) solution (20 mM Tris, 0.3% PEI, pH 7.4), and the filter was washed 3 times with a filtering buffer (50 mM Tris, 5 mM MgCl$_2$, 150 mM NaCl, 0.03% NaN$_3$, 0.05% CHAPS, pH 7.4). Thereafter, UniFilter-96 GF/C was dried in a mechanical drier for 1 hour, 15 µl of the liquid scintillator MicroScint O (PerkinElmer) was added to each well, and a measurement was taken using TopCount (PerkinElmer). The data obtained were analyzed using Prism to calculate the IC$_{50}$ value. The affinity of the test compound was expressed as a ratio to the IC$_{50}$ value of PYY(3-36) taken as 1 (IC$_{50}$ Ratio: IC$_{50}$ of test compound/IC$_{50}$ of PYY(3-36)). The results are shown in the RBA column in Table 5.

(3) Test Method: Human Y2 Receptor G Protein Binding Assay (GBA)

The agonist activity of the compound of the present invention against the human Y2 receptor was measured by the method described below.

2 µL of the test compound, serially diluted with DMSO from 100 µM to 1 nM, was dispensed to a 96-well plate, and 100 µL of the membrane fraction, previously diluted with an assay buffer (50 mM Tris, 5 mM MgCl$_2$, 150 mM NaCl, 1 µl GDP, 0.03% NaN$_3$, 0.1% BSA, pH 7.4) to 1 µg protein/mL, was dispensed thereto, subsequently, 100 µL of a [$^{35}$S]GTPγS (NEG030H, PerkinElmer, previously diluted with the assay buffer to 1 nM) was added, and they were mixed by pipetting. After incubation at room temperature for 120 minutes, the mixture was filtered through the cell harvester FilterMate (PerkinElmer) using the UniFilter-96 GF/C (PerkinElmer), and the filter was washed 3 times with a filtering buffer (50 mM Tris, 5 mM MgCl$_2$, 150 mM NaCl, 0.03% NaN$_3$, 0.05%

CHAPS, pH 7.4). Thereafter, UniFilter-96 GF/C was dried in a mechanical drier for 1 hour, 15 μl of the liquid scintillator MicroScint O (PerkinElmer) was added to each well, and a measurement was taken using TopCount (PerkinElmer). The data obtained were analyzed using Prism to calculate the $EC_{50}$ value. The agonist activity of the test compound was expressed as a ratio to the $EC_{50}$ value of $PYY_{3-36}$ taken as 1 ($EC_{50}$ Ratio: $EC_{50}$ of test compound/$EC_{50}$ of PYY(3-36)). The results are shown in the GBA column in Table 5 (Table 5-1-Table 5-10).

TABLE 5

| compound No. | RBA $IC_{50}$ Ratio | GBA $EC_{50}$ Ratio |
|---|---|---|
| 1 | 50 | 13 |
| 2 | 4.9 | 2.1 |
| 3 | 6.0 | 2.7 |
| 4 | 2.4 | 1.1 |
| 5 | 9.8 | 8.1 |
| 6 | 5.1 | 5.9 |
| 7 | 5.0 | 4.7 |
| 8 | 30 | 24 |
| 9 | 92 | 23 |
| 10 | 39 | 18 |
| 11 | 260 | 63 |
| 12 | 12 | 5.0 |
| 13 | 7.6 | 3.6 |
| 14 | 14 | 6.9 |
| 15 | 8.7 | 5.5 |
| 16 | 120 | 45 |
| 17 | 180 | 66 |
| 18 | 4.0 | 3.0 |
| 19 | 45 | 25 |
| 20 | 2.8 | 2.0 |
| 21 | 4.1 | 3.6 |
| 22 | 4.1 | 3.5 |
| 23 | 3.4 | 5.0 |
| 24 | 14 | 9.4 |
| 25 | 30 | 16 |
| 26 | 18 | 11 |
| 27 | 4.5 | 3.6 |
| 28 | 14 | 12 |
| 29 | 6.8 | 4.3 |
| 30 | 25 | 14 |
| 31 | 42 | 29 |
| 32 | 9.1 | 7.4 |
| 33 | 23 | 17 |
| 34 | 25 | 14 |
| 35 | 14 | 8.7 |
| 36 | 17 | 13 |
| 37 | 7.6 | 4.6 |
| 38 | 52 | 26 |
| 39 | 7.2 | 4.0 |
| 40 | 71 | 27 |
| 41 | 15 | 8.7 |
| 42 | 10 | 5.7 |
| 43 | 4.6 | 2.3 |
| 44 | 3.8 | 2.6 |
| 45 | 21 | 12 |
| 46 | 87 | 34 |
| 47 | 49 | 23 |
| 48 | 8.1 | 4.1 |
| 49 | 34 | 24 |
| 50 | 7.1 | 4.6 |
| 51 | 9.5 | 5.3 |
| 52 | 11 | 5.7 |
| 53 | 18 | 7.5 |
| 54 | 5.7 | 3.4 |
| 55 | 3.4 | 3.0 |
| 56 | 4.1 | 2.4 |
| 57 | 2.8 | 1.9 |
| 58 | 4.1 | 2.9 |
| 59 | 16 | 6.6 |
| 60 | 180 | 44 |
| 61 | 29 | 17 |
| 62 | 18 | 15 |
| 63 | 34 | 25 |

TABLE 5-continued

| compound No. | RBA $IC_{50}$ Ratio | GBA $EC_{50}$ Ratio |
|---|---|---|
| 64 | 28 | 18 |
| 65 | 15 | 16 |
| 66 | 4.8 | 2.9 |
| 67 | 34 | 22 |
| 68 | 19 | 15 |
| 69 | 37 | 28 |
| 70 | 18 | 15 |
| 71 | 7.6 | 8.5 |
| 72 | 5.0 | 5.4 |
| 73 | 12 | 6.6 |
| 74 | 14 | 24 |
| 75 | 76 | 37 |
| 76 | 7.2 | 4.5 |
| 77 | 50 | 33 |
| 78 | 15 | 23 |
| 79 | 23 | 20 |
| 80 | 17 | 12 |
| 81 | 51 | 26 |
| 82 | 25 | 19 |
| 83 | 26 | 22 |
| 84 | 15 | 13 |
| 85 | 15 | 11 |
| 86 | 19 | 11 |
| 87 | 26 | 20 |
| 88 | 25 | 16 |
| 89 | 26 | 28 |
| 90 | 19 | 22 |
| 91 | 20 | 21 |
| 92 | 22 | 20 |
| 93 | 52 | 41 |
| 94 | 31 | 37 |
| 95 | 70 | 49 |
| 96 | 1.9 | 1.1 |
| 97 | 13 | 6.0 |
| 98 | 18 | 8.7 |
| 99 | 19 | 21 |
| 100 | 45 | 30 |
| 101 | 19 | 13 |
| 102 | 49 | 35 |
| 103 | 13 | 8.6 |
| 104 | 5.6 | 4.3 |
| 105 | 6.9 | 4.0 |
| 106 | 5.2 | 3.8 |
| 107 | 12 | 5.9 |
| 108 | 20 | 8.4 |
| 109 | 6.1 | 5.1 |
| 110 | 3.4 | 2.2 |
| 111 | 6.6 | 5.3 |
| 112 | 6.3 | 3.9 |
| 113 | 11 | 4.7 |
| 114 | 1.1 | 0.9 |
| 115 | 2.4 | 1.7 |
| 116 | 1.7 | 1.2 |
| 117 | 2.1 | 1.9 |
| 118 | 0.9 | 0.9 |
| 119 | 9.9 | 5.8 |
| 120 | 17 | 10 |
| 121 | 1.2 | 1.3 |
| 122 | 17 | 14 |
| 123 | 0.6 | 0.72 |
| 124 | 3.5 | 6.1 |
| 125 | 4 | 3.4 |
| 126 | 7.3 | 5.0 |
| 127 | 2.6 | 3.1 |
| 128 | 11 | 5.4 |
| 129 | 12 | 7.8 |
| 130 | 1.8 | 1 |
| 131 | 7.0 | 3.6 |
| 132 | 6.1 | 3.1 |
| 133 | 5.8 | 2.4 |
| 134 | 2.0 | 1.2 |
| 135 | 1.9 | 0.84 |
| 136 | 0.57 | 0.63 |
| 137 | 3.6 | 1.8 |
| 138 | 1.8 | 1.3 |
| 139 | 2.2 | 1.2 |
| 140 | 20 | 2.6 |

TABLE 5-continued

| compound No. | RBA IC$_{50}$ Ratio | GBA EC$_{50}$ Ratio |
|---|---|---|
| 141 | 4.6 | 1.3 |
| 142 | 3.2 | 1.1 |
| 143 | 2.9 | 0.85 |
| 144 | 22 | 4.5 |
| 145 | 160 | 17 |
| 146 | 36 | 5.6 |
| 147 | 9.3 | 2.1 |
| 148 | 3.3 | 1.2 |
| 149 | 12 | 2.2 |
| 150 | 4.2 | 2.2 |
| 151 | 68 | 9.5 |
| 152 | 5.5 | 1.7 |
| 153 | 1.7 | 1.3 |
| 154 | 2.8 | 1.3 |
| 155 | 4.5 | 2.6 |
| 156 | 5.8 | 3.0 |
| 157 | 2.5 | 1.6 |
| 158 | 7.1 | 2.6 |
| 159 | 2.8 | 1.2 |
| 160 | 0.92 | 1.3 |
| 161 | 4.1 | 2.4 |
| 162 | 5.2 | 2.6 |
| 163 | 5.4 | 2.5 |
| 164 | 0.44 | 0.66 |
| 165 | 2.6 | 1.6 |
| 166 | 0.8 | 0.7 |
| 167 | 0.64 | 1.1 |
| 168 | 0.73 | 1.1 |
| 169 | 0.48 | 0.86 |
| 170 | 0.43 | 0.88 |
| 171 | 2.9 | 1.6 |
| 172 | 2.3 | 1.3 |
| 173 | 2.9 | 1.4 |
| 174 | 1.9 | 1.0 |
| 175 | 6.4 | 2.6 |
| 176 | 5.2 | 4.2 |
| 177 | 4.5 | 3.7 |
| 178 | 13 | 17 |
| 179 | 71 | 37 |
| 180 | 8.1 | 6.0 |
| 181 | 19 | 13 |
| 182 | 14 | 11 |
| 183 | 20 | 31 |
| 184 | 1.5 | 2.9 |
| 185 | 1.7 | 1.2 |
| 186 | 0.43 | 0.69 |
| 187 | 0.66 | 0.84 |
| 188 | 0.6 | 0.71 |
| 189 | 1.7 | 1.1 |
| 190 | 0.66 | 0.77 |
| 191 | 1.4 | 1.4 |
| 192 | 1.3 | 1.2 |
| 193 | 3.3 | 2.4 |
| 194 | 1.4 | 1.3 |
| 195 | 2.1 | 1.5 |
| 196 | 1.6 | 1.6 |
| 197 | 1.3 | 1.9 |
| 198 | 12 | 7.1 |
| 199 | 20 | 8.5 |
| 200 | 16 | 10 |
| 201 | 1.6 | 2.0 |
| 202 | 43 | 20 |
| 203 | 0.38 | 0.76 |
| 204 | 0.8 | 1.3 |
| 205 | 2.5 | 2.4 |
| 206 | 1.5 | 0.83 |
| 207 | 1.1 | 0.86 |
| 208 | 3.4 | 2.2 |
| 209 | 2.7 | 1.9 |
| 210 | 1.3 | 0.9 |
| 211 | 1.1 | 0.69 |
| 212 | 0.79 | 0.89 |
| 213 | 0.76 | 1.1 |
| 214 | 1.9 | 2.0 |
| 215 | 1.9 | 1.8 |
| 216 | 1.3 | 1.3 |
| 217 | 0.96 | 1.2 |
| 218 | 2 | 1.9 |
| 219 | 2.3 | 1.7 |
| 220 | 5.3 | 3.5 |
| 221 | 3.1 | 1.4 |
| 222 | 1.9 | 1.1 |
| 223 | 7.4 | 3.9 |
| 224 | 3.0 | 2.4 |
| 225 | 2.8 | 2.2 |
| 226 | 6.2 | 4.6 |
| 227 | 7.5 | 6.9 |
| 228 | 8.1 | 5.7 |
| 229 | 0.45 | 0.50 |
| 230 | 0.89 | 2.5 |
| 231 | 0.85 | 2.1 |
| 232 | 0.55 | 1.6 |
| 233 | 0.33 | 1.2 |
| 234 | 1.7 | 2.6 |
| 235 | 2.1 | 2.7 |
| 236 | 8.4 | 1.7 |
| 237 | 2.9 | 2.9 |
| 238 | 24 | 11 |
| 239 | 8.8 | 5.2 |
| 240 | 0.81 | 1.1 |
| 241 | 0.58 | 0.91 |
| 242 | 0.39 | 1.3 |
| 243 | 1.3 | 2 |
| 244 | 2.4 | 2.8 |
| 245 | 0.85 | 1.9 |
| 246 | 0.31 | 1 |
| 247 | 0.70 | 1.6 |
| 248 | 3.4 | 1.1 |
| 249 | 0.36 | 0.67 |
| 250 | 2 | 1.1 |
| 251 | 0.68 | 0.56 |
| 252 | 6.3 | 2.8 |
| 253 | 1.1 | 0.85 |
| 254 | 2.8 | 1.5 |
| 255 | 0.80 | 0.86 |
| 256 | 1.7 | 1.2 |
| 257 | 1.0 | 0.98 |
| 258 | 0.61 | 0.78 |
| 259 | 1.1 | 0.93 |
| 260 | 0.91 | 1.2 |
| 261 | 0.54 | 0.81 |
| 262 | 0.5 | 1.7 |
| 263 | 1.1 | 1.8 |
| 264 | 1.1 | 1.7 |
| 265 | 5.8 | 5.7 |
| 266 | 2.7 | 3.1 |
| 267 | 0.96 | 1.4 |
| 268 | 0.89 | 0.57 |
| 269 | 0.91 | 0.65 |
| 270 | 0.52 | 0.61 |
| 271 | 0.82 | 0.82 |
| 272 | 1.1 | 1.0 |
| 273 | 1.2 | 1.6 |
| 274 | 1.2 | 1.0 |
| 275 | 1.2 | 0.89 |
| 276 | 0.54 | 0.78 |
| 277 | 0.36 | 0.79 |
| 278 | 0.97 | 1.1 |
| 279 | 1.0 | 1.3 |
| 280 | 6.6 | 4.2 |
| 281 | 1.8 | 1.8 |
| 282 | 1.1 | 1.6 |
| 283 | 2.2 | 2.5 |
| 284 | 0.93 | 1.3 |
| 285 | 0.95 | 1.2 |
| 286 | 0.78 | 0.94 |
| 287 | 1.2 | 1.2 |
| 288 | 0.52 | 1.3 |
| 289 | 0.82 | 1.4 |
| 290 | 1.1 | 1.8 |
| 291 | 1.2 | 2.7 |
| 292 | 1.2 | 0.74 |
| 293 | 1.2 | 0.97 |
| 294 | 1.2 | 1.5 |

TABLE 5-continued

| compound No. | RBA IC$_{50}$ Ratio | GBA EC$_{50}$ Ratio |
|---|---|---|
| 295 | 0.76 | 1.2 |
| 296 | 1.1 | 1.0 |
| 297 | 1.5 | 1.4 |
| 298 | 0.86 | 1.0 |
| 299 | 1.3 | 0.92 |
| 300 | 0.77 | 0.91 |
| 301 | 1.0 | 1.1 |
| 302 | 1.7 | 1.2 |
| 303 | 1.2 | 1.2 |
| 304 | 0.32 | 1.1 |
| 305 | 10 | 3.9 |
| 306 | 2.9 | 1.7 |
| 307 | 7.2 | 4.0 |
| 308 | 17 | 11 |
| 309 | 3.8 | 3.9 |
| 310 | 1.2 | 1.5 |
| 311 | 18 | 14 |
| 312 | 4.3 | 5.8 |
| 313 | 0.72 | 0.8 |
| 314 | 1.1 | 1.2 |
| 315 | 1.5 | 1.5 |
| 316 | 2.4 | 1.7 |
| 317 | 0.65 | 1.0 |
| 318 | 2.3 | 1.9 |
| 319 | 1.1 | 1.3 |
| 320 | 2.3 | 0.98 |
| 321 | 0.88 | 0.78 |
| 322 | 6.1 | 2.8 |
| 323 | 1.3 | 0.95 |
| 324 | 1.1 | 0.71 |
| 325 | 0.82 | 0.7 |
| 326 | 1.3 | 0.94 |
| 327 | 3.0 | 1.6 |
| 328 | 1.6 | 1.9 |
| 329 | 0.52 | 0.59 |
| 330 | 1.7 | 1.8 |
| 331 | 1.7 | 1.7 |
| 332 | 3.5 | 3.0 |
| 333 | 0.93 | 1.6 |
| 334 | 1.3 | 1.6 |
| 335 | 0.97 | 1.5 |
| 336 | 0.75 | 1.4 |
| 337 | 0.99 | 1.3 |
| 338 | 1.9 | 2.1 |
| 339 | 1.76 | 2.0 |
| 340 | 1.7 | 1.9 |
| 341 | 3.2 | 2.4 |
| 342 | 3.3 | 1.9 |
| 343 | 0.65 | 1.0 |
| 344 | 1.9 | 1.7 |
| 345 | 1.1 | 1.4 |
| 346 | 1.0 | 1.3 |
| 347 | 0.76 | 1.3 |
| 348 | 0.88 | 1.4 |
| 349 | 0.57 | 1.7 |
| 350 | 0.92 | 1.9 |
| 351 | 1.2 | 1.9 |
| 352 | 1.6 | 1.3 |
| 353 | 9.1 | 4.8 |
| 354 | 68 | 33 |
| 355 | 1.4 | 1.1 |

(4) Test Method: 3-Days Continuous Subcutaneous Administration Test-1

The food intake suppressing activity of the compound of the present invention was examined by the method described below.

The test compound was dissolved in 50% DMSO so that sustained release would occur at 0.03 mg/kg/day, and the solution was filled in the Alzet Pump (Alzet model: 1003D, sustained release rate: 1 μL/hr, capacity: 100 μL). After the filling, the pump was placed in a 2 mL Eppendorf tube containing 330 μL of physiological saline, and incubated at 37° C. for 2 hours or more. Thereafter, this pump was subcutaneously embedded in the back of each mouse by the method described below. After weighing, each male C57EL/6J mice at 12-13 weeks of age (25° C., allowed to take food and water ad libitum; 12-hour bright-12-hour dark cycle, lighting turned on at 08:00) was anesthetized with diethyl ether; the skin in the upper back thereof was incised, and the above-mentioned pump was embedded subcutaneously. Thereafter, several drops of penicillin solution (100000 units/mL) were added to the incised part, and the incision was sutured using Michel's surgical needle. This mouse was returned to the rearing cage (reared alone), and given previously weighed food; 3 days later, the amount of remaining food was measured. Food consumption was calculated by subtracting the amount of remaining food after 3 days from the weight of the food given on the day of pump embedding. The food intake suppressing activity of each test compound was expressed as a food intake suppression rate (%) relative to the food intake suppression rate for PYY(3-36) (1 mg/kg/day) taken as 100%. The results are shown in Table 6 (Table 6-1-Table 6-3).

TABLE 6

| compound No. | food intake suppression rate (%) |
|---|---|
| 136 | 10 |
| 137 | 25 |
| 138 | 38 |
| 169 | 55 |
| 204 | 16 |
| 213 | 33 |
| 216 | 36 |
| 217 | 28 |
| 218 | 27 |
| 224 | 30 |
| 232 | 34 |
| 233 | 36 |
| 237 | 46 |
| 240 | 36 |
| 241 | 16 |
| 242 | 25 |
| 249 | 39 |
| 253 | 19 |
| 268 | 16 |
| 269 | 11 |
| 270 | 28 |
| 271 | 28 |
| 276 | 16 |
| 282 | 30 |
| 283 | 18 |
| 284 | 21 |
| 285 | 28 |
| 286 | 37 |
| 287 | 42 |
| 288 | 28 |
| 292 | 36 |
| 293 | 51 |
| 294 | 45 |
| 295 | 52 |
| 296 | 36 |
| 297 | 45 |
| 298 | 56 |
| 299 | 46 |
| 300 | 35 |
| 301 | 35 |
| 302 | 22 |
| 303 | 20 |
| 307 | 22 |
| 310 | 12 |
| 312 | 10 |
| 313 | 23 |
| 314 | 21 |
| 315 | 45 |
| 316 | 29 |
| 317 | 49 |
| 318 | 18 |
| 319 | 40 |
| 320 | 18 |

TABLE 6-continued

| compound No. | food intake suppression rate (%) |
|---|---|
| 322 | 31 |
| 324 | 42 |
| 325 | 47 |
| 326 | 57 |
| 327 | 58 |
| 328 | 75 |
| 329 | 51 |
| 330 | 36 |
| 331 | 35 |
| 332 | 32 |
| 333 | 28 |
| 334 | 14 |
| 335 | 27 |
| 336 | 52 |
| 337 | 49 |
| 338 | 27 |
| 339 | 51 |
| 340 | 27 |
| 341 | 35 |
| 342 | 36 |
| 343 | 15 |
| 344 | 22 |
| 345 | 10 |
| 349 | 52 |
| 350 | 41 |
| 351 | 27 |

(5) Test Method: 3-Day Continuous Subcutaneous Administration Test-2

The food intake suppressing activity of the compound of the present invention was examined by the following method.

The test compound was dissolved in a solvent (50% DMSO) so that sustained release would occur at 0.03 mg/kg/day, and the solution was filled in the Alzet Pump (DURECT Corporation, model: 1003D). After the filling, the pump was immersed in physiological saline for priming, and then used. The pump was embedded by the following method. Each male C57BL/6J mouse at 9-10 weeks of age (25° C., allowed to take food and water ad libitum; 12-hour bright-12-hour dark cycle) was anesthetized; the skin in the upper back thereof was incised, and the above-mentioned pump was embedded subcutaneously; the incision was sutured. After weighing, this mouse was returned to the rearing cage (reared alone), and given previously weighed food; food consumption as of 2 days after the start of administration was measured. The food consumption was calculated by subtracting the amount of remaining food from the weight of the food given on the day of the start of administration. From the food consumption obtained, the food intake suppression rate (%) of each test compound was calculated using the following the formula. The results are shown in Table 7.
A group receiving administration of the aforementioned solvent alone was the control group.
Food intake suppression rate (%):

(Food consumption for control group–food consumption for test compound administration group)/
food consumption for control group×100

TABLE 7

| compound No. | food intake suppression rate (%) |
|---|---|
| 356 | 48.5 |
| 357 | 46.3 |
| 358 | 62.5 |
| 359 | 43.4 |
| 360 | 36.7 |
| 361 | 23.3 |

TABLE 7-continued

| compound No. | food intake suppression rate (%) |
|---|---|
| 362 | 54.2 |
| 363 | 27.7 |
| 364 | 37.3 |
| 365 | 37.8 |
| 366 | 32.9 |
| 367 | 24.0 |
| 368 | 34.9 |
| 369 | 47.8 |
| 370 | 17.9 |
| 371 | 18.6 |
| 372 | 27.2 |
| 373 | 17.5 |
| 374 | 22.6 |

As shown in Table 5, Table 6 and Table 7, the compound of the present invention has a superior Y2 receptor agonist action and food intake suppressive action.

Formulation Example 1

| | |
|---|---|
| (1) compound No. 1 | 10.0 mg |
| (2) lactose | 70.0 mg |
| (3) cornstarch | 50.0 mg |
| (4) soluble starch | 7.0 mg |
| (5) magnesium stearate | 3.0 mg |

Compound No. 1 (10.0 mg) and magnesium stearate (3.0 mg) are granulated with an aqueous soluble starch solution (0.07 ml) (7.0 mg as soluble starch), dried and mixed with lactose (70.0 mg) and cornstarch (50.0 mg). The mixture is compressed to give a tablet.

Formulation Example 2

| | |
|---|---|
| (1) compound No. 1 | 5.0 mg |
| (2) sodium chloride | 20.0 mg |
| (3) distilled water | to total amount 2 ml |

Compound No. 1 (5.0 mg) and sodium chloride (20.0 mg) are dissolved in distilled water, and water is added to a total amount of 2.0 ml. The solution is filtered, and filled in a 2 ml ampoule under aseptic conditions. The ampoule is sterilized and tightly sealed to give a solution for injection.

INDUSTRIAL APPLICABILITY

The compound of the present invention has a superior Y2 receptor agonist action and is useful as an agent for the prophylaxis or treatment of obesity and the like.

This application is based on a patent application No. 2009-158278 filed in Japan, the contents of which are incorporated in full herein.

[Sequence Listing]

The invention claimed is:

1. A peptide represented by the formula (I):

$$P^1-X^1-A25-A26-A27-A28-A29-A30-A31-A32-A33-A34-A35-A36-NH_2 \quad (I)$$

wherein $P^1$ is:

acetyl, 3-carboxypropionyl, 4-imidazolecarbonyl, tetrahydro-2H-pyran-4-ylcarbonyl, 3-carboxypropylcarbamoyl, carboxymethylcarbamoyl, [(1S)-1-carboxy-3-methylbutyl]carbamoyl, or tetrahydro-2H-pyran-4-ylcarbamoyl;

$X^1$ is a group represented by the formula:

-A23-A24- wherein A23 is Ser or Glu; and A24 is D-Pro or D-Hyp;

A25 is Iva, Arg or Nle;

A26 is Pya(4) or His;

A27 is Cha;

A28 is Aib, Iva, or Leu(Me);

A29 is Asn;

A30 is Lys;

A31 is Aib;

A32 is Thr;

A33 is Arg;

A34 is Gln;

A35 is Arg; and

A36 is Cha;

or a salt thereof.

2. A peptide comprising the sequence Thp(4)-NHCO-Ser-D-Pro-Arg-Pya(4)-Cha-Aib-Asn-Lys-Aib-Thr-Arg-Gln-Arg-Cha-NH$_2$ or a salt thereof.

3. A peptide comprising the sequence Ac-Ser-D-Hyp-Iva-Pya(4)-Cha-Iva-Asn-Lys-Aib-Thr-Arg-Gln-Arg-Cha-NH$_2$ or a salt thereof.

4. A peptide comprising the sequence 4-Imidazolecarbonyl-Ser-D-Hyp-Iva-Pya(4)-Cha-Leu(Me)-Asn-Lys-Aib-Thr-Arg-Gln-Arg-Cha-NH$_2$ or a salt thereof.

5. A peptide comprising the sequence CC(GABA)-Ser-D-Hyp-Iva-Pya(4)-Cha-Leu(Me)-Asn-Lys-Aib-Thr-Arg-Gln-Arg-Cha-NH$_2$ or a salt thereof.

6. A pharmaceutical drug comprising the peptide according to claim 1, or a salt thereof.

7. The pharmaceutical drug according to claim 6, which is a Y2 receptor agonist.

8. The pharmaceutical drug according to claim 6, which is a feeding suppressant.

9. The pharmaceutical drug according to claim 6, which is an agent for the treatment of obesity.

10. A method for the treatment of obesity in a mammal, comprising administering an effective amount of the peptide according to claim 1 or a salt thereof to the mammal.

\* \* \* \* \*

```
                             SEQUENCE LISTING

<160> NUMBER OF SEQ ID NOS: 187

<210> SEQ ID NO 1
<211> LENGTH: 36
<212> TYPE: PRT
<213> ORGANISM: Homo sapiens
<220> FEATURE:
<221> NAME/KEY: MOD_RES
<222> LOCATION: (36)..(36)
<223> OTHER INFORMATION: AMIDATION

<400> SEQUENCE: 1

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
                20                  25                  30

Arg Gln Arg Tyr
            35

<210> SEQ ID NO 2
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: NON_TER
<222> LOCATION: (4)..(4)

<400> SEQUENCE: 2

Ser Pro Glu Glu
1

<210> SEQ ID NO 3
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: NON_TER
<222> LOCATION: (5)..(5)

<400> SEQUENCE: 3

Ala Ser Pro Glu Glu
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: NON_TER
<222> LOCATION: (6)..(6)

<400> SEQUENCE: 4

Asp Ala Ser Pro Glu Glu
1               5

<210> SEQ ID NO 5
<211> LENGTH: 7
<212> TYPE: PRT
<213> ORGANISM: Artificial Sequence
<220> FEATURE:
```

-continued

```
<223> OTHER INFORMATION: Synthetic peptide
<220> FEATURE:
<221> NAME/KEY: NON_TER
<222> LOCATION: (7)..(7)

<400> SEQUENCE: 5

Glu Asp Ala Ser Pro Glu Glu
1               5

<210> SEQ ID NO 6
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: NON_TER
<222> LOCATION: (15)..(15)

<400> SEQUENCE: 6

Glu Asp Ala Ser Pro Glu Glu Leu Ala Arg Tyr Tyr Ala Ser Leu
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: NON_TER
<222> LOCATION: (15)..(15)

<400> SEQUENCE: 7

Glu Asp Ala Ser Pro Glu Glu Leu Asn Arg Tyr Tyr Ala Ser Leu
1               5                   10                  15

<210> SEQ ID NO 8
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: NON_TER
<222> LOCATION: (10)..(10)

<400> SEQUENCE: 8

Glu Glu Leu Ala Arg Tyr Tyr Ala Ser Leu
1               5                   10

<210> SEQ ID NO 9
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: NON_TER
<222> LOCATION: (8)..(8)

<400> SEQUENCE: 9

Leu Asn Arg Tyr Tyr Ala Ser Leu
1               5

<210> SEQ ID NO 10
<211> LENGTH: 8
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa stands for Acp.
<220> FEATURE:
<221> NAME/KEY: NON_TER
<222> LOCATION: (8)..(8)

<400> SEQUENCE: 10

Tyr Pro Ile Lys Xaa Ala Ser Leu
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: NON_TER
<222> LOCATION: (7)..(7)

<400> SEQUENCE: 11

Asn Arg Tyr Tyr Ala Ser Leu
1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: NON_TER
<222> LOCATION: (6)..(6)

<400> SEQUENCE: 12

Arg Tyr Tyr Ala Ser Leu
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: NON_TER
<222> LOCATION: (6)..(6)

<400> SEQUENCE: 13

Arg Arg Tyr Ala Ser Leu
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa stands for Acp.
<220> FEATURE:
<221> NAME/KEY: NON_TER
<222> LOCATION: (6)..(6)

<400> SEQUENCE: 14
```

```
Ile Lys Xaa Ala Ser Leu
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: NON_TER
<222> LOCATION: (5)..(5)

<400> SEQUENCE: 15

Arg Tyr Ala Ser Leu
1               5

<210> SEQ ID NO 16
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: NON_TER
<222> LOCATION: (5)..(5)

<400> SEQUENCE: 16

Tyr Tyr Ala Ser Leu
1               5

<210> SEQ ID NO 17
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa stands for Acp.
<220> FEATURE:
<221> NAME/KEY: NON_TER
<222> LOCATION: (5)..(5)

<400> SEQUENCE: 17

Tyr Pro Ile Lys Xaa
1               5

<210> SEQ ID NO 18
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (14)..(14)
<223> OTHER INFORMATION: AMIDATION

<400> SEQUENCE: 18

Ser Leu Arg His Tyr Leu Asn Leu Val Thr Arg Gln Arg Tyr
1               5                   10

<210> SEQ ID NO 19
<211> LENGTH: 14
<212> TYPE: PRT
<213> ORGANISM: Artificial Sequence
<220> FEATURE:
```

```
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (14)..(14)
<223> OTHER INFORMATION: AMIDATION

<400> SEQUENCE: 19

Ser Leu Arg His Tyr Leu Asn Leu Val Thr Arg Gln Arg Tyr
1               5                   10

<210> SEQ ID NO 20
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (13)..(13)
<223> OTHER INFORMATION: METHYLATION
<220> FEATURE:
<221> NAME/KEY: MOD_RES
<222> LOCATION: (14)..(14)
<223> OTHER INFORMATION: AMIDATION

<400> SEQUENCE: 20

Ser Leu Arg Ala Tyr Ile Asn Leu Ile Thr Arg Gln Arg Tyr
1               5                   10

<210> SEQ ID NO 21
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (14)..(14)
<223> OTHER INFORMATION: METHYLATION
<220> FEATURE:
<221> NAME/KEY: MOD_RES
<222> LOCATION: (15)..(15)
<223> OTHER INFORMATION: AMIDATION

<400> SEQUENCE: 21

Ala Ser Leu Arg Ala Tyr Ile Asn Leu Ile Thr Gln Arg Arg Tyr
1               5                   10                  15

<210> SEQ ID NO 22
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (18)..(18)
<223> OTHER INFORMATION: AMIDATION

<400> SEQUENCE: 22
```

Arg Tyr Tyr Ala Ser Leu Arg Ala Tyr Ile Asn Leu Ile Thr Arg Gln
1               5                   10                  15

Arg Tyr

<210> SEQ ID NO 23
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for
      4-guanidinomethylbenzoylarginine.
<220> FEATURE:
<221> NAME/KEY: MOD_RES
<222> LOCATION: (12)..(12)
<223> OTHER INFORMATION: AMIDATION

<400> SEQUENCE: 23

Xaa Ala Tyr Ile Asn Leu Ile Thr Arg Gln Arg Tyr
1               5                   10

<210> SEQ ID NO 24
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (17)..(17)
<223> OTHER INFORMATION: AMIDATION

<400> SEQUENCE: 24

Tyr Tyr Ala Ser Leu Arg Ala Tyr Ile Asn Leu Ile Thr Arg Gln Arg
1               5                   10                  15

Tyr

<210> SEQ ID NO 25
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for 4-aminomethylbenzoylarginine.
<220> FEATURE:
<221> NAME/KEY: MOD_RES
<222> LOCATION: (12)..(12)
<223> OTHER INFORMATION: AMIDATION

<400> SEQUENCE: 25

Xaa Ala Tyr Ile Asn Leu Ile Thr Arg Gln Arg Phe
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Synthetic peptide
<220> FEATURE:

```
<221> NAME/KEY: MISC_FEATURE
<222> LOCATION: (1)..(1)
<223> OTHER INFORMATION: Xaa stands for 4-aminomethylbenzoylarginine.
<220> FEATURE:
<221> NAME/KEY: MOD_RES
<222> LOCATION: (12)..(12)
<223> OTHER INFORMATION: METHYLATION
<220> FEATURE:
<221> NAME/KEY: MOD_RES
<222> LOCATION: (12)..(12)
<223> OTHER INFORMATION: AMIDATION

<400> SEQUENCE: 26

Xaa Ala Tyr Ile Asn Leu Ile Thr Arg Gln Arg Tyr
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for 4-aminomethylbenzoylarginine.
<220> FEATURE:
<221> NAME/KEY: MISC_FEATURE
<222> LOCATION: (12)..(12)
<223> OTHER INFORMATION: Xaa stands for 4-fluorophenylalanine.
<220> FEATURE:
<221> NAME/KEY: MOD_RES
<222> LOCATION: (12)..(12)
<223> OTHER INFORMATION: AMIDATION

<400> SEQUENCE: 27

Xaa Ala Tyr Ile Asn Leu Ile Thr Arg Gln Arg Xaa
1               5                   10

<210> SEQ ID NO 28
<211> LENGTH: 12
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Xaa stands for 4-aminomethylbenzoylornithine.
<220> FEATURE:
<221> NAME/KEY: MOD_RES
<222> LOCATION: (12)..(12)
<223> OTHER INFORMATION: AMIDATION

<400> SEQUENCE: 28

Xaa Ala Tyr Ile Asn Leu Ile Thr Arg Gln Arg Tyr
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for 4-aminomethylbenzoylarginine.
<220> FEATURE:
<221> NAME/KEY: MISC_FEATURE
<222> LOCATION: (9)..(9)
<223> OTHER INFORMATION: Xaa stands for homoarginine.
<220> FEATURE:
```

<221> NAME/KEY: MOD_RES
<222> LOCATION: (12)..(12)
<223> OTHER INFORMATION: AMIDATION

<400> SEQUENCE: 29

Xaa Ala Tyr Ile Asn Leu Ile Thr Xaa Gln Arg Tyr
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for 4-aminomethylbenzoylarginine.
<220> FEATURE:
<221> NAME/KEY: MISC_FEATURE
<222> LOCATION: (12)..(12)
<223> OTHER INFORMATION: Xaa stands for 4-aminophenylalanine.
<220> FEATURE:
<221> NAME/KEY: MOD_RES
<222> LOCATION: (12)..(12)
<223> OTHER INFORMATION: AMIDATION

<400> SEQUENCE: 30

Xaa Ala Tyr Ile Asn Leu Ile Thr Arg Gln Arg Xaa
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for 4-aminomethylbenzoylarginine.
<220> FEATURE:
<221> NAME/KEY: MISC_FEATURE
<222> LOCATION: (12)..(12)
<223> OTHER INFORMATION: Xaa stands for 1-naphthylalanine.
<220> FEATURE:
<221> NAME/KEY: MOD_RES
<222> LOCATION: (12)..(12)
<223> OTHER INFORMATION: AMIDATION

<400> SEQUENCE: 31

Xaa Ala Tyr Ile Asn Leu Ile Thr Arg Gln Arg Xaa
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for 4-aminomethylbenzoylarginine.
<220> FEATURE:
<221> NAME/KEY: MISC_FEATURE
<222> LOCATION: (12)..(12)
<223> OTHER INFORMATION: Xaa stands for 2-naphthylalanine.
<220> FEATURE:
<221> NAME/KEY: MOD_RES
<222> LOCATION: (12)..(12)
<223> OTHER INFORMATION: AMIDATION

```
<400> SEQUENCE: 32

Xaa Ala Tyr Ile Asn Leu Ile Thr Arg Gln Arg Xaa
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for 4-aminomethylbenzoylarginine.
<220> FEATURE:
<221> NAME/KEY: MISC_FEATURE
<222> LOCATION: (12)..(12)
<223> OTHER INFORMATION: Xaa stands for 4-methylphenylalanine.
<220> FEATURE:
<221> NAME/KEY: MOD_RES
<222> LOCATION: (12)..(12)
<223> OTHER INFORMATION: AMIDATION

<400> SEQUENCE: 33

Xaa Ala Tyr Ile Asn Leu Ile Thr Arg Gln Arg Xaa
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for 4-aminomethylbenzoylarginine.
<220> FEATURE:
<221> NAME/KEY: MISC_FEATURE
<222> LOCATION: (12)..(12)
<223> OTHER INFORMATION: Xaa stands for N-alpha-methylphenylalanine.
<220> FEATURE:
<221> NAME/KEY: MOD_RES
<222> LOCATION: (12)..(12)
<223> OTHER INFORMATION: AMIDATION

<400> SEQUENCE: 34

Xaa Ala Tyr Ile Asn Leu Ile Thr Arg Gln Arg Xaa
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for 4-aminomethylbenzoylarginine.
<220> FEATURE:
<221> NAME/KEY: MISC_FEATURE
<222> LOCATION: (12)..(12)
<223> OTHER INFORMATION: Xaa stands for 1,2,3,4-tetrahydroisoquinoline-
      3-carboxylic acid.
<220> FEATURE:
<221> NAME/KEY: MOD_RES
<222> LOCATION: (12)..(12)
<223> OTHER INFORMATION: AMIDATION

<400> SEQUENCE: 35

Xaa Ala Tyr Ile Asn Leu Ile Thr Arg Gln Arg Xaa
```

```
1               5                   10
```

<210> SEQ ID NO 36
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for 4-aminomethylbenzoylarginine.
<220> FEATURE:
<221> NAME/KEY: MOD_RES
<222> LOCATION: (12)..(12)
<223> OTHER INFORMATION: AMIDATION

<400> SEQUENCE: 36

```
Xaa Arg Tyr Ile Asn Leu Ile Thr Arg Gln Arg Tyr
1               5                   10
```

<210> SEQ ID NO 37
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for 4-aminomethylbenzoylarginine.
<220> FEATURE:
<221> NAME/KEY: MOD_RES
<222> LOCATION: (12)..(12)
<223> OTHER INFORMATION: AMIDATION

<400> SEQUENCE: 37

```
Xaa Pro Tyr Ile Asn Leu Ile Thr Arg Gln Arg Tyr
1               5                   10
```

<210> SEQ ID NO 38
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for 4-aminomethylbenzoylarginine.
<220> FEATURE:
<221> NAME/KEY: MOD_RES
<222> LOCATION: (12)..(12)
<223> OTHER INFORMATION: AMIDATION

<400> SEQUENCE: 38

```
Xaa Ala Tyr Leu Asn Leu Ile Thr Arg Gln Arg Tyr
1               5                   10
```

<210> SEQ ID NO 39
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for 4-aminomethylbenzoylarginine.
<220> FEATURE:
<221> NAME/KEY: MISC_FEATURE
<222> LOCATION: (4)..(4)

```
<223> OTHER INFORMATION: Xaa stands for Nle.
<220> FEATURE:
<221> NAME/KEY: MOD_RES
<222> LOCATION: (12)..(12)
<223> OTHER INFORMATION: AMIDATION

<400> SEQUENCE: 39

Xaa Ala Tyr Xaa Asn Leu Ile Thr Arg Gln Arg Tyr
1               5                   10

<210> SEQ ID NO 40
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for 4-aminomethylbenzoylarginine.
<220> FEATURE:
<221> NAME/KEY: MOD_RES
<222> LOCATION: (12)..(12)
<223> OTHER INFORMATION: AMIDATION

<400> SEQUENCE: 40

Xaa Ala Tyr Phe Asn Leu Ile Thr Arg Gln Arg Tyr
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for 4-aminomethylbenzoylarginine.
<220> FEATURE:
<221> NAME/KEY: MOD_RES
<222> LOCATION: (12)..(12)
<223> OTHER INFORMATION: AMIDATION

<400> SEQUENCE: 41

Xaa Ala Tyr Trp Asn Leu Ile Thr Arg Gln Arg Tyr
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for
      4-({[imino(octylamino)methyl]amino}methyl)benzoylarginine.
<220> FEATURE:
<221> NAME/KEY: MOD_RES
<222> LOCATION: (12)..(12)
<223> OTHER INFORMATION: AMIDATION

<400> SEQUENCE: 42

Xaa Ala Tyr Ile Asn Leu Ile Thr Arg Gln Arg Tyr
1               5                   10

<210> SEQ ID NO 43
<211> LENGTH: 12
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for 4-aminomethylbenzoylarginine.
<220> FEATURE:
<221> NAME/KEY: MOD_RES
<222> LOCATION: (12)..(12)
<223> OTHER INFORMATION: AMIDATION

<400> SEQUENCE: 43

Xaa Ala Arg Ile Asn Leu Ile Thr Arg Gln Arg Tyr
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for 4-aminomethylbenzoylarginine.
<220> FEATURE:
<221> NAME/KEY: MOD_RES
<222> LOCATION: (12)..(12)
<223> OTHER INFORMATION: AMIDATION

<400> SEQUENCE: 44

Xaa Ala Gln Ile Asn Leu Ile Thr Arg Gln Arg Tyr
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for 4-aminomethylbenzoylarginine.
<220> FEATURE:
<221> NAME/KEY: MOD_RES
<222> LOCATION: (12)..(12)
<223> OTHER INFORMATION: AMIDATION

<400> SEQUENCE: 45

Xaa Ala Tyr Ala Asn Leu Ile Thr Arg Gln Arg Tyr
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for 4-aminomethylbenzoylarginine.
<220> FEATURE:
<221> NAME/KEY: MOD_RES
<222> LOCATION: (12)..(12)
<223> OTHER INFORMATION: AMIDATION

<400> SEQUENCE: 46

Xaa Ala Tyr Ile Asn Ala Ile Thr Arg Gln Arg Tyr
1               5                   10
```

```
<210> SEQ ID NO 47
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for 4-aminomethylbenzoylarginine.
<220> FEATURE:
<221> NAME/KEY: MOD_RES
<222> LOCATION: (12)..(12)
<223> OTHER INFORMATION: AMIDATION

<400> SEQUENCE: 47

Xaa Ala Tyr Ile Asn Leu Ala Thr Arg Gln Arg Tyr
1               5                   10

<210> SEQ ID NO 48
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (13)..(13)
<223> OTHER INFORMATION: AMIDATION

<400> SEQUENCE: 48

Phe Arg Ala Tyr Ile Asn Leu Ile Thr Arg Gln Arg Tyr
1               5                   10

<210> SEQ ID NO 49
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for cyclohexylalanine.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (13)..(13)
<223> OTHER INFORMATION: AMIDATION

<400> SEQUENCE: 49

Xaa Arg Ala Tyr Ile Asn Leu Ile Thr Arg Gln Arg Tyr
1               5                   10

<210> SEQ ID NO 50
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
```

```
<220> FEATURE:
<221> NAME/KEY: MOD_RES
<222> LOCATION: (13)..(13)
<223> OTHER INFORMATION: AMIDATION

<400> SEQUENCE: 50

Pro Arg Ala Tyr Ile Asn Leu Ile Thr Arg Gln Arg Tyr
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for 4-aminomethylbenzoylarginine.
<220> FEATURE:
<221> NAME/KEY: MOD_RES
<222> LOCATION: (12)..(12)
<223> OTHER INFORMATION: AMIDATION

<400> SEQUENCE: 51

Xaa Ala Tyr Ile Asn Leu Val Thr Arg Gln Arg Tyr
1               5                   10

<210> SEQ ID NO 52
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for 4-aminomethylbenzoylarginine.
<220> FEATURE:
<221> NAME/KEY: MISC_FEATURE
<222> LOCATION: (7)..(7)
<223> OTHER INFORMATION: Xaa stands for phenylglycine.
<220> FEATURE:
<221> NAME/KEY: MOD_RES
<222> LOCATION: (12)..(12)
<223> OTHER INFORMATION: AMIDATION

<400> SEQUENCE: 52

Xaa Ala Tyr Ile Asn Leu Xaa Thr Arg Gln Arg Tyr
1               5                   10

<210> SEQ ID NO 53
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for 4-aminomethylbenzoylarginine.
<220> FEATURE:
<221> NAME/KEY: MISC_FEATURE
<222> LOCATION: (7)..(7)
<223> OTHER INFORMATION: Xaa stands for cyclohexylalanine.
<220> FEATURE:
<221> NAME/KEY: MOD_RES
<222> LOCATION: (12)..(12)
<223> OTHER INFORMATION: AMIDATION

<400> SEQUENCE: 53

Xaa Ala Tyr Ile Asn Leu Xaa Thr Arg Gln Arg Tyr
```

```
1               5                   10
```

<210> SEQ ID NO 54
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for 4-aminomethylbenzoylarginine.
<220> FEATURE:
<221> NAME/KEY: MISC_FEATURE
<222> LOCATION: (7)..(7)
<223> OTHER INFORMATION: Xaa stands for Nle.
<220> FEATURE:
<221> NAME/KEY: MOD_RES
<222> LOCATION: (12)..(12)
<223> OTHER INFORMATION: AMIDATION

<400> SEQUENCE: 54

```
Xaa Ala Tyr Ile Asn Leu Xaa Thr Arg Gln Arg Tyr
1               5                   10
```

<210> SEQ ID NO 55
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for 4-aminomethylbenzoylarginine.
<220> FEATURE:
<221> NAME/KEY: MISC_FEATURE
<222> LOCATION: (3)..(3)
<223> OTHER INFORMATION: Xaa stands for Nle.
<220> FEATURE:
<221> NAME/KEY: MOD_RES
<222> LOCATION: (12)..(12)
<223> OTHER INFORMATION: AMIDATION

<400> SEQUENCE: 55

```
Xaa Ala Xaa Ile Asn Leu Ile Thr Arg Gln Arg Tyr
1               5                   10
```

<210> SEQ ID NO 56
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for 4-aminomethylbenzoylarginine.
<220> FEATURE:
<221> NAME/KEY: MISC_FEATURE
<222> LOCATION: (3)..(3)
<223> OTHER INFORMATION: Xaa stands for 4-pyridylalanine.
<220> FEATURE:
<221> NAME/KEY: MOD_RES
<222> LOCATION: (12)..(12)
<223> OTHER INFORMATION: AMIDATION

<400> SEQUENCE: 56

```
Xaa Ala Xaa Ile Asn Leu Ile Thr Arg Gln Arg Tyr
1               5                   10
```

<210> SEQ ID NO 57

```
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for 4-aminomethylbenzoylarginine.
<220> FEATURE:
<221> NAME/KEY: MOD_RES
<222> LOCATION: (12)..(12)
<223> OTHER INFORMATION: AMIDATION

<400> SEQUENCE: 57

Xaa Ala Tyr Ile Asn Gly Ile Thr Arg Gln Arg Tyr
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for 4-aminomethylbenzoylarginine.
<220> FEATURE:
<221> NAME/KEY: MISC_FEATURE
<222> LOCATION: (5)..(5)
<223> OTHER INFORMATION: Xaa stands for Aib.
<220> FEATURE:
<221> NAME/KEY: MOD_RES
<222> LOCATION: (12)..(12)
<223> OTHER INFORMATION: AMIDATION

<400> SEQUENCE: 58

Xaa Ala Tyr Ile Xaa Leu Ile Thr Arg Gln Arg Tyr
1               5                   10

<210> SEQ ID NO 59
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for 4-aminomethylbenzoylarginine.
<220> FEATURE:
<221> NAME/KEY: MISC_FEATURE
<222> LOCATION: (6)..(6)
<223> OTHER INFORMATION: Xaa stands for Aib.
<220> FEATURE:
<221> NAME/KEY: MOD_RES
<222> LOCATION: (12)..(12)
<223> OTHER INFORMATION: AMIDATION

<400> SEQUENCE: 59

Xaa Ala Tyr Ile Asn Xaa Ile Thr Arg Gln Arg Tyr
1               5                   10

<210> SEQ ID NO 60
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
```

-continued

```
<223> OTHER INFORMATION: Xaa stands for 4-aminomethylbenzoylarginine.
<220> FEATURE:
<221> NAME/KEY: MISC_FEATURE
<222> LOCATION: (2)..(2)
<223> OTHER INFORMATION: Xaa stands for cyclopropylalanine.
<220> FEATURE:
<221> NAME/KEY: MOD_RES
<222> LOCATION: (12)..(12)
<223> OTHER INFORMATION: AMIDATION

<400> SEQUENCE: 60

Xaa Xaa Tyr Ile Asn Leu Ile Thr Arg Gln Arg Tyr
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for 4-aminomethylbenzoyllysine.
<220> FEATURE:
<221> NAME/KEY: MOD_RES
<222> LOCATION: (12)..(12)
<223> OTHER INFORMATION: AMIDATION

<400> SEQUENCE: 61

Xaa Ala Tyr Ile Asn Leu Ile Thr Arg Gln Arg Tyr
1               5                   10

<210> SEQ ID NO 62
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for 4-aminomethylbenzoylarginine.
<220> FEATURE:
<221> NAME/KEY: MOD_RES
<222> LOCATION: (12)..(12)
<223> OTHER INFORMATION: AMIDATION

<400> SEQUENCE: 62

Xaa Gly Tyr Ile Asn Leu Ile Thr Arg Gln Arg Tyr
1               5                   10

<210> SEQ ID NO 63
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for 4-aminomethylbenzoylarginine.
<220> FEATURE:
<221> NAME/KEY: MOD_RES
<222> LOCATION: (12)..(12)
<223> OTHER INFORMATION: AMIDATION

<400> SEQUENCE: 63

Xaa Ala Trp Ile Asn Leu Ile Thr Arg Gln Arg Tyr
1               5                   10
```

```
<210> SEQ ID NO 64
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for 4-aminomethylbenzoylarginine.
<220> FEATURE:
<221> NAME/KEY: MISC_FEATURE
<222> LOCATION: (3)..(3)
<223> OTHER INFORMATION: Xaa stands for 4-aminophenylalanine.
<220> FEATURE:
<221> NAME/KEY: MOD_RES
<222> LOCATION: (12)..(12)
<223> OTHER INFORMATION: AMIDATION

<400> SEQUENCE: 64

Xaa Ala Xaa Ile Asn Leu Ile Thr Arg Gln Arg Tyr
1               5                   10

<210> SEQ ID NO 65
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for 4-aminomethylbenzoylarginine.
<220> FEATURE:
<221> NAME/KEY: MISC_FEATURE
<222> LOCATION: (3)..(3)
<223> OTHER INFORMATION: Xaa stands for Aib.
<220> FEATURE:
<221> NAME/KEY: MOD_RES
<222> LOCATION: (12)..(12)
<223> OTHER INFORMATION: AMIDATION

<400> SEQUENCE: 65

Xaa Ala Xaa Ile Asn Leu Ile Thr Arg Gln Arg Tyr
1               5                   10

<210> SEQ ID NO 66
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for 4-aminomethylbenzoylarginine.
<220> FEATURE:
<221> NAME/KEY: MOD_RES
<222> LOCATION: (12)..(12)
<223> OTHER INFORMATION: AMIDATION

<400> SEQUENCE: 66

Xaa Ala Tyr Ile Asn Phe Ile Thr Arg Gln Arg Tyr
1               5                   10

<210> SEQ ID NO 67
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
```

```
<222> LOCATION: (1)..(1)
<223> OTHER INFORMATION: Xaa stands for 4-aminomethylbenzoylarginine.
<220> FEATURE:
<221> NAME/KEY: MISC_FEATURE
<222> LOCATION: (6)..(6)
<223> OTHER INFORMATION: Xaa stands for 1-naphthylalanine.
<220> FEATURE:
<221> NAME/KEY: MOD_RES
<222> LOCATION: (12)..(12)
<223> OTHER INFORMATION: AMIDATION

<400> SEQUENCE: 67

Xaa Ala Tyr Ile Asn Xaa Ile Thr Arg Gln Arg Tyr
1               5                   10

<210> SEQ ID NO 68
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for 4-aminomethylbenzoylarginine.
<220> FEATURE:
<221> NAME/KEY: MISC_FEATURE
<222> LOCATION: (6)..(6)
<223> OTHER INFORMATION: Xaa stands for 2-naphthylalanine.
<220> FEATURE:
<221> NAME/KEY: MOD_RES
<222> LOCATION: (12)..(12)
<223> OTHER INFORMATION: AMIDATION

<400> SEQUENCE: 68

Xaa Ala Tyr Ile Asn Xaa Ile Thr Arg Gln Arg Tyr
1               5                   10

<210> SEQ ID NO 69
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for 4-aminomethylbenzoylarginine.
<220> FEATURE:
<221> NAME/KEY: MOD_RES
<222> LOCATION: (12)..(12)
<223> OTHER INFORMATION: AMIDATION

<400> SEQUENCE: 69

Xaa Ala Tyr Ile Asn Tyr Ile Thr Arg Gln Arg Tyr
1               5                   10

<210> SEQ ID NO 70
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for 4-aminomethylbenzoylarginine.
<220> FEATURE:
<221> NAME/KEY: MISC_FEATURE
<222> LOCATION: (6)..(6)
<223> OTHER INFORMATION: Xaa stands for 4-fluorophenylalanine.
<220> FEATURE:
<221> NAME/KEY: MOD_RES
```

```
<222> LOCATION: (12)..(12)
<223> OTHER INFORMATION: AMIDATION

<400> SEQUENCE: 70

Xaa Ala Tyr Ile Asn Xaa Ile Thr Arg Gln Arg Tyr
1               5                   10

<210> SEQ ID NO 71
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for 4-aminomethylbenzoylarginine.
<220> FEATURE:
<221> NAME/KEY: MOD_RES
<222> LOCATION: (12)..(12)
<223> OTHER INFORMATION: AMIDATION

<400> SEQUENCE: 71

Xaa Ala Tyr Ile Asn Leu Phe Thr Arg Gln Arg Tyr
1               5                   10

<210> SEQ ID NO 72
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for 4-aminomethylbenzoylarginine.
<220> FEATURE:
<221> NAME/KEY: MOD_RES
<222> LOCATION: (12)..(12)
<223> OTHER INFORMATION: AMIDATION

<400> SEQUENCE: 72

Xaa Ala Tyr Ile Asn Leu Ile Ser Arg Gln Arg Tyr
1               5                   10

<210> SEQ ID NO 73
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for 4-aminomethylbenzoylarginine.
<220> FEATURE:
<221> NAME/KEY: MISC_FEATURE
<222> LOCATION: (8)..(8)
<223> OTHER INFORMATION: Xaa stands for Nva.
<220> FEATURE:
<221> NAME/KEY: MOD_RES
<222> LOCATION: (12)..(12)
<223> OTHER INFORMATION: AMIDATION

<400> SEQUENCE: 73

Xaa Ala Tyr Ile Asn Leu Ile Xaa Arg Gln Arg Tyr
1               5                   10

<210> SEQ ID NO 74
<211> LENGTH: 12
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for 4-aminomethylbenzoylarginine.
<220> FEATURE:
<221> NAME/KEY: MOD_RES
<222> LOCATION: (12)..(12)
<223> OTHER INFORMATION: AMIDATION

<400> SEQUENCE: 74

Xaa Ala Tyr Ile Asn Leu Ile Leu Arg Gln Arg Tyr
1               5                   10

<210> SEQ ID NO 75
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for benzoylarginine.
<220> FEATURE:
<221> NAME/KEY: MISC_FEATURE
<222> LOCATION: (3)..(3)
<223> OTHER INFORMATION: Xaa stands for cyclohexylalanine.
<220> FEATURE:
<221> NAME/KEY: MISC_FEATURE
<222> LOCATION: (4)..(4)
<223> OTHER INFORMATION: Xaa stands for 1-naphthylalanine.
<220> FEATURE:
<221> NAME/KEY: MISC_FEATURE
<222> LOCATION: (7)..(7)
<223> OTHER INFORMATION: Xaa stands for Aib.
<220> FEATURE:
<221> NAME/KEY: MISC_FEATURE
<222> LOCATION: (12)..(12)
<223> OTHER INFORMATION: Xaa stands for cyclohexylalanine.
<220> FEATURE:
<221> NAME/KEY: MOD_RES
<222> LOCATION: (12)..(12)
<223> OTHER INFORMATION: AMIDATION

<400> SEQUENCE: 75

Xaa His Xaa Xaa Asn Leu Xaa Thr Arg Gln Arg Xaa
1               5                   10

<210> SEQ ID NO 76
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for benzoylarginine.
<220> FEATURE:
<221> NAME/KEY: MISC_FEATURE
<222> LOCATION: (3)..(3)
<223> OTHER INFORMATION: Xaa stands for cyclohexylalanine.
<220> FEATURE:
<221> NAME/KEY: MISC_FEATURE
<222> LOCATION: (4)..(4)
<223> OTHER INFORMATION: Xaa stands for cyclohexylalanine.
<220> FEATURE:
<221> NAME/KEY: MISC_FEATURE
<222> LOCATION: (7)..(7)
<223> OTHER INFORMATION: Xaa stands for Aib.
<220> FEATURE:
<221> NAME/KEY: MISC_FEATURE
```

```
<222> LOCATION: (12)..(12)
<223> OTHER INFORMATION: Xaa stands for cyclohexylalanine.
<220> FEATURE:
<221> NAME/KEY: MOD_RES
<222> LOCATION: (12)..(12)
<223> OTHER INFORMATION: AMIDATION

<400> SEQUENCE: 76

Xaa His Xaa Xaa Asn Leu Xaa Thr Arg Gln Arg Xaa
1               5                   10

<210> SEQ ID NO 77
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for benzoylarginine.
<220> FEATURE:
<221> NAME/KEY: MISC_FEATURE
<222> LOCATION: (3)..(3)
<223> OTHER INFORMATION: Xaa stands for cyclohexylalanine.
<220> FEATURE:
<221> NAME/KEY: MISC_FEATURE
<222> LOCATION: (12)..(12)
<223> OTHER INFORMATION: Xaa stands for cyclohexylalanine.
<220> FEATURE:
<221> NAME/KEY: MOD_RES
<222> LOCATION: (12)..(12)
<223> OTHER INFORMATION: AMIDATION

<400> SEQUENCE: 77

Xaa His Xaa Ile Asn Leu Arg Thr Arg Gln Arg Xaa
1               5                   10

<210> SEQ ID NO 78
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for benzoylarginine.
<220> FEATURE:
<221> NAME/KEY: MISC_FEATURE
<222> LOCATION: (3)..(3)
<223> OTHER INFORMATION: Xaa stands for 4-piperidinylalanine.
<220> FEATURE:
<221> NAME/KEY: MISC_FEATURE
<222> LOCATION: (12)..(12)
<223> OTHER INFORMATION: Xaa stands for cyclohexylalanine.
<220> FEATURE:
<221> NAME/KEY: MOD_RES
<222> LOCATION: (12)..(12)
<223> OTHER INFORMATION: AMIDATION

<400> SEQUENCE: 78

Xaa His Xaa Ile Asn Trp Ile Thr Arg Gln Arg Xaa
1               5                   10

<210> SEQ ID NO 79
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
```

```
<222> LOCATION: (1)..(1)
<223> OTHER INFORMATION: Xaa stands for benzoylarginine.
<220> FEATURE:
<221> NAME/KEY: MISC_FEATURE
<222> LOCATION: (3)..(3)
<223> OTHER INFORMATION: Xaa stands for 2,3-diaminopropionic acid.
<220> FEATURE:
<221> NAME/KEY: MISC_FEATURE
<222> LOCATION: (12)..(12)
<223> OTHER INFORMATION: Xaa stands for cyclohexylalanine.
<220> FEATURE:
<221> NAME/KEY: MOD_RES
<222> LOCATION: (12)..(12)
<223> OTHER INFORMATION: AMIDATION

<400> SEQUENCE: 79

Xaa His Xaa Ile Asn Trp Ile Thr Arg Gln Arg Xaa
1               5                   10

<210> SEQ ID NO 80
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for 2-aminobenzoic acid.
<220> FEATURE:
<221> NAME/KEY: MISC_FEATURE
<222> LOCATION: (4)..(4)
<223> OTHER INFORMATION: Xaa stands for cyclohexylalanine.
<220> FEATURE:
<221> NAME/KEY: MISC_FEATURE
<222> LOCATION: (13)..(13)
<223> OTHER INFORMATION: Xaa stands for cyclohexylalanine.
<220> FEATURE:
<221> NAME/KEY: MOD_RES
<222> LOCATION: (13)..(13)
<223> OTHER INFORMATION: AMIDATION

<400> SEQUENCE: 80

Xaa Arg His Xaa Ile Asn Trp Ile Thr Arg Gln Arg Xaa
1               5                   10

<210> SEQ ID NO 81
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for benzoylarginine.
<220> FEATURE:
<221> NAME/KEY: MISC_FEATURE
<222> LOCATION: (3)..(3)
<223> OTHER INFORMATION: Xaa stands for cyclohexylalanine.
<220> FEATURE:
<221> NAME/KEY: MISC_FEATURE
<222> LOCATION: (7)..(7)
<223> OTHER INFORMATION: Xaa stands for 2,3-diaminopropionic acid.
<220> FEATURE:
<221> NAME/KEY: MISC_FEATURE
<222> LOCATION: (12)..(12)
<223> OTHER INFORMATION: Xaa stands for cyclohexylalanine.
<220> FEATURE:
<221> NAME/KEY: MOD_RES
<222> LOCATION: (12)..(12)
<223> OTHER INFORMATION: AMIDATION

<400> SEQUENCE: 81
```

```
Xaa His Xaa Ile Asn Leu Xaa Thr Arg Gln Arg Xaa
1               5                   10

<210> SEQ ID NO 82
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for benzoylarginine.
<220> FEATURE:
<221> NAME/KEY: MISC_FEATURE
<222> LOCATION: (3)..(3)
<223> OTHER INFORMATION: Xaa stands for cyclohexylalanine.
<220> FEATURE:
<221> NAME/KEY: MISC_FEATURE
<222> LOCATION: (7)..(7)
<223> OTHER INFORMATION: Xaa stands for N-omega-methylarginine.
<220> FEATURE:
<221> NAME/KEY: MISC_FEATURE
<222> LOCATION: (12)..(12)
<223> OTHER INFORMATION: Xaa stands for cyclohexylalanine.
<220> FEATURE:
<221> NAME/KEY: MOD_RES
<222> LOCATION: (12)..(12)
<223> OTHER INFORMATION: AMIDATION

<400> SEQUENCE: 82

Xaa His Xaa Ile Asn Leu Xaa Thr Arg Gln Arg Xaa
1               5                   10

<210> SEQ ID NO 83
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for benzoylarginine.
<220> FEATURE:
<221> NAME/KEY: MISC_FEATURE
<222> LOCATION: (3)..(3)
<223> OTHER INFORMATION: Xaa stands for cyclohexylalanine.
<220> FEATURE:
<221> NAME/KEY: MISC_FEATURE
<222> LOCATION: (7)..(7)
<223> OTHER INFORMATION: Xaa stands for 4-pyridylalanine.
<220> FEATURE:
<221> NAME/KEY: MISC_FEATURE
<222> LOCATION: (12)..(12)
<223> OTHER INFORMATION: Xaa stands for cyclohexylalanine.
<220> FEATURE:
<221> NAME/KEY: MOD_RES
<222> LOCATION: (12)..(12)
<223> OTHER INFORMATION: AMIDATION

<400> SEQUENCE: 83

Xaa His Xaa Ile Asn Leu Xaa Thr Arg Gln Arg Xaa
1               5                   10

<210> SEQ ID NO 84
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
```

```
<223> OTHER INFORMATION: Xaa stands for benzoylarginine.
<220> FEATURE:
<221> NAME/KEY: MISC_FEATURE
<222> LOCATION: (3)..(3)
<223> OTHER INFORMATION: Xaa stands for cyclohexylalanine.
<220> FEATURE:
<221> NAME/KEY: MISC_FEATURE
<222> LOCATION: (7)..(7)
<223> OTHER INFORMATION: Xaa stands for 4-aminophenylalanine.
<220> FEATURE:
<221> NAME/KEY: MISC_FEATURE
<222> LOCATION: (12)..(12)
<223> OTHER INFORMATION: Xaa stands for cyclohexylalanine.
<220> FEATURE:
<221> NAME/KEY: MOD_RES
<222> LOCATION: (12)..(12)
<223> OTHER INFORMATION: AMIDATION

<400> SEQUENCE: 84

Xaa His Xaa Ile Asn Leu Xaa Thr Arg Gln Arg Xaa
1               5                   10

<210> SEQ ID NO 85
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for benzoylarginine.
<220> FEATURE:
<221> NAME/KEY: MISC_FEATURE
<222> LOCATION: (3)..(3)
<223> OTHER INFORMATION: Xaa stands for cyclohexylalanine.
<220> FEATURE:
<221> NAME/KEY: MISC_FEATURE
<222> LOCATION: (6)..(6)
<223> OTHER INFORMATION: Xaa stands for 4-aminophenylalanine.
<220> FEATURE:
<221> NAME/KEY: MISC_FEATURE
<222> LOCATION: (12)..(12)
<223> OTHER INFORMATION: Xaa stands for cyclohexylalanine.
<220> FEATURE:
<221> NAME/KEY: MOD_RES
<222> LOCATION: (12)..(12)
<223> OTHER INFORMATION: AMIDATION

<400> SEQUENCE: 85

Xaa His Xaa Ile Asn Xaa Ile Thr Arg Gln Arg Xaa
1               5                   10

<210> SEQ ID NO 86
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for benzoylarginine.
<220> FEATURE:
<221> NAME/KEY: MISC_FEATURE
<222> LOCATION: (8)..(8)
<223> OTHER INFORMATION: Xaa stands for O-methylthreonine.
<220> FEATURE:
<221> NAME/KEY: MOD_RES
<222> LOCATION: (12)..(12)
<223> OTHER INFORMATION: AMIDATION

<400> SEQUENCE: 86

Xaa Ala Tyr Ile Asn Leu Ile Xaa Arg Gln Arg Tyr
```

```
<210> SEQ ID NO 87
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for cyclohexanecarbonylarginine.
<220> FEATURE:
<221> NAME/KEY: MISC_FEATURE
<222> LOCATION: (3)..(3)
<223> OTHER INFORMATION: Xaa stands for cyclohexylalanine.
<220> FEATURE:
<221> NAME/KEY: MISC_FEATURE
<222> LOCATION: (5)..(5)
<223> OTHER INFORMATION: Xaa stands for N-omega-methylasparagine.
<220> FEATURE:
<221> NAME/KEY: MISC_FEATURE
<222> LOCATION: (12)..(12)
<223> OTHER INFORMATION: Xaa stands for cyclohexylalanine.
<220> FEATURE:
<221> NAME/KEY: MOD_RES
<222> LOCATION: (12)..(12)
<223> OTHER INFORMATION: AMIDATION

<400> SEQUENCE: 87

Xaa His Xaa Ile Xaa Leu Ile Thr Arg Gln Arg Xaa
1               5                   10

<210> SEQ ID NO 88
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for
      4-guanidinomethylbenzoylnorleucine.
<220> FEATURE:
<221> NAME/KEY: MISC_FEATURE
<222> LOCATION: (3)..(3)
<223> OTHER INFORMATION: Xaa stands for cyclohexylalanine.
<220> FEATURE:
<221> NAME/KEY: MISC_FEATURE
<222> LOCATION: (4)..(4)
<223> OTHER INFORMATION: Xaa stands for cyclohexylalanine.
<220> FEATURE:
<221> NAME/KEY: MISC_FEATURE
<222> LOCATION: (7)..(7)
<223> OTHER INFORMATION: Xaa stands for cyclohexylalanine.
<220> FEATURE:
<221> NAME/KEY: MISC_FEATURE
<222> LOCATION: (12)..(12)
<223> OTHER INFORMATION: Xaa stands for cyclohexylalanine.
<220> FEATURE:
<221> NAME/KEY: MOD_RES
<222> LOCATION: (12)..(12)
<223> OTHER INFORMATION: AMIDATION

<400> SEQUENCE: 88

Xaa His Xaa Xaa Asn Arg Xaa Thr Arg Gln Arg Xaa
1               5                   10

<210> SEQ ID NO 89
<211> LENGTH: 12
<212> TYPE: PRT
<213> ORGANISM: Artificial Sequence
<220> FEATURE:
```

```
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for cyclohexanecarbonylarginine.
<220> FEATURE:
<221> NAME/KEY: MISC_FEATURE
<222> LOCATION: (2)..(2)
<223> OTHER INFORMATION: Xaa stands for Nle.
<220> FEATURE:
<221> NAME/KEY: MISC_FEATURE
<222> LOCATION: (3)..(3)
<223> OTHER INFORMATION: Xaa stands for cyclohexylalanine.
<220> FEATURE:
<221> NAME/KEY: MISC_FEATURE
<222> LOCATION: (4)..(4)
<223> OTHER INFORMATION: Xaa stands for cyclohexylalanine.
<220> FEATURE:
<221> NAME/KEY: MISC_FEATURE
<222> LOCATION: (7)..(7)
<223> OTHER INFORMATION: Xaa stands for Aib.
<220> FEATURE:
<221> NAME/KEY: MISC_FEATURE
<222> LOCATION: (12)..(12)
<223> OTHER INFORMATION: Xaa stands for cyclohexylalanine.
<220> FEATURE:
<221> NAME/KEY: MOD_RES
<222> LOCATION: (12)..(12)
<223> OTHER INFORMATION: AMIDATION

<400> SEQUENCE: 89

Xaa Xaa Xaa Xaa Asn Leu Xaa Thr Arg Gln Arg Xaa
1               5                   10

<210> SEQ ID NO 90
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for cyclohexanecarbonylarginine.
<220> FEATURE:
<221> NAME/KEY: MISC_FEATURE
<222> LOCATION: (3)..(3)
<223> OTHER INFORMATION: Xaa stands for cyclohexylalanine.
<220> FEATURE:
<221> NAME/KEY: MISC_FEATURE
<222> LOCATION: (4)..(4)
<223> OTHER INFORMATION: Xaa stands for cyclopropylalanine.
<220> FEATURE:
<221> NAME/KEY: MISC_FEATURE
<222> LOCATION: (7)..(7)
<223> OTHER INFORMATION: Xaa stands for Aib.
<220> FEATURE:
<221> NAME/KEY: MISC_FEATURE
<222> LOCATION: (12)..(12)
<223> OTHER INFORMATION: Xaa stands for cyclohexylalanine.
<220> FEATURE:
<221> NAME/KEY: MOD_RES
<222> LOCATION: (12)..(12)
<223> OTHER INFORMATION: AMIDATION

<400> SEQUENCE: 90

Xaa His Xaa Xaa Asn Leu Xaa Thr Arg Gln Arg Xaa
1               5                   10

<210> SEQ ID NO 91
<211> LENGTH: 12
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: MISC_FEATURE
<222> LOCATION: (1)..(1)
<223> OTHER INFORMATION: Xaa stands for isobutanoylarginine.
<220> FEATURE:
<221> NAME/KEY: MISC_FEATURE
<222> LOCATION: (2)..(2)
<223> OTHER INFORMATION: Xaa stands for Abu.
<220> FEATURE:
<221> NAME/KEY: MISC_FEATURE
<222> LOCATION: (3)..(3)
<223> OTHER INFORMATION: Xaa stands for cyclohexylalanine.
<220> FEATURE:
<221> NAME/KEY: MISC_FEATURE
<222> LOCATION: (4)..(4)
<223> OTHER INFORMATION: Xaa stands for 4-fluorophenylalanine.
<220> FEATURE:
<221> NAME/KEY: MISC_FEATURE
<222> LOCATION: (7)..(7)
<223> OTHER INFORMATION: Xaa stands for Aib.
<220> FEATURE:
<221> NAME/KEY: MISC_FEATURE
<222> LOCATION: (12)..(12)
<223> OTHER INFORMATION: Xaa stands for cyclohexylalanine.
<220> FEATURE:
<221> NAME/KEY: MOD_RES
<222> LOCATION: (12)..(12)
<223> OTHER INFORMATION: AMIDATION

<400> SEQUENCE: 91

Xaa Xaa Xaa Xaa Asn Leu Xaa Thr Arg Gln Arg Xaa
1               5                   10

<210> SEQ ID NO 92
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for isobutanoylarginine.
<220> FEATURE:
<221> NAME/KEY: MISC_FEATURE
<222> LOCATION: (2)..(2)
<223> OTHER INFORMATION: Xaa stands for Abu.
<220> FEATURE:
<221> NAME/KEY: MISC_FEATURE
<222> LOCATION: (3)..(3)
<223> OTHER INFORMATION: Xaa stands for cyclohexylalanine.
<220> FEATURE:
<221> NAME/KEY: MISC_FEATURE
<222> LOCATION: (4)..(4)
<223> OTHER INFORMATION: Xaa stands for cyclohexylalanine.
<220> FEATURE:
<221> NAME/KEY: MISC_FEATURE
<222> LOCATION: (6)..(6)
<223> OTHER INFORMATION: Xaa stands for cyclopropylalanine.
<220> FEATURE:
<221> NAME/KEY: MISC_FEATURE
<222> LOCATION: (7)..(7)
<223> OTHER INFORMATION: Xaa stands for Aib.
<220> FEATURE:
<221> NAME/KEY: MISC_FEATURE
<222> LOCATION: (12)..(12)
<223> OTHER INFORMATION: Xaa stands for cyclohexylalanine.
<220> FEATURE:
<221> NAME/KEY: MOD_RES
<222> LOCATION: (12)..(12)
<223> OTHER INFORMATION: AMIDATION

<400> SEQUENCE: 92

Xaa Xaa Xaa Xaa Asn Xaa Xaa Thr Arg Gln Arg Xaa
1               5                   10
```

```
<210> SEQ ID NO 93
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for isobutanoylarginine.
<220> FEATURE:
<221> NAME/KEY: MISC_FEATURE
<222> LOCATION: (2)..(2)
<223> OTHER INFORMATION: Xaa stands for Abu.
<220> FEATURE:
<221> NAME/KEY: MISC_FEATURE
<222> LOCATION: (3)..(3)
<223> OTHER INFORMATION: Xaa stands for cyclohexylalanine.
<220> FEATURE:
<221> NAME/KEY: MISC_FEATURE
<222> LOCATION: (4)..(4)
<223> OTHER INFORMATION: Xaa stands for cyclohexylalanine.
<220> FEATURE:
<221> NAME/KEY: MISC_FEATURE
<222> LOCATION: (6)..(6)
<223> OTHER INFORMATION: Xaa stands for gamma-methylleucine.
<220> FEATURE:
<221> NAME/KEY: MISC_FEATURE
<222> LOCATION: (7)..(7)
<223> OTHER INFORMATION: Xaa stands for Aib.
<220> FEATURE:
<221> NAME/KEY: MISC_FEATURE
<222> LOCATION: (12)..(12)
<223> OTHER INFORMATION: Xaa stands for cyclohexylalanine.
<220> FEATURE:
<221> NAME/KEY: MOD_RES
<222> LOCATION: (12)..(12)
<223> OTHER INFORMATION: AMIDATION

<400> SEQUENCE: 93

Xaa Xaa Xaa Xaa Asn Xaa Xaa Thr Arg Gln Arg Xaa
1               5                   10

<210> SEQ ID NO 94
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for isobutanoylarginine.
<220> FEATURE:
<221> NAME/KEY: MISC_FEATURE
<222> LOCATION: (2)..(2)
<223> OTHER INFORMATION: Xaa stands for Abu.
<220> FEATURE:
<221> NAME/KEY: MISC_FEATURE
<222> LOCATION: (3)..(3)
<223> OTHER INFORMATION: Xaa stands for cyclohexylalanine.
<220> FEATURE:
<221> NAME/KEY: MISC_FEATURE
<222> LOCATION: (4)..(4)
<223> OTHER INFORMATION: Xaa stands for cyclohexylalanine.
<220> FEATURE:
<221> NAME/KEY: MISC_FEATURE
<222> LOCATION: (7)..(7)
<223> OTHER INFORMATION: Xaa stands for 3-pyridylalanine.
<220> FEATURE:
<221> NAME/KEY: MISC_FEATURE
<222> LOCATION: (12)..(12)
<223> OTHER INFORMATION: Xaa stands for cyclohexylalanine.
<220> FEATURE:
<221> NAME/KEY: MOD_RES
<222> LOCATION: (12)..(12)
```

```
<223> OTHER INFORMATION: AMIDATION

<400> SEQUENCE: 94

Xaa Xaa Xaa Xaa Asn Leu Xaa Thr Arg Gln Arg Xaa
1               5                   10

<210> SEQ ID NO 95
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for isobutanoylarginine.
<220> FEATURE:
<221> NAME/KEY: MISC_FEATURE
<222> LOCATION: (2)..(2)
<223> OTHER INFORMATION: Xaa stands for Abu.
<220> FEATURE:
<221> NAME/KEY: MISC_FEATURE
<222> LOCATION: (3)..(3)
<223> OTHER INFORMATION: Xaa stands for cyclohexylalanine.
<220> FEATURE:
<221> NAME/KEY: MISC_FEATURE
<222> LOCATION: (4)..(4)
<223> OTHER INFORMATION: Xaa stands for 4-pyridylalanine.
<220> FEATURE:
<221> NAME/KEY: MISC_FEATURE
<222> LOCATION: (7)..(7)
<223> OTHER INFORMATION: Xaa stands for Aib.
<220> FEATURE:
<221> NAME/KEY: MISC_FEATURE
<222> LOCATION: (12)..(12)
<223> OTHER INFORMATION: Xaa stands for cyclohexylalanine.
<220> FEATURE:
<221> NAME/KEY: MOD_RES
<222> LOCATION: (12)..(12)
<223> OTHER INFORMATION: AMIDATION

<400> SEQUENCE: 95

Xaa Xaa Xaa Xaa Asn Leu Xaa Thr Arg Gln Arg Xaa
1               5                   10

<210> SEQ ID NO 96
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for isobutanoylarginine.
<220> FEATURE:
<221> NAME/KEY: MISC_FEATURE
<222> LOCATION: (2)..(2)
<223> OTHER INFORMATION: Xaa stands for Abu.
<220> FEATURE:
<221> NAME/KEY: MISC_FEATURE
<222> LOCATION: (3)..(3)
<223> OTHER INFORMATION: Xaa stands for cyclohexylalanine.
<220> FEATURE:
<221> NAME/KEY: MISC_FEATURE
<222> LOCATION: (4)..(4)
<223> OTHER INFORMATION: Xaa stands for cyclohexylalanine.
<220> FEATURE:
<221> NAME/KEY: MISC_FEATURE
<222> LOCATION: (7)..(7)
<223> OTHER INFORMATION: Xaa stands for Aib.
<220> FEATURE:
<221> NAME/KEY: MISC_FEATURE
<222> LOCATION: (12)..(12)
<223> OTHER INFORMATION: Xaa stands for 2-fluorotyrosine.
```

```
<220> FEATURE:
<221> NAME/KEY: MOD_RES
<222> LOCATION: (12)..(12)
<223> OTHER INFORMATION: AMIDATION

<400> SEQUENCE: 96

Xaa Xaa Xaa Xaa Asn Leu Xaa Thr Arg Gln Arg Xaa
1               5                   10

<210> SEQ ID NO 97
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for isobutanoylarginine.
<220> FEATURE:
<221> NAME/KEY: MISC_FEATURE
<222> LOCATION: (2)..(2)
<223> OTHER INFORMATION: Xaa stands for Abu.
<220> FEATURE:
<221> NAME/KEY: MISC_FEATURE
<222> LOCATION: (3)..(3)
<223> OTHER INFORMATION: Xaa stands for cyclohexylalanine.
<220> FEATURE:
<221> NAME/KEY: MISC_FEATURE
<222> LOCATION: (4)..(4)
<223> OTHER INFORMATION: Xaa stands for cyclohexylalanine.
<220> FEATURE:
<221> NAME/KEY: MISC_FEATURE
<222> LOCATION: (7)..(7)
<223> OTHER INFORMATION: Xaa stands for Aib.
<220> FEATURE:
<221> NAME/KEY: MISC_FEATURE
<222> LOCATION: (12)..(12)
<223> OTHER INFORMATION: Xaa stands for 3-fluorotyrosine.
<220> FEATURE:
<221> NAME/KEY: MOD_RES
<222> LOCATION: (12)..(12)
<223> OTHER INFORMATION: AMIDATION

<400> SEQUENCE: 97

Xaa Xaa Xaa Xaa Asn Leu Xaa Thr Arg Gln Arg Xaa
1               5                   10

<210> SEQ ID NO 98
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for isobutanoylarginine.
<220> FEATURE:
<221> NAME/KEY: MISC_FEATURE
<222> LOCATION: (2)..(2)
<223> OTHER INFORMATION: Xaa stands for Abu.
<220> FEATURE:
<221> NAME/KEY: MISC_FEATURE
<222> LOCATION: (3)..(3)
<223> OTHER INFORMATION: Xaa stands for cyclohexylalanine.
<220> FEATURE:
<221> NAME/KEY: MISC_FEATURE
<222> LOCATION: (4)..(4)
<223> OTHER INFORMATION: Xaa stands for cyclohexylalanine.
<220> FEATURE:
<221> NAME/KEY: MISC_FEATURE
<222> LOCATION: (7)..(7)
<223> OTHER INFORMATION: Xaa stands for cyclopropylglycine.
<220> FEATURE:
```

<221> NAME/KEY: MISC_FEATURE
<222> LOCATION: (12)..(12)
<223> OTHER INFORMATION: Xaa stands for cyclohexylalanine.
<220> FEATURE:
<221> NAME/KEY: MOD_RES
<222> LOCATION: (12)..(12)
<223> OTHER INFORMATION: AMIDATION

<400> SEQUENCE: 98

Xaa Xaa Xaa Xaa Asn Leu Xaa Thr Arg Gln Arg Xaa
1               5                   10

<210> SEQ ID NO 99
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for isobutanoylarginine.
<220> FEATURE:
<221> NAME/KEY: MISC_FEATURE
<222> LOCATION: (2)..(2)
<223> OTHER INFORMATION: Xaa stands for Abu.
<220> FEATURE:
<221> NAME/KEY: MISC_FEATURE
<222> LOCATION: (3)..(3)
<223> OTHER INFORMATION: Xaa stands for cyclohexylalanine.
<220> FEATURE:
<221> NAME/KEY: MISC_FEATURE
<222> LOCATION: (4)..(4)
<223> OTHER INFORMATION: Xaa stands for cyclohexylalanine.
<220> FEATURE:
<221> NAME/KEY: MISC_FEATURE
<222> LOCATION: (7)..(7)
<223> OTHER INFORMATION: Xaa stands for Aib.
<220> FEATURE:
<221> NAME/KEY: MISC_FEATURE
<222> LOCATION: (12)..(12)
<223> OTHER INFORMATION: Xaa stands for cyclohexylalanine.
<220> FEATURE:
<221> NAME/KEY: MOD_RES
<222> LOCATION: (12)..(12)
<223> OTHER INFORMATION: AMIDATION

<400> SEQUENCE: 99

Xaa Xaa Xaa Xaa Asn Ser Xaa Thr Arg Gln Arg Xaa
1               5                   10

<210> SEQ ID NO 100
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for isobutanoylarginine.
<220> FEATURE:
<221> NAME/KEY: MISC_FEATURE
<222> LOCATION: (2)..(2)
<223> OTHER INFORMATION: Xaa stands for Abu.
<220> FEATURE:
<221> NAME/KEY: MISC_FEATURE
<222> LOCATION: (3)..(3)
<223> OTHER INFORMATION: Xaa stands for cyclohexylalanine.
<220> FEATURE:
<221> NAME/KEY: MISC_FEATURE
<222> LOCATION: (4)..(4)
<223> OTHER INFORMATION: Xaa stands for cyclohexylalanine.
<220> FEATURE:
<221> NAME/KEY: MISC_FEATURE

```
<222> LOCATION: (7)..(7)
<223> OTHER INFORMATION: Xaa stands for Aib.
<220> FEATURE:
<221> NAME/KEY: MISC_FEATURE
<222> LOCATION: (12)..(12)
<223> OTHER INFORMATION: Xaa stands for cyclohexylalanine.
<220> FEATURE:
<221> NAME/KEY: MOD_RES
<222> LOCATION: (12)..(12)
<223> OTHER INFORMATION: AMIDATION

<400> SEQUENCE: 100

Xaa Xaa Xaa Xaa Asn Gln Xaa Thr Arg Gln Arg Xaa
1               5                   10

<210> SEQ ID NO 101
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for isobutanoylarginine.
<220> FEATURE:
<221> NAME/KEY: MISC_FEATURE
<222> LOCATION: (2)..(2)
<223> OTHER INFORMATION: Xaa stands for Abu.
<220> FEATURE:
<221> NAME/KEY: MISC_FEATURE
<222> LOCATION: (3)..(3)
<223> OTHER INFORMATION: Xaa stands for cyclohexylalanine.
<220> FEATURE:
<221> NAME/KEY: MISC_FEATURE
<222> LOCATION: (4)..(4)
<223> OTHER INFORMATION: Xaa stands for cyclohexylalanine.
<220> FEATURE:
<221> NAME/KEY: MISC_FEATURE
<222> LOCATION: (6)..(6)
<223> OTHER INFORMATION: Xaa stands for Abu.
<220> FEATURE:
<221> NAME/KEY: MISC_FEATURE
<222> LOCATION: (7)..(7)
<223> OTHER INFORMATION: Xaa stands for Aib.
<220> FEATURE:
<221> NAME/KEY: MISC_FEATURE
<222> LOCATION: (12)..(12)
<223> OTHER INFORMATION: Xaa stands for cyclohexylalanine.
<220> FEATURE:
<221> NAME/KEY: MOD_RES
<222> LOCATION: (12)..(12)
<223> OTHER INFORMATION: AMIDATION

<400> SEQUENCE: 101

Xaa Xaa Xaa Xaa Asn Xaa Xaa Thr Arg Gln Arg Xaa
1               5                   10

<210> SEQ ID NO 102
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for isobutanoylarginine.
<220> FEATURE:
<221> NAME/KEY: MISC_FEATURE
<222> LOCATION: (2)..(2)
<223> OTHER INFORMATION: Xaa stands for Abu.
<220> FEATURE:
<221> NAME/KEY: MISC_FEATURE
<222> LOCATION: (3)..(3)
```

<223> OTHER INFORMATION: Xaa stands for cyclohexylalanine.
<220> FEATURE:
<221> NAME/KEY: MISC_FEATURE
<222> LOCATION: (4)..(4)
<223> OTHER INFORMATION: Xaa stands for cyclohexylalanine.
<220> FEATURE:
<221> NAME/KEY: MISC_FEATURE
<222> LOCATION: (7)..(7)
<223> OTHER INFORMATION: Xaa stands for Aib.
<220> FEATURE:
<221> NAME/KEY: MISC_FEATURE
<222> LOCATION: (12)..(12)
<223> OTHER INFORMATION: Xaa stands for cyclohexylalanine.
<220> FEATURE:
<221> NAME/KEY: MOD_RES
<222> LOCATION: (12)..(12)
<223> OTHER INFORMATION: AMIDATION

<400> SEQUENCE: 102

Xaa Xaa Xaa Xaa Asn His Xaa Thr Arg Gln Arg Xaa
1               5                   10

<210> SEQ ID NO 103
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for isobutanoylarginine.
<220> FEATURE:
<221> NAME/KEY: MISC_FEATURE
<222> LOCATION: (2)..(2)
<223> OTHER INFORMATION: Xaa stands for Abu.
<220> FEATURE:
<221> NAME/KEY: MISC_FEATURE
<222> LOCATION: (3)..(3)
<223> OTHER INFORMATION: Xaa stands for cyclohexylalanine.
<220> FEATURE:
<221> NAME/KEY: MISC_FEATURE
<222> LOCATION: (4)..(4)
<223> OTHER INFORMATION: Xaa stands for cyclopropylglycine.
<220> FEATURE:
<221> NAME/KEY: MISC_FEATURE
<222> LOCATION: (7)..(7)
<223> OTHER INFORMATION: Xaa stands for Aib.
<220> FEATURE:
<221> NAME/KEY: MISC_FEATURE
<222> LOCATION: (12)..(12)
<223> OTHER INFORMATION: Xaa stands for cyclohexylalanine.
<220> FEATURE:
<221> NAME/KEY: MOD_RES
<222> LOCATION: (12)..(12)
<223> OTHER INFORMATION: AMIDATION

<400> SEQUENCE: 103

Xaa Xaa Xaa Xaa Asn Leu Xaa Thr Arg Gln Arg Xaa
1               5                   10

<210> SEQ ID NO 104
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for isobutanoylarginine.
<220> FEATURE:
<221> NAME/KEY: MISC_FEATURE
<222> LOCATION: (2)..(2)
<223> OTHER INFORMATION: Xaa stands for Abu.

```
<220> FEATURE:
<221> NAME/KEY: MISC_FEATURE
<222> LOCATION: (3)..(3)
<223> OTHER INFORMATION: Xaa stands for Abu.
<220> FEATURE:
<221> NAME/KEY: MISC_FEATURE
<222> LOCATION: (4)..(4)
<223> OTHER INFORMATION: Xaa stands for cyclohexylalanine.
<220> FEATURE:
<221> NAME/KEY: MISC_FEATURE
<222> LOCATION: (7)..(7)
<223> OTHER INFORMATION: Xaa stands for Aib.
<220> FEATURE:
<221> NAME/KEY: MISC_FEATURE
<222> LOCATION: (12)..(12)
<223> OTHER INFORMATION: Xaa stands for cyclohexylalanine.
<220> FEATURE:
<221> NAME/KEY: MOD_RES
<222> LOCATION: (12)..(12)
<223> OTHER INFORMATION: AMIDATION

<400> SEQUENCE: 104

Xaa Xaa Xaa Xaa Asn Leu Xaa Thr Arg Gln Arg Xaa
1               5                   10

<210> SEQ ID NO 105
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for isobutanoylarginine.
<220> FEATURE:
<221> NAME/KEY: MISC_FEATURE
<222> LOCATION: (2)..(2)
<223> OTHER INFORMATION: Xaa stands for Abu.
<220> FEATURE:
<221> NAME/KEY: MISC_FEATURE
<222> LOCATION: (4)..(4)
<223> OTHER INFORMATION: Xaa stands for cyclohexylalanine.
<220> FEATURE:
<221> NAME/KEY: MISC_FEATURE
<222> LOCATION: (7)..(7)
<223> OTHER INFORMATION: Xaa stands for Aib.
<220> FEATURE:
<221> NAME/KEY: MISC_FEATURE
<222> LOCATION: (12)..(12)
<223> OTHER INFORMATION: Xaa stands for cyclohexylalanine.
<220> FEATURE:
<221> NAME/KEY: MOD_RES
<222> LOCATION: (12)..(12)
<223> OTHER INFORMATION: AMIDATION

<400> SEQUENCE: 105

Xaa Xaa Gly Xaa Asn Leu Xaa Thr Arg Gln Arg Xaa
1               5                   10

<210> SEQ ID NO 106
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for amidinoglycine.
<220> FEATURE:
<221> NAME/KEY: MISC_FEATURE
<222> LOCATION: (2)..(2)
<223> OTHER INFORMATION: Xaa stands for piperidine-4-carboxylic acid.
<220> FEATURE:
```

```
<221> NAME/KEY: MISC_FEATURE
<222> LOCATION: (5)..(5)
<223> OTHER INFORMATION: Xaa stands for cyclohexylalanine.
<220> FEATURE:
<221> NAME/KEY: MISC_FEATURE
<222> LOCATION: (14)..(14)
<223> OTHER INFORMATION: Xaa stands for cyclohexylalanine.
<220> FEATURE:
<221> NAME/KEY: MOD_RES
<222> LOCATION: (14)..(14)
<223> OTHER INFORMATION: AMIDATION

<400> SEQUENCE: 106

Xaa Xaa Arg His Xaa Ile Asn Trp Ile Thr Arg Gln Arg Xaa
1               5                   10

<210> SEQ ID NO 107
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for benzoylarginine.
<220> FEATURE:
<221> NAME/KEY: MISC_FEATURE
<222> LOCATION: (3)..(3)
<223> OTHER INFORMATION: Xaa stands for cyclohexylalanine.
<220> FEATURE:
<221> NAME/KEY: MISC_FEATURE
<222> LOCATION: (4)..(4)
<223> OTHER INFORMATION: Xaa stands for cyclohexylalanine.
<220> FEATURE:
<221> NAME/KEY: MISC_FEATURE
<222> LOCATION: (7)..(7)
<223> OTHER INFORMATION: Xaa stands for Aib.
<220> FEATURE:
<221> NAME/KEY: MISC_FEATURE
<222> LOCATION: (12)..(12)
<223> OTHER INFORMATION: Xaa stands for cyclohexylalanine.
<220> FEATURE:
<221> NAME/KEY: MOD_RES
<222> LOCATION: (12)..(12)
<223> OTHER INFORMATION: AMIDATION

<400> SEQUENCE: 107

Xaa Ser Xaa Xaa Asn Leu Xaa Thr Arg Gln Arg Xaa
1               5                   10

<210> SEQ ID NO 108
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for benzoylarginine.
<220> FEATURE:
<221> NAME/KEY: MISC_FEATURE
<222> LOCATION: (2)..(2)
<223> OTHER INFORMATION: Xaa stands for O-methylserine.
<220> FEATURE:
<221> NAME/KEY: MISC_FEATURE
<222> LOCATION: (3)..(3)
<223> OTHER INFORMATION: Xaa stands for cyclohexylalanine.
<220> FEATURE:
<221> NAME/KEY: MISC_FEATURE
<222> LOCATION: (4)..(4)
<223> OTHER INFORMATION: Xaa stands for cyclohexylalanine.
<220> FEATURE:
<221> NAME/KEY: MISC_FEATURE
```

```
<222> LOCATION: (7)..(7)
<223> OTHER INFORMATION: Xaa stands for Aib.
<220> FEATURE:
<221> NAME/KEY: MISC_FEATURE
<222> LOCATION: (12)..(12)
<223> OTHER INFORMATION: Xaa stands for cyclohexylalanine.
<220> FEATURE:
<221> NAME/KEY: MOD_RES
<222> LOCATION: (12)..(12)
<223> OTHER INFORMATION: AMIDATION

<400> SEQUENCE: 108

Xaa Xaa Xaa Xaa Asn Leu Xaa Thr Arg Gln Arg Xaa
1               5                   10

<210> SEQ ID NO 109
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for benzoylarginine.
<220> FEATURE:
<221> NAME/KEY: MISC_FEATURE
<222> LOCATION: (3)..(3)
<223> OTHER INFORMATION: Xaa stands for cyclohexylalanine.
<220> FEATURE:
<221> NAME/KEY: MISC_FEATURE
<222> LOCATION: (4)..(4)
<223> OTHER INFORMATION: Xaa stands for cyclohexylalanine.
<220> FEATURE:
<221> NAME/KEY: MISC_FEATURE
<222> LOCATION: (7)..(7)
<223> OTHER INFORMATION: Xaa stands for Aib.
<220> FEATURE:
<221> NAME/KEY: MISC_FEATURE
<222> LOCATION: (12)..(12)
<223> OTHER INFORMATION: Xaa stands for cyclohexylalanine.
<220> FEATURE:
<221> NAME/KEY: MOD_RES
<222> LOCATION: (12)..(12)
<223> OTHER INFORMATION: AMIDATION

<400> SEQUENCE: 109

Xaa Asn Xaa Xaa Asn Leu Xaa Thr Arg Gln Arg Xaa
1               5                   10

<210> SEQ ID NO 110
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for isobutanoylarginine.
<220> FEATURE:
<221> NAME/KEY: MISC_FEATURE
<222> LOCATION: (2)..(2)
<223> OTHER INFORMATION: Xaa stands for Abu.
<220> FEATURE:
<221> NAME/KEY: MISC_FEATURE
<222> LOCATION: (3)..(3)
<223> OTHER INFORMATION: Xaa stands for cyclohexylalanine.
<220> FEATURE:
<221> NAME/KEY: MISC_FEATURE
<222> LOCATION: (7)..(7)
<223> OTHER INFORMATION: Xaa stands for Aib.
<220> FEATURE:
<221> NAME/KEY: MISC_FEATURE
<222> LOCATION: (12)..(12)
```

```
<223> OTHER INFORMATION: Xaa stands for cyclohexylalanine.
<220> FEATURE:
<221> NAME/KEY: MOD_RES
<222> LOCATION: (12)..(12)
<223> OTHER INFORMATION: AMIDATION

<400> SEQUENCE: 110

Xaa Xaa Xaa Gln Asn Leu Xaa Thr Arg Gln Arg Xaa
1               5                   10

<210> SEQ ID NO 111
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for isobutanoylarginine.
<220> FEATURE:
<221> NAME/KEY: MISC_FEATURE
<222> LOCATION: (2)..(2)
<223> OTHER INFORMATION: Xaa stands for Abu.
<220> FEATURE:
<221> NAME/KEY: MISC_FEATURE
<222> LOCATION: (3)..(3)
<223> OTHER INFORMATION: Xaa stands for cyclohexylalanine.
<220> FEATURE:
<221> NAME/KEY: MISC_FEATURE
<222> LOCATION: (7)..(7)
<223> OTHER INFORMATION: Xaa stands for Aib.
<220> FEATURE:
<221> NAME/KEY: MISC_FEATURE
<222> LOCATION: (12)..(12)
<223> OTHER INFORMATION: Xaa stands for cyclohexylalanine.
<220> FEATURE:
<221> NAME/KEY: MOD_RES
<222> LOCATION: (12)..(12)
<223> OTHER INFORMATION: AMIDATION

<400> SEQUENCE: 111

Xaa Xaa Xaa His Asn Leu Xaa Thr Arg Gln Arg Xaa
1               5                   10

<210> SEQ ID NO 112
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for isobutanoylarginine.
<220> FEATURE:
<221> NAME/KEY: MISC_FEATURE
<222> LOCATION: (2)..(2)
<223> OTHER INFORMATION: Xaa stands for Abu.
<220> FEATURE:
<221> NAME/KEY: MISC_FEATURE
<222> LOCATION: (3)..(3)
<223> OTHER INFORMATION: Xaa stands for cyclohexylalanine.
<220> FEATURE:
<221> NAME/KEY: MISC_FEATURE
<222> LOCATION: (7)..(7)
<223> OTHER INFORMATION: Xaa stands for Aib.
<220> FEATURE:
<221> NAME/KEY: MISC_FEATURE
<222> LOCATION: (12)..(12)
<223> OTHER INFORMATION: Xaa stands for cyclohexylalanine.
<220> FEATURE:
<221> NAME/KEY: MOD_RES
<222> LOCATION: (12)..(12)
<223> OTHER INFORMATION: AMIDATION
```

<400> SEQUENCE: 112

Xaa Xaa Xaa Ser Asn Leu Xaa Thr Arg Gln Arg Xaa
1               5                   10

<210> SEQ ID NO 113
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for benzoylarginine.
<220> FEATURE:
<221> NAME/KEY: MISC_FEATURE
<222> LOCATION: (3)..(3)
<223> OTHER INFORMATION: Xaa stands for Nva
<220> FEATURE:
<221> NAME/KEY: MISC_FEATURE
<222> LOCATION: (4)..(4)
<223> OTHER INFORMATION: Xaa stands for cyclohexylalanine.
<220> FEATURE:
<221> NAME/KEY: MISC_FEATURE
<222> LOCATION: (7)..(7)
<223> OTHER INFORMATION: Xaa stands for Aib
<220> FEATURE:
<221> NAME/KEY: MOD_RES
<222> LOCATION: (12)..(12)
<223> OTHER INFORMATION: AMIDATION
<220> FEATURE:
<221> NAME/KEY: MISC_FEATURE
<222> LOCATION: (12)..(12)
<223> OTHER INFORMATION: Xaa stands for cyclohexylalanine.

<400> SEQUENCE: 113

Xaa His Xaa Xaa Asn Leu Xaa Thr Arg Gln Arg Xaa
1               5                   10

<210> SEQ ID NO 114
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for benzoylarginine.
<220> FEATURE:
<221> NAME/KEY: MISC_FEATURE
<222> LOCATION: (4)..(4)
<223> OTHER INFORMATION: Xaa stands for cyclohexylalanine.
<220> FEATURE:
<221> NAME/KEY: MISC_FEATURE
<222> LOCATION: (7)..(7)
<223> OTHER INFORMATION: Xaa stands for Aib
<220> FEATURE:
<221> NAME/KEY: MISC_FEATURE
<222> LOCATION: (12)..(12)
<223> OTHER INFORMATION: Xaa stands for cyclohexylalanine.
<220> FEATURE:
<221> NAME/KEY: MOD_RES
<222> LOCATION: (12)..(12)
<223> OTHER INFORMATION: AMIDATION

<400> SEQUENCE: 114

Xaa His His Xaa Asn Leu Xaa Thr Arg Gln Arg Xaa
1               5                   10

<210> SEQ ID NO 115
<211> LENGTH: 14

```
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa stands for N-isobutylglycine.
<220> FEATURE:
<221> NAME/KEY: MISC_FEATURE
<222> LOCATION: (5)..(5)
<223> OTHER INFORMATION: Xaa stands for cyclohexylalanine.
<220> FEATURE:
<221> NAME/KEY: MISC_FEATURE
<222> LOCATION: (6)..(6)
<223> OTHER INFORMATION: Xaa stands for cyclohexylalanine.
<220> FEATURE:
<221> NAME/KEY: MISC_FEATURE
<222> LOCATION: (9)..(9)
<223> OTHER INFORMATION: Xaa stands for Aib.
<220> FEATURE:
<221> NAME/KEY: MISC_FEATURE
<222> LOCATION: (14)..(14)
<223> OTHER INFORMATION: Xaa stands for cyclohexylalanine.
<220> FEATURE:
<221> NAME/KEY: MOD_RES
<222> LOCATION: (14)..(14)
<223> OTHER INFORMATION: AMIDATION

<400> SEQUENCE: 115

Ser Xaa Arg His Xaa Xaa Asn Leu Xaa Thr Arg Gln Arg Xaa
1               5                   10

<210> SEQ ID NO 116
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (5)..(5)
<223> OTHER INFORMATION: Xaa stands for cyclohexylalanine.
<220> FEATURE:
<221> NAME/KEY: MISC_FEATURE
<222> LOCATION: (6)..(6)
<223> OTHER INFORMATION: Xaa stands for cyclohexylalanine.
<220> FEATURE:
<221> NAME/KEY: MISC_FEATURE
<222> LOCATION: (9)..(9)
<223> OTHER INFORMATION: Xaa stands for Aib.
<220> FEATURE:
<221> NAME/KEY: MISC_FEATURE
<222> LOCATION: (14)..(14)
<223> OTHER INFORMATION: Xaa stands for cyclohexylalanine.
<220> FEATURE:
<221> NAME/KEY: MOD_RES
<222> LOCATION: (14)..(14)
<223> OTHER INFORMATION: AMIDATION

<400> SEQUENCE: 116

Ser Gly Arg His Xaa Xaa Asn Leu Xaa Thr Arg Gln Arg Xaa
1               5                   10

<210> SEQ ID NO 117
<211> LENGTH: 14
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa stands for azetidine-3-carboxylic acid.
<220> FEATURE:
<221> NAME/KEY: MISC_FEATURE
<222> LOCATION: (5)..(5)
<223> OTHER INFORMATION: Xaa stands for cyclohexylalanine.
<220> FEATURE:
<221> NAME/KEY: MISC_FEATURE
<222> LOCATION: (6)..(6)
<223> OTHER INFORMATION: Xaa stands for cyclohexylalanine.
<220> FEATURE:
<221> NAME/KEY: MISC_FEATURE
<222> LOCATION: (9)..(9)
<223> OTHER INFORMATION: Xaa stands for Aib.
<220> FEATURE:
<221> NAME/KEY: MISC_FEATURE
<222> LOCATION: (14)..(14)
<223> OTHER INFORMATION: Xaa stands for cyclohexylalanine.
<220> FEATURE:
<221> NAME/KEY: MOD_RES
<222> LOCATION: (14)..(14)
<223> OTHER INFORMATION: AMIDATION

<400> SEQUENCE: 117

Ser Xaa Arg His Xaa Xaa Asn Leu Xaa Thr Arg Gln Arg Xaa
1               5                   10

<210> SEQ ID NO 118
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: binding
<222> LOCATION: (1)..(2)
<223> OTHER INFORMATION: -CONH- is replaced by -CH=CH- (E type).
<220> FEATURE:
<221> NAME/KEY: MISC_FEATURE
<222> LOCATION: (5)..(5)
<223> OTHER INFORMATION: Xaa stands for cyclohexylalanine.
<220> FEATURE:
<221> NAME/KEY: MISC_FEATURE
<222> LOCATION: (6)..(6)
<223> OTHER INFORMATION: Xaa stands for cyclohexylalanine.
<220> FEATURE:
<221> NAME/KEY: MISC_FEATURE
<222> LOCATION: (9)..(9)
<223> OTHER INFORMATION: Xaa stands for Aib.
<220> FEATURE:
<221> NAME/KEY: MISC_FEATURE
<222> LOCATION: (14)..(14)
<223> OTHER INFORMATION: Xaa stands for cyclohexylalanine.
<220> FEATURE:
<221> NAME/KEY: MOD_RES
<222> LOCATION: (14)..(14)
<223> OTHER INFORMATION: AMIDATION

<400> SEQUENCE: 118

Gly Leu Arg His Xaa Xaa Asn Leu Xaa Thr Arg Gln Arg Xaa
1               5                   10
```

```
<210> SEQ ID NO 119
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa stands for alpha-methylproline.
<220> FEATURE:
<221> NAME/KEY: MISC_FEATURE
<222> LOCATION: (5)..(5)
<223> OTHER INFORMATION: Xaa stands for cyclohexylalanine.
<220> FEATURE:
<221> NAME/KEY: MISC_FEATURE
<222> LOCATION: (6)..(6)
<223> OTHER INFORMATION: Xaa stands for cyclohexylalanine.
<220> FEATURE:
<221> NAME/KEY: MISC_FEATURE
<222> LOCATION: (9)..(9)
<223> OTHER INFORMATION: Xaa stands for Aib.
<220> FEATURE:
<221> NAME/KEY: MISC_FEATURE
<222> LOCATION: (14)..(14)
<223> OTHER INFORMATION: Xaa stands for cyclohexylalanine.
<220> FEATURE:
<221> NAME/KEY: MOD_RES
<222> LOCATION: (14)..(14)
<223> OTHER INFORMATION: AMIDATION

<400> SEQUENCE: 119

Ser Xaa Arg His Xaa Xaa Asn Leu Xaa Thr Arg Gln Arg Xaa
1               5                   10

<210> SEQ ID NO 120
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa stands for gamma-aminobutyric acid.
<220> FEATURE:
<221> NAME/KEY: MISC_FEATURE
<222> LOCATION: (5)..(5)
<223> OTHER INFORMATION: Xaa stands for cyclohexylalanine.
<220> FEATURE:
<221> NAME/KEY: MISC_FEATURE
<222> LOCATION: (6)..(6)
<223> OTHER INFORMATION: Xaa stands for cyclohexylalanine.
<220> FEATURE:
<221> NAME/KEY: MISC_FEATURE
<222> LOCATION: (9)..(9)
<223> OTHER INFORMATION: Xaa stands for Aib.
<220> FEATURE:
<221> NAME/KEY: MISC_FEATURE
<222> LOCATION: (14)..(14)
<223> OTHER INFORMATION: Xaa stands for cyclohexylalanine.
<220> FEATURE:
<221> NAME/KEY: MOD_RES
<222> LOCATION: (14)..(14)
<223> OTHER INFORMATION: AMIDATION

<400> SEQUENCE: 120

Ser Xaa Arg His Xaa Xaa Asn Leu Xaa Thr Arg Gln Arg Xaa
```

```
<210> SEQ ID NO 121
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa stands for beta-alanine.
<220> FEATURE:
<221> NAME/KEY: MISC_FEATURE
<222> LOCATION: (4)..(4)
<223> OTHER INFORMATION: Xaa stands for 4-pyridylalanine.
<220> FEATURE:
<221> NAME/KEY: MISC_FEATURE
<222> LOCATION: (5)..(5)
<223> OTHER INFORMATION: Xaa stands for cyclohexylalanine.
<220> FEATURE:
<221> NAME/KEY: MISC_FEATURE
<222> LOCATION: (6)..(6)
<223> OTHER INFORMATION: Xaa stands for Aib.
<220> FEATURE:
<221> NAME/KEY: MISC_FEATURE
<222> LOCATION: (9)..(9)
<223> OTHER INFORMATION: Xaa stands for Aib.
<220> FEATURE:
<221> NAME/KEY: MISC_FEATURE
<222> LOCATION: (14)..(14)
<223> OTHER INFORMATION: Xaa stands for cyclohexylalanine.
<220> FEATURE:
<221> NAME/KEY: MOD_RES
<222> LOCATION: (14)..(14)
<223> OTHER INFORMATION: AMIDATION

<400> SEQUENCE: 121

Ser Xaa Arg Xaa Xaa Xaa Asn Lys Xaa Thr Arg Gln Arg Xaa
1               5                   10

<210> SEQ ID NO 122
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa stands for beta-alanine.
<220> FEATURE:
<221> NAME/KEY: MISC_FEATURE
<222> LOCATION: (4)..(4)
<223> OTHER INFORMATION: Xaa stands for 4-pyridylalanine.
<220> FEATURE:
<221> NAME/KEY: MISC_FEATURE
<222> LOCATION: (5)..(5)
<223> OTHER INFORMATION: Xaa stands for cyclohexylalanine.
<220> FEATURE:
<221> NAME/KEY: MISC_FEATURE
<222> LOCATION: (6)..(6)
<223> OTHER INFORMATION: Xaa stands for Aib.
<220> FEATURE:
<221> NAME/KEY: MISC_FEATURE
<222> LOCATION: (9)..(9)
<223> OTHER INFORMATION: Xaa stands for Aib.
<220> FEATURE:
```

-continued

```
<221> NAME/KEY: MISC_FEATURE
<222> LOCATION: (14)..(14)
<223> OTHER INFORMATION: Xaa stands for cyclohexylalanine.
<220> FEATURE:
<221> NAME/KEY: MOD_RES
<222> LOCATION: (14)..(14)
<223> OTHER INFORMATION: AMIDATION

<400> SEQUENCE: 122

Glu Xaa Arg Xaa Xaa Xaa Asn Lys Xaa Thr Arg Gln Arg Xaa
1               5                   10

<210> SEQ ID NO 123
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa stands for Aib.
<220> FEATURE:
<221> NAME/KEY: MISC_FEATURE
<222> LOCATION: (4)..(4)
<223> OTHER INFORMATION: Xaa stands for 4-pyridylalanine.
<220> FEATURE:
<221> NAME/KEY: MISC_FEATURE
<222> LOCATION: (5)..(5)
<223> OTHER INFORMATION: Xaa stands for cyclohexylalanine.
<220> FEATURE:
<221> NAME/KEY: MISC_FEATURE
<222> LOCATION: (6)..(6)
<223> OTHER INFORMATION: Xaa stands for Aib.
<220> FEATURE:
<221> NAME/KEY: MISC_FEATURE
<222> LOCATION: (9)..(9)
<223> OTHER INFORMATION: Xaa stands for Aib.
<220> FEATURE:
<221> NAME/KEY: MISC_FEATURE
<222> LOCATION: (14)..(14)
<223> OTHER INFORMATION: Xaa stands for cyclohexylalanine.
<220> FEATURE:
<221> NAME/KEY: MOD_RES
<222> LOCATION: (14)..(14)
<223> OTHER INFORMATION: AMIDATION

<400> SEQUENCE: 123

Ser Xaa Arg Xaa Xaa Xaa Asn Lys Xaa Thr Arg Gln Arg Xaa
1               5                   10

<210> SEQ ID NO 124
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa stands for isovaline.
<220> FEATURE:
<221> NAME/KEY: MISC_FEATURE
<222> LOCATION: (4)..(4)
<223> OTHER INFORMATION: Xaa stands for 4-pyridylalanine.
<220> FEATURE:
<221> NAME/KEY: MISC_FEATURE
```

<222> LOCATION: (5)..(5)
<223> OTHER INFORMATION: Xaa stands for cyclohexylalanine.
<220> FEATURE:
<221> NAME/KEY: MISC_FEATURE
<222> LOCATION: (6)..(6)
<223> OTHER INFORMATION: Xaa stands for Aib.
<220> FEATURE:
<221> NAME/KEY: MISC_FEATURE
<222> LOCATION: (9)..(9)
<223> OTHER INFORMATION: Xaa stands for Aib.
<220> FEATURE:
<221> NAME/KEY: MISC_FEATURE
<222> LOCATION: (14)..(14)
<223> OTHER INFORMATION: Xaa stands for cyclohexylalanine.
<220> FEATURE:
<221> NAME/KEY: MOD_RES
<222> LOCATION: (14)..(14)
<223> OTHER INFORMATION: AMIDATION

<400> SEQUENCE: 124

Ser Xaa Arg Xaa Xaa Xaa Asn Lys Xaa Thr Arg Gln Arg Xaa
1               5                   10

<210> SEQ ID NO 125
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa stands for 3-aminobutanoic acid.
<220> FEATURE:
<221> NAME/KEY: MISC_FEATURE
<222> LOCATION: (4)..(4)
<223> OTHER INFORMATION: Xaa stands for 4-pyridylalanine.
<220> FEATURE:
<221> NAME/KEY: MISC_FEATURE
<222> LOCATION: (5)..(5)
<223> OTHER INFORMATION: Xaa stands for cyclohexylalanine.
<220> FEATURE:
<221> NAME/KEY: MISC_FEATURE
<222> LOCATION: (6)..(6)
<223> OTHER INFORMATION: Xaa stands for Aib.
<220> FEATURE:
<221> NAME/KEY: MISC_FEATURE
<222> LOCATION: (9)..(9)
<223> OTHER INFORMATION: Xaa stands for Aib.
<220> FEATURE:
<221> NAME/KEY: MISC_FEATURE
<222> LOCATION: (14)..(14)
<223> OTHER INFORMATION: Xaa stands for cyclohexylalanine.
<220> FEATURE:
<221> NAME/KEY: MOD_RES
<222> LOCATION: (14)..(14)
<223> OTHER INFORMATION: AMIDATION

<400> SEQUENCE: 125

Ser Xaa Arg Xaa Xaa Xaa Asn Lys Xaa Thr Arg Gln Arg Xaa
1               5                   10

<210> SEQ ID NO 126
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)

```
<223> OTHER INFORMATION: ACETYLATION
<220> FEATURE:
<221> NAME/KEY: MISC_FEATURE
<222> LOCATION: (2)..(2)
<223> OTHER INFORMATION: Xaa stands for beta-homoalanine.
<220> FEATURE:
<221> NAME/KEY: MISC_FEATURE
<222> LOCATION: (4)..(4)
<223> OTHER INFORMATION: Xaa stands for 4-pyridylalanine.
<220> FEATURE:
<221> NAME/KEY: MISC_FEATURE
<222> LOCATION: (5)..(5)
<223> OTHER INFORMATION: Xaa stands for cyclohexylalanine.
<220> FEATURE:
<221> NAME/KEY: MISC_FEATURE
<222> LOCATION: (6)..(6)
<223> OTHER INFORMATION: Xaa stands for Aib.
<220> FEATURE:
<221> NAME/KEY: MISC_FEATURE
<222> LOCATION: (9)..(9)
<223> OTHER INFORMATION: Xaa stands for Aib.
<220> FEATURE:
<221> NAME/KEY: MISC_FEATURE
<222> LOCATION: (14)..(14)
<223> OTHER INFORMATION: Xaa stands for cyclohexylalanine.
<220> FEATURE:
<221> NAME/KEY: MOD_RES
<222> LOCATION: (14)..(14)
<223> OTHER INFORMATION: AMIDATION

<400> SEQUENCE: 126

Ser Xaa Arg Xaa Xaa Xaa Asn Lys Xaa Thr Arg Gln Arg Xaa
1               5                   10

<210> SEQ ID NO 127
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for 4-guanidinomethylbenzoyl
      isovaline.
<220> FEATURE:
<221> NAME/KEY: MISC_FEATURE
<222> LOCATION: (3)..(3)
<223> OTHER INFORMATION: Xaa stands for cyclohexylalanine.
<220> FEATURE:
<221> NAME/KEY: MISC_FEATURE
<222> LOCATION: (4)..(4)
<223> OTHER INFORMATION: Xaa stands for Aib.
<220> FEATURE:
<221> NAME/KEY: MISC_FEATURE
<222> LOCATION: (7)..(7)
<223> OTHER INFORMATION: Xaa stands for Aib.
<220> FEATURE:
<221> NAME/KEY: MISC_FEATURE
<222> LOCATION: (12)..(12)
<223> OTHER INFORMATION: Xaa stands for cyclohexylalanine.
<220> FEATURE:
<221> NAME/KEY: MOD_RES
<222> LOCATION: (12)..(12)
<223> OTHER INFORMATION: AMIDATION

<400> SEQUENCE: 127

Xaa His Xaa Xaa Asn Lys Xaa Thr Arg Gln Arg Xaa
1               5                   10

<210> SEQ ID NO 128
<211> LENGTH: 14
<212> TYPE: PRT
<213> ORGANISM: Artificial Sequence
<220> FEATURE:
```

```
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for 4-imidazolecarbonyl serine.
<220> FEATURE:
<221> NAME/KEY: MISC_FEATURE
<222> LOCATION: (2)..(2)
<223> OTHER INFORMATION: Xaa stands for Aib.
<220> FEATURE:
<221> NAME/KEY: MISC_FEATURE
<222> LOCATION: (3)..(3)
<223> OTHER INFORMATION: Xaa stands for isovaline.
<220> FEATURE:
<221> NAME/KEY: MISC_FEATURE
<222> LOCATION: (4)..(4)
<223> OTHER INFORMATION: Xaa stands for 4-pyridylalanine.
<220> FEATURE:
<221> NAME/KEY: MISC_FEATURE
<222> LOCATION: (5)..(5)
<223> OTHER INFORMATION: Xaa stands for cyclohexylalanine.
<220> FEATURE:
<221> NAME/KEY: MISC_FEATURE
<222> LOCATION: (6)..(6)
<223> OTHER INFORMATION: Xaa stands for Aib.
<220> FEATURE:
<221> NAME/KEY: MISC_FEATURE
<222> LOCATION: (9)..(9)
<223> OTHER INFORMATION: Xaa stands for Aib.
<220> FEATURE:
<221> NAME/KEY: MISC_FEATURE
<222> LOCATION: (14)..(14)
<223> OTHER INFORMATION: Xaa stands for cyclohexylalanine.
<220> FEATURE:
<221> NAME/KEY: MOD_RES
<222> LOCATION: (14)..(14)
<223> OTHER INFORMATION: AMIDATION

<400> SEQUENCE: 128

Xaa Xaa Xaa Xaa Xaa Xaa Asn Lys Xaa Thr Arg Gln Arg Xaa
1               5                   10

<210> SEQ ID NO 129
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa stands for Acp.
<220> FEATURE:
<221> NAME/KEY: MOD_RES
<222> LOCATION: (15)..(15)
<223> OTHER INFORMATION: AMIDATION

<400> SEQUENCE: 129

Ile Lys Xaa Arg Ala Tyr Ile Asn Leu Ile Thr Arg Gln Arg Tyr
1               5                   10                  15

<210> SEQ ID NO 130
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for 4-aminomethylbenzoyl arginine.
<220> FEATURE:
<221> NAME/KEY: MISC_FEATURE
<222> LOCATION: (8)..(8)
<223> OTHER INFORMATION: Xaa stands for Abu.
```

```
<220> FEATURE:
<221> NAME/KEY: MOD_RES
<222> LOCATION: (12)..(12)
<223> OTHER INFORMATION: AMIDATION

<400> SEQUENCE: 130

Xaa Ala Tyr Ile Asn Leu Ile Xaa Arg Gln Arg Tyr
1               5                   10

<210> SEQ ID NO 131
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: NON_TER
<222> LOCATION: (4)..(4)

<400> SEQUENCE: 131

Arg Tyr Tyr Ala
1

<210> SEQ ID NO 132
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: NON_TER
<222> LOCATION: (5)..(5)

<400> SEQUENCE: 132

Asn Arg Tyr Tyr Ala
1               5

<210> SEQ ID NO 133
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: NON_TER
<222> LOCATION: (6)..(6)

<400> SEQUENCE: 133

Leu Asn Arg Tyr Tyr Ala
1               5

<210> SEQ ID NO 134
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: NON_TER
<222> LOCATION: (7)..(7)

<400> SEQUENCE: 134

Glu Leu Asn Arg Tyr Tyr Ala
1               5

<210> SEQ ID NO 135
<211> LENGTH: 8
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: NON_TER
<222> LOCATION: (8)..(8)

<400> SEQUENCE: 135

Glu Glu Leu Asn Arg Tyr Tyr Ala
1               5

<210> SEQ ID NO 136
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: NON_TER
<222> LOCATION: (9)..(9)

<400> SEQUENCE: 136

Pro Glu Glu Leu Asn Arg Tyr Tyr Ala
1               5

<210> SEQ ID NO 137
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: NON_TER
<222> LOCATION: (10)..(10)

<400> SEQUENCE: 137

Ser Pro Glu Glu Leu Asn Arg Tyr Tyr Ala
1               5                   10

<210> SEQ ID NO 138
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: NON_TER
<222> LOCATION: (11)..(11)

<400> SEQUENCE: 138

Ala Ser Pro Glu Glu Leu Asn Arg Tyr Tyr Ala
1               5                   10

<210> SEQ ID NO 139
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: NON_TER
<222> LOCATION: (12)..(12)

<400> SEQUENCE: 139

Asp Ala Ser Pro Glu Glu Leu Asn Arg Tyr Tyr Ala
1               5                   10

<210> SEQ ID NO 140
<211> LENGTH: 13
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: NON_TER
<222> LOCATION: (13)..(13)

<400> SEQUENCE: 140

Glu Asp Ala Ser Pro Glu Glu Leu Asn Arg Tyr Tyr Ala
1               5                   10

<210> SEQ ID NO 141
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: NON_TER
<222> LOCATION: (14)..(14)

<400> SEQUENCE: 141

Gly Glu Asp Ala Ser Pro Glu Glu Leu Asn Arg Tyr Tyr Ala
1               5                   10

<210> SEQ ID NO 142
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: NON_TER
<222> LOCATION: (15)..(15)

<400> SEQUENCE: 142

Pro Gly Glu Asp Ala Ser Pro Glu Glu Leu Asn Arg Tyr Tyr Ala
1               5                   10                  15

<210> SEQ ID NO 143
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: NON_TER
<222> LOCATION: (16)..(16)

<400> SEQUENCE: 143

Ala Pro Gly Glu Asp Ala Ser Pro Glu Glu Leu Asn Arg Tyr Tyr Ala
1               5                   10                  15

<210> SEQ ID NO 144
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: NON_TER
<222> LOCATION: (17)..(17)

<400> SEQUENCE: 144

Glu Ala Pro Gly Glu Asp Ala Ser Pro Glu Glu Leu Asn Arg Tyr Tyr
1               5                   10                  15

Ala
```

```
<210> SEQ ID NO 145
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: NON_TER
<222> LOCATION: (18)..(18)

<400> SEQUENCE: 145

Pro Glu Ala Pro Gly Glu Asp Ala Ser Pro Glu Glu Leu Asn Arg Tyr
1               5                   10                  15

Tyr Ala

<210> SEQ ID NO 146
<211> LENGTH: 19
<212> TYPE: PRT
<213> ORGANISM: Artificial Sequence
<220> FEATURE:
<223> OTHER INFORMATION: Synthetic peptide
<220> FEATURE:
<221> NAME/KEY: NON_TER
<222> LOCATION: (19)..(19)

<400> SEQUENCE: 146

Lys Pro Glu Ala Pro Gly Glu Asp Ala Ser Pro Glu Glu Leu Asn Arg
1               5                   10                  15

Tyr Tyr Ala

<210> SEQ ID NO 147
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: NON_TER
<222> LOCATION: (20)..(20)

<400> SEQUENCE: 147

Ile Lys Pro Glu Ala Pro Gly Glu Asp Ala Ser Pro Glu Glu Leu Asn
1               5                   10                  15

Arg Tyr Tyr Ala
            20

<210> SEQ ID NO 148
<211> LENGTH: 21
<212> TYPE: PRT
<213> ORGANISM: Artificial Sequence
<220> FEATURE:
<223> OTHER INFORMATION: Synthetic peptide
<220> FEATURE:
<221> NAME/KEY: NON_TER
<222> LOCATION: (21)..(21)

<400> SEQUENCE: 148

Pro Ile Lys Pro Glu Ala Pro Gly Glu Asp Ala Ser Pro Glu Glu Leu
1               5                   10                  15

Asn Arg Tyr Tyr Ala
            20

<210> SEQ ID NO 149
<211> LENGTH: 22
<212> TYPE: PRT
<213> ORGANISM: Artificial Sequence
<220> FEATURE:
```

```
<223> OTHER INFORMATION: Synthetic peptide
<220> FEATURE:
<221> NAME/KEY: NON_TER
<222> LOCATION: (22)..(22)

<400> SEQUENCE: 149

Tyr Pro Ile Lys Pro Glu Ala Pro Gly Glu Asp Ala Ser Pro Glu Glu
1               5                   10                  15

Leu Asn Arg Tyr Tyr Ala
            20

<210> SEQ ID NO 150
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for Fmoc-arginine protected by Pbf.
<220> FEATURE:
<221> NAME/KEY: MISC_FEATURE
<222> LOCATION: (3)..(3)
<223> OTHER INFORMATION: Xaa stands for tyrosine protected by tert-
      Butyl.
<220> FEATURE:
<221> NAME/KEY: MISC_FEATURE
<222> LOCATION: (5)..(5)
<223> OTHER INFORMATION: Xaa stands for asparagine protected by Trt.
<220> FEATURE:
<221> NAME/KEY: MISC_FEATURE
<222> LOCATION: (8)..(8)
<223> OTHER INFORMATION: Xaa stands for threonine protected by tert-
      Butyl.
<220> FEATURE:
<221> NAME/KEY: MISC_FEATURE
<222> LOCATION: (9)..(9)
<223> OTHER INFORMATION: Xaa stands for arginine protected by Pbf.
<220> FEATURE:
<221> NAME/KEY: MISC_FEATURE
<222> LOCATION: (10)..(10)
<223> OTHER INFORMATION: Xaa stands for glutamine protected by Trt.
<220> FEATURE:
<221> NAME/KEY: MISC_FEATURE
<222> LOCATION: (11)..(11)
<223> OTHER INFORMATION: Xaa stands for arginine protected by Pbf.
<220> FEATURE:
<221> NAME/KEY: MISC_FEATURE
<222> LOCATION: (12)..(12)
<223> OTHER INFORMATION: Xaa stands for tyrosine protected by tert-
      Butyl.

<400> SEQUENCE: 150

Xaa Ala Xaa Ile Xaa Leu Ile Xaa Xaa Xaa Xaa Xaa
1               5                   10

<210> SEQ ID NO 151
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for arginine protected by Pbf.
<220> FEATURE:
<221> NAME/KEY: MISC_FEATURE
<222> LOCATION: (2)..(2)
<223> OTHER INFORMATION: Xaa stands for tyrosine protected by tert-
      Butyl.
<220> FEATURE:
<221> NAME/KEY: MISC_FEATURE
```

```
<222> LOCATION: (3)..(3)
<223> OTHER INFORMATION: Xaa stands for tyrosine protected by tert-
      Butyl.
<220> FEATURE:
<221> NAME/KEY: MISC_FEATURE
<222> LOCATION: (5)..(5)
<223> OTHER INFORMATION: Xaa stands for serine protected by tert-Butyl.
<220> FEATURE:
<221> NAME/KEY: MISC_FEATURE
<222> LOCATION: (7)..(7)
<223> OTHER INFORMATION: Xaa stands for arginine protected by Pbf.
<220> FEATURE:
<221> NAME/KEY: MISC_FEATURE
<222> LOCATION: (9)..(9)
<223> OTHER INFORMATION: Xaa stands for tyrosine protected by tert-
      Butyl.
<220> FEATURE:
<221> NAME/KEY: MISC_FEATURE
<222> LOCATION: (11)..(11)
<223> OTHER INFORMATION: Xaa stands for asparagine protected by Trt.
<220> FEATURE:
<221> NAME/KEY: MISC_FEATURE
<222> LOCATION: (14)..(14)
<223> OTHER INFORMATION: Xaa stands for threonine protected by tert-
      Butyl.
<220> FEATURE:
<221> NAME/KEY: MISC_FEATURE
<222> LOCATION: (15)..(15)
<223> OTHER INFORMATION: Xaa stands for arginine protected by Pbf.
<220> FEATURE:
<221> NAME/KEY: MISC_FEATURE
<222> LOCATION: (16)..(16)
<223> OTHER INFORMATION: Xaa stands for glutamine protected by Trt.
<220> FEATURE:
<221> NAME/KEY: MISC_FEATURE
<222> LOCATION: (17)..(17)
<223> OTHER INFORMATION: Xaa stands for arginine protected by Pbf.
<220> FEATURE:
<221> NAME/KEY: MISC_FEATURE
<222> LOCATION: (18)..(18)
<223> OTHER INFORMATION: Xaa stands for tyrosine protected by tert-
      Butyl.

<400> SEQUENCE: 151

Xaa Xaa Xaa Ala Xaa Leu Xaa Ala Xaa Ile Xaa Leu Ile Xaa Xaa Xaa
1               5                   10                  15

Xaa Xaa

<210> SEQ ID NO 152
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for 4-aminomethylbenzoylarginine.
<220> FEATURE:
<221> NAME/KEY: MOD_RES
<222> LOCATION: (12)..(12)
<223> OTHER INFORMATION: AMIDATION

<400> SEQUENCE: 152

Xaa Ala Glu Ile Asn Leu Lys Thr Arg Gln Arg Tyr
1               5                   10

<210> SEQ ID NO 153
<211> LENGTH: 12
<212> TYPE: PRT
<213> ORGANISM: Artificial Sequence
<220> FEATURE:
<223> OTHER INFORMATION: Synthetic peptide
<220> FEATURE:
```

```
<221> NAME/KEY: MISC_FEATURE
<222> LOCATION: (1)..(1)
<223> OTHER INFORMATION: Xaa stands for N,N'-bis-Boc-
      guanidinomethylbenzoyl arginine protected by Pbf.
<220> FEATURE:
<221> NAME/KEY: MISC_FEATURE
<222> LOCATION: (3)..(3)
<223> OTHER INFORMATION: Xaa stands for tyrosine protected by tert-
      Butyl.
<220> FEATURE:
<221> NAME/KEY: MISC_FEATURE
<222> LOCATION: (5)..(5)
<223> OTHER INFORMATION: Xaa stands for asparagine protected by Trt.
<220> FEATURE:
<221> NAME/KEY: MISC_FEATURE
<222> LOCATION: (8)..(8)
<223> OTHER INFORMATION: Xaa stands for threonine protected by tert-
      Butyl.
<220> FEATURE:
<221> NAME/KEY: MISC_FEATURE
<222> LOCATION: (9)..(9)
<223> OTHER INFORMATION: Xaa stands for arginine protected by Pbf.
<220> FEATURE:
<221> NAME/KEY: MISC_FEATURE
<222> LOCATION: (10)..(10)
<223> OTHER INFORMATION: Xaa stands for glutamine protected by Trt.
<220> FEATURE:
<221> NAME/KEY: MISC_FEATURE
<222> LOCATION: (11)..(11)
<223> OTHER INFORMATION: Xaa stands for arginine protected by Pbf.
<220> FEATURE:
<221> NAME/KEY: MISC_FEATURE
<222> LOCATION: (12)..(12)
<223> OTHER INFORMATION: Xaa stands for tyrosine protected by tert-
      Butyl.

<400> SEQUENCE: 153

Xaa Ala Xaa Ile Xaa Leu Ile Xaa Xaa Xaa Xaa Xaa
1               5                   10

<210> SEQ ID NO 154
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for Fmoc-arginine protected by Pbf.
<220> FEATURE:
<221> NAME/KEY: MISC_FEATURE
<222> LOCATION: (3)..(3)
<223> OTHER INFORMATION: Xaa stands for tyrosine protected by tert-
      Butyl.
<220> FEATURE:
<221> NAME/KEY: MISC_FEATURE
<222> LOCATION: (5)..(5)
<223> OTHER INFORMATION: Xaa stands for asparagine protected by Trt.
<220> FEATURE:
<221> NAME/KEY: MISC_FEATURE
<222> LOCATION: (7)..(7)
<223> OTHER INFORMATION: Xaa stands for Ile-Thr(gamma Me, Me Pro).
<220> FEATURE:
<221> NAME/KEY: MOD_RES
<222> LOCATION: (7)..(7)
<223> OTHER INFORMATION: HYDROXYLATION

<400> SEQUENCE: 154

Xaa Ala Xaa Ile Xaa Leu Xaa
1               5

<210> SEQ ID NO 155
<211> LENGTH: 7
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for Fmoc-4-aminomethylbenzoyl
      arginine protected by Pbf.
<220> FEATURE:
<221> NAME/KEY: MISC_FEATURE
<222> LOCATION: (3)..(3)
<223> OTHER INFORMATION: Xaa stands for tyrosine protected by tert-
      Butyl.
<220> FEATURE:
<221> NAME/KEY: MISC_FEATURE
<222> LOCATION: (5)..(5)
<223> OTHER INFORMATION: Xaa stands for asparagine protected by Trt.
<220> FEATURE:
<221> NAME/KEY: MISC_FEATURE
<222> LOCATION: (7)..(7)
<223> OTHER INFORMATION: Xaa stands for Ile-Thr(gamma Me, Me Pro).

<400> SEQUENCE: 155

Xaa Ala Xaa Ile Xaa Leu Xaa
1               5

<210> SEQ ID NO 156
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for Fmoc-arginine protected by Pbf.
<220> FEATURE:
<221> NAME/KEY: MISC_FEATURE
<222> LOCATION: (2)..(2)
<223> OTHER INFORMATION: Xaa stands for glutamine protected by Trt.
<220> FEATURE:
<221> NAME/KEY: MISC_FEATURE
<222> LOCATION: (3)..(3)
<223> OTHER INFORMATION: Xaa stands for arginine protected by Pbf.

<400> SEQUENCE: 156

Xaa Xaa Xaa Phe
1

<210> SEQ ID NO 157
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for Fmoc-homoarginine protected by
      BOC.
<220> FEATURE:
<221> NAME/KEY: MISC_FEATURE
<222> LOCATION: (2)..(2)
<223> OTHER INFORMATION: Xaa stands for glutamine protected by Trt.
<220> FEATURE:
<221> NAME/KEY: MISC_FEATURE
<222> LOCATION: (3)..(3)
<223> OTHER INFORMATION: Xaa stands for arginine protected by Pbf.
<220> FEATURE:
<221> NAME/KEY: MISC_FEATURE
<222> LOCATION: (4)..(4)
<223> OTHER INFORMATION: Xaa stand for tyrosine protected by tert-Butyl.

<400> SEQUENCE: 157
```

Xaa Xaa Xaa Xaa
1

<210> SEQ ID NO 158
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for arginine protected by Pbf.
<220> FEATURE:
<221> NAME/KEY: MISC_FEATURE
<222> LOCATION: (3)..(3)
<223> OTHER INFORMATION: Xaa stands for tyrosine protected by tert-
      Butyl.
<220> FEATURE:
<221> NAME/KEY: MISC_FEATURE
<222> LOCATION: (5)..(5)
<223> OTHER INFORMATION: Xaa stands for asparagine protected by Trt.
<220> FEATURE:
<221> NAME/KEY: MISC_FEATURE
<222> LOCATION: (8)..(8)
<223> OTHER INFORMATION: Xaa stands for threonine protected by tert-
      Butyl.
<220> FEATURE:
<221> NAME/KEY: MISC_FEATURE
<222> LOCATION: (9)..(9)
<223> OTHER INFORMATION: Xaa stands for arginine protected by Pbf.
<220> FEATURE:
<221> NAME/KEY: MISC_FEATURE
<222> LOCATION: (10)..(10)
<223> OTHER INFORMATION: Xaa stands for glutamine protected by Trt.
<220> FEATURE:
<221> NAME/KEY: MISC_FEATURE
<222> LOCATION: (11)..(11)
<223> OTHER INFORMATION: Xaa stands for arginine protected by Pbf.
<220> FEATURE:
<221> NAME/KEY: MISC_FEATURE
<222> LOCATION: (12)..(12)
<223> OTHER INFORMATION: Xaa stands for tyrosine protected by tert-
      Butyl.

<400> SEQUENCE: 158

Xaa Ala Xaa Ile Xaa Leu Ile Xaa Xaa Xaa Xaa Xaa
1               5                   10

<210> SEQ ID NO 159
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for 4-aminomethylbenzoyl arginine
      protected by Pbf.
<220> FEATURE:
<221> NAME/KEY: MISC_FEATURE
<222> LOCATION: (3)..(3)
<223> OTHER INFORMATION: Xaa stands for tyrosine protected by tert-
      Butyl.
<220> FEATURE:
<221> NAME/KEY: MISC_FEATURE
<222> LOCATION: (5)..(5)
<223> OTHER INFORMATION: Xaa stands for asparagine protected by Trt.
<220> FEATURE:
<221> NAME/KEY: MISC_FEATURE
<222> LOCATION: (8)..(8)
<223> OTHER INFORMATION: Xaa stands for threonine protected by tert-
      Butyl.
<220> FEATURE:
<221> NAME/KEY: MISC_FEATURE

```
<222> LOCATION: (9)..(9)
<223> OTHER INFORMATION: Xaa stands for arginine protected by Pbf.
<220> FEATURE:
<221> NAME/KEY: MISC_FEATURE
<222> LOCATION: (10)..(10)
<223> OTHER INFORMATION: Xaa stands for glutamine protected by Trt.
<220> FEATURE:
<221> NAME/KEY: MISC_FEATURE
<222> LOCATION: (11)..(11)
<223> OTHER INFORMATION: Xaa stands for arginine protected by Pbf.
<220> FEATURE:
<221> NAME/KEY: MISC_FEATURE
<222> LOCATION: (12)..(12)
<223> OTHER INFORMATION: Xaa stands for tyrosine protected by tert-
      Butyl.

<400> SEQUENCE: 159

Xaa Ala Xaa Ile Xaa Leu Ile Xaa Xaa Xaa Xaa Xaa
1               5                   10

<210> SEQ ID NO 160
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for
      (4-N-Boc-N'-n-octyl-1-guanidinomethyl)benzoylarginine protected
      by Pbf.
<220> FEATURE:
<221> NAME/KEY: MISC_FEATURE
<222> LOCATION: (3)..(3)
<223> OTHER INFORMATION: Xaa stands for tyrosine protected by tert-
      Butyl.
<220> FEATURE:
<221> NAME/KEY: MISC_FEATURE
<222> LOCATION: (5)..(5)
<223> OTHER INFORMATION: Xaa stands for asparagine protected by Trt.
<220> FEATURE:
<221> NAME/KEY: MISC_FEATURE
<222> LOCATION: (8)..(8)
<223> OTHER INFORMATION: Xaa stands for threonine protected by tert-
      Butyl.
<220> FEATURE:
<221> NAME/KEY: MISC_FEATURE
<222> LOCATION: (9)..(9)
<223> OTHER INFORMATION: Xaa stands for arginine protected by Pbf.
<220> FEATURE:
<221> NAME/KEY: MISC_FEATURE
<222> LOCATION: (10)..(10)
<223> OTHER INFORMATION: Xaa stands for glutamine protected by Trt.
<220> FEATURE:
<221> NAME/KEY: MISC_FEATURE
<222> LOCATION: (11)..(11)
<223> OTHER INFORMATION: Xaa stands for arginine protected by Pbf.
<220> FEATURE:
<221> NAME/KEY: MISC_FEATURE
<222> LOCATION: (12)..(12)
<223> OTHER INFORMATION: Xaa stands for tyrosine protected by tert-
      Butyl.

<400> SEQUENCE: 160

Xaa Ala Xaa Ile Xaa Leu Ile Xaa Xaa Xaa Xaa Xaa
1               5                   10

<210> SEQ ID NO 161
<211> LENGTH: 4
<212> TYPE: PRT
<213> ORGANISM: Artificial Sequence
<220> FEATURE:
<223> OTHER INFORMATION: Synthetic peptide
<220> FEATURE:
```

```
<221> NAME/KEY: MISC_FEATURE
<222> LOCATION: (1)..(1)
<223> OTHER INFORMATION: Xaa stands for arginine protected by Pbf.
<220> FEATURE:
<221> NAME/KEY: MISC_FEATURE
<222> LOCATION: (2)..(2)
<223> OTHER INFORMATION: Xaa stands for glutamine protected by Trt.
<220> FEATURE:
<221> NAME/KEY: MISC_FEATURE
<222> LOCATION: (3)..(3)
<223> OTHER INFORMATION: Xaa stands for arginine protected by Pbf.
<220> FEATURE:
<221> NAME/KEY: MISC_FEATURE
<222> LOCATION: (4)..(4)
<223> OTHER INFORMATION: Xaa stands for tyrosine protected by tert-
      Butyl.

<400> SEQUENCE: 161

Xaa Xaa Xaa Xaa
1

<210> SEQ ID NO 162
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa stands for asparagine protected by Trt.
<220> FEATURE:
<221> NAME/KEY: MISC_FEATURE
<222> LOCATION: (5)..(5)
<223> OTHER INFORMATION: Xaa stands for threonine protected by tert-
      Butyl.
<220> FEATURE:
<221> NAME/KEY: MISC_FEATURE
<222> LOCATION: (6)..(6)
<223> OTHER INFORMATION: Xaa stands for arginine protected by Pbf.
<220> FEATURE:
<221> NAME/KEY: MISC_FEATURE
<222> LOCATION: (7)..(7)
<223> OTHER INFORMATION: Xaa stands for glutamine protected by Trt.
<220> FEATURE:
<221> NAME/KEY: MISC_FEATURE
<222> LOCATION: (8)..(8)
<223> OTHER INFORMATION: Xaa stands for arginine protected by Pbf.
<220> FEATURE:
<221> NAME/KEY: MISC_FEATURE
<222> LOCATION: (9)..(9)
<223> OTHER INFORMATION: Xaa stands for tyrosine protected by tert-
      Butyl.

<400> SEQUENCE: 162

Ala Xaa Leu Ile Xaa Xaa Xaa Xaa Xaa
1               5

<210> SEQ ID NO 163
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for Boc-4-aminomethylbenzoyl
      arginine protected by Pbf.
<220> FEATURE:
<221> NAME/KEY: MISC_FEATURE
<222> LOCATION: (3)..(3)
<223> OTHER INFORMATION: Xaa stands for tyrosine protected by tert-
      Butyl.
<220> FEATURE:
```

```
<221> NAME/KEY: MISC_FEATURE
<222> LOCATION: (5)..(5)
<223> OTHER INFORMATION: Xaa stands for asparagine protected by Trt.
<220> FEATURE:
<221> NAME/KEY: MISC_FEATURE
<222> LOCATION: (8)..(8)
<223> OTHER INFORMATION: Xaa stands for threonine protected by tert-
      Butyl.
<220> FEATURE:
<221> NAME/KEY: MISC_FEATURE
<222> LOCATION: (9)..(9)
<223> OTHER INFORMATION: Xaa stands for arginine protected by Pbf.
<220> FEATURE:
<221> NAME/KEY: MISC_FEATURE
<222> LOCATION: (10)..(10)
<223> OTHER INFORMATION: Xaa stands for glutamine protected by Trt.
<220> FEATURE:
<221> NAME/KEY: MISC_FEATURE
<222> LOCATION: (11)..(11)
<223> OTHER INFORMATION: Xaa stands for arginine protected by Pbf.
<220> FEATURE:
<221> NAME/KEY: MISC_FEATURE
<222> LOCATION: (12)..(12)
<223> OTHER INFORMATION: Xaa stands for tyrosine protected by tert-
      Butyl.

<400> SEQUENCE: 163

Xaa Ala Xaa Ala Xaa Leu Ile Xaa Xaa Xaa Xaa Xaa
1               5                   10

<210> SEQ ID NO 164
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for arginine protected by Pbf.
<220> FEATURE:
<221> NAME/KEY: MISC_FEATURE
<222> LOCATION: (2)..(2)
<223> OTHER INFORMATION: Xaa stands for histidine protected by Trt.
<220> FEATURE:
<221> NAME/KEY: MISC_FEATURE
<222> LOCATION: (3)..(3)
<223> OTHER INFORMATION: Xaa stands for cyclohexylalanine.
<220> FEATURE:
<221> NAME/KEY: MISC_FEATURE
<222> LOCATION: (4)..(4)
<223> OTHER INFORMATION: Xaa stands for cyclohexylalanine.
<220> FEATURE:
<221> NAME/KEY: MISC_FEATURE
<222> LOCATION: (5)..(5)
<223> OTHER INFORMATION: Xaa stands for asparagine protected by Trt.
<220> FEATURE:
<221> NAME/KEY: MISC_FEATURE
<222> LOCATION: (7)..(7)
<223> OTHER INFORMATION: Xaa stands for Aib.
<220> FEATURE:
<221> NAME/KEY: MISC_FEATURE
<222> LOCATION: (8)..(8)
<223> OTHER INFORMATION: Xaa stands for threonine protected by tert-
      Butyl.
<220> FEATURE:
<221> NAME/KEY: MISC_FEATURE
<222> LOCATION: (9)..(9)
<223> OTHER INFORMATION: Xaa stands for arginine protected by Pbf.
<220> FEATURE:
<221> NAME/KEY: MISC_FEATURE
<222> LOCATION: (10)..(10)
<223> OTHER INFORMATION: Xaa stands for glutamine protected by Trt.
<220> FEATURE:
<221> NAME/KEY: MISC_FEATURE
<222> LOCATION: (11)..(11)
<223> OTHER INFORMATION: Xaa stands for arginine protected by Pbf.
```

```
<220> FEATURE:
<221> NAME/KEY: MISC_FEATURE
<222> LOCATION: (12)..(12)
<223> OTHER INFORMATION: Xaa stands for cyclohexylalanine.

<400> SEQUENCE: 164

Xaa Xaa Xaa Xaa Xaa Leu Xaa Xaa Xaa Xaa Xaa Xaa
1               5                   10

<210> SEQ ID NO 165
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for benzoylarginine protected by
      Pbf.
<220> FEATURE:
<221> NAME/KEY: MISC_FEATURE
<222> LOCATION: (2)..(2)
<223> OTHER INFORMATION: Xaa stands for histidine protected by Pbf.
<220> FEATURE:
<221> NAME/KEY: MISC_FEATURE
<222> LOCATION: (3)..(3)
<223> OTHER INFORMATION: Xaa stands for cyclohexylalanine.
<220> FEATURE:
<221> NAME/KEY: MISC_FEATURE
<222> LOCATION: (4)..(4)
<223> OTHER INFORMATION: Xaa stands for cyclohexylalanine.
<220> FEATURE:
<221> NAME/KEY: MISC_FEATURE
<222> LOCATION: (5)..(5)
<223> OTHER INFORMATION: Xaa stands for asparagine protected by Trt.
<220> FEATURE:
<221> NAME/KEY: MISC_FEATURE
<222> LOCATION: (7)..(7)
<223> OTHER INFORMATION: Xaa stands for Aib.
<220> FEATURE:
<221> NAME/KEY: MISC_FEATURE
<222> LOCATION: (8)..(8)
<223> OTHER INFORMATION: Xaa stands for threonine protected by tert-
      Butyl.
<220> FEATURE:
<221> NAME/KEY: MISC_FEATURE
<222> LOCATION: (9)..(9)
<223> OTHER INFORMATION: Xaa stands for arginine protected by Pbf.
<220> FEATURE:
<221> NAME/KEY: MISC_FEATURE
<222> LOCATION: (10)..(10)
<223> OTHER INFORMATION: Xaa stands for glutamine protected by Trt.
<220> FEATURE:
<221> NAME/KEY: MISC_FEATURE
<222> LOCATION: (11)..(11)
<223> OTHER INFORMATION: Xaa stands for arginine protected by Pbf.
<220> FEATURE:
<221> NAME/KEY: MISC_FEATURE
<222> LOCATION: (12)..(12)
<223> OTHER INFORMATION: Xaa stands for cyclohexylalanine.

<400> SEQUENCE: 165

Xaa Xaa Xaa Xaa Xaa Leu Xaa Xaa Xaa Xaa Xaa Xaa
1               5                   10

<210> SEQ ID NO 166
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
```

```
<223> OTHER INFORMATION: Xaa stands for arginine protected by Pbf.
<220> FEATURE:
<221> NAME/KEY: MISC_FEATURE
<222> LOCATION: (2)..(2)
<223> OTHER INFORMATION: Xaa stands for glutamine protected by Trt.
<220> FEATURE:
<221> NAME/KEY: MISC_FEATURE
<222> LOCATION: (3)..(3)
<223> OTHER INFORMATION: Xaa stands for arginine protected by Pbf.
<220> FEATURE:
<221> NAME/KEY: MISC_FEATURE
<222> LOCATION: (4)..(4)
<223> OTHER INFORMATION: Xaa stands for cyclohexylalanine.

<400> SEQUENCE: 166

Xaa Xaa Xaa Xaa
1

<210> SEQ ID NO 167
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for Nle.
<220> FEATURE:
<221> NAME/KEY: MISC_FEATURE
<222> LOCATION: (2)..(2)
<223> OTHER INFORMATION: Xaa stands for histidine protected by Trt.
<220> FEATURE:
<221> NAME/KEY: MISC_FEATURE
<222> LOCATION: (3)..(3)
<223> OTHER INFORMATION: Xaa stands for cyclohexylalanine.
<220> FEATURE:
<221> NAME/KEY: MISC_FEATURE
<222> LOCATION: (4)..(4)
<223> OTHER INFORMATION: Xaa stands for cyclohexylalanine.
<220> FEATURE:
<221> NAME/KEY: MISC_FEATURE
<222> LOCATION: (5)..(5)
<223> OTHER INFORMATION: Xaa stands for asparagine protected by Trt.
<220> FEATURE:
<221> NAME/KEY: MISC_FEATURE
<222> LOCATION: (6)..(6)
<223> OTHER INFORMATION: Xaa stands for arginine protected by Pbf.
<220> FEATURE:
<221> NAME/KEY: MISC_FEATURE
<222> LOCATION: (7)..(7)
<223> OTHER INFORMATION: Xaa stands for cyclohexylalanine.
<220> FEATURE:
<221> NAME/KEY: MISC_FEATURE
<222> LOCATION: (8)..(8)
<223> OTHER INFORMATION: Xaa stands for threonine protected by tert-
      Butyl.
<220> FEATURE:
<221> NAME/KEY: MISC_FEATURE
<222> LOCATION: (9)..(9)
<223> OTHER INFORMATION: Xaa stands for arginine protected by Pbf.
<220> FEATURE:
<221> NAME/KEY: MISC_FEATURE
<222> LOCATION: (10)..(10)
<223> OTHER INFORMATION: Xaa stands for glutamine protected by Trt.
<220> FEATURE:
<221> NAME/KEY: MISC_FEATURE
<222> LOCATION: (11)..(11)
<223> OTHER INFORMATION: Xaa stands for arginine protected by Pbf.
<220> FEATURE:
<221> NAME/KEY: MISC_FEATURE
<222> LOCATION: (12)..(12)
<223> OTHER INFORMATION: Xaa stands for cyclohexylalanine.

<400> SEQUENCE: 167

Xaa Xaa Xaa Xaa Xaa Xaa Xaa Xaa Xaa Xaa Xaa Xaa
```

```
1               5                   10

<210> SEQ ID NO 168
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for 4-(N,N'-bis-Boc-
      guanidinomethyl)benzoyl Nle.
<220> FEATURE:
<221> NAME/KEY: MISC_FEATURE
<222> LOCATION: (2)..(2)
<223> OTHER INFORMATION: Xaa stands for Histidine protected by Trt.
<220> FEATURE:
<221> NAME/KEY: MISC_FEATURE
<222> LOCATION: (3)..(3)
<223> OTHER INFORMATION: Xaa stands for cyclohexylalanine.
<220> FEATURE:
<221> NAME/KEY: MISC_FEATURE
<222> LOCATION: (4)..(4)
<223> OTHER INFORMATION: Xaa stands for cyclohexylalanine.
<220> FEATURE:
<221> NAME/KEY: MISC_FEATURE
<222> LOCATION: (5)..(5)
<223> OTHER INFORMATION: Xaa stands for asparagine protected by Trt.
<220> FEATURE:
<221> NAME/KEY: MISC_FEATURE
<222> LOCATION: (6)..(6)
<223> OTHER INFORMATION: Xaa stands for arginine protected by Pbf.
<220> FEATURE:
<221> NAME/KEY: MISC_FEATURE
<222> LOCATION: (7)..(7)
<223> OTHER INFORMATION: Xaa stands for cyclohexylalanine.
<220> FEATURE:
<221> NAME/KEY: MISC_FEATURE
<222> LOCATION: (8)..(8)
<223> OTHER INFORMATION: Xaa stands for threonine protected by tert-
      Butyl.
<220> FEATURE:
<221> NAME/KEY: MISC_FEATURE
<222> LOCATION: (9)..(9)
<223> OTHER INFORMATION: Xaa stands for arginine protected by Pbf.
<220> FEATURE:
<221> NAME/KEY: MISC_FEATURE
<222> LOCATION: (10)..(10)
<223> OTHER INFORMATION: Xaa stands for glutamine protected by Trt.
<220> FEATURE:
<221> NAME/KEY: MISC_FEATURE
<222> LOCATION: (11)..(11)
<223> OTHER INFORMATION: Xaa stands for arginine protected by Pbf.
<220> FEATURE:
<221> NAME/KEY: MISC_FEATURE
<222> LOCATION: (12)..(12)
<223> OTHER INFORMATION: Xaa stands for cyclohexylalanine.

<400> SEQUENCE: 168

Xaa Xaa Xaa Xaa Xaa Xaa Xaa Xaa Xaa Xaa Xaa Xaa
1               5                   10

<210> SEQ ID NO 169
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for arginine protected by Pbf.
<220> FEATURE:
<221> NAME/KEY: MISC_FEATURE
<222> LOCATION: (2)..(2)
```

<223> OTHER INFORMATION: Xaa stands for Abu.
<220> FEATURE:
<221> NAME/KEY: MISC_FEATURE
<222> LOCATION: (3)..(3)
<223> OTHER INFORMATION: Xaa stands for cyclohexylalanine.
<220> FEATURE:
<221> NAME/KEY: MISC_FEATURE
<222> LOCATION: (4)..(4)
<223> OTHER INFORMATION: Xaa stands for cyclohexylalanine.
<220> FEATURE:
<221> NAME/KEY: MISC_FEATURE
<222> LOCATION: (5)..(5)
<223> OTHER INFORMATION: Xaa stands for asparagine protected by Trt.
<220> FEATURE:
<221> NAME/KEY: MISC_FEATURE
<222> LOCATION: (7)..(7)
<223> OTHER INFORMATION: Xaa stands for Aib.
<220> FEATURE:
<221> NAME/KEY: MISC_FEATURE
<222> LOCATION: (8)..(8)
<223> OTHER INFORMATION: Xaa stands for threonine protected by tert-
      Butyl.
<220> FEATURE:
<221> NAME/KEY: MISC_FEATURE
<222> LOCATION: (9)..(9)
<223> OTHER INFORMATION: Xaa stands for arginine protected by Pbf.
<220> FEATURE:
<221> NAME/KEY: MISC_FEATURE
<222> LOCATION: (10)..(10)
<223> OTHER INFORMATION: Xaa stands for glutamine protected by Trt.
<220> FEATURE:
<221> NAME/KEY: MISC_FEATURE
<222> LOCATION: (11)..(11)
<223> OTHER INFORMATION: Xaa stands for arginine protected by Pbf.
<220> FEATURE:
<221> NAME/KEY: MISC_FEATURE
<222> LOCATION: (12)..(12)
<223> OTHER INFORMATION: Xaa stands for cyclohexylalanine.

<400> SEQUENCE: 169

Xaa Xaa Xaa Xaa Xaa Leu Xaa Xaa Xaa Xaa Xaa Xaa
1               5                   10

<210> SEQ ID NO 170
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for arginine protected by Pbf.
<220> FEATURE:
<221> NAME/KEY: MISC_FEATURE
<222> LOCATION: (3)..(3)
<223> OTHER INFORMATION: Xaa stands for cyclohexylalanine.
<220> FEATURE:
<221> NAME/KEY: MISC_FEATURE
<222> LOCATION: (4)..(4)
<223> OTHER INFORMATION: Xaa stands for cyclohexylalanine.
<220> FEATURE:
<221> NAME/KEY: MISC_FEATURE
<222> LOCATION: (5)..(5)
<223> OTHER INFORMATION: Xaa stands for asparagine protected by Trt.
<220> FEATURE:
<221> NAME/KEY: MISC_FEATURE
<222> LOCATION: (7)..(7)
<223> OTHER INFORMATION: Xaa stands for Aib.
<220> FEATURE:
<221> NAME/KEY: MISC_FEATURE
<222> LOCATION: (8)..(8)
<223> OTHER INFORMATION: Xaa stands for threonine protected by tert-
      Butyl.
<220> FEATURE:
<221> NAME/KEY: MISC_FEATURE
<222> LOCATION: (9)..(9)

```
<223> OTHER INFORMATION: Xaa stands for arginine protected by Pbf.
<220> FEATURE:
<221> NAME/KEY: MISC_FEATURE
<222> LOCATION: (10)..(10)
<223> OTHER INFORMATION: Xaa stands for glutamine protected by Trt.
<220> FEATURE:
<221> NAME/KEY: MISC_FEATURE
<222> LOCATION: (11)..(11)
<223> OTHER INFORMATION: Xaa stands for arginine protected by Pbf.
<220> FEATURE:
<221> NAME/KEY: MISC_FEATURE
<222> LOCATION: (12)..(12)
<223> OTHER INFORMATION: Xaa stands for cyclohexylalanine.

<400> SEQUENCE: 170

Xaa His Xaa Xaa Xaa Leu Xaa Xaa Xaa Xaa Xaa Xaa
1               5                   10

<210> SEQ ID NO 171
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for 4-aminomethylbenzoylarginine.
<220> FEATURE:
<221> NAME/KEY: MISC_FEATURE
<222> LOCATION: (12)..(12)
<223> OTHER INFORMATION: AMIDATION

<400> SEQUENCE: 171

Xaa Ala Tyr Lys Asn Leu Ile Glu Arg Gln Arg Tyr
1               5                   10

<210> SEQ ID NO 172
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for Aib.
<220> FEATURE:
<221> NAME/KEY: MISC_FEATURE
<222> LOCATION: (2)..(2)
<223> OTHER INFORMATION: Xaa stands for threonine protected by tert-
      Butyl.
<220> FEATURE:
<221> NAME/KEY: MISC_FEATURE
<222> LOCATION: (3)..(3)
<223> OTHER INFORMATION: Xaa stands for arginine protected by Pbf.
<220> FEATURE:
<221> NAME/KEY: MISC_FEATURE
<222> LOCATION: (4)..(4)
<223> OTHER INFORMATION: Xaa stands for glutamine protected by Trt.
<220> FEATURE:
<221> NAME/KEY: MISC_FEATURE
<222> LOCATION: (5)..(5)
<223> OTHER INFORMATION: Xaa stands for arginine protected by Pbf.
<220> FEATURE:
<221> NAME/KEY: MISC_FEATURE
<222> LOCATION: (6)..(6)
<223> OTHER INFORMATION: Xaa stands for cyclohexylalanine.

<400> SEQUENCE: 172

Xaa Xaa Xaa Xaa Xaa Xaa
1               5
```

```
<210> SEQ ID NO 173
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for Fmoc-cyclohexylalanine.
<220> FEATURE:
<221> NAME/KEY: MISC_FEATURE
<222> LOCATION: (2)..(2)
<223> OTHER INFORMATION: Xaa stands for Aib.
<220> FEATURE:
<221> NAME/KEY: MISC_FEATURE
<222> LOCATION: (3)..(3)
<223> OTHER INFORMATION: Xaa stands for asparagine protected by Trt.
<220> FEATURE:
<221> NAME/KEY: MISC_FEATURE
<222> LOCATION: (4)..(4)
<223> OTHER INFORMATION: Xaa stands for lysine protected by Boc.
<220> FEATURE:
<221> NAME/KEY: MISC_FEATURE
<222> LOCATION: (5)..(5)
<223> OTHER INFORMATION: Xaa stands for Aib.
<220> FEATURE:
<221> NAME/KEY: MISC_FEATURE
<222> LOCATION: (6)..(6)
<223> OTHER INFORMATION: Xaa stands for threonine protected by tert-
      Butyl.
<220> FEATURE:
<221> NAME/KEY: MISC_FEATURE
<222> LOCATION: (7)..(7)
<223> OTHER INFORMATION: Xaa stands for arginine protected by Pbf.
<220> FEATURE:
<221> NAME/KEY: MISC_FEATURE
<222> LOCATION: (8)..(8)
<223> OTHER INFORMATION: Xaa stands for glutamine protected by Trt.
<220> FEATURE:
<221> NAME/KEY: MISC_FEATURE
<222> LOCATION: (9)..(9)
<223> OTHER INFORMATION: Xaa stands for arginine protected by Pbf.
<220> FEATURE:
<221> NAME/KEY: MISC_FEATURE
<222> LOCATION: (10)..(10)
<223> OTHER INFORMATION: Xaa stands for cyclohexylalanine.

<400> SEQUENCE: 173

Xaa Xaa Xaa Xaa Xaa Xaa Xaa Xaa Xaa Xaa
1               5                   10

<210> SEQ ID NO 174
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for 4-imidazolecarbonylserine.
<220> FEATURE:
<221> NAME/KEY: MISC_FEATURE
<222> LOCATION: (2)..(2)
<223> OTHER INFORMATION: Xaa stands for Aib.
<220> FEATURE:
<221> NAME/KEY: MISC_FEATURE
<222> LOCATION: (3)..(3)
<223> OTHER INFORMATION: Xaa stands for isovaline.
<220> FEATURE:
<221> NAME/KEY: MISC_FEATURE
<222> LOCATION: (4)..(4)
<223> OTHER INFORMATION: Xaa stands for 4-pyridylalanine.
<220> FEATURE:
<221> NAME/KEY: MISC_FEATURE
<222> LOCATION: (5)..(5)
```

```
<223> OTHER INFORMATION: Xaa stands for cyclohexylalanine.
<220> FEATURE:
<221> NAME/KEY: MOD_RES
<222> LOCATION: (6)..(6)
<223> OTHER INFORMATION: METHYLATION
<220> FEATURE:
<221> NAME/KEY: MOD_RES
<222> LOCATION: (8)..(8)
<223> OTHER INFORMATION: ACETYLATION
<220> FEATURE:
<221> NAME/KEY: MISC_FEATURE
<222> LOCATION: (9)..(9)
<223> OTHER INFORMATION: Xaa stands for Aib.
<220> FEATURE:
<221> NAME/KEY: MISC_FEATURE
<222> LOCATION: (14)..(14)
<223> OTHER INFORMATION: Xaa stands for cyclohexylalanine.
<220> FEATURE:
<221> NAME/KEY: MOD_RES
<222> LOCATION: (14)..(14)
<223> OTHER INFORMATION: AMIDATION

<400> SEQUENCE: 174

Xaa Xaa Xaa Xaa Xaa Leu Asn Lys Xaa Thr Arg Gln Arg Xaa
1               5                   10

<210> SEQ ID NO 175
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for F-moc lysine protected by Mtt.
<220> FEATURE:
<221> NAME/KEY: MISC_FEATURE
<222> LOCATION: (2)..(2)
<223> OTHER INFORMATION: Xaa stands for glutamine protected by Trt.
<220> FEATURE:
<221> NAME/KEY: MISC_FEATURE
<222> LOCATION: (3)..(3)
<223> OTHER INFORMATION: Xaa stands for arginine protected by Pbf.
<220> FEATURE:
<221> NAME/KEY: MISC_FEATURE
<222> LOCATION: (4)..(4)
<223> OTHER INFORMATION: Xaa stands for tyrosine protected by tert-
      Butyl.

<400> SEQUENCE: 175

Xaa Xaa Xaa Xaa
1

<210> SEQ ID NO 176
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for Aib.
<220> FEATURE:
<221> NAME/KEY: MISC_FEATURE
<222> LOCATION: (2)..(2)
<223> OTHER INFORMATION: Xaa stands for threonine protected by tert-
      Butyl.
<220> FEATURE:
<221> NAME/KEY: MISC_FEATURE
<222> LOCATION: (3)..(3)
<223> OTHER INFORMATION: Xaa stands for arginine protected by Pbf.
<220> FEATURE:
<221> NAME/KEY: MISC_FEATURE
```

```
<222> LOCATION: (4)..(4)
<223> OTHER INFORMATION: Xaa stands for glutamine protected by Trt.
<220> FEATURE:
<221> NAME/KEY: MISC_FEATURE
<222> LOCATION: (5)..(5)
<223> OTHER INFORMATION: Xaa stands for arginine protected by Pbf.
<220> FEATURE:
<221> NAME/KEY: MISC_FEATURE
<222> LOCATION: (6)..(6)
<223> OTHER INFORMATION: Xaa stands for cyclohexylalanine.

<400> SEQUENCE: 176

Xaa Xaa Xaa Xaa Xaa Xaa
1               5

<210> SEQ ID NO 177
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for asparagine protected by Trt.
<220> FEATURE:
<221> NAME/KEY: MISC_FEATURE
<222> LOCATION: (2)..(2)
<223> OTHER INFORMATION: Xaa stands for lysine protected by Boc.
<220> FEATURE:
<221> NAME/KEY: MISC_FEATURE
<222> LOCATION: (3)..(3)
<223> OTHER INFORMATION: Xaa stands for Aib.
<220> FEATURE:
<221> NAME/KEY: MISC_FEATURE
<222> LOCATION: (4)..(4)
<223> OTHER INFORMATION: Xaa stands for threonine protected by tert-
      Butyl.
<220> FEATURE:
<221> NAME/KEY: MISC_FEATURE
<222> LOCATION: (5)..(5)
<223> OTHER INFORMATION: Xaa stands for arginine protected by Pbf.
<220> FEATURE:
<221> NAME/KEY: MISC_FEATURE
<222> LOCATION: (6)..(6)
<223> OTHER INFORMATION: Xaa stands for glutamine protected by Trt.
<220> FEATURE:
<221> NAME/KEY: MISC_FEATURE
<222> LOCATION: (7)..(7)
<223> OTHER INFORMATION: Xaa stands for arginine protected by Pbf.
<220> FEATURE:
<221> NAME/KEY: MISC_FEATURE
<222> LOCATION: (8)..(8)
<223> OTHER INFORMATION: Xaa stands for cyclohexylalanine.

<400> SEQUENCE: 177

Xaa Xaa Xaa Xaa Xaa Xaa Xaa Xaa
1               5

<210> SEQ ID NO 178
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for Aib.
<220> FEATURE:
<221> NAME/KEY: MISC_FEATURE
<222> LOCATION: (2)..(2)
<223> OTHER INFORMATION: Xaa stands for threonine protected by tert-
      Butyl.
<220> FEATURE:
```

```
<221> NAME/KEY: MISC_FEATURE
<222> LOCATION: (3)..(3)
<223> OTHER INFORMATION: Xaa stands for arginine protected by Pbf.
<220> FEATURE:
<221> NAME/KEY: MISC_FEATURE
<222> LOCATION: (4)..(4)
<223> OTHER INFORMATION: Xaa stands for glutamine protected by Trt.
<220> FEATURE:
<221> NAME/KEY: MISC_FEATURE
<222> LOCATION: (5)..(5)
<223> OTHER INFORMATION: Xaa stands for arginine protected by Pbf.
<220> FEATURE:
<221> NAME/KEY: MISC_FEATURE
<222> LOCATION: (6)..(6)
<223> OTHER INFORMATION: Xaa stands for cyclohexylalanine.

<400> SEQUENCE: 178

Xaa Xaa Xaa Xaa Xaa Xaa
1               5

<210> SEQ ID NO 179
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for cyclohexylalanine.
<220> FEATURE:
<221> NAME/KEY: MISC_FEATURE
<222> LOCATION: (2)..(2)
<223> OTHER INFORMATION: Xaa stands for Aib.
<220> FEATURE:
<221> NAME/KEY: MISC_FEATURE
<222> LOCATION: (3)..(3)
<223> OTHER INFORMATION: Xaa stands for asparagine protected by Trt.
<220> FEATURE:
<221> NAME/KEY: MISC_FEATURE
<222> LOCATION: (4)..(4)
<223> OTHER INFORMATION: Xaa stands for lysine protected by Boc.
<220> FEATURE:
<221> NAME/KEY: MISC_FEATURE
<222> LOCATION: (5)..(5)
<223> OTHER INFORMATION: Xaa stands for Aib.
<220> FEATURE:
<221> NAME/KEY: MISC_FEATURE
<222> LOCATION: (6)..(6)
<223> OTHER INFORMATION: Xaa stands for threonine protected by tert-
      Butyl.
<220> FEATURE:
<221> NAME/KEY: MISC_FEATURE
<222> LOCATION: (7)..(7)
<223> OTHER INFORMATION: Xaa stands for arginine protected by Pbf.
<220> FEATURE:
<221> NAME/KEY: MISC_FEATURE
<222> LOCATION: (8)..(8)
<223> OTHER INFORMATION: Xaa stands for glutamine protected by Trt.
<220> FEATURE:
<221> NAME/KEY: MISC_FEATURE
<222> LOCATION: (9)..(9)
<223> OTHER INFORMATION: Xaa stands for arginine protected by Pbf.
<220> FEATURE:
<221> NAME/KEY: MISC_FEATURE
<222> LOCATION: (10)..(10)
<223> OTHER INFORMATION: Xaa stands for cyclohexylalanine.

<400> SEQUENCE: 179

Xaa Xaa Xaa Xaa Xaa Xaa Xaa Xaa Xaa Xaa
1               5                   10

<210> SEQ ID NO 180
<211> LENGTH: 12
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for isovaline.
<220> FEATURE:
<221> NAME/KEY: MISC_FEATURE
<222> LOCATION: (2)..(2)
<223> OTHER INFORMATION: Xaa stands for 4-pyridylalanine.
<220> FEATURE:
<221> NAME/KEY: MISC_FEATURE
<222> LOCATION: (3)..(3)
<223> OTHER INFORMATION: Xaa stands for cyclohexylalanine.
<220> FEATURE:
<221> NAME/KEY: MOD_RES
<222> LOCATION: (4)..(4)
<223> OTHER INFORMATION: METHYLATION
<220> FEATURE:
<221> NAME/KEY: MISC_FEATURE
<222> LOCATION: (5)..(5)
<223> OTHER INFORMATION: Xaa stands for asparagine protected by Trt.
<220> FEATURE:
<221> NAME/KEY: MISC_FEATURE
<222> LOCATION: (6)..(6)
<223> OTHER INFORMATION: Xaa stands for lysine protected by Boc.
<220> FEATURE:
<221> NAME/KEY: MISC_FEATURE
<222> LOCATION: (7)..(7)
<223> OTHER INFORMATION: Xaa stands for Aib.
<220> FEATURE:
<221> NAME/KEY: MISC_FEATURE
<222> LOCATION: (8)..(8)
<223> OTHER INFORMATION: Xaa stands for threonine protected by tert-
      Butyl.
<220> FEATURE:
<221> NAME/KEY: MISC_FEATURE
<222> LOCATION: (9)..(9)
<223> OTHER INFORMATION: Xaa stands for arginine protected by Pbf.
<220> FEATURE:
<221> NAME/KEY: MISC_FEATURE
<222> LOCATION: (10)..(10)
<223> OTHER INFORMATION: Xaa stands for glutamine protected by Trt.
<220> FEATURE:
<221> NAME/KEY: MISC_FEATURE
<222> LOCATION: (11)..(11)
<223> OTHER INFORMATION: Xaa stands for arginine protected by Pbf.
<220> FEATURE:
<221> NAME/KEY: MISC_FEATURE
<222> LOCATION: (12)..(12)
<223> OTHER INFORMATION: Xaa stands for cyclohexylalanine.

<400> SEQUENCE: 180

Xaa Xaa Xaa Leu Xaa Xaa Xaa Xaa Xaa Xaa Xaa Xaa
1               5                   10

<210> SEQ ID NO 181
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for isovaline.
<220> FEATURE:
<221> NAME/KEY: MISC_FEATURE
<222> LOCATION: (2)..(2)
<223> OTHER INFORMATION: Xaa stands for 4-pyridylalanine.
<220> FEATURE:
<221> NAME/KEY: MISC_FEATURE
<222> LOCATION: (3)..(3)
<223> OTHER INFORMATION: Xaa stands for cyclohexylalanine.
<220> FEATURE:
<221> NAME/KEY: MOD_RES
```

```
<222> LOCATION: (4)..(4)
<223> OTHER INFORMATION: METHYLATION
<220> FEATURE:
<221> NAME/KEY: MISC_FEATURE
<222> LOCATION: (5)..(5)
<223> OTHER INFORMATION: Xaa stands for asparagine protected by Trt.
<220> FEATURE:
<221> NAME/KEY: MISC_FEATURE
<222> LOCATION: (6)..(6)
<223> OTHER INFORMATION: Xaa stands for lysine protected by Boc.
<220> FEATURE:
<221> NAME/KEY: MISC_FEATURE
<222> LOCATION: (7)..(7)
<223> OTHER INFORMATION: Xaa stands for Aib.
<220> FEATURE:
<221> NAME/KEY: MISC_FEATURE
<222> LOCATION: (8)..(8)
<223> OTHER INFORMATION: Xaa stands for threonine protected by tert-
      Butyl.
<220> FEATURE:
<221> NAME/KEY: MISC_FEATURE
<222> LOCATION: (9)..(9)
<223> OTHER INFORMATION: Xaa stands for arginine protected by Pbf.
<220> FEATURE:
<221> NAME/KEY: MISC_FEATURE
<222> LOCATION: (10)..(10)
<223> OTHER INFORMATION: Xaa stands for glutamine protected by Trt.
<220> FEATURE:
<221> NAME/KEY: MISC_FEATURE
<222> LOCATION: (11)..(11)
<223> OTHER INFORMATION: Xaa stands for arginine protected by Pbf.
<220> FEATURE:
<221> NAME/KEY: MISC_FEATURE
<222> LOCATION: (12)..(12)
<223> OTHER INFORMATION: Xaa stands for cyclohexylalanine.

<400> SEQUENCE: 181

Xaa Xaa Xaa Leu Xaa Xaa Xaa Xaa Xaa Xaa Xaa Xaa
1               5                   10

<210> SEQ ID NO 182
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for 4-pyridylalanine.
<220> FEATURE:
<221> NAME/KEY: MISC_FEATURE
<222> LOCATION: (2)..(2)
<223> OTHER INFORMATION: Xaa stands for cyclohexylalanine.
<220> FEATURE:
<221> NAME/KEY: MISC_FEATURE
<222> LOCATION: (3)..(3)
<223> OTHER INFORMATION: Xaa stands for Aib.
<220> FEATURE:
<221> NAME/KEY: MISC_FEATURE
<222> LOCATION: (4)..(4)
<223> OTHER INFORMATION: Xaa stands for asparagine protected by Trt.
<220> FEATURE:
<221> NAME/KEY: MISC_FEATURE
<222> LOCATION: (5)..(5)
<223> OTHER INFORMATION: Xaa stands for lysine protected by Boc.
<220> FEATURE:
<221> NAME/KEY: MISC_FEATURE
<222> LOCATION: (6)..(6)
<223> OTHER INFORMATION: Xaa stands for Aib.
<220> FEATURE:
<221> NAME/KEY: MISC_FEATURE
<222> LOCATION: (7)..(7)
<223> OTHER INFORMATION: Xaa stands for threonine protected by tert-
      Butyl.
<220> FEATURE:
<221> NAME/KEY: MISC_FEATURE
```

```
<222> LOCATION: (8)..(8)
<223> OTHER INFORMATION: Xaa stands for arginine protected by Pbf.
<220> FEATURE:
<221> NAME/KEY: MISC_FEATURE
<222> LOCATION: (9)..(9)
<223> OTHER INFORMATION: Xaa stands for glutamine protected by Trt.
<220> FEATURE:
<221> NAME/KEY: MISC_FEATURE
<222> LOCATION: (10)..(10)
<223> OTHER INFORMATION: Xaa stands for arginine protected by Pbf.
<220> FEATURE:
<221> NAME/KEY: MISC_FEATURE
<222> LOCATION: (11)..(11)
<223> OTHER INFORMATION: Xaa stands for cyclohexylalanine.

<400> SEQUENCE: 182

Xaa Xaa Xaa Xaa Xaa Xaa Xaa Xaa Xaa Xaa Xaa
1               5                   10

<210> SEQ ID NO 183
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for cyclohexylalanine.
<220> FEATURE:
<221> NAME/KEY: MOD_RES
<222> LOCATION: (2)..(2)
<223> OTHER INFORMATION: METHYLATION
<220> FEATURE:
<221> NAME/KEY: MISC_FEATURE
<222> LOCATION: (3)..(3)
<223> OTHER INFORMATION: Xaa stands for asparagine protected by Trt.
<220> FEATURE:
<221> NAME/KEY: MISC_FEATURE
<222> LOCATION: (4)..(4)
<223> OTHER INFORMATION: Xaa stands for lysine protected by Boc.
<220> FEATURE:
<221> NAME/KEY: MISC_FEATURE
<222> LOCATION: (5)..(5)
<223> OTHER INFORMATION: Xaa stands for Aib.
<220> FEATURE:
<221> NAME/KEY: MISC_FEATURE
<222> LOCATION: (6)..(6)
<223> OTHER INFORMATION: Xaa stands for threonine protected by tert-
      Butyl.
<220> FEATURE:
<221> NAME/KEY: MISC_FEATURE
<222> LOCATION: (7)..(7)
<223> OTHER INFORMATION: Xaa stands for arginine protected by Pbf.
<220> FEATURE:
<221> NAME/KEY: MISC_FEATURE
<222> LOCATION: (8)..(8)
<223> OTHER INFORMATION: Xaa stands for glutamine protected by Trt.
<220> FEATURE:
<221> NAME/KEY: MISC_FEATURE
<222> LOCATION: (9)..(9)
<223> OTHER INFORMATION: Xaa stands for arginine protected by Pbf.
<220> FEATURE:
<221> NAME/KEY: MISC_FEATURE
<222> LOCATION: (10)..(10)
<223> OTHER INFORMATION: Xaa stands for cyclohexylalanine.

<400> SEQUENCE: 183

Xaa Leu Xaa Xaa Xaa Xaa Xaa Xaa Xaa Xaa
1               5                   10

<210> SEQ ID NO 184
<211> LENGTH: 33
<212> TYPE: DNA
<213> ORGANISM: Artificial Sequence
```

```
<220> FEATURE:
<223> OTHER INFORMATION: primer

<400> SEQUENCE: 184
ccaccatggg tccaataggt gcagaggctg atg                                    33

<210> SEQ ID NO 185
<211> LENGTH: 30
<212> TYPE: DNA
<213> ORGANISM: Artificial Sequence
<220> FEATURE:
<223> OTHER INFORMATION: primer

<400> SEQUENCE: 185
ttagacattg gtagcctctg tgaaagagtc                                        30

<210> SEQ ID NO 186
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa stands for cyclohexylalanine.
<220> FEATURE:
<221> NAME/KEY: MOD_RES
<222> LOCATION: (2)..(2)
<223> OTHER INFORMATION: METHYLATION.
<220> FEATURE:
<221> NAME/KEY: MISC_FEATURE
<222> LOCATION: (3)..(3)
<223> OTHER INFORMATION: Xaa stands for asparagine protected by Trt.
<220> FEATURE:
<221> NAME/KEY: MISC_FEATURE
<222> LOCATION: (4)..(4)
<223> OTHER INFORMATION: Xaa stands for lysine protected by Boc.
<220> FEATURE:
<221> NAME/KEY: MISC_FEATURE
<222> LOCATION: (5)..(5)
<223> OTHER INFORMATION: Xaa stands for Aib.
<220> FEATURE:
<221> NAME/KEY: MISC_FEATURE
<222> LOCATION: (6)..(6)
<223> OTHER INFORMATION: Xaa stands for threonine protected by tert-
      Butyl.
<220> FEATURE:
<221> NAME/KEY: MISC_FEATURE
<222> LOCATION: (7)..(7)
<223> OTHER INFORMATION: Xaa stands for arginine protected by Pbf.
<220> FEATURE:
<221> NAME/KEY: MISC_FEATURE
<222> LOCATION: (8)..(8)
<223> OTHER INFORMATION: Xaa stands for glutamine protected by Trt.
<220> FEATURE:
<221> NAME/KEY: MISC_FEATURE
<222> LOCATION: (9)..(9)
<223> OTHER INFORMATION: Xaa stands for arginine protected by Pbf.
<220> FEATURE:
<221> NAME/KEY: MISC_FEATURE
<222> LOCATION: (10)..(10)
<223> OTHER INFORMATION: Xaa stands for cyclohexylalanine.

<400> SEQUENCE: 186

Xaa Leu Xaa Xaa Xaa Xaa Xaa Xaa Xaa Xaa
1               5                   10

<210> SEQ ID NO 187
<211> LENGTH: 14
<212> TYPE: PRT
<213> ORGANISM: Artificial Sequence
<220> FEATURE:
```

```
<223> OTHER INFORMATION: Synthetic peptide
<220> FEATURE:
<221> NAME/KEY: misc_feature
<222> LOCATION: (1)..(1)
<223> OTHER INFORMATION: Xaa stands for Ser, Glu, or Gln.
<220> FEATURE:
<221> NAME/KEY: BINDING
<222> LOCATION: (1)..(1)
<223> OTHER INFORMATION: Binding to P1-X4-, wherein P1 shows acetyl etc.
      and X4 shows a bond or any amino acid residue(s) bound
      continuously or discontinuously to each other from the C-terminal
      of the 1st-22nd amino acid of the amino acid sequence shown by SEQ
      ID NO:1.
<220> FEATURE:
<221> NAME/KEY: misc_feature
<222> LOCATION: (2)..(2)
<223> OTHER INFORMATION: Xaa stands for D-Pro, D-Hyp, Aib, D-Iva, or
      Iva.
<220> FEATURE:
<221> NAME/KEY: misc_feature
<222> LOCATION: (3)..(3)
<223> OTHER INFORMATION: Xaa stands for Iva, Arg, Nle, Arg(Me), or
      Ala(4Pip).
<220> FEATURE:
<221> NAME/KEY: misc_feature
<222> LOCATION: (4)..(4)
<223> OTHER INFORMATION: Xaa stands for Pya(4), His, Abu, Ala(4Pip), or
      Phe.
<220> FEATURE:
<221> NAME/KEY: misc_feature
<222> LOCATION: (5)..(5)
<223> OTHER INFORMATION: Xaa stands for Cha, or Nal(2).
<220> FEATURE:
<221> NAME/KEY: misc_feature
<222> LOCATION: (6)..(6)
<223> OTHER INFORMATION: Xaa stands for Aib, Iva, Leu(Me), Cha, or
      alpha-MePhe.
<220> FEATURE:
<221> NAME/KEY: misc_feature
<222> LOCATION: (8)..(8)
<223> OTHER INFORMATION: Xaa stands for Lys, Har, Arg(Me), Ala(4Pip),
      Cha, or Lys(Ac).
<220> FEATURE:
<221> NAME/KEY: misc_feature
<222> LOCATION: (9)..(9)
<223> OTHER INFORMATION: Xaa stands for Aib, D-Iva or Iva.
<220> FEATURE:
<221> NAME/KEY: misc_feature
<222> LOCATION: (14)..(14)
<223> OTHER INFORMATION: Xaa stands for Cha, or Phe(2,6-Me2).
<220> FEATURE:
<221> NAME/KEY: MOD_RES
<222> LOCATION: (14)..(14)
<223> OTHER INFORMATION: AMIDATION

<400> SEQUENCE: 187

Xaa Xaa Xaa Xaa Xaa Xaa Asn Xaa Xaa Thr Arg Gln Arg Xaa
1               5                   10
```